(12) United States Patent
Alam et al.

(10) Patent No.: US 9,981,964 B2
(45) Date of Patent: May 29, 2018

(54) MALEIMIDE DERIVATIVES AS MODULATORS OF WNT PATHWAY

(71) Applicant: Agency for Science, Technology and Research, Singapore (SG)

(72) Inventors: Jenefer Alam, Singapore (SG); Anders Poulsen, Singapore (SG); Soo Yei Ho, Singapore (SG); Wei Ling Wang, Singapore (SG); Athisayamani Jeyaraj Duraiswamy, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days. days.

(21) Appl. No.: 15/105,312

(22) PCT Filed: Dec. 17, 2014

(86) PCT No.: PCT/SG2014/000601
§ 371 (c)(1),
(2) Date: Jun. 16, 2016

(87) PCT Pub. No.: WO2015/094118
PCT Pub. Date: Jun. 25, 2015

(65) Prior Publication Data
US 2016/0318926 A1 Nov. 3, 2016

(30) Foreign Application Priority Data
Dec. 17, 2013 (GB) .................................. 1322334.2

(51) Int. Cl.
C07D 471/04 (2006.01)
C07D 487/04 (2006.01)

(52) U.S. Cl.
CPC ......... *C07D 471/04* (2013.01); *C07D 487/04* (2013.01)

(58) Field of Classification Search
CPC .................................................. C07D 471/104
See application file for complete search history.

(56) References Cited

U.S. PATENT DOCUMENTS

| | | |
|---|---|---|
| 4,798,619 A | 1/1989 | Los |
| 4,990,517 A | 2/1991 | Petersen et al. |
| 2009/0163545 A1 | 6/2009 | Goldfarb |

FOREIGN PATENT DOCUMENTS

| | | |
|---|---|---|
| WO | WO 2000/06549 A1 | 2/2000 |
| WO | WO 2004/049803 A1 | 6/2004 |

(Continued)

OTHER PUBLICATIONS

Vippagunta et al. (2001).*
Pinedo et al. (2000).*
McMahon et al. (2000).*
International Search Report and Written Opinion dated Jan. 20, 2015 for PCT/SG2014/000601.
International Preliminary Report on Patentability dated Jun. 30, 2016 for PCT/SG2014/000601.
Amann et al., The siderophores of Pseudomonas fluorescens 18.1 and the importance of cyclopeptidic substructures for the recognition at the cell surface. Z Naturforsch C. Sep.-Oct. 2000;55(9-10):671-80.
Amit et al., Axin mediated CKI phosphorylation of beta-catenin at Ser 45: a molecular switch for the Wnt pathway. Genes Dev. 2002;16:1066-76.
Austin et al., A role for the Wnt gene family in hematopoiesis: expansion of multilineage progenitor cells. Blood. 1997;89:3624-35.
Barker et al., Mining the Wnt pathway for cancer therapeutics. Nat. Rev. Drug Discov. 2006;5:997-1014.
Bergmann et al., Inhibition of glycogen synthase kinase 3β induces dermal fibrosis by activation of the canonical Wnt pathway. Ann. Rheum. Dis. 2011;70:2191-8.

(Continued)

*Primary Examiner* — Paul V Ward
(74) *Attorney, Agent, or Firm* — Wolf, Greenfield & Sacks, P.C.

(57) ABSTRACT

The present invention relates to compounds of formula (I), combinations and uses thereof for disease therapy, or a pharmaceutically acceptable salt, solvate or polymorph thereof, including all tautomers and stereoisomers thereof wherein $R_1$ represents optionally substituted alkyl (wherein optional substituents include one or more substituents each independently selected from $C_{1-6}$alkoxy); optionally substituted carbocyclyl (wherein optional substituents include one or more substituents each independently selected from $C_1$-6alkyl, $C_{1-6}$alkoxy, $C_{1-6}$haloalkyl, $C_{1-6}$haloalkoxy and halo); or -alkylaryl; $R_2$ represents H; or alkyl; $R_3$ represents H; or alkyl; U, V and W represent —(CH$_2$)—; or U and V together represent —CH=CH— and W represents C=O; Y represents aryl; heteroaryl; optionally substituted carbocyclyl (wherein optional substituents include one or more substituents each independently selected from $C_{1-6}$alkyl, $C_{1-6}$alkoxy, $C_{1-6}$haloalkyl, $C_{1-6}$haloalkoxy and halo); or optionally substituted heterocyclyl (wherein optional substituents include one or more substituents each independently selected from $C_{1-6}$alkyl, $C_{1-6}$ alkoxy, —C(O)OC$_{1-6}$alkyl, —C(O)C$_{1-6}$alkyl and —C(O)NHC$_{1-6}$alkyl); and Z represents aryl; heteroaryl; optionally substituted carbocyclyl (wherein optional substituents include one or more substituents each independently selected from $C_{1-6}$alkyl, $C_{1-6}$alkoxy, $C_{1-6}$haloalkyl, $C_{1-6}$haloalkoxy and halo); or optionally substituted heterocyclyl (wherein optional substituents include one or more substituents each independently selected from $C_{1-6}$alkyl, $C_{1-6}$ alkoxy, —C(O)OC$_{1-6}$alkyl, —C(O)C$_{1-6}$alkyl and —C(O)NHC$_{1-6}$alkyl).

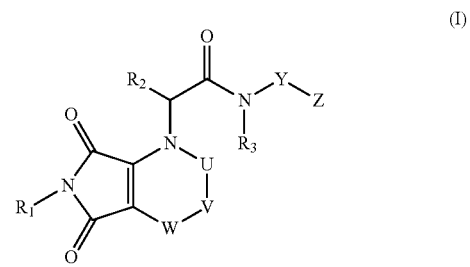

19 Claims, 7 Drawing Sheets

(56) References Cited

FOREIGN PATENT DOCUMENTS

| WO | WO 2006/103399 A1 | 10/2006 |
|----|-------------------|---------|
| WO | WO 2008/155572 A2 | 12/2008 |
| WO | WO 2009/132068 A2 | 10/2009 |
| WO | WO 2010/075282 A1 | 7/2010 |
| WO | WO 2010/122774 A1 | 10/2010 |
| WO | WO 2011/056630 A2 | 5/2011 |
| WO | WO 2013/000994 A1 | 1/2013 |
| WO | WO 2014/189466 A1 | 11/2014 |
| WO | WO 2015/094118 A1 | 6/2015 |

OTHER PUBLICATIONS

Bourderioux et al., Corrigendum to "Synthesis of new fused and substituted benzo and pyrido carbazoles via C-2 (het)arylindoles" [Tetrahedron 64(49) (2008) 11012-11019]. Tetrahedron. 2009;65:696-7.

Bourderioux et al., Synthesis of new fused and substituted benzo and pyrido carbazoles via C-2 (het)arylindoles. Tetrahedron. 2008;64(49):11012-19.

Budzikiewicz et al., Characterization of the chromophores of pyoverdins and related siderophores by electrospray tandem mass spectrometry. Biometals. 2007;20(2):135-44.

Cheng et al., Wnt antagonism inhibits hepatic stellate cell activation and liver fibrosis. Am. J. Physiol. Gastrointest. Liver Physiol. 2008;294:G39-G49.

Chilosi et al., Aberrant Wnt/beta-catenin pathway activation in idiopathic pulmonary fibrosis. Am. J. Pathol. 2003;162(5):1495-1502.

Chiurato et al., New efficient access to fused (Het)aryltetrahydroindolizinones via N-acyl iminium intermediates. Tetrahedron. 2010;66(25):4647-53.

Clevers, Wnt/beta-catenin signaling in development and disease. Cell. 2006;127:469-80.

Cobas et al., Beta-catenin is dispensable for hematopoiesis and lymphopoiesis. J. Exp. Med. 2004;199:221-9.

Dahmen et al., Deletions of AXIN1, a Component of the WNT/wingless Pathway, in Sporadic Medulloblastomas. Cancer Res. 2001;61:7039-43.

Deady et al., Synthesis of perimidine and fused perimidine derivatives from reaction of 1,8-naphthalenediamine with an iminoisocoumarin. J Heterocycl Chem. 1998;35(6):1417-9.

Dealmeida et al., The soluble wnt receptor Frizzled8CRD-hFc inhibits the growth of teratocarcinomas in vivo. Cancer Res. 2007;67(11):5371-9.

Deslandes et al., Synthesis and biological evaluation of analogs of the marine alkaloids granulatimide and isogranulatimide. Eur J Med Chem. Aug. 2012;54:626-36. doi:10.1016/j.ejmech.2012.06.012.

Duffell et al., Nanoelectrospray ionization mass spectrometric study of Mycobacterium tuberculosis CYP121-ligand interactions. Anal Chem. Jun. 18, 2013;85(12):5707-14. doi:10.1021/ac400236z.

Fodde et al., Wnt/beta-catenin signaling in cancer stemness and malignant behavior. Curr Opin Cell Biol. Apr. 2007;19(2):150-8.

Gandhirajan et al., Wnt/β-catenin/LEF-1 signaling in chronic lymphocytic leukemia (CLL): a target for current and potential therapeutic options. Curr. Cancer Drug Targets. 2010;10:716-27.

Garcia-Rostan et al., Frequent Mutation and Nuclear Localization of β-Catenin in Anaplastic Thyroid Carcinoma. Cancer Res. 1999;59:1811-5.

He et al., Wnt/β-catenin signaling promotes renal interstitial fibrosis. J. Am. Soc. Nephrol. 2009;20(4):765-76.

Henderson et al., Inhibition of Wnt/beta-catenin/CREB binding protein (CBP) signaling reverses pulmonary fibrosis. Proc Natl Acad Sci U S A. 2010;107(32):14309-14.

Herr et al., WNT secretion and signalling inhuman disease. Trends Mol. Med. 2012;18(8):483-93.

Hoang et al., Expression of Ldl receptor-related protein 5 (Lrp5) as a novel marker for disease progression in high-grade osteosarcoma. Int. J. Cancer. 2004;109:106-11.

Holcombe et al., Expression of Wnt ligands and Frizzled receptors in colonic mucosa and in colon carcinoma, J Clin Pathol: Mol. Pathol. 2002;55:220-6.

Hugon et al., Synthesis and biological activities of isogranulatimide analogues. Bioorg Med Chem. 2007;15(17):5965-80.

Hugon et al., Synthesis of isogranulatimide analogues possessing a pyrrole moiety instead of an imidazole heterocycle. Tetrahedron Lett. 2003;44(20):3927-30.

Hugon et al., Synthesis of isogranulatimides A and B analogues possessing a 7-azaindole unit instead of an indole moiety. Tetrahedron Lett. Jun. 9, 2003;44(24):4607-11.

Jeannet et al., Long-term, multilineage hematopoiesis occurs in the combined absence of beta-catenin and gamma-catenin. Blood. 2008;111(1):142-9.

Kimura et al., Synthesis and assignment of the absolute configuration of indenotlyptoline bisindole alkaloid BE-54017. Org Lett. Sep. 7, 2012;14(17):4418-21. doi: 10.1021/ol3019314.

Kirikoshi et al., Up-regulation of Frizzled-7 (FZD7) in human gastric cancer. Int J Oncol 2001;19:111-15.

Klopocki et al., Loss of SFRP1 is associated with breast cancer progression and poor prognosis in early stage tumors. Int. J. Oncol. 2004;25:641-9.

Koesters et al., Nuclear accumulation of β-catenin protein in Wilms' tumours. J. Pathol. 2003;199:68-76.

Kuhnert et al., Essential requirement for Wnt signaling in proliferation of adult small intestine and colon revealed by adenoviral expression of Dickkopf-1. Proc Natl Acad Sci U S A. Jan. 6, 2004;101(1):266-71.

Lee et al., Expression of the secreted frizzled-related protein gene family is downregulated in human mesothelioma. Oncogene. 2004;23:6672-6.

Lee et al., Therapeutic potential of a monoclonal antibody blocking the wnt pathway in diabetic retinopathy. Diabetes. 2012;61:2948-57.

Li et al., Synthesis of Spiro thiazolo[3,2-a]pyrimidine compounds by one-pot sequential 1,3-dipolar cycloadditions. J Heterocycl Chem. 2011;48(4):776-9.

Lo Muzio et al., WNT-1 expression in basal cell carcinoma of head and neck. An immunohistochemical and confocal study with regard to the intracellular distribution of beta-catenin. Anticancer Res. 2002;22:565-76.

Logan et al., The Wnt signaling pathway in development and disease. Annu. Rev. Cell Dev. Biol. 2004;20:781-810.

MacDonald et al., Wnt/beta-catenin signaling: Components, mechanisms, and diseases. Dev. Cell. 2009;17(1):9-26.

Malamidou-Xenikaki et al., A study on the reactions of 3-indolecarbaldehyde oximes with electrophilic alkenes/alkynes. Generation of nitrones from the O-H oximes. 4π-Participation of the O-Me oximes in Diels-Alder reactions. Tetrahedron. 1997;53(2):747-58.

Molina-Ruiz et al., A TOPological Sub-structural Molecular Design (TOPS-MODE)-QSAR approach for modeling the antiproliferative activity against murine leukemia tumor cell line (L1210). Bioorg Med Chem. Jan. 15, 2009;17(2):537-47. doi: 10.1016/j.bmc.2008.11.084.

Mulcahy et al., Synthesis and cyclometalation of a pyrido[3,2-e]-2,10b-diaza-cyclopenta[c]fluorene-1,3-dione scaffold. Tetrahedron Lett. Dec. 11, 2006;47(50):8877-80.

Nicolaides et al., Diels-Alder Reactions of Ethyl [10-(Methoxyimino)phenanthren-9-ylidene]acetate with Dienophiles. Synthesis of Dibenzo[f,h]quinoline and Dibenzo[a,c]acridine Derivatives. J Org Chem. 1994;59(5):1083-6.

Noggle et al., A molecular basis for human embryonic stem cell pluripotency. Stem. Cell Rev. 2005;1:111-8.

Pallavicini et al., Corrigendum to "Highly efficient racemisation of a key intermediate of the antibiotic moxifloxacin" [Tetrahedron Asymmetry 22 (2011) 379-380]. Tetrahedron: Asymmetry. Apr. 11, 2011;22(7):818.

Pallavicini et al., Highly efficient racemisation of a key intermediate of the antibiotic moxifloxacin. Tetrahedron: Asymmetry. 2011;22(4):379-80.

(56) References Cited

OTHER PUBLICATIONS

Pin et al., Intermolecular and intramolecular alpha-amidoalkylation reactions using bismuth triflate as the catalyst. J Org Chem. Feb. 16, 2007;72(4):1181-91.
Pinto et al., Canonical Wnt signals are essential for homeostasis of the intestinal epithelium. Genes Dev. Jul. 15, 2003;17(14):1709-13.
Polakis, The many ways of Wnt in cancer. Curr. Opin. Genet. Dev. 2007;17:45-51.
Potts et al., Annulation to the quinazoline ring utilizing mesoionic ring systems. J Org Chem. 1985;50(10):1666-76.
Price et al., Some derivatives of oxanilide. J Org Chem. 1947;12:386-92.
Ramachandran et al., Wnt inhibitory factor 1 induces apoptosis and inhibits cervical cancer growth, invasion and angiogenesis in vivo. Oncogene. 2012;31:2725-37.
Reifenberger et al., Molecular genetic analysis of malignant melanomas for aberrations of the WNT signaling pathway genes CTNNB1, APC, ICAT and BTRC. Int. J. Cancer. 2002;100:549-56.
Reya et al., A role for Wnt signalling in self-renewal of haematopoietic stem cells. Nature. 2003;423:409-14.
Reya et al., Wnt signalling in stem cells and cancer. Nature. 2005;434:843-50.
Rhee et al., Wnt and frizzled receptors as potential targets for immunotherapy in headand neck squamous cell carcinomas. Oncogene. 2002;21:6598-6605.
Ricken et al., Wnt Signaling in the Ovary: Identification and Compartmentalized Expression of wnt-2, wnt-2b, and Frizzled-4 mRNAs. Endocrinology. 2002;143:2741-9.
Robinson et al., Wnt signaling and prostate cancer. Curr. Drug Targets. 2008;9:571-80.
Saiz-Urra et al., Theoretical prediction of antiproliferative activity against murine leukemia tumor cell line (L1210). 3D-morse descriptor and its application in computational chemistry. QSAR Comb. Sci. 2009;28(1):98-110.
Sato et al., Molecular signature of human embryonic stem cells and its comparison with the mouse. Dev. Biol. 2003;260:404-13.
Satoh et al., AXIN1 mutations in hepatocellular carcinomas, and growth suppression in cancer cells by virus-mediated transfer of AXIN. Nature Genet. 2000;24:245-50.
Schett et al., The role of Wnt proteins in arthritis. Nature clinical practice. Rheumatology. 2008;4:473-80.
Stoehr et al., Deletions of chromosome 8p and loss of sFRP1 expression are progression markers of papillary bladder cancer. Lab Invest. 2004;84:465-78.
Suzuki et al., Epigenetic inactivation of SFRP genes allows constitutive WNT signalling in colorectal cancer. Nature genet. 2004;36(4):417-22.
Tanaka et al., Reactions of 1H-pyrrolo[3,4-b]quinoline derivatives. Tetrahedron Letters. 1971;12(30):2803-6.
Torres et al., Activities of the Wnt-1 class of secreted signaling factors are antagonized by the Wnt-5A class and by a dominant negative cadherin in early Xenopus development. J. Cell bio. 1996;133:1123-37.
Ugolini et al., WNT pathway and mammary carcinogenesis: loss of expression of candidate tumor suppressor gene SFRP1 in most invasive carcinomas except of the medullary type, Oncogene 2001;20:5810-7.
Van Es et al., Production of 9-thioxo-2,3,4,9-tetrahydropyrrolo[3,4-b]quinolin-1-one derivatives from the aminolysis of 3,3,9-trichloro-3H-thieno[3,4-b]quinolin-1-one. S. Afr. J. Chem. 2003;56:30-3.
Van Es et al., Sulphur-substituted pyrrolo[3,4-b]quinolines: synthesis, chemistry and antimicrobial activity. S. Afr. J. Chem. 2005;58:74-81.
Van Es et al., The synthesis of 4-ethyl-2-propyl-3-substituted-pyrrolo[3,4-b]quinoline-1,9-dione derivatives from 3,3-dichloro-4-ethylthieno[3,4-b]quinoline-1,9-dione and propylamine. S. Afr. J. Chem. 2006;59:101-8.
Willert et al., Wnt proteins are lipid-modified and can act as stem cell growth factors. Nature. 2003;423:448-52.
Yap et al., Rapid and selective detection of fatty acylated proteins using omega-alkynyl-fatty acids and click chemistry. J Lipid Res. 2010;51(6):1566-80.
Yoshida et al., Synthesis of granulatimide positional analogues. Chem Pharm Bull (Tokyo). Feb. 2003;51(2):209-14.
You et al., Inhibition of Wnt-2-mediated signaling induces programmed cell death in non-small-cell lung cancer cells. Oncogene. 2004;23:6170-4.
Zeng et al., Aberrant Wnt/B-Catenin Signaling in Pancreatic Adenocarcinoma. Neoplasia. 2006;8(4):279-89.

* cited by examiner ated with TCF proteins; converting TCF from a repressor into an activator of Wnt-responsive gene transcription.

Wnt in Cancer & Stem Cell:

Deregulation of components of Writ/β-catenin signaling is implied in a wide spectrum of diseases including degenerative diseases, metabolic diseases, and a number of cancers such as cervical, colon, breast, bladder, head and neck, gastric, lung, ovarian, prostate, thyroid, non-small-cell lung, as well as chronic lymphocytic leukemia, mesothelioma, melanoma, pancreatic adenocarcinoma, basal cell carcinoma, osteosarcoma, hepatocellular carcinoma, Wilm's tumor and medulloblastoma.

MALEIMIDE DERIVATIVES AS MODULATORS OF WNT PATHWAY

RELATED APPLICATIONS

This application is a national stage filing under 35 U.S.C. § 371 of international application number PCT/SG2014/000601, filed Dec. 17, 2014, which claims the benefit of priority of United Kingdom application No. 1322334.2, filed Dec. 17, 2013, the contents of each of which are hereby incorporated by reference in their entirety for all purposes.

FIELD

The invention relates to WNT pathway modulators, processes for making them and methods for using them.

PRIORITY

This application claims priority from UK application GB 1322334.2, filed 17 Dec. 2013, the entire contents of which are incorporated herein by cross-reference.

BACKGROUND

Wnt proteins are secreted glycoproteins acting as growth factors that regulate various cellular functions include proliferation, differentiation, death, migration, and polarity, by activating multiple intracellular signaling cascades, including the β-catenin-dependent and -independent pathways. There are 19 Wnt members have been found in humans and mice, and they exhibit unique expression patterns and distinct functions during development. In humans and mice, the 10 members of the Frizzled (Fz) family comprise a series of seven-pass transmembrane receptors that have been identified as Wnt receptors. In addition to Fz proteins, single-pass transmembrane proteins, such as low-density lipoprotein receptor-related protein 5 (LRP5), LRP6, receptor tyrosine kinase (RTK)-like orphan receptor 1 (Ror1), Ror2, and receptor-like tyrosine kinase (Ryk), have been shown to function as co-receptors for Wnt signaling. Therefore, it has been assumed traditionally that the binding of different Wnts to their specific receptors selectively triggers different Wnts to their specific receptors selectively triggers different outcomes via distinct intracellular pathways.

Diverse Wnts, Wnt receptors, and downstream pathway all contribute to the role of Wnt. These pathways all play a role in development, stem cell maintenance, cancer and metastasis.

In the absence of Wnt signaling, β-catenin is bound and phosphorylated by a "destruction complex" containing the adenomatous polyposis coli (APC) and Axin proteins, as well as glycogen synthase kinase 3 (GSK3) and casein kinase I (CKI). Phosphorylated β-catenin is bound by the F box protein Slimb/β-TrCP and polyubiquitinated, leading to proteosomal degradation. In addition, the complex acts to prevent nuclear localization of b-catenin. Upon Wnt binding to Frizzled (Fz) and low-density lipoprotein-related proteins 5 and 6 (LRP5/6), GSK3, Axin, and other destruction complex components are recruited to the receptor complex. The function of the destruction complex is inhibited, and unphosphorylated β-catenin accumulates in the cytoplasm and eventually translocates to the nucleus. There, it associ- Wnt signaling plays a role both during development, and within stem cell niches in adults. This is best established in skin, hematopoietic stem cells, mammary gland and in intestinal proliferation. For example, high level expression of DKK1, an inhibitor of Wnt signaling, blocks normal stem cell proliferation in mouse intestine, suggesting there is an essential role for Wnt signaling in maintenance of stem cells in the digestive tract. Wnt roles in self renewal and expansion of stem cells have also been demonstrated for embryonic and neural stem cells, suggesting that Wnt signaling may be a general requirement of stem cell maintenance. Inhibition of Wnt signaling, e.g., by overexpression of axin or an extracellular Wnt-binding protein, sFRP, reduces hematopoietic stem cell (HSC) growth in vitro and the ability to reconstitute HSCs in vivo. Notably, while overexpression of activated β-catenin can expand HSC populations in culture for extended periods, two groups have reported that β-catenin is not required for HSC survival and serial transplantation, supporting the proposal that there is more to Wnt signaling than stabilization of β-catenin in stem cell survival. Diverse Wnts can regulate stem cell proliferation: Wnts 1, 5a, and 10b are able to stimulate expansion of HSC populations and Wnt5a acts synergistically with stem cell factor (SCF) to expand and promote self renewal of HSCs. The demonstration of a role for Wnt5a in HSC self renewal and its ability to synergize with stem cell factor is particularly interesting because Wnt5a often acts in a β-catenin independent manner. While Wnt signaling is critical for stem cell maintenance, it may therefore be via signaling pathways distinct from or in parallel to the β-catenin pathway.

Fibrosis:

Wnt/β-catenin signaling pathway is essential to embryonic development in general and organ morphogenesis, so it is not surprising that dysregulation of this pathway in adult has been linked to fibroblast biology and fibrosis. It has been demonstrated that Wnt/β-catenin signaling play a role in severe fibrotic diseases, such as pulmonary fibrosis, liver fibrosis, skin fibrosis and renal fibrosis.

Others:

Dysregulation of Wnt/β-catenin signaling contributes to the development of diabetic retinopathy by inducing retinal inflammation, vascular leakage, and neovascularization.

The binding of Wnt proteins to plasma membrane receptors on mesenchymal cells induces the differentiation of these cells into the osteoblast lineage and thereby supports bone formation. Wnts are also key signaling proteins in joint remodeling processes. Active Wnt signaling contributes to osteophyte formation and might have an essential role in the anabolic pattern of joint remodeling that is observed in ankylosing spondylitis and osteoarthritis. By contrast, blockade of Wnt signaling facilitates bone erosion and contributes to catabolic joint remodeling, a process that is observed in rheumatoid arthritis.

There is therefore a need for compounds that modulate and/or inhibit the WNT pathway so as to treat diseases associated with WNT activity.

DEFINITIONS

A measure of the binding of an inhibitor to and the subsequent release from an enzyme is the "$IC_{50}$" value, which reflects the inhibitor concentration, which at a given substrate concentration, results in 50% enzyme activity.

The term "subject" as used herein, refers to an animal, preferably a mammal, most preferably a human, who has been the object of treatment, observation or experiment. In one embodiment the subject is not a human. The subject may be for example a non-human mammal.

The term "therapeutically effective amount" as used herein, means that amount of active compound or pharmaceutical agent that elicits the biological or medicinal response in a tissue system, animal or human being sought by a researcher, veterinarian, medical doctor or other clinician, which includes alleviation of the symptoms of the disease or disorder being treated.

As used herein, the term "pharmaceutically acceptable" embraces both human and veterinary use: For example the term "pharmaceutically acceptable" embraces a veterinarily acceptable compound or a compound acceptable in human medicine and health care. In one embodiment, human medicine and health care is excluded.

Throughout the description and the claims the expression "alkyl", unless specifically limited, denotes a $C_{1-12}$ alkyl group, suitably a $C_{1-6}$ alkyl group, e.g. $C_{1-4}$ alkyl group. Alkyl groups may be straight chain or branched. Suitable alkyl groups include, for example, methyl, ethyl, propyl (e.g. n-propyl and isopropyl), butyl (e.g. n-butyl, iso-butyl, sec-butyl and tert-butyl), pentyl (e.g. n-pentyl), hexyl (e.g. n-hexyl), heptyl (e.g. n-heptyl) and octyl (e.g. n-octyl). The expression "alk", for example in the expressions "alkoxy", "haloalkyl" and "thioalkyl" should be interpreted in accordance with the definition of "alkyl". Exemplary alkoxy groups include methoxy, ethoxy, propoxy (e.g. n-propoxy), butoxy (e.g. n-butoxy), pentoxy (e.g. n-pentoxy), hexoxy (e.g. n-hexoxy), heptoxy (e.g. n-heptoxy) and octoxy (e.g. n-octoxy). Exemplary thioalkyl groups include methylthio-. Exemplary haloalkyl groups include fluoroalkyl e.g. $CF_3$.

The expression "alkenyl", unless specifically limited, denotes a $C_{2-12}$ alkenyl group, suitably a $C_{2-6}$ alkenyl group, e.g. a $C_{2-4}$ alkenyl group, which contains at least one double bond at any desired location and which does not contain any triple bonds. Alkenyl groups may be straight chain or branched. Exemplary alkenyl groups including one double bond include propenyl and butenyl. Exemplary alkenyl groups including two double bonds include pentadienyl, e.g. (1E, 3E)-pentadienyl.

The expression "alkynyl", unless specifically limited, denotes a $C_{2-12}$ alkynyl group, suitably a $C_{2-6}$ alkynyl group, e.g. a $C_{2-4}$ alkynyl group, which contains at least one triple bond at any desired location and may or may not also contain one or more double bonds. Alkynyl groups may be straight chain or branched. Exemplary alkynyl groups include propynyl and butynyl.

The expression "alkylene" denotes a chain of formula —$(CH_2)_n$— wherein n is an integer e.g. 1-12, 1-6, 2-6 or 2-5 (for example 1, 2, 3, 4, 5, 6, 7, 8, 9, 10, 11 or 12), unless specifically limited.

The expression "cycloalkyl", unless specifically limited, denotes a $C_{3-10}$ cycloalkyl group (i.e. 3 to 10 ring carbon atoms), more suitably a $C_{3-8}$ cycloalkyl group, e.g. a $C_{3-6}$ cycloalkyl group. Exemplary cycloalkyl groups include cyclopropyl, cyclobutyl, cyclopentyl, cyclohexyl, cycloheptyl and cyclooctyl. A most suitable number of ring carbon atoms is three to six or 4 to 8 or 5 to 7, but may be 3, 4, 5, 6, 7, 8, 9 or 10.

The expression "cycloalkenyl", unless specifically limited, denotes a $C_{3-10}$ cycloalkenyl group (i.e. 3 to 10 ring carbon atoms), suitably a $C_{5-10}$ cycloalkenyl group (i.e. 5 to 10 ring carbon atoms), more suitably a $C_{5-8}$ cycloalkenyl group e.g. a $C_{5-6}$ cycloalkenyl group. Exemplary cycloalkenyl groups include cyclopropenyl, cyclohexenyl, cycloheptenyl and cyclooctenyl. A most suitable number of ring carbon atoms is five to six.

The expression "carbocyclyl", unless specifically limited, denotes any ring system in which all the ring atoms are carbon and which contains between three and twelve ring carbon atoms, suitably between three and ten carbon atoms and more suitably between three and eight carbon atoms. Carbocyclyl groups may be saturated or partially unsaturated, but do not include aromatic rings. Examples of carbocyclyl groups include monocyclic, bicyclic, and tricyclic ring systems, in particular monocyclic and bicyclic ring systems. Other carbocyclyl groups include bridged ring systems (e.g. bicyclo[2.2.1]heptenyl). A specific example of a carbocyclyl group is a cycloalkyl group. A further example of a carbocyclyl group is a cycloalkenyl group.

The expression "heterocyclyl", unless specifically limited, refers to a carbocyclyl group wherein one or more (e.g. 1, 2 or 3) ring atoms are replaced by heteroatoms. The heteroatom(s) are commonly selected from N, S and O. A specific example of a heterocyclyl group is a cycloalkyl group (e.g. cyclopentyl or more particularly cyclohexyl) wherein one or more (e.g. 1, 2 or 3, particularly 1 or 2, especially 1) ring atoms are replaced by heteroatoms selected from N, S or O. Exemplary heterocyclyl groups containing one hetero atom include pyrrolidine, tetrahydrofuran and piperidine, and exemplary heterocyclyl groups containing two hetero atoms include morpholine and piperazine. A further specific example of a heterocyclyl group is a cycloalkenyl group (e.g. a cyclohexenyl group) wherein one or more (e.g. 1, 2 or 3, particularly 1 or 2, especially 1) ring atoms are replaced by heteroatoms selected from N, S and O. An example of such a group is dihydropyranyl (e.g. 3,4-dihydro-2H-pyran-2-yl-). The heterocyclyl group may be linked to other part or parts of the molecule by a carbon ring atom or nitrogen ring atom.

The expression "aryl", unless specifically limited, denotes a $C_{6-12}$ aryl group, suitably a $C_{6-10}$ aryl group, more suitably a $C_{6-8}$ aryl group. Aryl groups will contain at least one aromatic ring (e.g. one, two or three rings). Aryl groups with multiple aromatic rings include fused aromatic rings and aromatic rings connected to each other by one single bond. An example of a typical aryl group with one aromatic ring is phenyl. An example of a typical aryl group with two fused aromatic rings is naphthyl. An example of an aromatic group with two directly connected aromatic rings is biphenyl.

The expression "heteroaryl", unless specifically limited, denotes an aryl residue, wherein one or more (e.g. 1, 2, 3, or 4, suitably 1, 2 or 3) ring atoms are replaced by heteroatoms, said heteroatoms commonly being selected from N, S and O, or else a 5-membered aromatic ring containing one or more (e.g. 1, 2, 3, or 4, suitably 1, 2 or 3) ring atoms, said heteroatoms commonly being selected from N, S and O. In some embodiments a heteroaryl group will have no ring heteroatoms other than nitrogen. Exemplary monocyclic heteroaryl groups having one heteroatom include: five membered rings (e.g. pyrrole, furan, thiophene); and six membered rings (e.g. pyridine, such as pyridin-2-yl, pyridin-3-yl and pyridin-4-yl). Exemplary monocyclic heteroaryl groups having two heteroatoms include: five membered rings (e.g. pyrazole, oxazole, isoxazole, thiazole, isothiazole, imidazole, such as imidazol-1-yl, imidazol-2-yl imidazol-4-yl); and six membered rings (e.g. pyridazine, pyrimidine, pyrazine). Exemplary monocyclic heteroaryl groups having three heteroatoms include: 1,2,3-triazole, 1,2,4-triazole, 1,2,3-oxadiazole and 1,2,4-oxadiazole. Exemplary moniocyclic heteroaryl groups having four heteroatoms include tetrazole. Exemplary bicyclic heteroaryl groups include: indole (e.g. indol-6-yl), benzofuran, benzthiophene, quinoline, isoquinoline, indazole, benzimidazole, benzthiazole, quinazoline and purine. The heteroaryl group may be linked to other part or parts of the molecule by a carbon ring atom or nitrogen ring atom.

The aforementioned aryl and heteroaryl groups may, where appropriate, optionally be substituted by one or more (e.g. 1, 2 or 3, suitably 1 or 2) groups independently selected from monovalent or multivalent (i.e. having valency greater than 1) functional groups. Suitable substituent groups include alkyl, alkenyl, alkynyl, haloalkyl, -alkoxy (e.g. OMe), cycloalkyl, alkenyloxy-, alkynyloxy-, alkoxyalkyl-, nitro, halogen (e.g. fluoro, chloro and bromo), cyano, hydroxyl, oxo, —C(O)-alkyl (e.g. COMe), C(O)OH, —C(O)Oalkyl (e.g. —C(O)OMe), —OC(O)alkyl (e.g. —OC(O)Me), —NH$_2$, —NHalkyl (e.g. —NHMe), —N(alkyl)$_2$ (e.g. dimethylamino-), —C(O)NH$_2$, —C(O)NH(alkyl) (e.g. —C(O)NHMe), —NHC(O)alkyl (e.g. —NHC(O)Me), —C(NH)NH$_2$, thioalkyl (e.g. -thiomethyl), —SO$_2$alkyl (e.g. SO$_2$Me), —SOalkyl (e.g. —SOMe), —SO$_2$cycloalkyl and —SOcycloalkyl. More typically, substituents will be selected from alkyl (e.g. Me), fluoroalkyl (e.g. CF$_3$ and CHF$_2$), alkoxy (e.g. OMe), halogen and hydroxyl.

The expression "-alkylaryl", unless specifically limited, denotes an aryl residue which is connected via an alkylene moiety e.g. a C$_{1-4}$alkylene moiety. An example of such a group is benzyl: PhCH$_2$—.

The term "halogen" or "halo" comprises fluorine (F), chlorine (Cl) and bromine (Br).

The term "amino" refers to the group —NH$_2$.

The term "oxo" refers to an oxygen atom which, together with the carbon atom which it substitutes, forms a carbonyl group C═O.

Stereoisomers:

All possible stereoisomers of the claimed compounds are included in the present invention.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Preparation and Isolation of Stereoisomers:

Where the processes for the preparation of the compounds according to the invention give rise to a mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Pharmaceutically Acceptable Salts:

In view of the close relationship between the free compounds and the compounds in the form of their salts or solvates, whenever a compound is referred to in this context, a corresponding salt, solvate or polymorph is also intended, provided such is possible or appropriate under the circumstances.

Salts and solvates of the compounds of formula (I) and physiologically functional derivatives thereof which are suitable for use in medicine are those wherein the counter-ion or associated solvent is pharmaceutically acceptable. However, salts and solvates having non-pharmaceutically acceptable counter-ions or associated solvents are within the scope of the present invention, for example, for use as intermediates in the preparation of other compounds and their pharmaceutically acceptable salts and solvates.

Suitable salts according to the invention include those formed with both organic and inorganic acids or bases. Pharmaceutically acceptable acid addition salts include those formed from hydrochloric, hydrobromic, sulfuric, nitric, citric, tartaric, phosphoric, lactic, pyruvic, acetic, trifluoroacetic, triphenylacetic, sulfamic, sulfanilic, succinic, oxalic, fumaric, maleic, malic, mandelic, glutamic, aspartic, oxaloacetic, methanesulfonic, ethanesulfonic, arylsulfonic (for example p-toluenesulfonic, benzenesulfonic, naphthalenesulfonic or naphthalenedisulfonic), salicylic, glutaric, gluconic, tricarballylic, cinnamic, substituted cinnamic (for example, phenyl, methyl, methoxy or halo substituted cinnamic, including 4-methyl and 4-methoxycinnamic acid), ascorbic, oleic, naphthoic, hydroxynaphthoic (for example 1- or 3-hydroxy-2-naphthoic), naphthaleneacrylic (for example naphthalene-2-acrylic), benzoic, 4-methoxybenzoic, 2- or 4-hydroxybenzoic, 4-chlorobenzoic, 4-phenylbenzoic, benzeneacrylic (for example 1,4-benzenediacrylic), isethionic acids, perchloric, propionic, glycolic, hydroxyethanesulfonic, pamoic, cyclohexanesulfamic, salicylic, saccharinic and trifluoroacetic acid. Pharmaceutically acceptable base salts include ammonium salts, alkali metal salts such as those of sodium and potassium, alkaline earth metal salts such as those of calcium and magnesium and salts with organic bases such as dicyclohexylamine and N-methyl-D-glucamine.

All pharmaceutically acceptable acid addition salt forms of the compounds of the present invention are intended to be embraced by the scope of this invention.

Polymorph Crystal Forms:

Furthermore, some of the crystalline forms of the compounds may exist as polymorphs and as such are intended to be included in the present invention. In addition, some of the compounds may form solvates with water (i.e. hydrates) or common organic solvents, and such solvates are also intended to be encompassed within the scope of this invention. The compounds, including their salts, can also be obtained in the form of their hydrates, or include other solvents used for their crystallization.

Prodrugs:

The present invention further includes within its scope prodrugs of the compounds of this invention. In general, such prodrugs will be functional derivatives of the compounds which are readily convertible in vivo into the desired therapeutically active compound. Thus, in these cases, the methods of treatment of the present invention, the term "administering" shall encompass the treatment of the various disorders described with prodrug versions of one or more of the claimed compounds, but which converts to the above specified compound in vivo after administration to the subject. Conventional procedures for the selection and preparation of suitable prodrug derivatives are described, for example, in "Design of Prodrugs", ed. H. Bundgaard, Elsevier, 1985.

Protective Groups:

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991, fully incorporated herein by reference. The protecting groups may be removed at a convenient subsequent stage using methods known from the art.

As used herein, the term "composition" is intended to encompass a product comprising the claimed compounds in the therapeutically effective amounts, as well as any product which results, directly or indirectly, from combinations of the claimed compounds.

Carriers and Additives for Galenic Formulations:

Carriers, which can be added to the mixture, include necessary and inert pharmaceutical excipients, including, but not limited to, suitable binders, suspending agents, lubricants, flavorants, sweeteners, preservatives, coatings, disintegrating agents, dyes and coloring agents.

Thus, for liquid oral preparations, such as for example, suspensions, elixirs and solutions, suitable carriers and additives may advantageously include water, glycols, oils, alcohols, flavoring agents, preservatives, coloring agents and the like; for solid oral preparations such as, for example, powders, capsules, gelcaps and tablets, suitable carriers and additives include starches, sugars, diluents, granulating agents, lubricants, binders, disintegrating agents and the like.

Soluble polymers as targetable drug carriers can include polyvinylpyrrolidone, pyran copolymer, polyhydroxypropylmethacrylamidephenol, polyhydroxyethylaspartamide-phenol, or polyethyleneoxidepolyllysine substituted with palmitoyl residue. Furthermore, the compounds of the present invention may be coupled to a class of biodegradable polymers useful in achieving controlled release of a drug, for example, polyactic acid, polyepsilon caprolactone, polyhydroxy butyeric acid, polyorthoesters, polyacetals, polydihydropyrans, polycyanoacrylates and cross-linked or amphipathic block copolymers of hydrogels.

Suitable binders include, without limitation, starch, gelatin, natural sugars such as glucose or betalactose, corn sweeteners, natural and synthetic gums such as acacia, tragacanth or sodium oleate, sodium stearate, magnesium stearate, sodium benzoate, sodium acetate, sodium chloride and the like.

Disintegrators include, without limitation, starch, methyl cellulose, agar, bentonite, xanthan gum and the like.

SUMMARY OF INVENTION

According to the invention there is provided a compound of formula (I), (I)

or a pharmaceutically acceptable salt, solvate or polymorph thereof, including all tautomers and stereoisomers thereof wherein:

$R_1$ represents alkyl which is optionally substituted by one or more substituents each independently selected from $C_{1-6}$alkoxy; carbocyclyl which is optionally substituted by one or more substituents each independently selected from $C_{1-6}$alkyl, $C_{1-6}$alkoxy, $C_{1-6}$haloalkyl, $C_{1-6}$haloalkoxy and halo; or -alkylaryl;

$R_2$ represents H; or alkyl;

$R_3$ represents H; or alkyl;

U, V and W each represent —($CH_2$)—; or U and V together represent —CH=CH— and W represents C=O;

Y represents aryl; heteroaryl; carbocyclyl which is optionally substituted by one or more substituents each independently selected from $C_{1-6}$alkyl, $C_{1-6}$alkoxy, $C_{1-6}$haloalkyl, $C_{1-6}$haloalkoxy and halo; or heterocyclyl which is optionally substituted by one or more substituents each independently selected from $C_{1-6}$alkyl, $C_{1-6}$alkoxy, —C(O)O$C_{1-6}$alkyl, —C(O)$C_{1-6}$alkyl and —C(O)NH$C_{1-6}$alkyl; and Z represents aryl; heteroaryl; carbocyclyl which is optionally substituted by one or more substituents each independently selected from $C_{1-6}$alkyl, $C_{1-6}$alkoxy, $C_{1-6}$haloalkyl, $C_{1-6}$haloalkoxy and halo; or heterocyclyl which is optionally substituted by one or more substituents each independently selected from $C_{1-6}$alkyl, $C_{1-6}$alkoxy, —C(O)O$C_{1-6}$alkyl, —C(O)$C_{1-6}$alkyl and —C(O)NH$C_{1-6}$alkyl.

BRIEF DESCRIPTION OF DRAWINGS

FIG. 5 shows the results for Cell line AsPC-1 treated with Compound 43. FIG. 6 shows the results for Cell line HPAF-II treated with Compound 43. FIG. 7 shows the results for Cell line CFPAC-1 treated with Compound 43.

DETAILED DESCRIPTION

Figure 1:
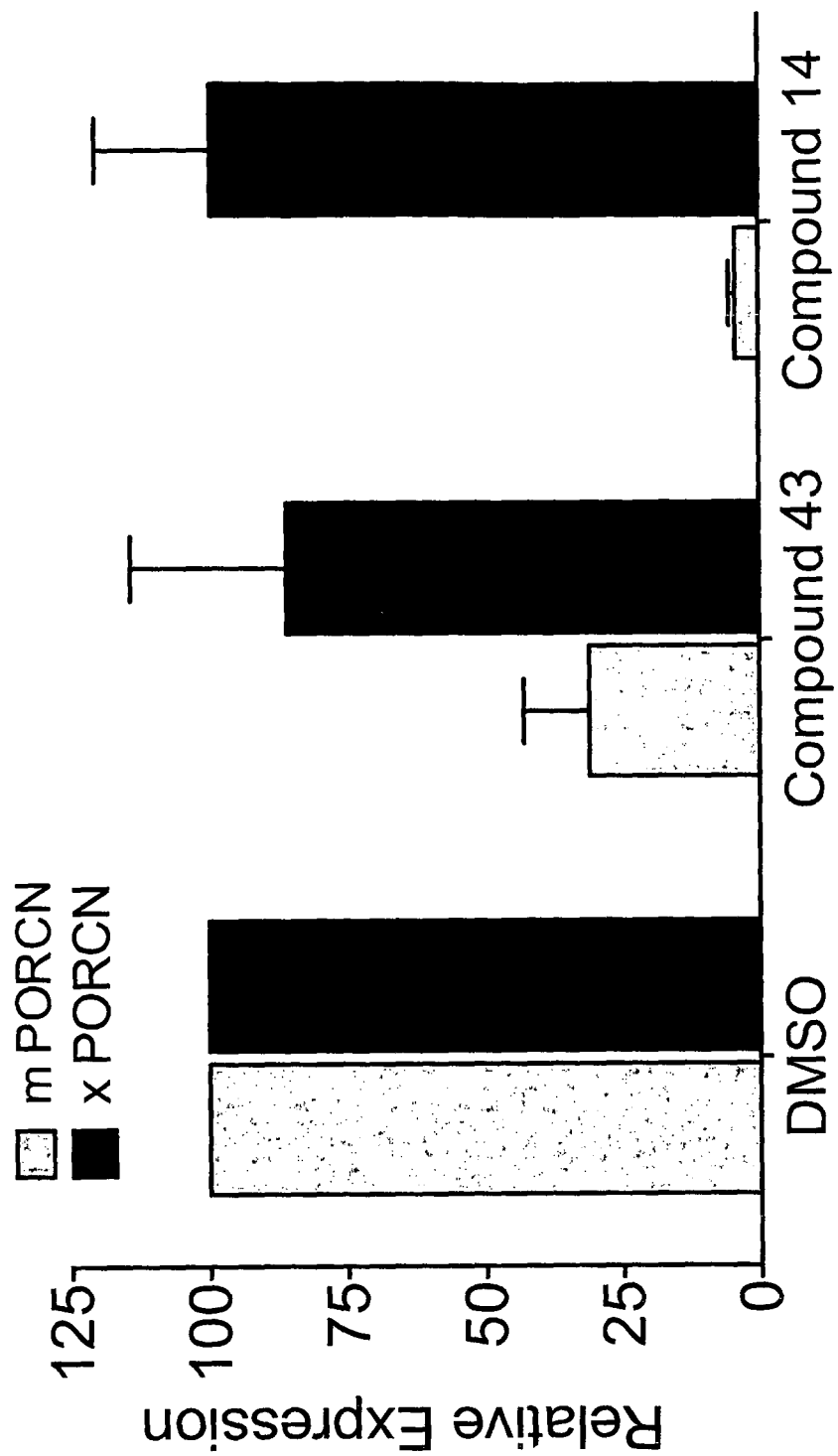
FIG. 1: A bar chart illustrating inhibition of the activity of mammalian porcupine by the two compounds, Compound 13 and 43.

According to the invention there is provided a compound of formula (I),

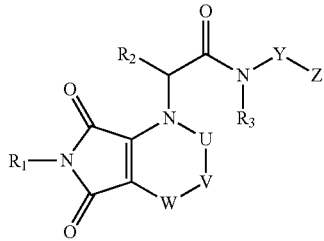

(I)

or a pharmaceutically acceptable salt, solvate or polymorph thereof, including all tautomers and stereoisomers thereof wherein:

$R_1$ represents optionally substituted alkyl (wherein optional substituents include one or more substituents each independently selected from $C_{1-6}$alkoxy); optionally substituted carbocyclyl (wherein optional substituents include one or more substituents each independently selected from $C_{1-6}$alkyl, $C_{1-6}$alkoxy, $C_{1-6}$haloalkyl, $C_{1-6}$haloalkoxy and halo); or -alkylaryl;

$R_2$ represents H; or alkyl;

$R_3$ represents H; or alkyl;

U, V and W represent —(CH$_2$)—; or U and V together represent —CH=CH— and W represents C=O;

Y represents aryl; heteroaryl; optionally substituted carbocyclyl (wherein optional substituents include one or more substituents each independently selected from $C_{1-6}$alkyl, $C_{1-6}$alkoxy, $C_{1-6}$haloalkyl, $C_{1-6}$haloalkoxy and halo); or optionally substituted heterocyclyl (wherein optional substituents include one or more substituents each independently selected from $C_{1-6}$alkyl, $C_{1-6}$alkoxy, —C(O)OC$_{1-6}$alkyl, —C(O)C$_{1-6}$alkyl and —C(O)NHC$_{1-6}$alkyl); and Z represents aryl; heteroaryl; optionally substituted carbocyclyl (wherein optional substituents include one or more substituents each independently selected from $C_{1-6}$alkyl, $C_{1-6}$alkoxy, $C_{1-6}$haloalkyl, $C_{1-6}$haloalkoxy and halo); or optionally substituted heterocyclyl (wherein optional substituents include one or more substituents each independently selected from $C_{1-6}$alkyl, $C_{1-6}$alkoxy, —C(O)OC$_{1-6}$alkyl, —C(O)C$_{1-6}$alkyl and —C(O)NHC$_{1-6}$alkyl).

Further, according to the invention there is provided a compound of formula (I),

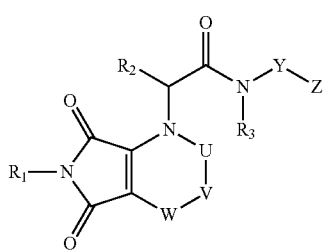

(I)

or a pharmaceutically acceptable salt, solvate or polymorph thereof, including all tautomers and stereoisomers thereof wherein:

$R_1$ represents alkyl which is optionally substituted by one or more substituents each independently selected from $C_{1-6}$alkoxy; carbocyclyl which is optionally substituted by one or more substituents each independently selected from $C_{1-6}$alkyl, $C_{1-6}$alkoxy, $C_{1-6}$haloalkyl, $C_{1-6}$haloalkoxy and halo; or -alkylaryl;

$R_2$ represents H; or alkyl;

$R_3$ represents H; or alkyl;

U, V and W represent —(CH$_2$)—; or U and V together represent —CH=CH— and W represents C=O;

Y represents aryl; heteroaryl; carbocyclyl which is optionally substituted by one or more substituents each independently selected from $C_{1-6}$alkyl, $C_{1-6}$alkoxy, $C_{1-6}$haloalkyl, $C_{1-6}$haloalkoxy and halo; or heterocyclyl which is optionally substituted by one or more substituents each independently selected from $C_{1-6}$alkyl, $C_{1-6}$alkoxy, —C(O)OC$_{1-6}$alkyl, —C(O)C$_{1-6}$alkyl and —C(O)NHC$_{1-6}$alkyl; and Z represents aryl; heteroaryl; carbocyclyl which is optionally substituted by one or more substituents each independently selected from $C_{1-6}$alkyl, $C_{1-6}$alkoxy, $C_{1-6}$haloalkyl, $C_{1-6}$haloalkoxy and halo; or heterocyclyl which is optionally substituted by one or more substituents each independently selected from $C_{1-6}$alkyl, $C_{1-6}$alkoxy, —C(O)OC$_{1-6}$alkyl, —C(O)C$_{1-6}$alkyl and —C(O)NHC$_{1-6}$alkyl:

In the context of variable Y, the term "aryl" is understood to mean "arylene" (e.g. "phenyl" is understood to mean "phenylene" (i.e. C$_6$H$_4$)) because Y is a linking group (in that it links the amide nitrogen atom to the group Z), not a terminal group. The terms for other Y rings (e.g. heteroaryl) are to be construed likewise. When Y is referred to as being unsubstituted, this is understood to mean no other substituents other than Z and NR$_3$. When Y is referred to as being monosubstituted, this is understood to mean one substituent other than Z and NR$_3$.

When $R_1$ represents alkyl which is optionally substituted by one or more substituents each independently selected from $C_{1-6}$alkoxy (e.g. methoxy), examples include $C_{1-6}$ alkyl (e.g. unsubstituted $C_{1-6}$alkyl) such as methyl, ethyl, propyl (e.g. n-propyl, isopropyl), butyl (e.g. n-butyl, isobutyl, sec-butyl, tert-butyl), pentyl (e.g. n-pentyl) and hexyl (e.g. n-hexyl). Exemplary $C_{1-6}$ alkyl groups are methyl, ethyl and isopropyl, particularly methyl and isopropyl, more particularly methyl.

When $R_1$ represents carbocyclyl which is optionally substituted by one or more substituents each independently selected from $C_{1-6}$alkyl (e.g. methyl), $C_{1-6}$alkoxy (e.g. methoxy), $C_{1-6}$haloalkyl (e.g. fluoromethyl), $C_{1-6}$haloalkoxy (e.g. fluoromethoxy) and halo (e.g. fluoro, e.g. chloro), examples include cycloalkyl, such as $C_{3-10}$ cycloalkyl (e.g $C_{3-6}$ cycloalkyl such as $C_{3-4}$ cycloalkyl). Examples include cyclopropyl, cyclobutyl, cyclopentyl and cyclohexyl. Exemplary $C_{3-4}$ cycloalkyl groups are cyclopropyl and cyclobutyl, particularly cyclopropyl.

When $R_1$ represents -alkylaryl, examples include benzyl.

When $R_2$ represents alkyl, examples include $C_{1-6}$ alkyl such as methyl, ethyl, propyl (e.g. n-propyl, isopropyol), butyl (e.g. n-butyl, iso-butyl, sec-butyl, tert-butyl), pentyl (e.g. n-pentyl) and hexyl (e.g. n-hexyl). Exemplary $C_{1-6}$ alkyl groups are methyl and ethyl, particularly methyl. When $R_2$ represents alkyl (e.g. methyl), the stereocentre adjacent to $R_2$ may have "S" or "R" stereochemistry.

When $R_3$ represents alkyl, examples include $C_{1-6}$ alkyl such as methyl, ethyl, propyl (e.g. n-propyl, isopropyl), butyl (e.g. n-butyl, iso-butyl, sec-butyl, tert-butyl), pentyl (e.g. n-pentyl) and hexyl (e.g. n-hexyl). Exemplary $C_{1-6}$ alkyl groups are methyl and ethyl, particularly methyl.

In one embodiment U, V and W each represent —(CH$_2$)—. In another embodiment U and V together represent —C=C— and W represents C=O.

When Y represents aryl, examples include optionally substituted phenyl. Exemplary substituents include one or more (e.g. one or two, especially one) substituents each independently selected from $C_{1-6}$ alkyl (e.g. methyl), C$_{1-6}$alkoxy (e.g. methoxy), halo (e.g. fluoro, e.g. chloro), —C$_{1-6}$haloalkyl (e.g. fluoromethyl such as trifluoromethyl) and —C$_{1-6}$haloalkoxy (e.g. trifluoromethoxy). Specific examples include phenyl, 2-methylphenyl, 3-methylphenyl, 2-fluorophenyl, 3-fluorophenyl, 2-methoxyphenyl and 3-methoxyphenyl. Z and NR$_3$ may be positioned on the phenyl ring at the 1- and 4-positions relative to each other (i.e. Z and NR$_3$ have a para relationship).

When Y represents heteroaryl, examples include monocyclic (e.g. 5 and 6 membered) and bicyclic (e.g. 9 and 10 membered) heteroaryl ring systems, especially monocyclic ring systems. The aforementioned heteroaryl group may either be unsubstituted or may be substituted by one or more (e.g. one or two, particularly one) substituents. Exemplary substituents are independently selected from C$_{1-6}$ alkyl (e.g. methyl), C$_{1-6}$alkoxy (e.g. methoxy), halo (e.g. fluoro, e.g. chloro), —C$_{1-6}$haloalkyl (e.g. fluoromethyl such as trifluoromethyl) and —C$_{1-6}$haloalkoxy (e.g. trifluoromethoxy), especially methyl and fluoro. When Y is 5-membered monocyclic heteroaryl, Z and NR$_3$ may be positioned on the ring at non-adjacent ring atoms. When Y is 6-membered monocyclic heteroaryl, Z and NR$_3$ may be positioned on the ring at 1- and 4-positions relative to each other (i.e. Z and NR$_3$ have a para relationship). Examples of unsubstituted 6-membered monocyclic heteroaryl include pyridinyl, pyridazinyl, pyrazinyl and pyrimidinyl. Examples of unsubstituted 5-membered monocyclic heteroaryl include imidazolyl, oxazolyl, thiazolyl, pyrazolyl, isoxazolyl and isothiazolyl. Specific examples of unsubstituted monocyclic heteroaryl include pyridinyl, pyridazinyl, pyrazinyl and isoxazolyl, particularly pyridinyl, pyridazinyl and pyrazinyl. Examples of substituted monocyclic heteroaryl include methylpyridinyl, methylpyridazinyl, methylpyrazinyl, methylpyrimidinyl, fluoropyridinyl, fluoropyridazinyl, fluoropyrazinyl and fluoropyrimidinyl. Specific examples of substituted monocyclic heteroaryl include methylpyridazinyl, methylpyridinyl and fluoropyridinyl.

When Y represents carbocyclyl which is optionally substituted by one or more substituents each independently selected from C$_{1-6}$alkyl (e.g. methyl), C$_{1-6}$alkoxy (e.g. methoxy), C$_{1-6}$haloalkyl (e.g. fluoromethyl), C$_{1-6}$haloalkoxy (e.g. fluoromethoxy) and halo (e.g. fluoro, e.g. chloro), Y may represent carbocyclyl which is optionally substituted by C$_{1-6}$ alkyl. Examples include monocyclic carbocyclyl which is optionally substituted by C$_{1-6}$ alkyl (such as methyl). Examples of carbocyclyl include C$_{3-8}$cycloalkyl (e.g. cyclohexyl) and C$_{5-8}$cycloalkenyl (e.g. cyclohexenyl). The carbocycyl ring is optionally substituted by one, two or three substituents (e.g. one or two, especially one, e.g. one methyl group). When Y represents carbocydlyl, Y may represent C$_{3-8}$cycloalkyl, for example C$_{5-6}$cycloalkyl. A specific example is cyclohexyl. When Y is cyclohexyl, Z and —NR$_3$ may be positioned on ring Y at the 1- and 4-positions relative to each other.

When Y represents heterocyclyl which is optionally substituted by one or more substituents each independently selected from C$_{1-6}$alkyl, C$_{1-6}$alkoxy, —C(O)OC$_{1-6}$alkyl, —C(O)C$_{1-6}$alkyl and —C(O)NHC$_{1-6}$alkyl, Y may represent heterocyclyl which is optionally substituted by C$_{1-6}$ alkyl (such as methyl). Examples include monocyclic heterocyclyl. The heterocyclyl group may be unsubstituted or may have for example one or two (e.g. one) substituent (e.g. one methyl group). Examples include pyrrolidinyl, piperidinyl, morpholinyl, 4,5-dihydropyrazolyl, 4,5-dihydroisoxazolyl and 4,5-dihydroisothiazolyl.

When Z represents aryl, exemplary substituents include C$_{1-6}$ alkyl (e.g. methyl), C$_{1-6}$alkoxy (e.g. methoxy), halo (e.g. fluoro, e.g. chloro), —C$_{1-6}$haloalkyl (e.g. fluoromethyl such as difluoromethyl or trifluoromethyl) and —C$_{1-6}$haloalkoxy (e.g. trifluoromethoxy). Examples include monocyclic aryl such as substituted or unsubstituted phenyl, e.g. phenyl, chlorophenyl (e.g. 2-chlorophenyl, 3-chlorophenyl, 4-chlorophenyl), fluorophenyl (e.g. 2-fluorophenyl, 3-fluorophenyl, 4-fluorophenyl), methylphenyl (2-methylphenyl, 3-methylphenyl, 4-methylphenyl), methoxyphenyl (e.g. 2-methoxyphenyl, 3-methoxyphenyl, 4-methoxyphenyl), haloalkylphenyl (e.g. 2-trifluoromethoxyphenyl, 3-trifluoromethylphenyl, 4-trifluoromethylphenyl, 2-difluoromethoxyphenyl 3-diflurormethylphenyl and 4-diflurom-ethylphenyl), haloalkoxyphenyl (e.g. 3-trifluoromethyloxyphenyl, 4-trifluoromethyloxyphenyl).

When Z represents heteroaryl, examples include monocyclic (e.g. 5 and 6 membered) and bicyclic (e.g. 9 and 10 membered) heteroaryl ring systems, especially monocyclic ring systems. The aforementioned heteroaryl group may either be unsubstituted or may be substituted by one or more (e.g. one or two, particularly one) substituents. Exemplary substituents are independently selected from C$_{1-6}$ alkyl (e.g. methyl), C$_{1-6}$alkoxy (e.g. methoxy), halo (e.g. fluoro, e.g. chloro), —C$_{1-6}$haloalkyl (e.g. fluoromethyl such as trifluoromethyl) and —C$_{1-6}$haloalkoxy (e.g. trifluoromethoxy). Unsubstituted examples include pyridinyl (e.g. 2-pyridinyl, 3-pyridinyl and 4-pyridinyl), pyrimidinyl (e.g. 2-pyrimidinyl, 4-pyrimidinyl and 5-pyrimidinyl), pyridazinyl (e.g. 3-pyradazinyl) and thiazolyl (e.g. 2-thiazolyl). Substituted examples wherein heteroaryl comprises one ring heteroatom include methylpyridinyl (e.g. 2-methyl-5-pyridinyl, 2-methyl-6-pyridinyl, 3-methyl-5-pyridinyl), fluoromethylpyridinyl (e.g. trifluoromethylpyridinyl such as 2-trifluoromethyl-5-pyridinyl and 3-trifluroromethyl-5-pyridinyl and difluoromethylpyridinyl such as 3-difluoromethyl-5-pyridinyl), fluoropyridinyl (e.g. 2-fluoro-5-pyridinyl, 3-fluoro-5-pyridinyl and 2-fluoro-3-pyridinyl) and chloropyridinyl (e.g. 3-chloro-5-pyridinyl). Substituted examples wherein heteroaryl comprises two ring heteroatoms include methylthiazolyl (e.g. 2-methyl-4-thiazolyl).

When Z represents carbocyclyl which is optionally substituted by one or more substituents each independently selected from C$_{1-6}$alkyl (e.g. methyl), C$_{1-6}$alkoxy (e.g. methoxy), C$_{1-6}$haloalkyl (e.g. fluoromethyl), C$_{1-6}$haloalkoxy (e.g. fluoromethoxy) and halo (e.g. fluoro, e.g. chloro), Z may represent carbocyclyl which is optionally substituted by C$_{1-6}$ alkyl. Examples include monocyclic carbocyclyl which is optionally substituted by C$_{1-6}$ alkyl (such as methyl). Examples of carbocyclyl include C$_{3-8}$cycloalkyl (e.g. cyclohexyl) and C$_{5-8}$cycloalkenyl (e.g. cyclohexenyl). The carbocycyl ring is optionally substituted by one, two or three substituents (e.g. one or two, especially one, e.g. one methyl group). When Z represents carbocyclyl, Z may represent C$_{3-8}$cycloalkyl, such as C$_{5-6}$cycloalkyl. A specific example is cyclohexyl.

When Z represents heterocyclyl which is optionally substituted by one or more substituents each independently selected from C$_{1-6}$alkyl, C$_{1-6}$alkoxy, —C(O)OC$_{1-6}$alkyl, —C(O)C$_{1-6}$alkyl and —C(O)NHC$_{1-6}$alkyl, Z may represent heterocyclyl which is optionally substituted by C$_{1-6}$ alkyl (such as methyl). Examples include monocyclic heterocyclyl. The heterocyclyl group may be unsubstituted or may have for example one or two (e.g. one) substituent (e.g. one methyl group). Examples include piperidinyl, pyrrolidinyl, piperazinyl, morpholinyl, 4,5-dihydropyrazolyl and 4,5-dihydroisoxazolyl.

Suitably R$_1$ represents alkyl or cycloalkyl optionally substituted by C$_{1-4}$alkyl (e.g. methyl). More suitably, R$_1$ represents C$_{1-3}$ alkyl or C$_{3-4}$ cycloalkyl. Most suitably, R$_1$ represents methyl, cyclopropyl, cyclobutyl or isopropyl, particularly methyl or cyclopropyl, most particularly cyclopropyl.

Suitably R$_2$ represents H or C$_{1-3}$ alkyl. More suitably, R$_2$ represents H or methyl, especially H.

Suitably $R_3$ represents H or $C_{1-3}$ alkyl. More suitably, $R_3$ represents H or methyl, especially H.

Suitably, U, V and W each represent —($CH_2$)—.

Suitably Y represents aryl (especially phenyl) or heteroaryl (especially monocyclic heteroaryl). More suitably Y represents phenyl which is optionally substituted by one or more groups (especially one group) selected from $C_{1-6}$ alkyl (particularly methyl), $C_{1-6}$ alkoxy (particularly methoxy) or fluoro; or monocyclic heteroaryl (particularly a monocyclic heteroaryl comprising one or two nitrogen ring atoms such as pyridinyl, pyridazinyl, pyrazinyl, pyrimidinyl or isoxazolyl, e.g. pyridinyl, pyridazinyl or pyrazinyl) optionally substituted by $C_{1-6}$ alkyl (particularly methyl) or halo (particularly fluoro). Suitably Y is phenyl or 6-membered heteroaryl. In one embodiment Y is phenyl. In one embodiment Y is 6-membered heteroaryl comprising one or two nitrogen ring atoms. In one embodiment Y is unsubstituted. In one embodiment, Y is unsubstituted phenyl. In one embodiment Y is unsubstituted heteroaryl. In one embodiment Y is monosubstituted, for example by methyl or fluoro. In one embodiment Y is monosubstituted phenyl. In one embodiment Y is monosubstituted heteroaryl. When Y is 6-membered aryl or 6-membered heteroaryl, Z and —$NR_3$ are suitably positioned on ring Y at the 1- and 4-positions relative to each other (that is Y and —$NR_3$ have a para relationship).

Suitably Z represents aryl (especially phenyl) or heteroaryl (especially monocyclic heteroaryl). More suitably Z represents phenyl optionally substituted by fluoro, chloro, methyl, methoxy, fluromethyl (e.g. difluoromethyl or trifluromethyl), or haloalkoxy (e.g. —$OCF_3$); or monocyclic heteroaryl (especially monocyclic heteroaryl comprising one or two nitrogen ring atoms such as pyridinyl, pyridizinyl, pyrazinyl, pyrimidinyl, oxazolyl or thiazolyl) optionally substituted by methyl, fluoromethyl (e.g. difluoromethyl or trifluromethyl), fluoro or chloro. In one embodiment Z is unsubstituted. In one embodiment, Z is unsubstituted phenyl. In one embodiment Z is unsubstituted monocyclic heteroaryl. In one embodiment Z is monosubstituted; for example by methyl, fluoromethyl, fluoro or chloro.

In one embodiment, $R_1$ represents methyl or cyclopropyl; $R_2$ represents H; $R_3$ represents H; U, V and W each represent —$CH_2$—; Y represents phenyl, pyridinyl, pyridazinyl, pyrazinyl or pyrimidinyl wherein Y is optionally substituted by one group selected from methyl and fluoro; and Z represents phenyl, thiazolyl, pyridinyl, pyridazinyl, pyrazinyl or pyrimidinyl wherein Z is optionally substituted by one group selected from methyl, fluoro, chloro, methoxy and fluoromethyl.

In one embodiment there are provided compounds of formula (I) which are compounds of formula (IA),

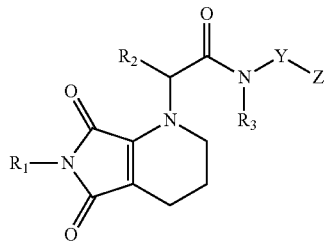

(IA)

or a pharmaceutically acceptable salt, solvate or polymorph thereof, including all tautomers and stereoisomers thereof wherein:
$R_1$ represents alkyl, or cycloalkyl;
$R_2$ represents H or alkyl;
$R_3$ represents H or alkyl;
Y represents aryl or heteroaryl; and
Z represents aryl or heteroaryl.

In one embodiment, the compounds of formula (I) have an $IC_{50}$ against HEK293-STF3A cells of less than about 10 micromolar.

In some embodiments $R_1$ is methyl and $R_2$ and $R_3$ are both H. In other embodiments $R_1$ is cyclopropyl and $R_2$ and $R_3$ are both H. In further embodiments $R_1$ and $R_2$ are both methyl and $R_3$ is H.

Processes

The present invention further provides a process for preparation of compounds of formula (I) or a protected derivative thereof comprises reaction of a compound of formula (II)

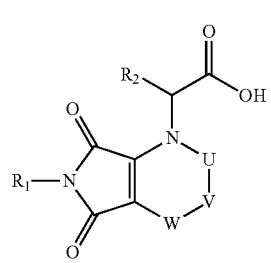

(II)

or a protected derivative thereof, wherein $R_1$, $R_2$, U, V and W are as defined above, with a compound of formula (III)

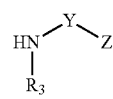

(III)

or a protected derivative thereof wherein $R_3$, Y and Z are as defined above.

Compounds of formula (II) may be prepared by ester hydrolysis of a compound of formula (IV)

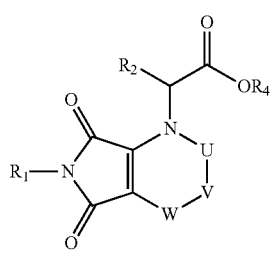

(IV)

wherein $R_1$, $R_2$, U, V and W are as defined above and wherein $R_4$ is $C_{1-6}$ alkyl.

When U, V and W each represent —($CH_2$)—, compounds of formula (IV) may be prepared by reaction of a compound of formula (V)

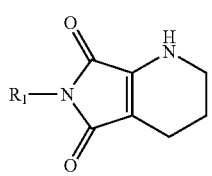
(V)

wherein $R_1$, is as defined above, with a compound of formula (VI)

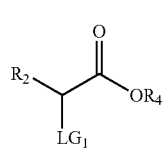
(VI)

wherein $R_2$ and $R_4$ are as defined above and wherein $LG_1$ is a leaving group such as Br.

Compounds of formula (V) may be prepared from compounds of formula (VI)

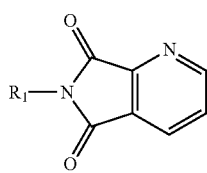
(VI)

wherein $R_1$ is as defined above, for example by catalytic hydrogenation.

Compounds of formula (VI) can be prepared from a compound of formula (VII)

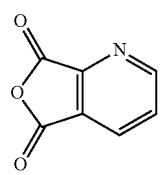
(VII)

and the corresponding amine, $R_1$—$NH_2$. Compound (VII) is commercially available.

Compounds of formula (IV) wherein U and V together represent —CH=CH— and W represents C=O may be prepared by reaction of a compound of formula (VIII)

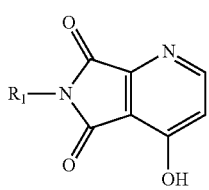
(VIII)

wherein $R_1$ is as defined above, with a compound of formula (VI)

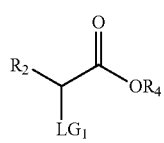
(VI)

wherein $R_2$, $R_4$ and $LG_1$ are as defined above.

Compounds of formula (VIII) may be prepared from a compound of formula (IX)

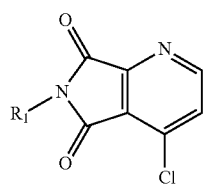
(IX)

wherein $R_1$ is as defined above, using a hydroxylating agent such as CsOAc.

Compounds of formula (IX) may be prepared from a compound of formula (X)

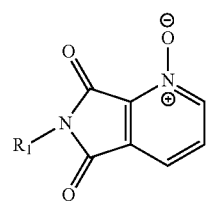
(X)

wherein $R_1$ is as defined above, for example by using a chlorinating agent such as $POCl_3$.

Compounds of formula (X) may be prepared from a compound of formula (XI)

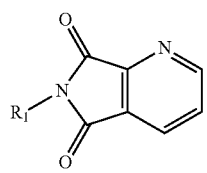
(XI)

wherein $R_1$ is as defined above, by using an oxidizing agent such as metachloroperbenzoic acid (mCPBA).

Compounds of formula (III) may be prepared by a coupling reaction, such as a Suzuki coupling. For example, compound of formula (III) may be prepared by a coupling reaction of a compound of formula (XII)

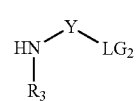
(XII)

wherein Y and R$_3$ are as defined above and LG$_2$ is a leaving group such as a boronic acid or boronic ester or Br or Cl; with a compound of formula (XIII)

(XIII)

wherein Z is as defined above and LG$_3$ is a leaving group such as boronic acid or boronic ester or Br or Cl.

Therapeutic Uses

The present invention provides a compound of formula (I) for use as a medicament.

The compounds of the present invention may have an IC50 against STF3A of less than 20 micromolar, e.g. less than 10 micromolar. The IC50 may be less than 5, 2, 1, 0.5, 0.2 or 0.1 micromolar. It may be between about 0.01 and about 10 micromolar, or between about 0.01 and 5, 0.01 and 1, 0.01 and 0.5, 0.01 and 0.1, 0.01 and 0.05, 0.1 and 5, 0.1 and 1, 0.1 and 0.5, 0.1 and 10, 0.5 and 10, 1 and 10, 5 and 10, 1 and 5 or 0.1 and 0.5, e.g. about 0.01, 0.02, 0.03, 0.04, 0.05, 0.1, 0.2, 0.3, 0.4, 0.5, 0.6, 0.7, 0.8, 0.9, 1, 2, 3, 4, 5, 6, 7, 8, 9 or 10 micromolar.

The present invention provides compounds of formula (I) for use in modulation of the WNT pathway.

The present invention also provides a method of modulating WNT activity comprising exposing a WNT protein or a WNT receptor to a compound of formula (I).

In addition, the present invention provides use of a compound of formula (I) for modulating WNT activity.

The present invention additionally provides compounds of formula (I) for use in the treatment of a disease or condition associated with WNT pathway activity.

A method of treating a disease or condition associated with WNT pathway activity comprising administering to a subject in need thereof a therapeutically effective amount of a compound of formula (I) is also provided by the present invention.

The present invention further provides use of a compound of formula (I) for treatment of a disease or condition associated with WNT pathway activity.

Also provided by the present invention is use of a compound of formula (I) in the manufacture of a medicament for the treatment of a disease or condition associated with WNT pathway activity.

The aforementioned disease or condition is suitably selected from the group consisting of cancer, fibrosis, stem cell and diabetic retinopathy, rheumatoid arthritis, psoriasis and myocardial infarction.

The cancer may be a cancer characterized by high WNT activity.

The disease or condition may be a cancer, such as cervical, colon, breast, bladder, head and neck, gastric, lung, ovarian, prostate, thyroid, non-small-cell lung, as well as chronic lymphocytic leukemia, mesothelioma, melanoma, pancreatic adenocarcinoma, basal cell carcinoma, osteosarcoma, hepatocellular carcinoma, Wilm's tumor or medulloblastoma, or a fibrotic disease, such as pulmonary fibrosis, liver fibrosis, skin fibrosis or renal fibrosis, or a degenerative disease, or a metabolic disease such as diabetic retinopathy.

The present invention also provides use of a compound of formula (I) in diagnosis.

Pharmaceutical Compositions

To prepare the pharmaceutical compositions of this invention, at least one compound of formula (I) optionally in combination with at least one of the other aforementioned agents can be used as the active ingredient(s). The active ingredient(s) is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included.

Injectable suspensions may also prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient(s) necessary to deliver an effective dose as described above. The pharmaceutical compositions herein will contain, per dosage unit, e.g., tablet, capsule, powder, injection, suppository, teaspoonful and the like, from about 0.03 mg to 100 mg/kg (preferred 0.1-30 mg/kg) and may be given at a dosage of from about 0.1-300 mg/kg per day (preferred 1-50 mg/kg per day) of each active ingredient or combination thereof. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of each active ingredient or combinations thereof of the present invention.

The tablets or pills of the compositions of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, acetyl alcohol and cellulose acetate.

This liquid forms in which the compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinylpyrrolidone or gelatin.

The pharmaceutical composition may contain between about 0.01 mg and 100 mg, preferably about 5 to 50 mg, of each compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or betalactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitable flavored suspending or dispersing agents such as the synthetic and natural gums, for example, tragacanth, acacia, methyl-cellulose and the like.

For parenteral administration, sterile suspensions and solutions are desired. Isotonic preparations which generally contain suitable preservatives are employed when intravenous administration is desired.

The compounds or combinations of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Compounds or combinations of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamid-ephenol, or polyethyl eneoxidepolyllysine substituted with palmitoyl residue. Furthermore, the compounds of the present invention may be coupled to a class of biodegradable polymers useful in achieving controlled release of a drug, for example, polyactic acid, polyepsilon caprolactone, polyhydroxy butyeric acid, polyorthoesters, polyacetals, polydihydropyrans, polycyanoacrylates and cross-linked or amphipathic block copolymers of hydrogels.

Compounds or combinations of this invention may be administered in any of the foregoing compositions and according to dosage regimens established in the art whenever treatment of the addressed disorders is required.

The daily dosage of the products may be varied over a wide range from 0.01 to 1.000 mg per mammal per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of each active ingredient or combinations thereof for the symptomatic adjustment of the dosage to the patient to be treated. An effective amount of the drug is ordinarily supplied at a dosage level of from about 0.1 mg/kg to about 300 mg/kg of body weight per day. Preferably, the range is from about 1 to about 50 mg/kg of body weight per day. The compounds or combinations may be administered on a regimen of 1 to 4 times per day.

Optimal dosages to be administered may be readily determined by those skilled in the art, and will vary with the particular compound used, the mode of administration, the strength of the preparation, the mode of administration, and the advancement of disease condition. In addition, factors associated with the particular patient being treated, including patient age, weight, diet and time of administration, will result in the need to adjust dosages.

In a further aspect, the invention also provides a process for preparing a pharmaceutical composition comprising at least one compound of formula (I), optionally in combination with at least one of the other aforementioned agents and a pharmaceutically acceptable carrier.

The compositions are preferably in a unit dosage form in an amount appropriate for the relevant daily dosage.

Suitable dosages, including especially unit dosages, of the compounds of the present invention include the known dosages including unit doses for these compounds as described or referred to in reference text such as the British and US Pharmacopoeias, Remington's Pharmaceutical Sciences (Mack Publishing Co.), Martindale The Extra Pharmacopoeia (London, The Pharmaceutical Press) (for example see the 31st Edition page 341 and pages cited therein) or the above mentioned publications.

EXAMPLES

| Cpd ID | Structure | IUPAC Name | STF3a IC$_{50}$ μM |
|---|---|---|---|
| 1 | 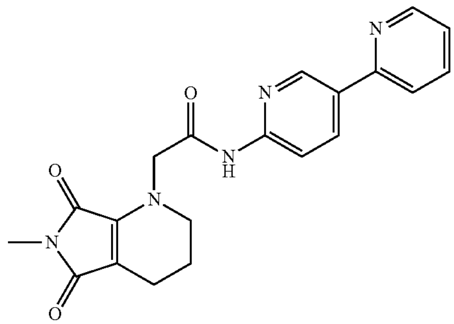 [SMILES: CN1C(=O)C2=C(C1=O)N(CC(=O)Nc1ccc(-c3ccccn3)cn1)CCC2] | N-([2,3'-bipyridin]-6'-yl)-2-(6-methyl-5,7-dioxo-2,3,4,5,6,7-hexahydro-1H-pyrrolo[3,4-b]pyridin-1-yl)acetamide | <0.1 |
| 2 | 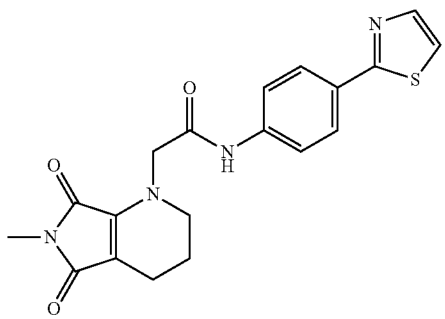 [SMILES: CN1C(=O)C2=C(C1=O)N(CC(=O)Nc1ccc(-c3nccs3)cc1)CCC2] | 2-(6-methyl-5,7-dioxo-2,3,4,5,6,7-hexahydro-1H-pyrrolo[3,4-b]pyridin-1-yl)-N-(4-(thiazol-2-yl)phenyl)acetamide | <0.1 |
| 3 | 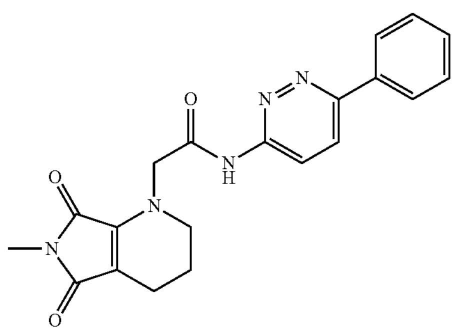 | 2-(6-methyl-5,7-dioxo-2,3,4,5,6,7-hexahydro-1H-pyrrolo[3,4-b]pyridin-1-yl)-N-(6-phenylpyridazin-3-yl)acetamide | <0.1 |
| 4 | 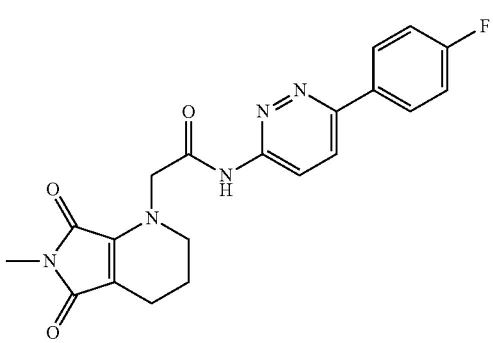 [SMILES: CN1C(=O)C2=C(C1=O)N(CC(=O)Nc1ccc(-c3ccc(F)cc3)nn1)CCC2] | N-(6-(4-fluorophenyl)pyridazin-3-yl)-2-(6-methyl-5,7-dioxo-2,3,4,5,6,7-hexahydro-1H-pyrrolo[3,4-b]pyridin-1-yl)acetamide | <0.1 |

-continued

| Cpd ID | Structure | IUPAC Name | STF3a IC$_{50}$ μM |
|---|---|---|---|
| 5 | 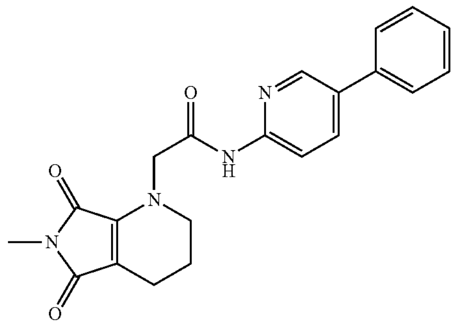 [SMILES: CN1C(=O)C2=C(C1=O)N(CC(=O)Nc1ccc(-c3ccccc3)cn1)CCC2] | 2-(6-methyl-5,7-dioxo-2,3,4,5,6,7-hexahydro-1H-pyrrolo[3,4-b]pyridin-1-yl)-N-(5-phenylpyridin-2-yl)acetamide | <0.1 |
| 6 | 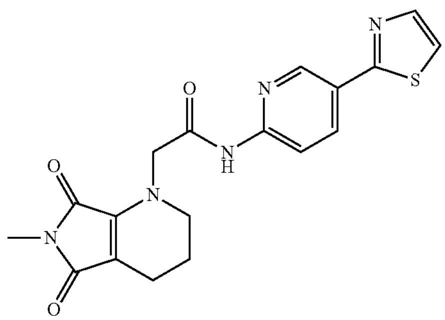 [SMILES: CN1C(=O)C2=C(C1=O)N(CC(=O)Nc1ccc(-c3nccs3)cn1)CCC2] | 2-(6-methyl-5,7-dioxo-2,3,4,5,6,7-hexahydro-1H-pyrrolo[3,4-b]pyridin-1-yl)-N-(5-(thiazol-2-yl)pyridin-2-yl)acetamide | <0.1 |
| 7 | 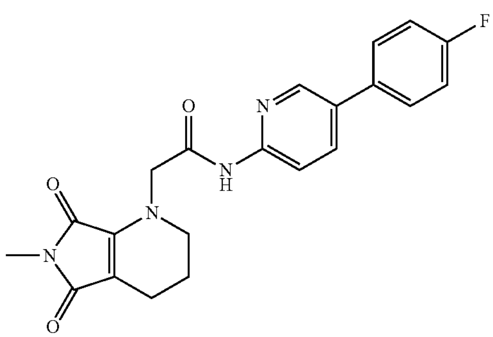 [SMILES: CN1C(=O)C2=C(C1=O)N(CC(=O)Nc1ccc(-c3ccc(F)cc3)cn1)CCC2] | N-(5-(4-fluorophenyl)pyridin-2-yl)-2-(6-methyl-5,7-dioxo-2,3,4,5,6,7-hexahydro-1H-pyrrolo[3,4-b]pyridin-1-yl)acetamide | <0.1 |
| 8 | 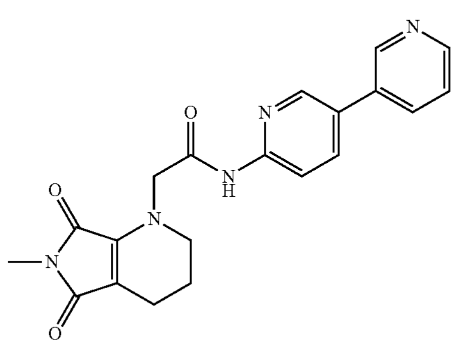 [SMILES: CN1C(=O)C2=C(C1=O)N(CC(=O)Nc1ccc(-c3cccnc3)cn1)CCC2] | N-([3,3'-bipyridin]-6-yl)-2-(6-methyl-5,7-dioxo-2,3,4,5,6,7-hexahydro-1H-pyrrolo[3,4-b]pyridin-1-yl)acetamide | <0.1 |

| Cpd ID | Structure | IUPAC Name | STF3a IC$_{50}$ μM |
|---|---|---|---|
| 9 | 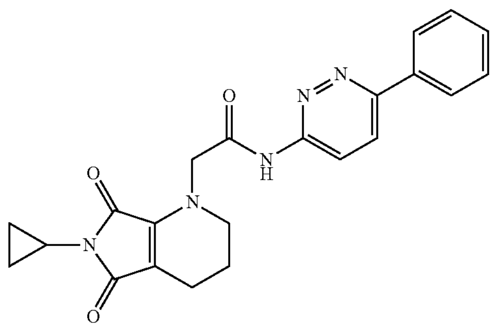 [SMILES: O=C(CN1CCCC2=C1C(=O)N(C1CC1)C2=O)Nc1ccc(-c2ccccc2)nn1] | N-(2,3'-bipyridin-6'-yl)-2-(6-cyclopropyl-5,7-dioxo-2,3,4,5,6,7-hexahydro-1H-pyrrolo[3,4-b]pyridin-1-yl)acetamide | <0.1 |
| 10 | 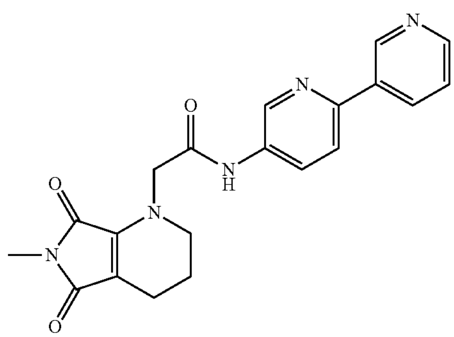 [SMILES: CN1C(=O)C2=C(C1=O)N(CC(=O)Nc1ccc(-c3cccnc3)nc1)CCC2] | N-([2,3'-bipyridin]-5-yl)-2-(6-methyl-5,7-dioxo-2,3,4,5,6,7-hexahydro-1H-pyrrolo[3,4-b]pyridin-1-yl)acetamide | <0.1 |
| 11 | 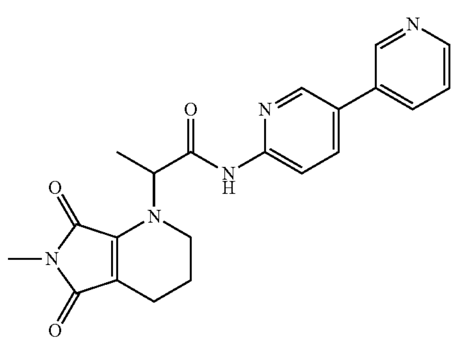 [SMILES: CC(C(=O)Nc1ccc(-c2cccnc2)cn1)N1CCCC2=C1C(=O)N(C)C2=O] | N-([3,3'-bipyridin]-6-yl)-2-(6-methyl-5,7-dioxo-2,3,4,5,6,7-hexahydro-1H-pyrrolo[3,4-b]pyridin-1-yl)propanamide | <0.1 |
| 12 | 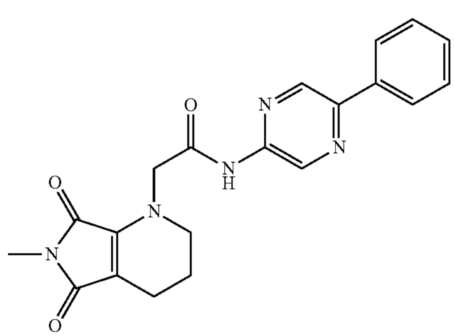 [SMILES: CN1C(=O)C2=C(C1=O)N(CC(=O)Nc1cnc(-c3ccccc3)cn1)CCC2] | 2-(6-methyl-5,7-dioxo-2,3,4,5,6,7-hexahydro-1H-pyrrolo[3,4-b]pyridin-1-yl)-N-(5-phenylpyrazin-2-yl)acetamide | <0.1 |

-continued

| Cpd ID | Structure | IUPAC Name | STF3a IC$_{50}$ μM |
|---|---|---|---|
| 13 | 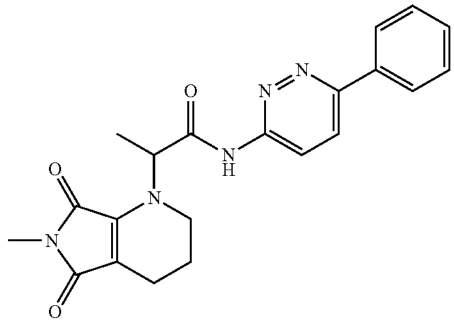 [SMILES: CC(C(=O)Nc1ccc(-c2ccccc2)nn1)N1CCCC2=C1C(=O)N(C)C2=O] | 2-(6-methyl-5,7-dioxo-2,3,4,5,6,7-hexahydro-1H-pyrrolo[3,4-b]pyridin-1-yl)-N-(6-phenylpyridazin-3-yl)propanamide | <0.1 |
| 14 | 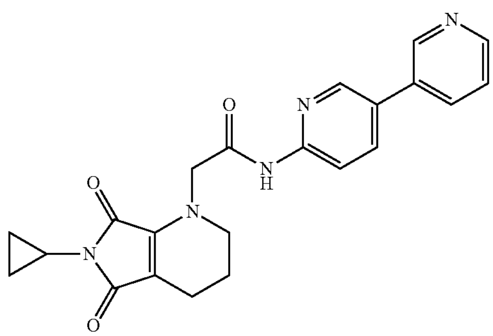 [SMILES: O=C(CN1CCCC2=C1C(=O)N(C1CC1)C2=O)Nc1ccc(-c2cccnc2)cn1] | N-([3,3'-bipyridin]-6-yl)-2-(6-cyclopropyl-5,7-dioxo-2,3,4,5,6,7-hexahydro-1H-pyrrolo[3,4-b]pyridin-1-yl)acetamide | <0.1 |
| 15 | 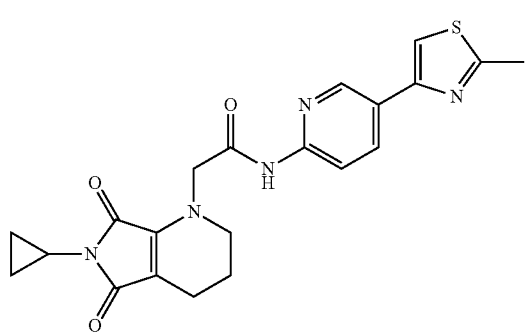 [SMILES: Cc1nc(-c2ccc(NC(=O)CN3CCCC4=C3C(=O)N(C3CC3)C4=O)nc2)cs1] | 2-(6-cyclopropyl-5,7-dioxo-2,3,4,5,6,7-hexahydro-1H-pyrrolo[3,4-b]pyridin-1-yl)-N-(5-(2-methylthiazol-4-yl)pyridin-2-yl)acetamide | <0.1 |
| 16 | 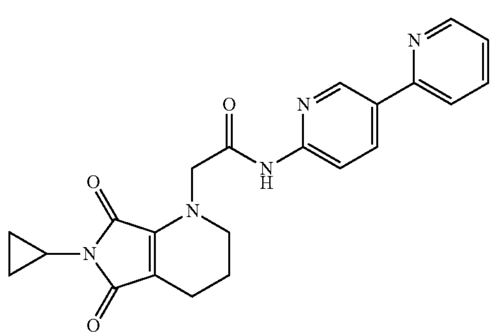 [SMILES: O=C(CN1CCCC2=C1C(=O)N(C1CC1)C2=O)Nc1ccc(-c2ccccn2)cn1] | N-([2,3'-bipyridin]-6'-yl)-2-(6-cyclopropyl-5,7-dioxo-2,3,4,5,6,7-hexahydro-1H-pyrrolo[3,4-b]pyridin-1-yl)acetamide | <0.1 |

| Cpd ID | Structure | IUPAC Name | STF3a IC$_{50}$ μM |
|---|---|---|---|
| 17 | 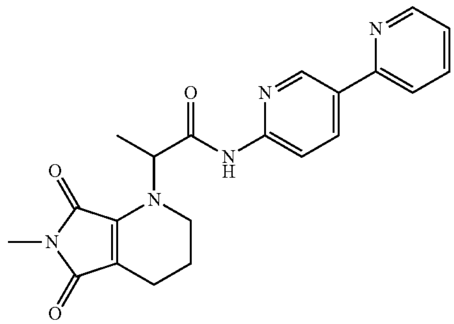 [SMILES: CC(C(=O)Nc1ccc(-c2ccccn2)cn1)N1CCCC2=C1C(=O)N(C)C2=O] | N-([2,3'-bipyridin]-6'-yl)-2-(6-methyl-5,7-dioxo-2,3,4,5,6,7-hexahydro-1H-pyrrolo[3,4-b]pyridin-1-yl)propanamide | <0.1 |
| 18 | 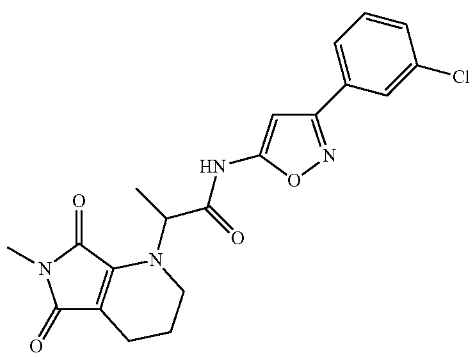 [SMILES: CC(C(=O)Nc1cc(-c2cccc(Cl)c2)no1)N1CCCC2=C1C(=O)N(C)C2=O] | N-(3-(3-chlorophenyl)isoxazol-5-yl)-2-(6-methyl-5,7-dioxo-2,3,4,5,6,7-hexahydro-1H-pyrrolo[3,4-b]pyridin-1-yl)propanamide | <5 |
| 19 | 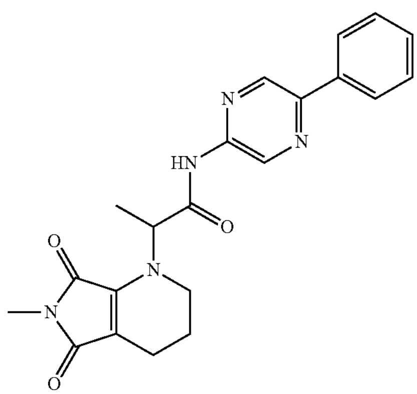 [SMILES: CC(C(=O)Nc1cnc(-c2ccccc2)cn1)N1CCCC2=C1C(=O)N(C)C2=O] | 2-(6-methyl-5,7-dioxo-2,3,4,5,6,7-hexahydro-1H-pyrrolo[3,4-b]pyridin-1-yl)-N-(5-phenylpyrazin-2-yl)propanamide | <0.1 |
| 20 | 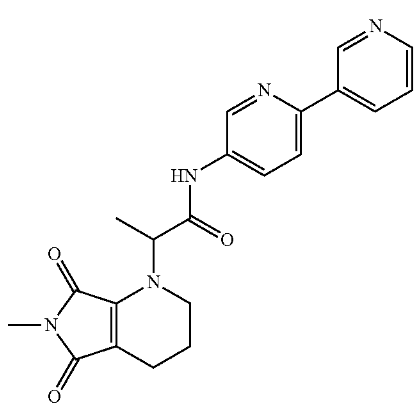 [SMILES: CC(C(=O)Nc1ccc(-c2cccnc2)nc1)N1CCCC2=C1C(=O)N(C)C2=O] | N-([2,3'-bipyridin]-5-yl)-2-(6-methyl-5,7-dioxo-2,3,4,5,6,7-hexahydro-1H-pyrrolo[3,4-b]pyridin-1-yl)propanamide | <0.1 |

-continued

| Cpd ID | Structure | IUPAC Name | STF3a IC$_{50}$ μM |
|---|---|---|---|
| 21 | 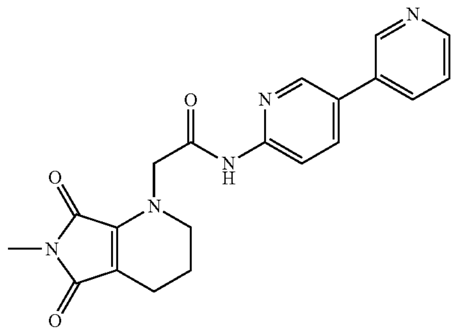 [SMILES: CN1C(=O)C2=C(C1=O)N(CC(=O)Nc1ccc(-c3cccnc3)cn1)CCC2] | 2-(6-methyl-5,7-dioxo-2,3,4,5,6,7-hexahydro-1H-pyrrolo[3,4-b]pyridin-1-yl)-N-(5-(pyridin-3-yl)pyrazin-2-yl)acetamide | <0.1 |
| 22 | 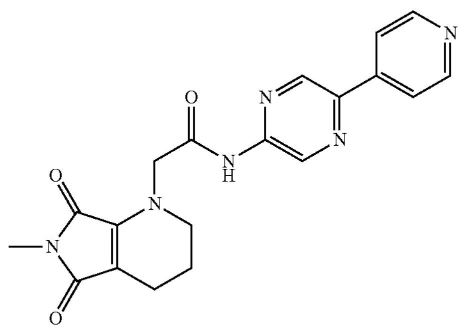 [SMILES: CN1C(=O)C2=C(C1=O)N(CC(=O)Nc1cnc(-c3ccncc3)cn1)CCC2] | 2-(6-methyl-5,7-dioxo-2,3,4,5,6,7-hexahydro-1H-pyrrolo[3,4-b]pyridin-1-yl)-N-(5-(pyridin-4-yl)pyrazin-2-yl)acetamide | >10 |
| 23 | 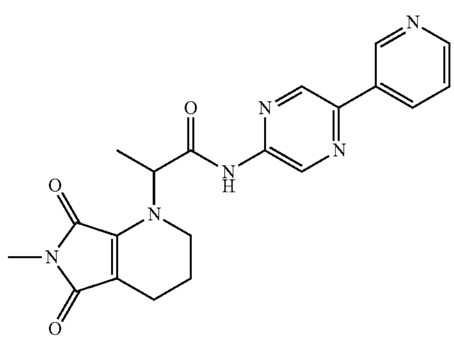 [SMILES: CC(C(=O)Nc1cnc(-c2cccnc2)cn1)N1CCCC2=C1C(=O)N(C)C2=O] | 2-(6-methyl-5,7-dioxo-2,3,4,5,6,7-hexahydro-1H-pyrrolo[3,4-b]pyridin-1-yl)-N-(5-(pyridin-3-yl)pyrazin-2-yl)propanamide | <0.1 |
| 24 | 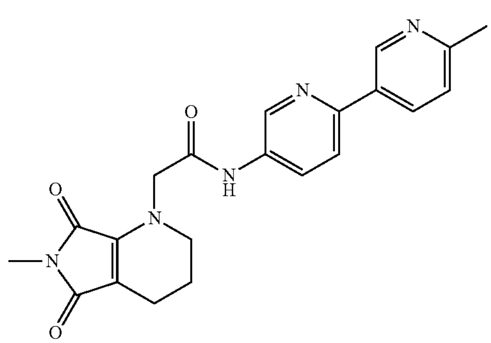 | 2-(6-methyl-5,7-dioxo-2,3,4,5,6,7-hexahydro-1H-pyrrolo[3,4-b]pyridin-1-yl)-N-(6'-methyl-[2,3'-bipyridin]-5-yl)acetamide | <0.1 |

-continued

| Cpd ID | Structure | IUPAC Name | STF3a IC$_{50}$ μM |
|---|---|---|---|
| 25 | 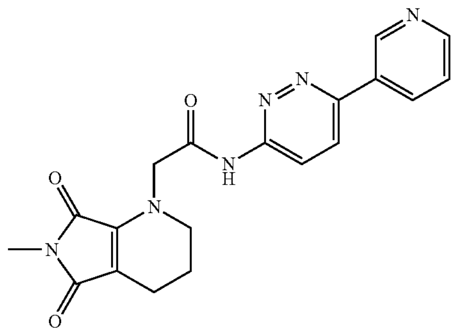 [SMILES: CN1C(=O)C2=C(C1=O)N(CC(=O)Nc1ccc(-c3cccnc3)nn1)CCC2] | 2-(6-methyl-5,7-dioxo-2,3,4,5,6,7-hexahydro-1H-pyrrolo[3,4-b]pyridin-1-yl)-N-(6-(pyridin-3-yl)pyridazin-3-yl)acetamide | <0.1 |
| 26 | 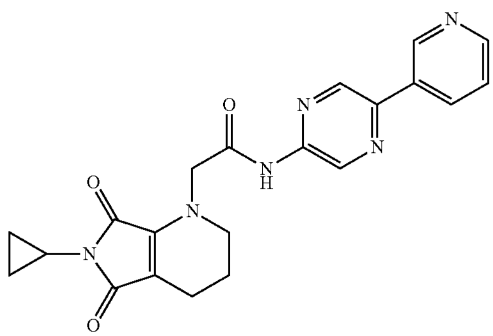 | 2-(6-cyclopropyl-5,7-dioxo-2,3,4,5,6,7-hexahydro-1H-pyrrolo[3,4-b]pyridin-1-yl)-N-(5-(pyridin-3-yl)pyrazin-2-yl)acetamide | <0.1 |
| 27 | 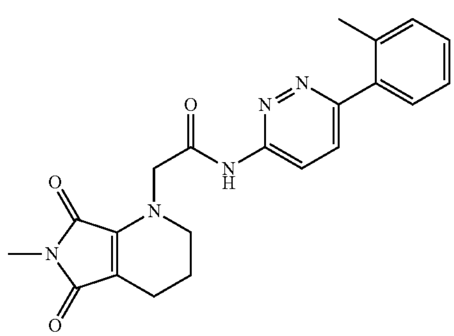 [SMILES: Cc1ccccc1-c1ccc(NC(=O)CN2CCCC3=C2C(=O)N(C)C3=O)nn1] | 2-(6-methyl-5,7-dioxo-2,3,4,5,6,7-hexahydro-1H-pyrrolo[3,4-b]pyridin-1-yl)-N-(6-(o-tolyl)pyridazin-3-yl)acetamide | <1 |
| 28 | 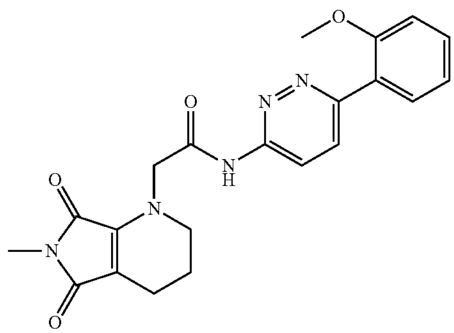 [SMILES: COc1ccccc1-c1ccc(NC(=O)CN2CCCC3=C2C(=O)N(C)C3=O)nn1] | N-(6-(2-methoxyphenyl)pyridazin-3-yl)-2-(6-methyl-5,7-dioxo-2,3,4,5,6,7-hexahydro-1H-pyrrolo[3,4-b]pyridin-1-yl)acetamide | >10 |

| Cpd ID | Structure | IUPAC Name | STF3a IC$_{50}$ μM |
|---|---|---|---|
| 29 | 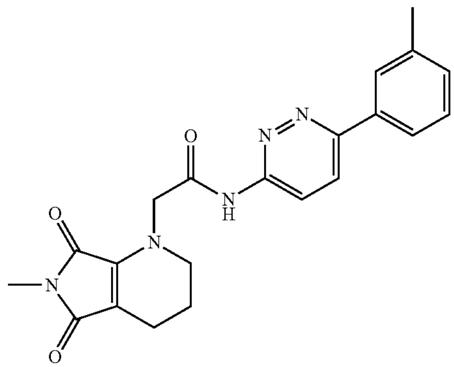 [SMILES: Cc1cccc(-c2ccc(NC(=O)CN3CCCC4=C3C(=O)N(C)C4=O)nn2)c1] | 2-(6-methyl-5,7-dioxo-2,3,4,5,6,7-hexahydro-1H-pyrrolo[3,4-b]pyridin-1-yl)-N-(6-(m-tolyl)pyridazin-3-yl)acetamide | <0.1 |
| 30 | 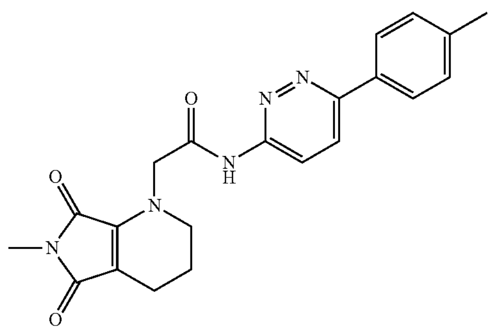 | 2-(6-methyl-5,7-dioxo-2,3,4,5,6,7-hexahydro-1H-pyrrolo[3,4-b]pyridin-1-yl)-N-(6-(p-tolyl)pyridazin-3-yl)acetamide | <0.1 |
| 31 | 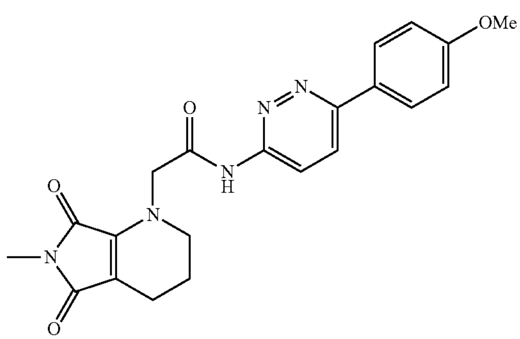 [SMILES: COc1ccc(-c2ccc(NC(=O)CN3CCCC4=C3C(=O)N(C)C4=O)nn2)cc1] | N-(6-(4-methoxyphenyl)pyridazin-3-yl)-2-(6-methyl-5,7-dioxo-2,3,4,5,6,7-hexahydro-1H-pyrrolo[3,4-b]pyridin-1-yl)acetamide | <0.1 |
| 32 | 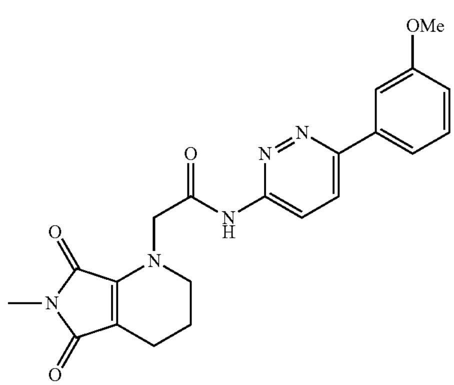 [SMILES: COc1cccc(-c2ccc(NC(=O)CN3CCCC4=C3C(=O)N(C)C4=O)nn2)c1] | N-(6-(3-methoxyphenyl)pyridazin-3-yl)-2-(6-methyl-5,7-dioxo-2,3,4,5,6,7-hexahydro-1H-pyrrolo[3,4-b]pyridin-1-yl)acetamide | <0.1 |

| Cpd ID | Structure | IUPAC Name | STF3a IC$_{50}$ μM |
|---|---|---|---|
| 33 | 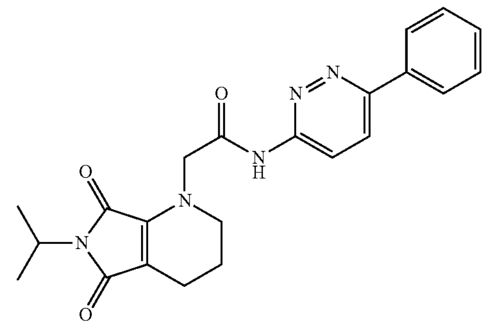 [SMILES: CC(C)N1C(=O)C2=C(C1=O)N(CC(=O)Nc1ccc(-c3ccccc3)nn1)CCC2] | 2-(6-isopropyl-5,7-dioxo-2,3,4,5,6,7-hexahydro-1H-pyrrolo[3,4-b]pyridin-1-yl)-N-(6-phenylpyridazin-3-yl)acetamide | <0.1 |
| 34 | 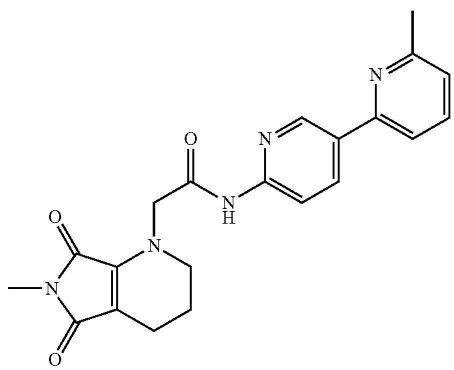 [SMILES: Cc1cccc(-c2ccc(NC(=O)CN3CCCC4=C3C(=O)N(C)C4=O)nc2)n1] | 2-(6-methyl-5,7-dioxo-2,3,4,5,6,7-hexahydro-1H-pyrrolo[3,4-b]pyridin-1-yl)-N-(6-methyl-[2,3'-bipyridin]-6'-yl)acetamide | <0.1 |
| 35 | 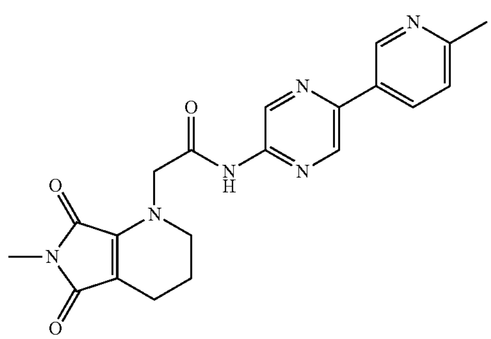 | N-(6-(3-methoxyphenyl)pyridazin-3-yl)-2-(6-methyl-5,7-dioxo-2,3,4,5,6,7-hexahydro-1H-pyrrolo[3,4-b]pyridin-1-yl)acetamide | <1.0 |
| 36 | 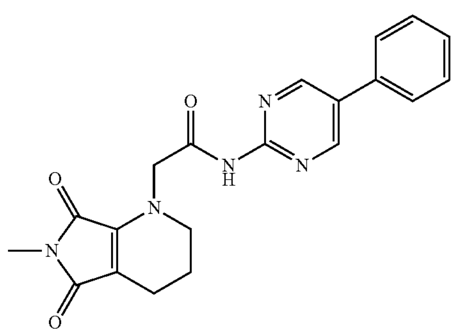 [SMILES: CN1C(=O)C2=C(C1=O)N(CC(=O)Nc1ncc(-c3ccccc3)cn1)CCC2] | 2-(6-methyl-5,7-dioxo-2,3,4,5,6,7-hexahydro-1H-pyrrolo[3,4-b]pyridin-1-yl)-N-(5-phenylpyrimidin-2-yl)acetamide | <0.1 |

| Cpd ID | Structure | IUPAC Name | STF3a IC$_{50}$ μM |
|---|---|---|---|
| 37 | 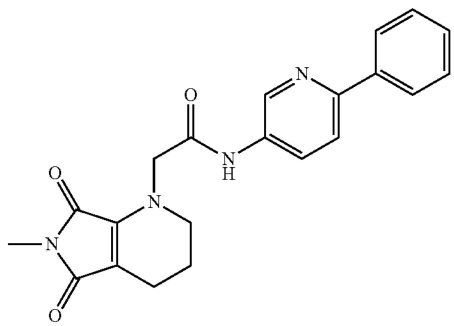 [SMILES: CN1C(=O)C2=C(C1=O)N(CC(=O)Nc1ccc(-c3ccccc3)nc1)CCC2] | 2-(6-methyl-5,7-dioxo-2,3,4,5,6,7-hexahydro-1H-pyrrolo[3,4-b]pyridin-1-yl)-N-(6-phenylpyridin-3-yl)acetamide | <0.1 |
| 38 | 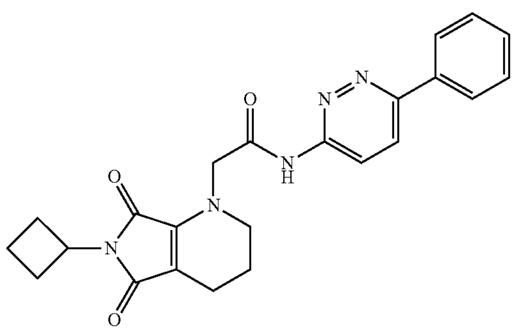 [SMILES: O=C(CN1CCCC2=C1C(=O)N(C1CCC1)C2=O)Nc1ccc(-c2ccccc2)nn1] | 2-(6-cyclobutyl-5,7-dioxo-2,3,4,5,6,7-hexahydro-1H-pyrrolo[3,4-b]pyridin-1-yl)-N-(6-phenylpyridazin-3-yl)acetamide | <0.1 |
| 39 | 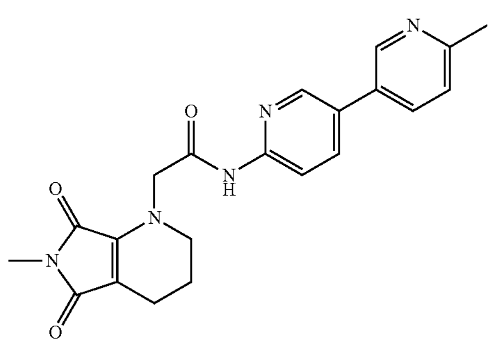 | 2-(6-methyl-5,7-dioxo-2,3,4,5,6,7-hexahydro-1H-pyrrolo[3,4-b]pyridin-1-yl)-N-(6'-methyl-[3,3'-bipyridin]-6-yl)acetamide | <0.1 |
| 40 | 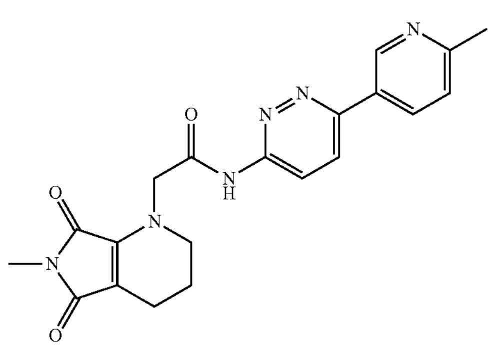 | 2-(6-methyl-5,7-dioxo-2,3,4,5,6,7-hexahydro-1H-pyrrolo[3,4-b]pyridin-1-yl)-N-(6-(6-methylpyridin-3-yl)pyridazin-3-yl)acetamide | <0.1 |

-continued

| Cpd ID | Structure | IUPAC Name | STF3a IC$_{50}$ μM |
|---|---|---|---|
| 41 | 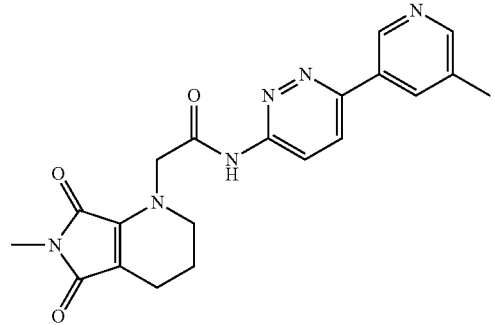 | 2-(6-methyl-5,7-dioxo-2,3,4,5,6,7-hexahydro-1H-pyrrolo[3,4-b]pyridin-1-yl)-N-(6-(5-methylpyridin-3-yl)pyridazin-3-yl)acetamide | <0.1 |
| 42 | 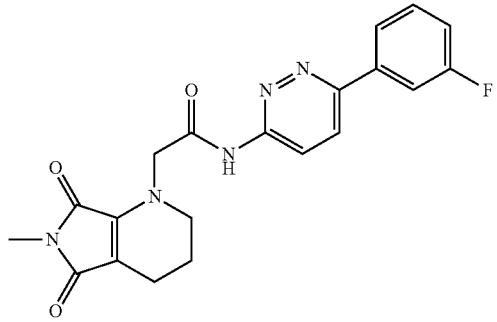 | N-(6-(3-fluorophenyl)pyridazin-3-yl)-2-(6-methyl-5,7-dioxo-2,3,4,5,6,7-hexahydro-1H-pyrrolo[3,4-b]pyridin-1-yl)acetamide | <0.1 |
| 43 | 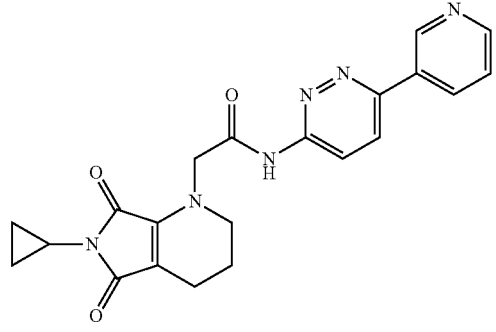 [SMILES: O=C(CN1CCCC2=C1C(=O)N(C1CC1)C2=O)Nc1ccc(-c2cccnc2)nn1] | 2-(6-cyclopropyl-5,7-dioxo-2,3,4,5,6,7-hexahydro-1H-pyrrolo[3,4-b]pyridin-1-yl)-N-(6-(pyridin-3-yl)pyridazin-3-yl)acetamide | <0.1 |
| 44 | 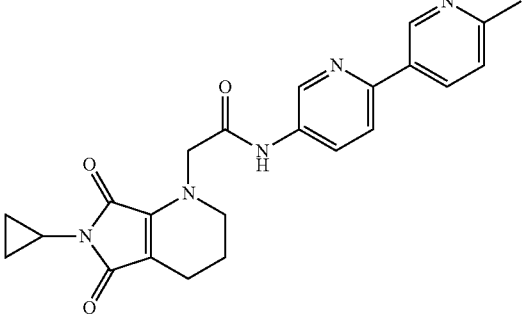 | 2-(6-cyclopropyl-5,7-dioxo-2,3,4,5,6,7-hexahydro-1H-pyrrolo[3,4-b]pyridin-1-yl)-N-(6'-methyl-[2,3'-bipyridin]-5-yl)acetamide | <0.1 |

-continued

| Cpd ID | Structure | IUPAC Name | STF3a IC$_{50}$ μM |
|---|---|---|---|
| 45 | 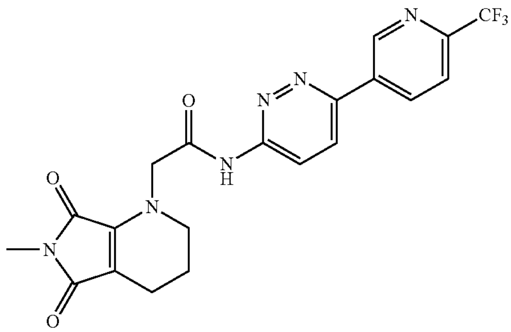 [SMILES: CN1C(=O)C2=C(C1=O)N(CC(=O)Nc1ccc(-c3ccc(C(F)(F)F)nc3)nn1)CCC2] | 2-(6-methyl-5,7-dioxo-2,3,4,5,6,7-hexahydro-1H-pyrrolo[3,4-b]pyridin-1-yl)-N-(6-(6-(trifluoromethyl)pyridin-3-yl)pyridazin-3-yl)acetamide | <5 |
| 46 | 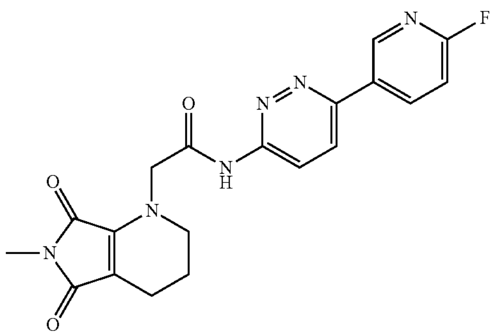 [SMILES: CN1C(=O)C2=C(C1=O)N(CC(=O)Nc1ccc(-c3ccc(F)nc3)nn1)CCC2] | N-(6-(6-fluoropyridin-3-yl)pyridazin-3-yl)-2-(6-methyl-5,7-dioxo-2,3,4,5,6,7-hexahydro-1H-pyrrolo[3,4-b]pyridin-1-yl)acetamide | <0.1 |
| 47 | 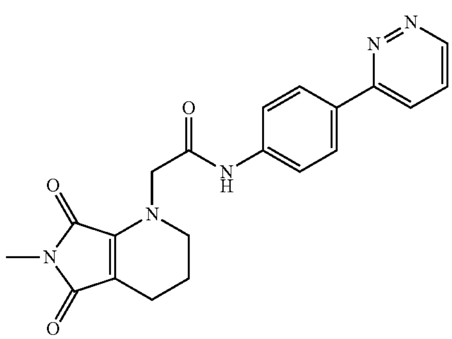 [SMILES: CN1C(=O)C2=C(C1=O)N(CC(=O)Nc1ccc(-c3cccnn3)cc1)CCC2] | 2-(6-methyl-5,7-dioxo-2,3,4,5,6,7-hexahydro-1H-pyrrolo[3,4-b]pyridin-1-yl)-N-(4-(pyridazin-3-yl)phenyl)acetamide | <1 |
| 48 | 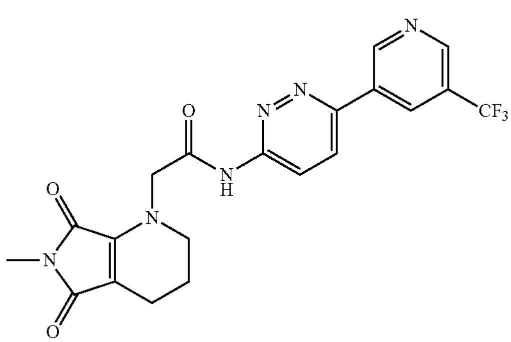 [SMILES: CN1C(=O)C2=C(C1=O)N(CC(=O)Nc1ccc(-c3cncc(C(F)(F)F)c3)nn1)CCC2] | 2-(6-methyl-5,7-dioxo-2,3,4,5,6,7-hexahydro-1H-pyrrolo[3,4-b]pyridin-1-yl)-N-(6-(5-(trifluoromethyl)pyridin-3-yl)pyridazin-3-yl)acetamide | <0.1 |

-continued

| Cpd ID | Structure | IUPAC Name | STF3a IC$_{50}$ μM |
|---|---|---|---|
| 49 | 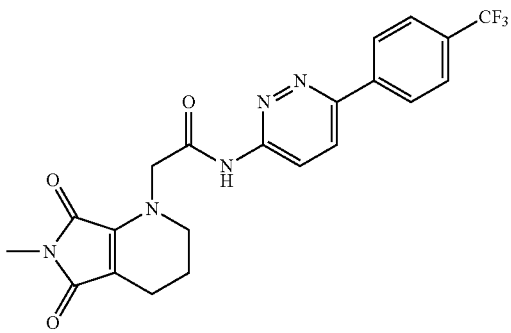 [SMILES: CN1C(=O)C2=C(C1=O)N(CC(=O)Nc1ccc(-c3ccc(C(F)(F)F)cc3)nn1)CCC2] | 2-(6-methyl-5,7-dioxo-2,3,4,5,6,7-hexahydro-1H-pyrrolo[3,4-b]pyridin-1-yl)-N-(6-(4-(trifluoromethyl)phenyl)pyridazin-3-yl)acetamide | <10 |
| 50 | 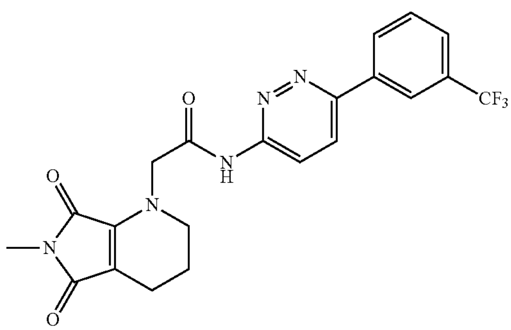 [SMILES: CN1C(=O)C2=C(C1=O)N(CC(=O)Nc1ccc(-c3cccc(C(F)(F)F)c3)nn1)CCC2] | 2-(6-methyl-5,7-dioxo-2,3,4,5,6,7-hexahydro-1H-pyrrolo[3,4-b]pyridin-1-yl)-N-(6-(3-(trifluoromethyl)phenyl)pyridazin-3-yl)acetamide | <0.1 |
| 51 | 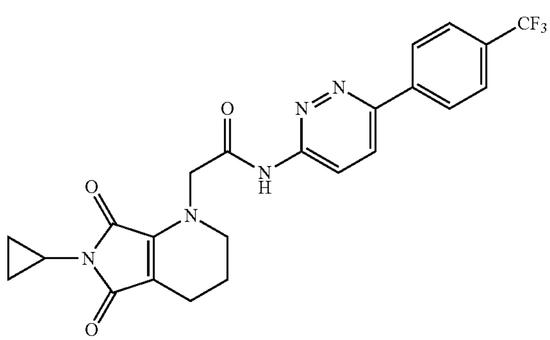 [SMILES: O=C(CN1CCCC2=C1C(=O)N(C1CC1)C2=O)Nc1ccc(-c2ccc(C(F)(F)F)cc2)nn1] | 2-(6-cyclopropyl-5,7-dioxo-2,3,4,5,6,7-hexahydro-1H-pyrrolo[3,4-b]pyridin-1-yl)-N-(6-(4-(trifluoromethyl)phenyl)pyridazin-3-yl)acetamide | <1 |
| 52 | 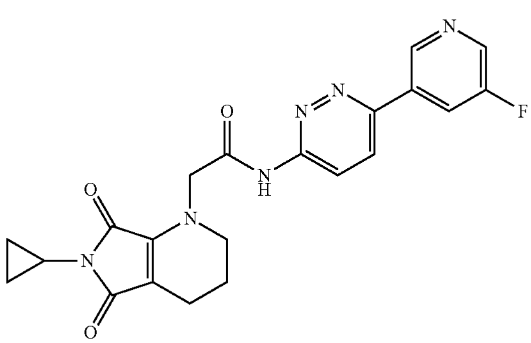 [SMILES: O=C(CN1CCCC2=C1C(=O)N(C1CC1)C2=O)Nc1ccc(-c2cncc(F)c2)nn1] | 2-(6-cyclopropyl-5,7-dioxo-2,3,4,5,6,7-hexahydro-1H-pyrrolo[3,4-b]pyridin-1-yl)-N-(6-(5-fluoropyridin-3-yl)pyridazin-3-yl)acetamide | <0.1 |

| Cpd ID | Structure | IUPAC Name | STF3a IC$_{50}$ μM |
|---|---|---|---|
| 53 | 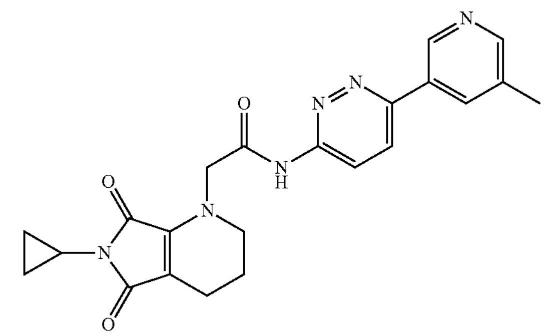 [SMILES: Cc1cncc(-c2ccc(NC(=O)CN3CCCC4=C3C(=O)N(C3CC3)C4=O)nn2)c1] | 2-(6-cyclopropyl-5,7-dioxo-2,3,4,5,6,7-hexahydro-1H-pyrrolo[3,4-b]pyridin-1-yl)-N-(6-(5-methylpyridin-3-yl)pyridazin-3-yl)acetamide | <0.1 |
| 54 | 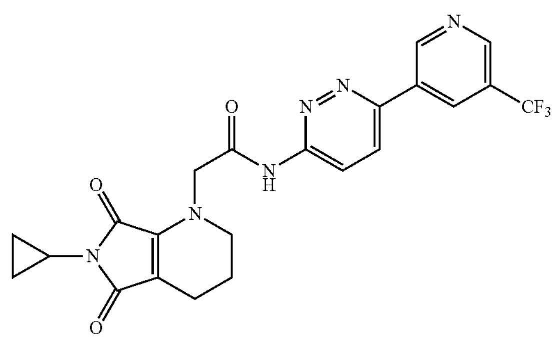 [SMILES: O=C(CN1CCCC2=C1C(=O)N(C1CC1)C2=O)Nc1ccc(-c2cncc(C(F)(F)F)c2)nn1] | 2-(6-cyclopropyl-5,7-dioxo-2,3,4,5,6,7-hexahydro-1H-pyrrolo[3,4-b]pyridin-1-yl)-N-(6-(5-(trifluoromethyl)pyridin-3-yl)pyridazin-3-yl)acetamide | <0.1 |
| 55 | 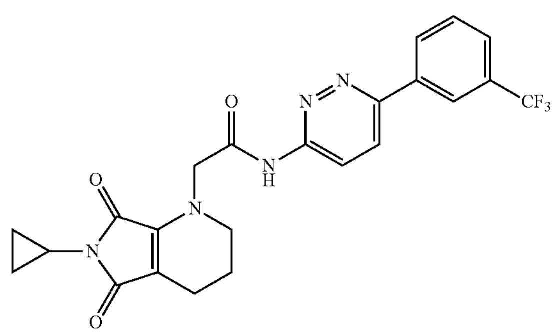 [SMILES: O=C(CN1CCCC2=C1C(=O)N(C1CC1)C2=O)Nc1ccc(-c2cccc(C(F)(F)F)c2)nn1] | 2-(6-cyclopropyl-5,7-dioxo-2,3,4,5,6,7-hexahydro-1H-pyrrolo[3,4-b]pyridin-1-yl)-N-(6-(3-(trifluoromethyl)phenyl)pyridazin-3-yl)acetamide | <0.1 |
| 56 | 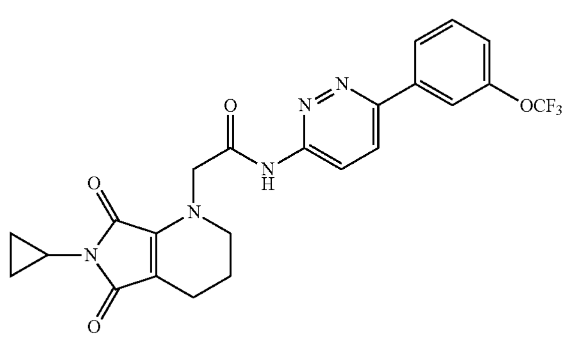 [SMILES: O=C(CN1CCCC2=C1C(=O)N(C1CC1)C2=O)Nc1ccc(-c2cccc(OC(F)(F)F)c2)nn1] | 2-(6-cyclopropyl-5,7-dioxo-2,3,4,5,6,7-hexahydro-1H-pyrrolo[3,4-b]pyridin-1-yl)-N-(6-(3-(trifluoromethoxy)phenyl)pyridazin-3-yl)acetamide | <1 |

| Cpd ID | Structure | IUPAC Name | STF3a IC$_{50}$ μM |
|---|---|---|---|
| 57 | 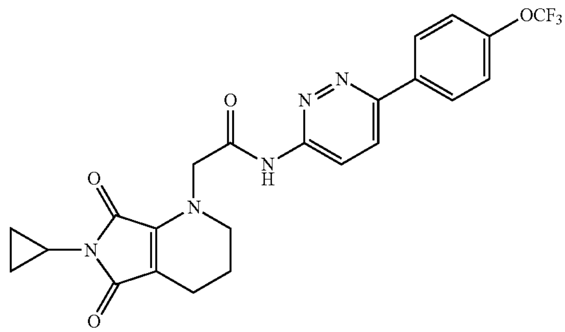 [SMILES: O=C(CN1CCCC2=C1C(=O)N(C1CC1)C2=O)Nc1ccc(-c2ccc(OC(F)(F)F)cc2)nn1] | 2-(6-cyclopropyl-5,7-dioxo-2,3,4,5,6,7-hexahydro-1H-pyrrolo[3,4-b]pyridin-1-yl)-N-(6-(4-(trifluoromethoxy)phenyl)pyridazin-3-yl)acetamide | <1 |
| 58 | 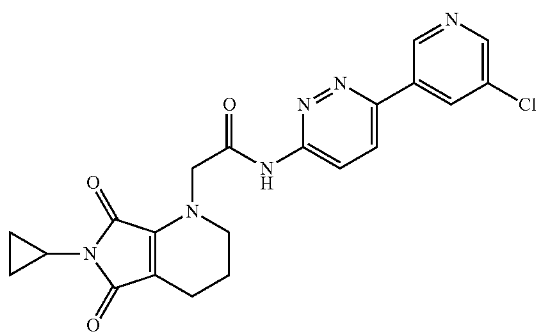 [SMILES: O=C(CN1CCCC2=C1C(=O)N(C1CC1)C2=O)Nc1ccc(-c2cncc(Cl)c2)nn1] | N-(6-(5-chloropyridin-3-yl)pyridazin-3-yl)-2-(6-cyclopropyl-5,7-dioxo-2,3,4,5,6,7-hexahydro-1H-pyrrolo[3,4-b]pyridin-1-yl)acetamide | <0.1 |
| 59 | 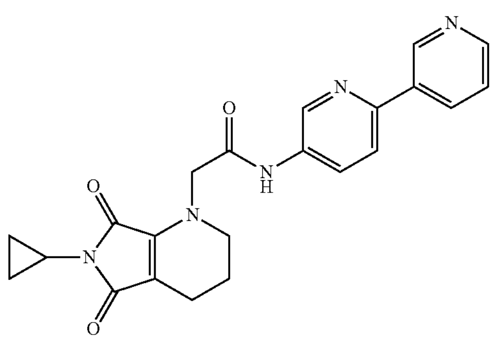 [SMILES: O=C(CN1CCCC2=C1C(=O)N(C1CC1)C2=O)Nc1ccc(-c2cccnc2)nc1] | N-(2,3'-bipyridin-5-yl)-2-(6-cyclopropyl-5,7-dioxo-2,3,4,5,6,7-hexahydro-1H-pyrrolo[3,4-b]pyridin-1-yl)acetamide | <0.1 |
| 60 | 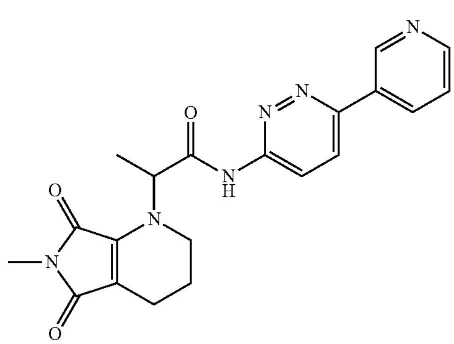 [SMILES: CC(C(=O)Nc1ccc(-c2cccnc2)nn1)N1CCCC2=C1C(=O)N(C)C2=O] | 2-(6-methyl-5,7-dioxo-2,3,4,5,6,7-hexahydro-1H-pyrrolo[3,4-b]pyridin-1-yl)-N-(6-(pyridin-3-yl)pyridazin-3-yl)propanamide | <0.1 |

| Cpd ID | Structure | IUPAC Name | STF3a IC$_{50}$ μM |
|---|---|---|---|
| 61 | 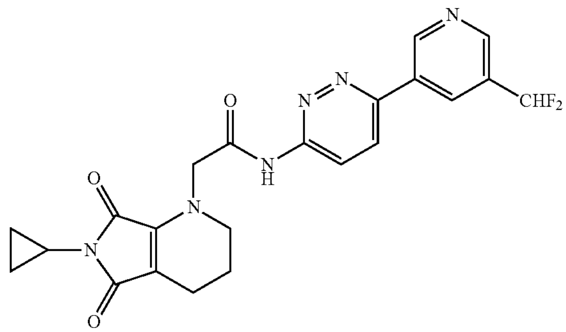 [SMILES: O=C(CN1CCCC2=C1C(=O)N(C1CC1)C2=O)Nc1ccc(-c2cncc(C(F)F)c2)nn1] | 2-(6-cyclopropyl-5,7-dioxo-2,3,4,5,6,7-hexahydro-1H-pyrrolo[3,4-b]pyridin-1-yl)-N-(6-(5-(difluoromethoxy)pyridin-3-yl)pyridazin-3-yl)acetamide | <0.1 |
| 62 | 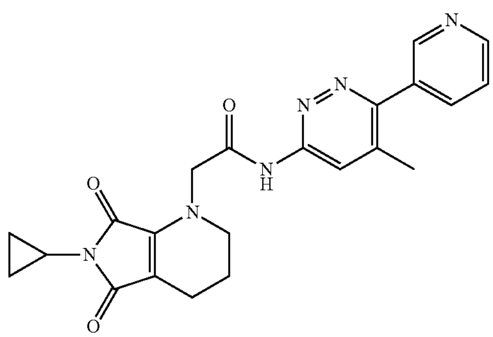 [SMILES: Cc1cc(NC(=O)CN2CCCC3=C2C(=O)N(C2CC2)C3=O)nnc1-c1cccnc1] | 2-(6-cyclopropyl-5,7-dioxo-2,3,4,5,6,7-hexahydro-1H-pyrrolo[3,4-b]pyridin-1-yl)-N-(5-methyl-6-(pyridin-3-yl)pyridazin-3-yl)acetamide | <5 |
| 63 | 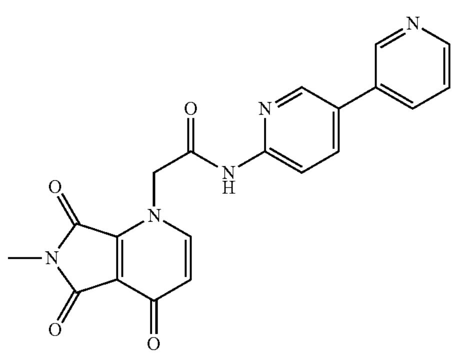 [SMILES: CN1C(=O)c2c(n(CC(=O)Nc3ccc(-c4cccnc4)cn3)ccc2=O)C1=O] | N-(3,3'-bipyridin-6-yl)-2-(6-methyl-4,5,7-trioxo-4,5,6,7-tetrahydro-1H-pyrrolo[3,4-b]pyridin-1-yl)acetamide | <1 |
| 64 | 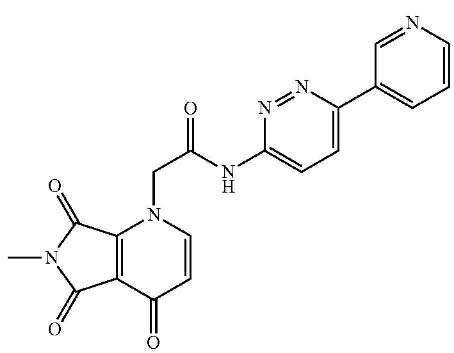 [SMILES: CN1C(=O)c2c(n(CC(=O)Nc3ccc(-c4cccnc4)nn3)ccc2=O)C1=O] | 2-(6-methyl-4,5,7-trioxo-4,5,6,7-tetrahydro-1H-pyrrolo[3,4-b]pyridin-1-yl)-N-(6-(pyridin-3-yl)pyridazin-3-yl)acetamide | <1 |

-continued

| Cpd ID | Structure | IUPAC Name | STF3a IC$_{50}$ μM |
|---|---|---|---|
| 65 | 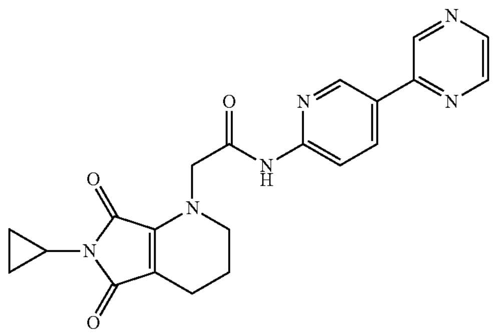 [SMILES: O=C(CN1CCCC2=C1C(=O)N(C1CC1)C2=O)Nc1ccc(-c2cnccn2)cn1] | 2-(6-cyclopropyl-5,7-dioxo-2,3,4,5,6,7-hexahydro-1H-pyrrolo[3,4-b]pyridin-1-yl)-N-(6-(pyrazin-2-yl)pyridin-3-yl)acetamide | <0.1 |
| 66 | 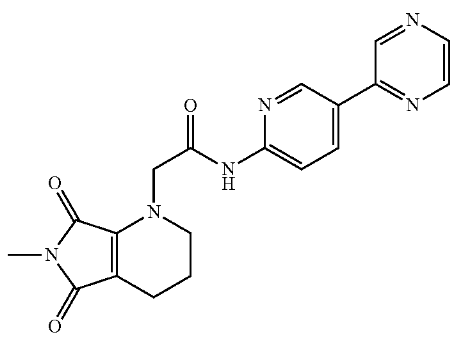 [SMILES: CN1C(=O)C2=C(C1=O)N(CC(=O)Nc1ccc(-c3cnccn3)cn1)CCC2] | 2-(6-methyl-5,7-dioxo-2,3,4,5,6,7-hexahydro-1H-pyrrolo[3,4-b]pyridin-1-yl)-N-(6-(pyrazin-2-yl)pyridin-3-yl)acetamide | <0.1 |
| 67 | 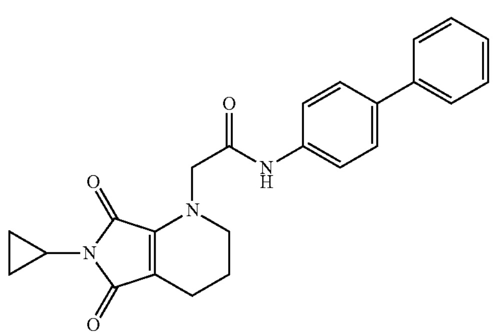 [SMILES: O=C(CN1CCCC2=C1C(=O)N(C1CC1)C2=O)Nc1ccc(-c2ccccc2)cc1] | N-([1,1'-biphenyl]-4-yl)-2-(6-cyclopropyl-5,7-dioxo-2,3,4,5,6,7-hexahydro-1H-pyrrolo[3,4-b]pyridin-1-yl)acetamide | <0.1 |
| 68 | 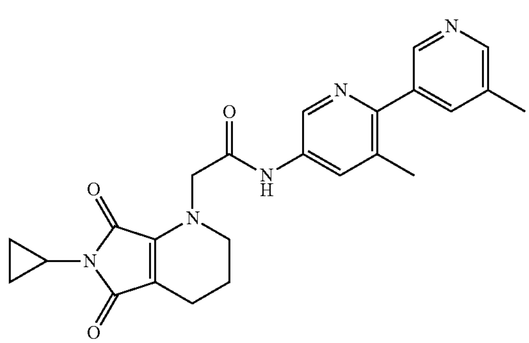 [SMILES: Cc1cncc(-c2ncc(NC(=O)CN3CCCC4=C3C(=O)N(C3CC3)C4=O)cc2C)c1] | 2-(6-cyclopropyl-5,7-dioxo-2,3,4,5,6,7-hexahydro-1H-pyrrolo[3,4-b]pyridin-1-yl)-N-(3,5'-dimethyl-[2,3'-bipyridin]-5-yl)acetamide | <0.1 |

| Cpd ID | Structure | IUPAC Name | STF3a IC$_{50}$ μM |
|---|---|---|---|
| 69 | 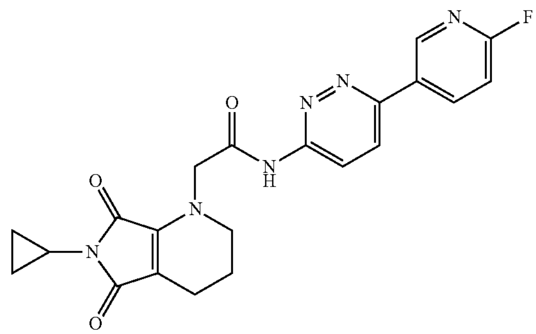 [SMILES: O=C(CN1CCCC2=C1C(=O)N(C1CC1)C2=O)Nc1ccc(-c2ccc(F)nc2)nn1] | 2-(6-cyclopropyl-5,7-dioxo-2,3,4,5,6,7-hexahydro-1H-pyrrolo[3,4-b]pyridin-1-yl)-N-(6-(6-fluoropyridin-3-yl)pyridazin-3-yl)acetamide | <0.1 |
| 70 | 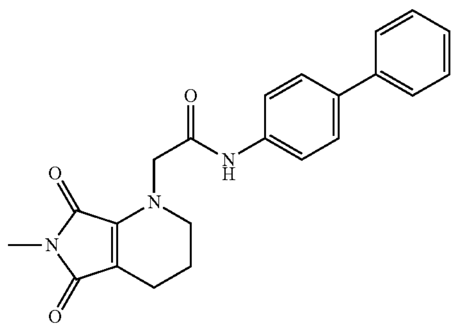 [SMILES: CN1C(=O)C2=C(C1=O)N(CC(=O)Nc1ccc(-c3ccccc3)cc1)CCC2] | N-([1,1'-biphenyl]-4-yl)-2-(6-methyl-5,7-dioxo-2,3,4,5,6,7-hexahydro-1H-pyrrolo[3,4-b]pyridin-1-yl)acetamide | <0.1 |
| 71 | 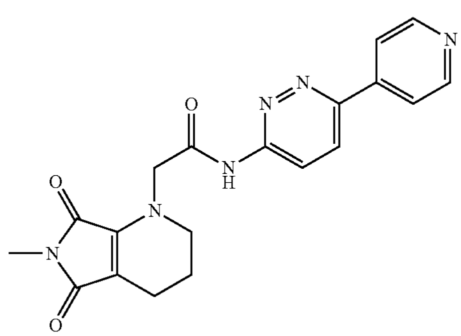 [SMILES: CN1C(=O)C2=C(C1=O)N(CC(=O)Nc1ccc(-c3ccncc3)nn1)CCC2] | 2-(6-methyl-5,7-dioxo-2,3,4,5,6,7-hexahydro-1H-pyrrolo[3,4-b]pyridin-1-yl)-N-(6-(pyridin-4-yl)pyridazin-3-yl)acetamide | <1 |
| 72 | 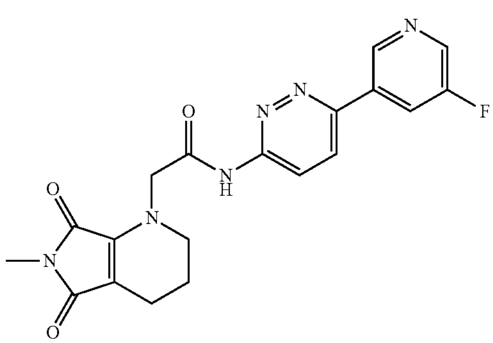 [SMILES: CN1C(=O)C2=C(C1=O)N(CC(=O)Nc1ccc(-c3cncc(F)c3)nn1)CCC2] | N-(6-(5-fluoropyridin-3-yl)pyridazin-3-yl)-2-(6-methyl-5,7-dioxo-2,3,4,5,6,7-hexahydro-1H-pyrrolo[3,4-b]pyridin-1-yl)acetamide | <0.1 |

| Cpd ID | Structure | IUPAC Name | STF3a IC$_{50}$ μM |
|---|---|---|---|
| 73 | 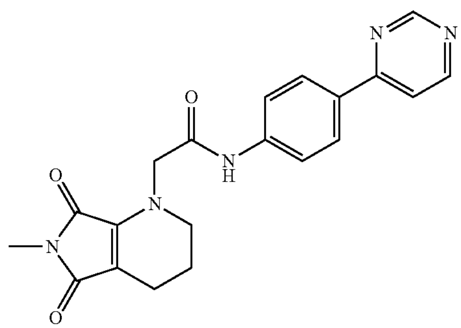 [SMILES: CN1C(=O)C2=C(C1=O)N(CC(=O)Nc1ccc(-c3ccncn3)cc1)CCC2] | 2-(6-methyl-5,7-dioxo-2,3,4,5,6,7-hexahydro-1H-pyrrolo[3,4-b]pyridin-1-yl)-N-(4-(pyrimidin-4-yl)phenyl)acetamide | >10 |
| 74 | 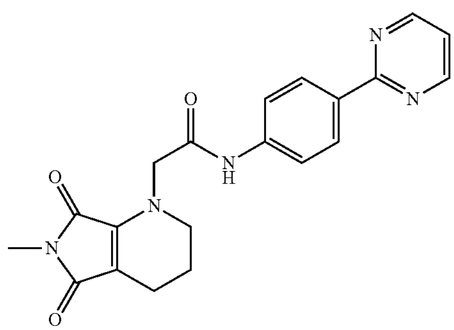 | 2-(6-methyl-5,7-dioxo-2,3,4,5,6,7-hexahydro-1H-pyrrolo[3,4-b]pyridin-1-yl)-N-(4-(pyrimidin-2-yl)phenyl)acetamide | <1.0 |
| 75 | 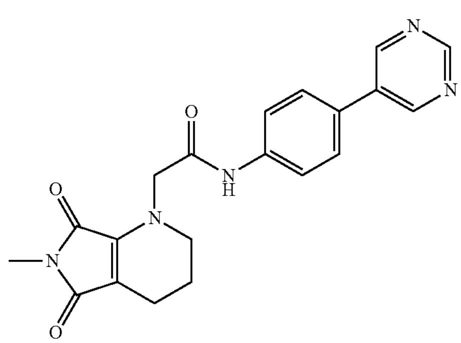 [SMILES: CN1C(=O)C2=C(C1=O)N(CC(=O)Nc1ccc(-c3cncnc3)cc1)CCC2] | 2-(6-methyl-5,7-dioxo-2,3,4,5,6,7-hexahydro-1H-pyrrolo[3,4-b]pyridin-1-yl)-N-(4-(pyrimidin-5-yl)phenyl)acetamide | <0.1 |
| 76 | 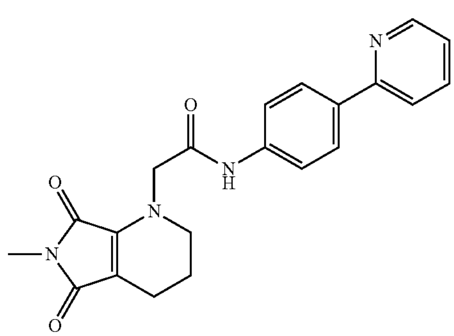 [SMILES: CN1C(=O)C2=C(C1=O)N(CC(=O)Nc1ccc(-c3ccccn3)cc1)CCC2] | 2-(6-methyl-5,7-dioxo-2,3,4,5,6,7-hexahydro-1H-pyrrolo[3,4-b]pyridin-1-yl)-N-(4-(pyridin-2-yl)phenyl)acetamide | <0.1 |

| Cpd ID | Structure | IUPAC Name | STF3a IC$_{50}$ μM |
|---|---|---|---|
| 77 | 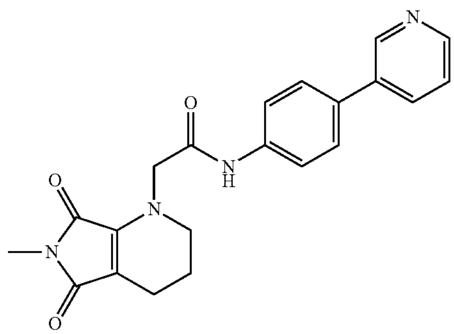 [SMILES: CN1C(=O)C2=C(C1=O)N(CC(=O)Nc1ccc(-c3cccnc3)cc1)CCC2] | 2-(6-methyl-5,7-dioxo-2,3,4,5,6,7-hexahydro-1H-pyrrolo[3,4-b]pyridin-1-yl)-N-(4-(pyridin-3-yl)phenyl)acetamide | <0.1 |
| 78 | 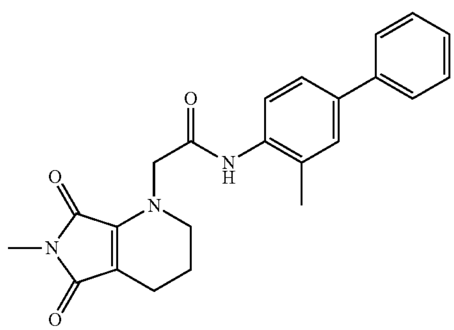 [SMILES: Cc1cc(-c2ccccc2)ccc1NC(=O)CN1CCCC2=C1C(=O)N(C)C2=O] | 2-(6-methyl-5,7-dioxo-2,3,4,5,6,7-hexahydro-1H-pyrrolo[3,4-b]pyridin-1-yl)-N-(3-methyl-[1,1'-biphenyl]-4-yl)acetamide | >10 |
| 79 | 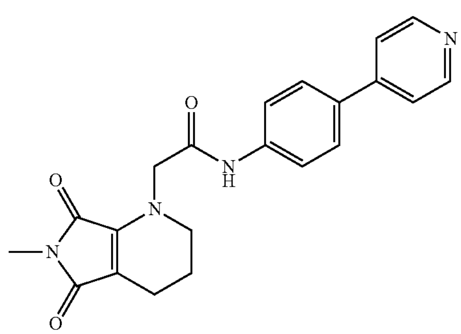 [SMILES: CN1C(=O)C2=C(C1=O)N(CC(=O)Nc1ccc(-c3ccncc3)cc1)CCC2] | 2-(6-methyl-5,7-dioxo-2,3,4,5,6,7-hexahydro-1H-pyrrolo[3,4-b]pyridin-1-yl)-N-(4-(pyridin-4-yl)phenyl)acetamide | <0.1 |
| 80 | 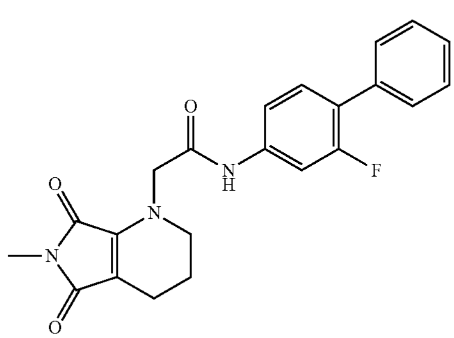 [SMILES: CN1C(=O)C2=C(C1=O)N(CC(=O)Nc1ccc(-c3ccccc3)c(F)c1)CCC2] | N-(2-fluoro-[1,1'-biphenyl]-4-yl)-2-(6-methyl-5,7-dioxo-2,3,4,5,6,7-hexahydro-1H-pyrrolo[3,4-b]pyridin-1-yl)acetamide | <0.1 |

| Cpd ID | Structure | IUPAC Name | STF3a IC$_{50}$ μM |
|---|---|---|---|
| 81 | 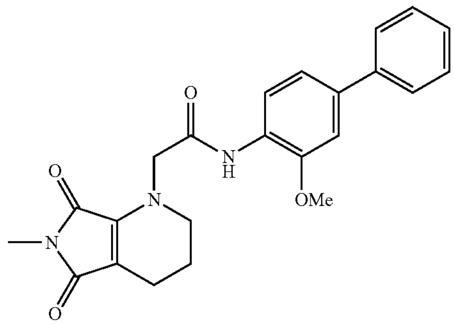 [SMILES: COc1cc(-c2ccccc2)ccc1NC(=O)CN1CCCC2=C1C(=O)N(C)C2=O] | N-(3-methoxy-[1,1'-biphenyl]-4-yl)-2-(6-methyl-5,7-dioxo-2,3,4,5,6,7-hexahydro-1H-pyrrolo[3,4-b]pyridin-1-yl)acetamide | >10 |
| 82 | 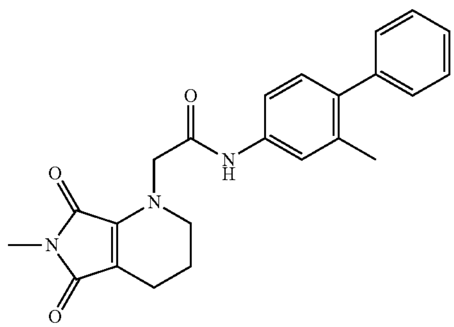 [SMILES: Cc1cc(NC(=O)CN2CCCC3=C2C(=O)N(C)C3=O)ccc1-c1ccccc1] | 2-(6-methyl-5,7-dioxo-2,3,4,5,6,7-hexahydro-1H-pyrrolo[3,4-b]pyridin-1-yl)-N-(2-methyl-[1,1'-biphenyl]-4-yl)acetamide | <0.1 |
| 83 | 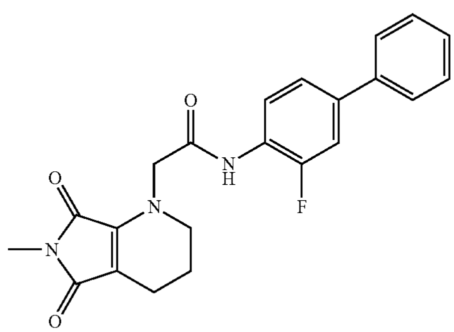 [SMILES: CN1C(=O)C2=C(C1=O)N(CC(=O)Nc1ccc(-c3ccccc3)cc1F)CCC2] | N-(3-fluorobiphenyl-4-yl)-2-(6-methyl-5,7-dioxo-2,3,4,5,6,7-hexahydro-1H-pyrrolo[3,4-b]pyridin-1-yl)acetamide | <0.1 |
| 84 | 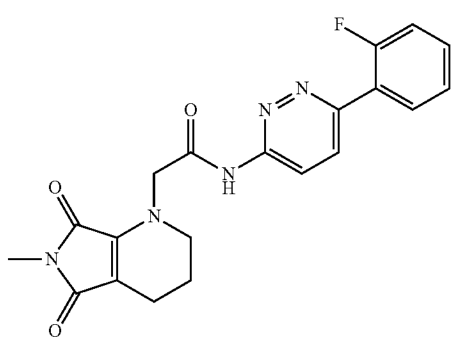 [SMILES: CN1C(=O)C2=C(C1=O)N(CC(=O)Nc1ccc(-c3ccccc3F)nn1)CCC2] | N-(6-(2-fluorophenyl)pyridazin-3-yl)-2-(6-methyl-5,7-dioxo-2,3,4,5,6,7-hexahydro-1H-pyrrolo[3,4-b]pyridin-1-yl)acetamide | <0.1 |

-continued

| Cpd ID | Structure | IUPAC Name | STF3a IC$_{50}$ μM |
|---|---|---|---|
| 85 | 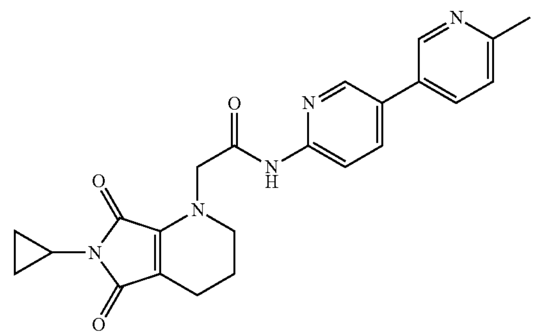 [SMILES: Cc1ccc(-c2ccc(NC(=O)CN3CCCC4=C3C(=O)N(C3CC3)C4=O)nc2)cn1] | 2-(6-cyclopropyl-5,7-dioxo-2,3,4,5,6,7-hexahydro-1H-pyrrolo[3,4-b]pyridin-1-yl)-N-(6'-methyl-[3,3'-bipyridin]-6-yl)acetamide | <0.1 |
| 86 | 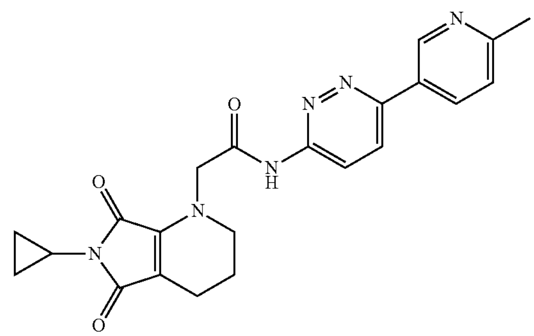 [SMILES: Cc1ccc(-c2ccc(NC(=O)CN3CCCC4=C3C(=O)N(C3CC3)C4=O)nn2)cn1] | 2-(6-cyclopropyl-5,7-dioxo-2,3,4,5,6,7-hexahydro-1H-pyrrolo[3,4-b]pyridin-1-yl)-N-(6-(6-methylpyridin-3-yl)pyridazin-3-yl)acetamide | <0.1 |
| 87 | 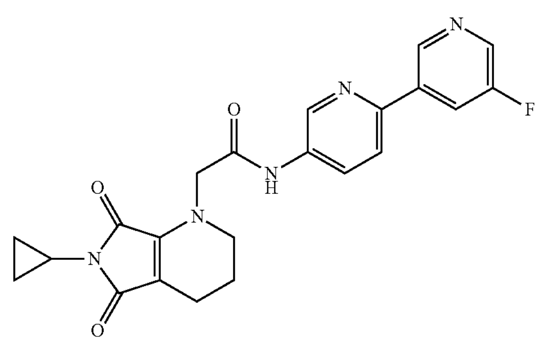 [SMILES: O=C(CN1CCCC2=C1C(=O)N(C1CC1)C2=O)Nc1ccc(-c2cncc(F)c2)nc1] | 2-(6-cyclopropyl-5,7-dioxo-2,3,4,5,6,7-hexahydro-1H-pyrrolo[3,4-b]pyridin-1-yl)-N-(5'-fluoro-[2,3'-bipyridin]-5-yl)acetamide | <0.1 |
| 88 | 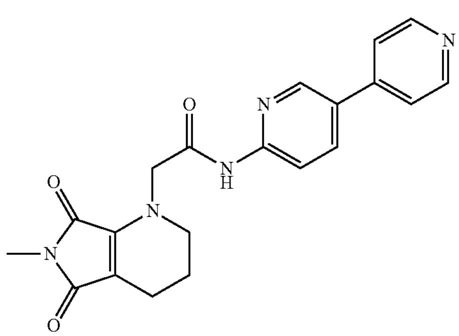 [SMILES: CN1C(=O)C2=C(C1=O)N(CC(=O)Nc1ccc(-c3ccncc3)cn1)CCC2] | N-([3,4'-bipyridin]-6-yl)-2-(6-methyl-5,7-dioxo-2,3,4,5,6,7-hexahydro-1H-pyrrolo[3,4-b]pyridin-1-yl)acetamide | <1 |

| Cpd ID | Structure | IUPAC Name | STF3a IC$_{50}$ μM |
|---|---|---|---|
| 89 | 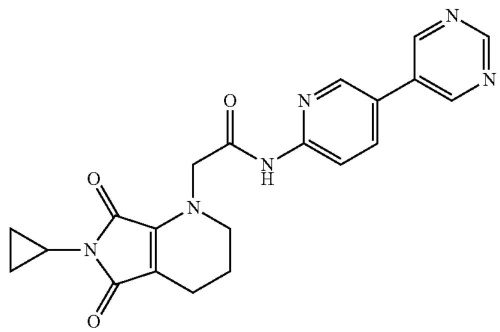 [SMILES: O=C(CN1CCCC2=C1C(=O)N(C1CC1)C2=O)Nc1ccc(-c2cncnc2)cn1] | 2-(6-cyclopropyl-5,7-dioxo-2,3,4,5,6,7-hexahydro-1H-pyrrolo[3,4-b]pyridin-1-yl)-N-(5-(pyrimidin-5-yl)pyridin-2-yl)acetamide | <0.1 |
| 90 | 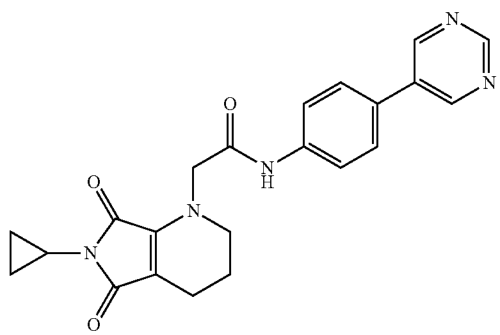 [SMILES: O=C(CN1CCCC2=C1C(=O)N(C1CC1)C2=O)Nc1ccc(-c2cncnc2)cc1] | 2-(6-cyclopropyl-5,7-dioxo-2,3,4,5,6,7-hexahydro-1H-pyrrolo[3,4-b]pyridin-1-yl)-N-(4-(pyrimidin-5-yl)phenyl)acetamide | <0.1 |
| 91 | 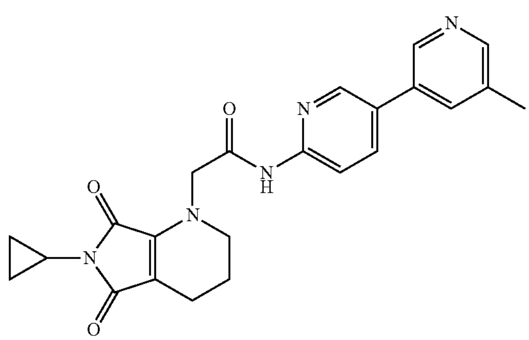 [SMILES: Cc1cncc(-c2ccc(NC(=O)CN3CCCC4=C3C(=O)N(C3CC3)C4=O)nc2)c1] | 2-(6-cyclopropyl-5,7-dioxo-2,3,4,5,6,7-hexahydro-1H-pyrrolo[3,4-b]pyridin-1-yl)-N-(5'-methyl-2,3'-bipyridin-5-yl)acetamide | <0.1 |
| 92 | 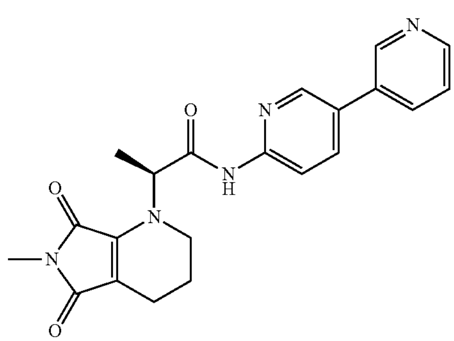 [SMILES: C[C@@H](C(=O)Nc1ccc(-c2cccnc2)cn1)N1CCCC2=C1C(=O)N(C)C2=O] | (S)-N-([3,3'-bipyridin]-6-yl)-2-(6-methyl-5,7-dioxo-2,3,4,5,6,7-hexahydro-1H-pyrrolo[3,4-b]pyridin-1-yl)propanamide | <0.1 |

-continued

| Cpd ID | Structure | IUPAC Name | STF3a IC$_{50}$ μM |
|---|---|---|---|
| 93 | 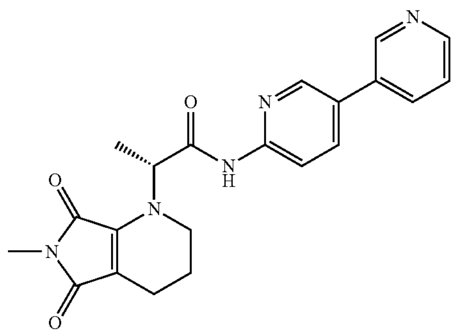 [SMILES: C[C@H](C(=O)Nc1ccc(-c2cccnc2)cn1)N1CCCC2=C1C(=O)N(C)C2=O] | (R)-N-([3,3'-bipyridin]-6-yl)-2-(6-methyl-5,7-dioxo-2,3,4,5,6,7-hexahydro-1H-pyrrolo[3,4-b]pyridin-1-yl)propanamide | <1 |
| 94 | 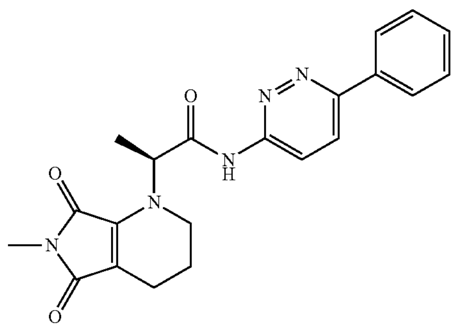 [SMILES: C[C@@H](C(=O)Nc1ccc(-c2ccccc2)nn1)N1CCCC2=C1C(=O)N(C)C2=O] | (S)-2-(6-methyl-5,7-dioxo-2,3,4,5,6,7-hexahydro-1H-pyrrolo[3,4-b]pyridin-1-yl)-N-(6-phenylpyridazin-3-yl)propanamide | <0.1 |
| 95 | 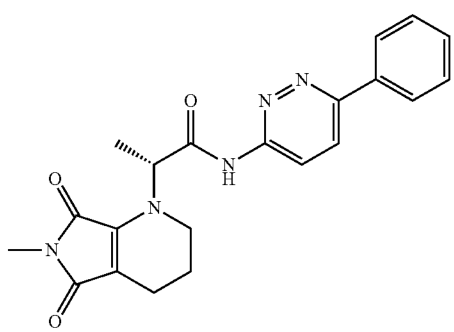 [SMILES: C[C@H](C(=O)Nc1ccc(-c2ccccc2)nn1)N1CCCC2=C1C(=O)N(C)C2=O] | (R)-2-(6-methyl-5,7-dioxo-2,3,4,5,6,7-hexahydro-1H-pyrrolo[3,4-b]pyridin-1-yl)-N-(6-phenylpyridazin-3-yl)propanamide | >10 |
| 96 | 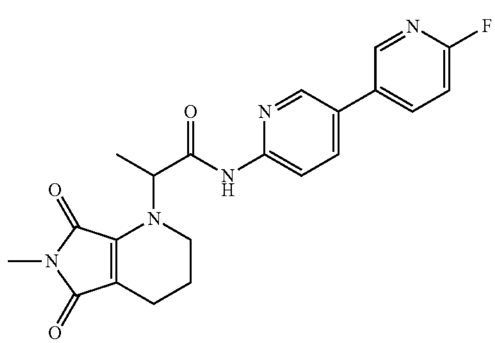 [SMILES: CC(C(=O)Nc1ccc(-c2ccc(F)nc2)cn1)N1CCCC2=C1C(=O)N(C)C2=O] | N-(6'-fluoro-3,3'-bipyridin-6-yl)-2-(6-methyl-5,7-dioxo-2,3,4,5,6,7-hexahydro-1H-pyrrolo[3,4-b]pyridin-1-yl)propanamide | <1 |

-continued

| Cpd ID | Structure | IUPAC Name | STF3a IC$_{50}$ μM |
|---|---|---|---|
| 97 | 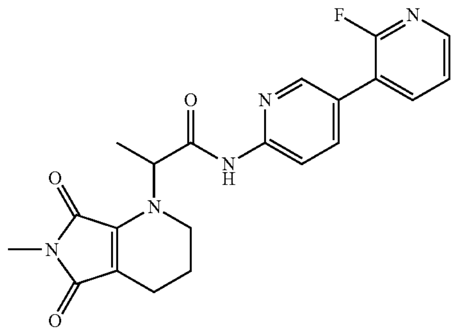 [SMILES: CC(C(=O)Nc1ccc(-c2cccnc2F)cn1)N1CCCC2=C1C(=O)N(C)C2=O] | N-(2'-fluoro-3,3'-bipyridin-6-yl)-2-(6-methyl-5,7-dioxo-2,3,4,5,6,7-hexahydro-1H-pyrrolo[3,4-b]pyridin-1-yl)propanamide | <0.1 |
| 99 | 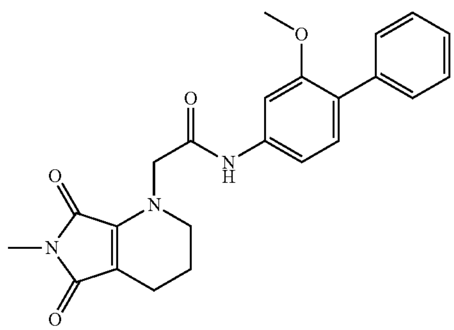 [SMILES: COc1cc(NC(=O)CN2CCCC3=C2C(=O)N(C)C3=O)ccc1-c1ccccc1] | N-(2-methoxy-[1,1'-biphenyl]-4-yl)-2-(6-methyl-5,7-dioxo-2,3,4,5,6,7-hexahydro-1H-pyrrolo[3,4-b]pyridin-1-yl)acetamide | <10 |
| 100 | 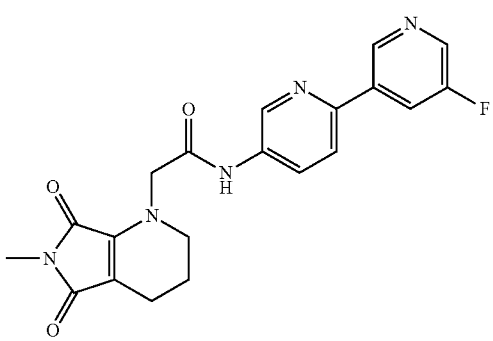 [SMILES: CN1C(=O)C2=C(C1=O)N(CC(=O)Nc1ccc(-c3cncc(F)c3)nc1)CCC2] | N-(5'-fluoro-[2,3'-bipyridin]-5-yl)-2-(6-methyl-5,7-dioxo-2,3,4,5,6,7-hexahydro-1H-pyrrolo[3,4-b]pyridin-1-yl)acetamide | <0.1 |
| 101 | 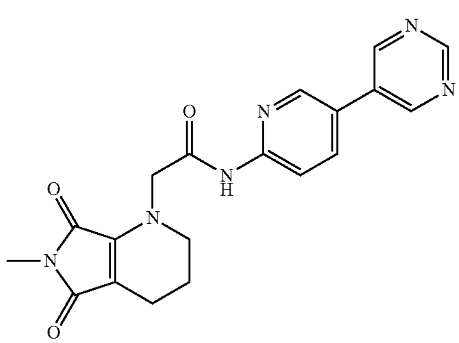 [SMILES: CN1C(=O)C2=C(C1=O)N(CC(=O)Nc1ccc(-c3cncnc3)cn1)CCC2] | 2-(6-methyl-5,7-dioxo-2,3,4,5,6,7-hexahydro-1H-pyrrolo[3,4-b]pyridin-1-yl)-N-(5-(pyrimidin-5-yl)pyridin-2-yl)acetamide | <0.1 |

-continued

| Cpd ID | Structure | IUPAC Name | STF3a IC$_{50}$ μM |
|---|---|---|---|
| 102 | 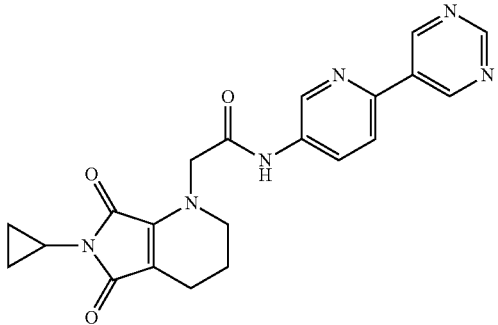 [SMILES: O=C(CN1CCCC2=C1C(=O)N(C1CC1)C2=O)Nc1ccc(-c2cncnc2)nc1] | 2-(6-cyclopropyl-5,7-dioxo-2,3,4,5,6,7-hexahydro-1H-pyrrolo[3,4-b]pyridin-1-yl)-N-(6-(pyrimidin-5-yl)pyridin-3-yl)acetamide | <0.1 |
| 103 | 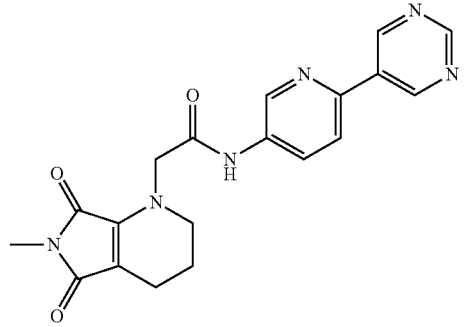 [SMILES: CN1C(=O)C2=C(C1=O)N(CC(=O)Nc1ccc(-c3cncnc3)nc1)CCC2] | 2-(6-methyl-5,7-dioxo-2,3,4,5,6,7-hexahydro-1H-pyrrolo[3,4-b]pyridin-1-yl)-N-(6-(pyrimidin-5-yl)pyridin-3-yl)acetamide | <1 |
| 104 | 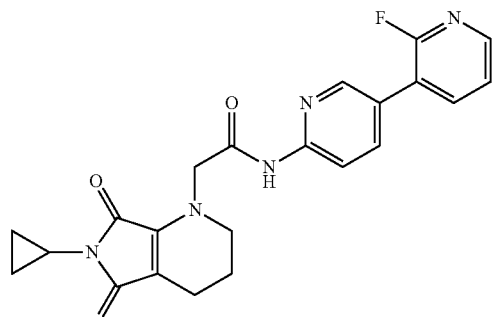 | 2-(6-cyclopropyl-5,7-dioxo-2,3,4,5,6,7-hexahydro-1H-pyrrolo[3,4-b]pyridin-1-yl)-N-(2'-fluoro-[3,3'-bipyridin]-6-yl)acetamide | <0.1 |
| 105 | 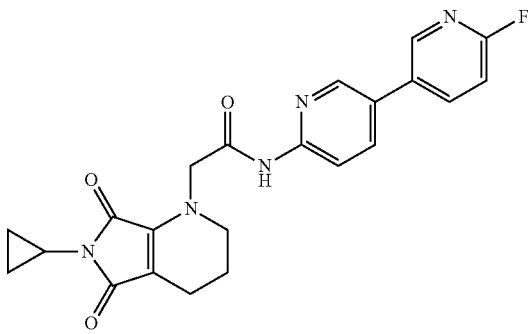 [SMILES: O=C(CN1CCCC2=C1C(=O)N(C1CC1)C2=O)Nc1ccc(-c2ccc(F)nc2)cn1] | 2-(6-cyclopropyl-5,7-dioxo-2,3,4,5,6,7-hexahydro-1H-pyrrolo[3,4-b]pyridin-1-yl)-N-(6'-fluoro[3,3'-bipyridin]-6-yl)acetamide | <0.1 |

| Cpd ID | Structure | IUPAC Name | STF3a IC$_{50}$ μM |
|---|---|---|---|
| 106 | 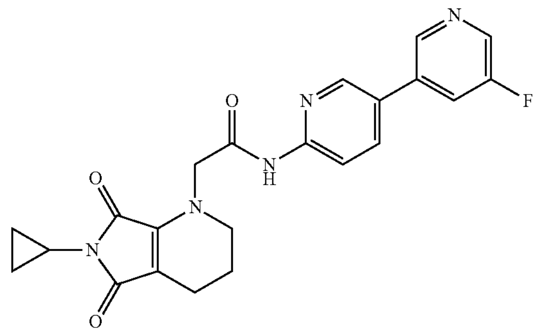 [SMILES: O=C(CN1CCCC2=C1C(=O)N(C1CC1)C2=O)Nc1ccc(-c2cncc(F)c2)cn1] | 2-(6-cyclopropyl-5,7-dioxo-2,3,4,5,6,7-hexahydro-1H-pyrrolo[3,4-b]pyridin-1-yl)-N-(5'-fluoro-[3,3'-bipyridin]-6-yl)acetamide | <0.1 |
| 107 | 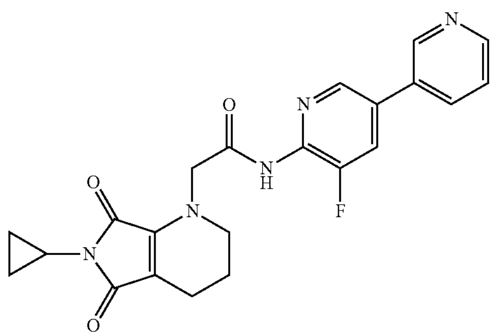 | 2-(6-cyclopropyl-5,7-dioxo-2,3,4,5,6,7-hexahydro-1H-pyrrolo[3,4-b]pyridin-1-yl)-N-(5-fluoro-[3,3'-bipyridin]-6-yl)acetamide | <1 |
| 108 | 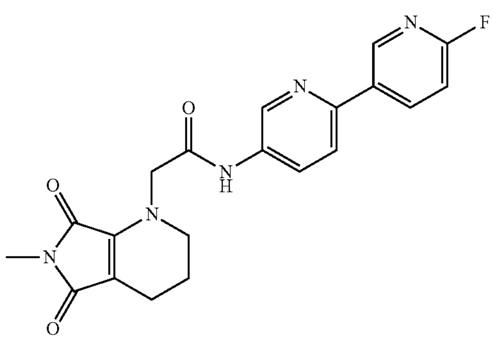 [SMILES: CN1C(=O)C2=C(C1=O)N(CC(=O)Nc1ccc(-c3ccc(F)nc3)nc1)CCC2] | N-(6'-fluoro-[2,3'-bipyridin]-5-yl)-2-(6-methyl-5,7-dioxo-2,3,4,5,6,7-hexahydro-1H-pyrrolo[3,4-b]pyridin-1-yl)acetamide | <1 |
| 109 | 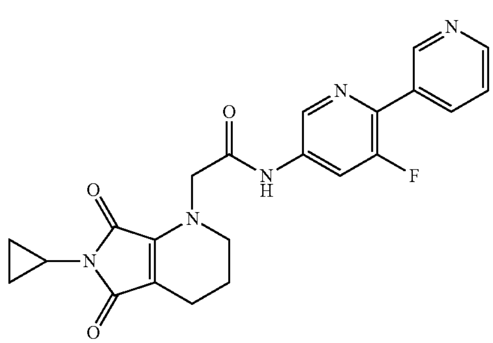 [SMILES: O=C(CN1CCCC2=C1C(=O)N(C1CC1)C2=O)Nc1cnc(-c2cccnc2)c(F)c1] | 2-(6-cyclopropyl-5,7-dioxo-2,3,4,5,6,7-hexahydro-1H-pyrrolo[3,4-b]pyridin-1-yl)-N-(4-fluoro-[3,3'-bipyridin]-6-yl)acetamide | <0.1 |

-continued

| Cpd ID | Structure | IUPAC Name | STF3a IC$_{50}$ μM |
|---|---|---|---|
| 110 | 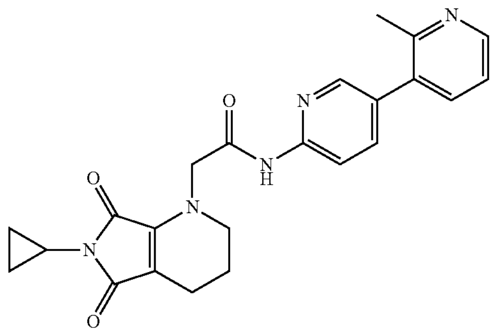 [SMILES: Cc1ncccc1-c1ccc(NC(=O)CN2CCCC3=C2C(=O)N(C2CC2)C3=O)nc1] | 2-(6-cyclopropyl-5,7-dioxo-2,3,4,5,6,7-hexahydro-1H-pyrrolo[3,4-b]pyridin-1-yl)-N-(2'-methyl-[3,3'-bipyridin]-6-yl)acetamide | <1 |
| 111 | 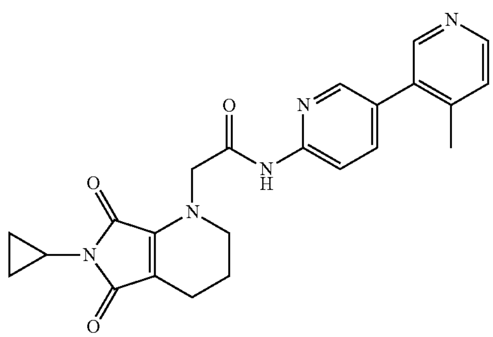 [SMILES: Cc1ccncc1-c1ccc(NC(=O)CN2CCCC3=C2C(=O)N(C2CC2)C3=O)nc1] | 2-(6-cyclopropyl-5,7-dioxo-2,3,4,5,6,7-hexahydro-1H-pyrrolo[3,4-b]pyridin-1-yl)-N-(4'-methyl-[3,3'-bipyridin]-6-yl)acetamide | <1 |
| 112 | 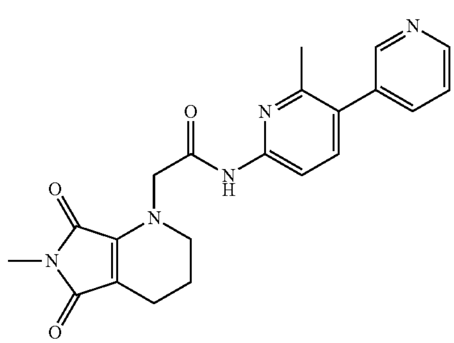 [SMILES: Cc1nc(NC(=O)CN2CCCC3=C2C(=O)N(C)C3=O)ccc1-c1cccnc1] | N-(6'-fluoro-[2,3'-bipyridin]-5-yl)-2-(6-methyl-5,7-dioxo-2,3,4,5,6,7-hexahydro-1H-pyrrolo[3,4-b]pyridin-1-yl)acetamide | <10 |
| 113 | 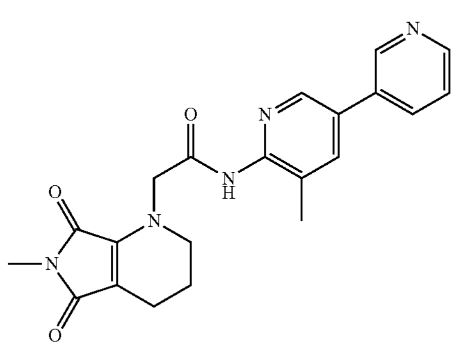 [SMILES: Cc1cc(-c2cccnc2)cnc1NC(=O)CN1CCCC2=C1C(=O)N(C)C2=O] | 2-(6-methyl-5,7-dioxo-2,3,4,5,6,7-hexahydro-1H-pyrrolo[3,4-b]pyridin-1-yl)-N-(5-methyl-[3,3'-bipyridin]-6-yl)acetamide | >10 |

| Cpd ID | Structure | IUPAC Name | STF3a IC$_{50}$ μM |
|---|---|---|---|
| 114 | 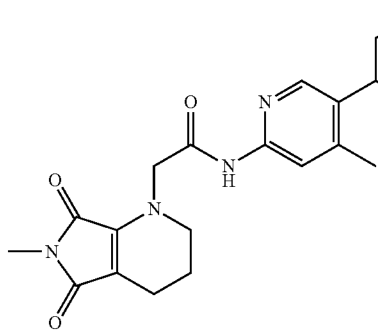 | 2-(6-methyl-5,7-dioxo-2,3,4,5,6,7-hexahydro-1H-pyrrolo[3,4-b]pyridin-1-yl)-N-(4-methyl-[3,3'-bipyridin]-6-yl)acetamide | <5 |
| 115 | 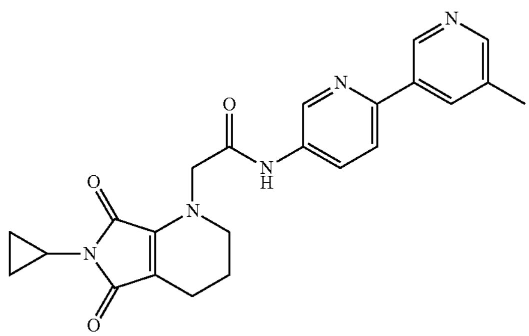 [SMILES: Cc1cncc(-c2ccc(NC(=O)CN3CCCC4=C3C(=O)N(C3CC3)C4=O)cn2)c1] | 2-(6-cyclopropyl-5,7-dioxo-2,3,4,5,6,7-hexahydro-1H-pyrrolo[3,4-b]pyridin-1-yl)-N-(5'-methyl-[3,3'-bipyridin]-6-yl)acetamide | <0.1 |
| 116 | 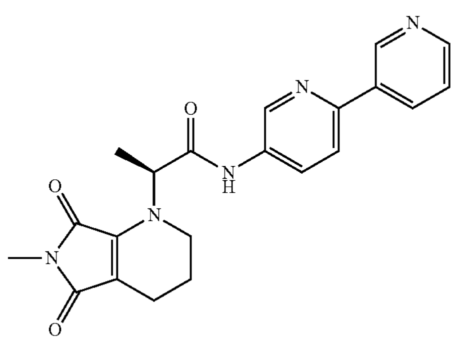 [SMILES: C[C@@H](C(=O)Nc1ccc(-c2cccnc2)nc1)N1CCCC2=C1C(=O)N(C)C2=O] | (S)-N-([2,3'-bipyridin]-5-yl)-2-(6-methyl-5,7-dioxo-2,3,4,5,6,7-hexahydro-1H-pyrrolo[3,4-b]pyridin-1-yl)propanamide | <0.1 |
| 117 | 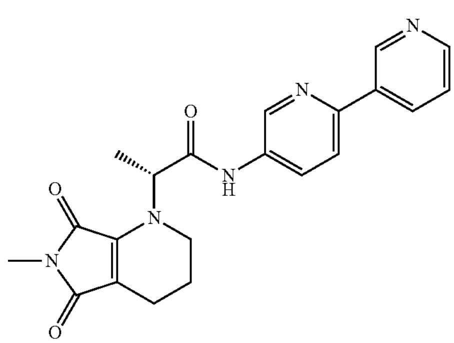 [SMILES: C[C@H](C(=O)Nc1ccc(-c2cccnc2)nc1)N1CCCC2=C1C(=O)N(C)C2=O] | (R)-N-([2,3'-bipyridin]-5-yl)-2-(6-methyl-5,7-dioxo-2,3,4,5,6,7-hexahydro-1H-pyrrolo[3,4-b]pyridin-1-yl)propanamide | <1 |

-continued

| Cpd ID | Structure | IUPAC Name | STF3a IC$_{50}$ μM |
|---|---|---|---|
| 118 | 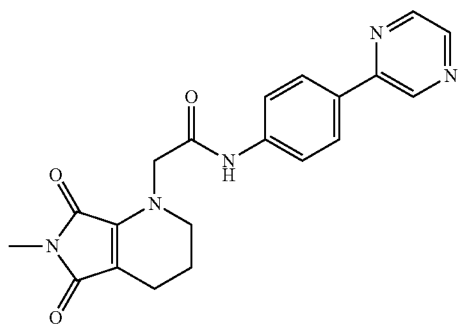 [SMILES: CN1C(=O)C2=C(C1=O)N(CC(=O)Nc1ccc(-c3cnccn3)cc1)CCC2] | 2-(6-methyl-5,7-dioxo-2,3,4,5,6,7-hexahydro-1H-pyrrolo[3,4-b]pyridin-1-yl)-N-(4-(pyrazin-2-yl)phenyl)acetamide | <0.1 |
| 119 | 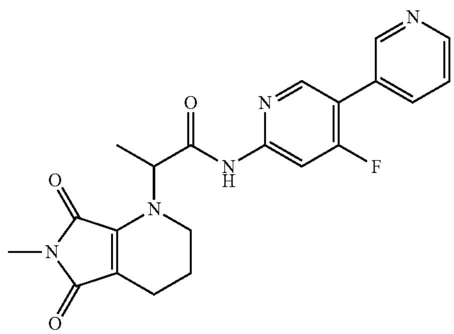 [SMILES: CC(C(=O)Nc1cc(F)c(-c2cccnc2)cn1)N1CCCC2=C1C(=O)N(C)C2=O] | N-(4-fluoro-3,3'-bipyridin-6-yl)-2-(6-methyl-5,7-dioxo-2,3,4,5,6,7-hexahydro-1H-pyrrolo[3,4-b]pyridin-1-yl)propanamide | <0.1 |
| 120 | 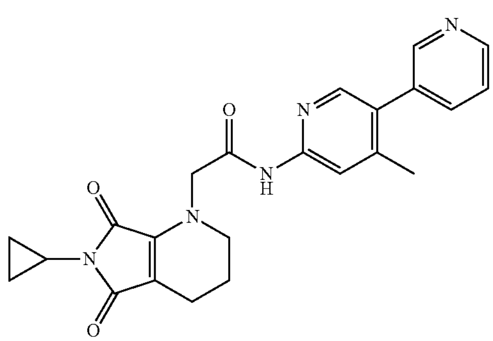 [SMILES: Cc1cc(NC(=O)CN2CCCC3=C2C(=O)N(C2CC2)C3=O)ncc1-c1cccnc1] | 2-(6-cyclopropyl-5,7-dioxo-2,3,4,5,6,7-hexahydro-1H-pyrrolo[3,4-b]pyridin-1-yl)-N-(4-methyl-[3,3'-bipyridin]-6-yl)acetamide | <1 |
| 121 | 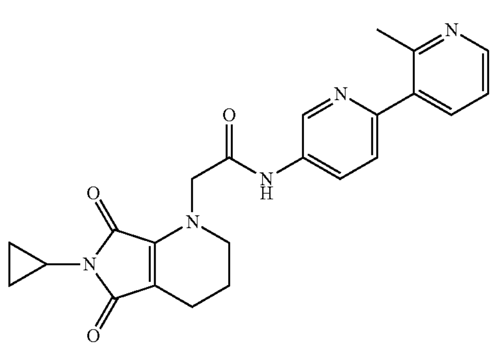 [SMILES: Cc1ncccc1-c1ccc(NC(=O)CN2CCCC3=C2C(=O)N(C2CC2)C3=O)cn1] | 2-(6-cyclopropyl-5,7-dioxo-2,3,4,5,6,7-hexahydro-1H-pyrrolo[3,4-b]pyridin-1-yl)-N-(2'-methyl-2,3'-bipyridin-5-yl)acetamide | <0.1 |

-continued

| Cpd ID | Structure | IUPAC Name | STF3a IC$_{50}$ μM |
|---|---|---|---|
| 122 | 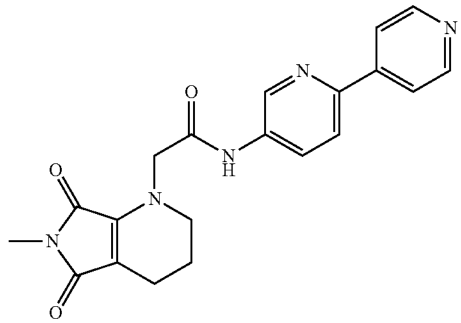 [SMILES: CN1C(=O)C2=C(C1=O)N(CC(=O)Nc1ccc(-c3ccncc3)nc1)CCC2] | N-(2,4'-bipyridin-5-yl)-2-(6-methyl-5,7-dioxo-2,3,4,5,6,7-hexahydro-1H-pyrrolo[3,4-b]pyridin-1-yl)acetamide | <1 |
| 123 | 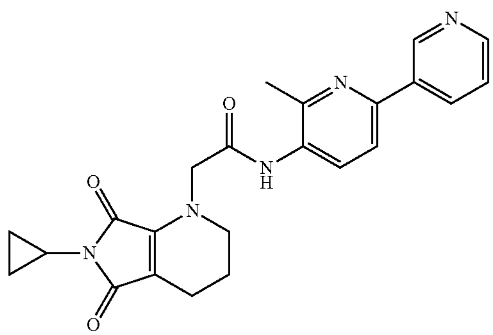 [SMILES: Cc1nc(-c2cccnc2)ccc1NC(=O)CN1CCCC2=C1C(=O)N(C1CC1)C2=O] | 2-(6-cyclopropyl-5,7-dioxo-2,3,4,5,6,7-hexahydro-1H-pyrrolo[3,4-b]pyridin-1-yl)-N-(6-methyl-2,3'-bipyridin-5-yl)acetamide | >10 |
| 124 | 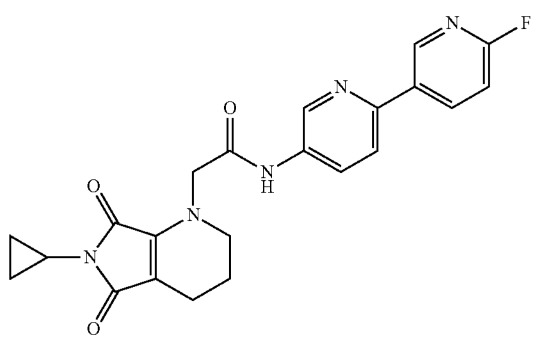 [SMILES: O=C(CN1CCCC2=C1C(=O)N(C1CC1)C2=O)Nc1ccc(-c2ccc(F)nc2)nc1] | 2-(6-cyclopropyl-5,7-dioxo-2,3,4,5,6,7-hexahydro-1H-pyrrolo[3,4-b]pyridin-1-yl)-N-(6'-fluoro-[2,3'-bipyridin]-5-yl)acetamide | <0.1 |
| 125 | 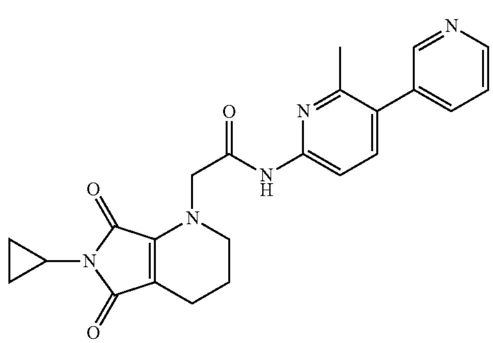 [SMILES: Cc1nc(NC(=O)CN2CCCC3=C2C(=O)N(C2CC2)C3=O)ccc1-c1cccnc1] | 2-(6-cyclopropyl-5,7-dioxo-2,3,4,5,6,7-hexahydro-1H-pyrrolo[3,4-b]pyridin-1-yl)-N-(2-methyl-[3,3'-bipyridin]-6-yl)acetamide | <1 |

| Cpd ID | Structure | IUPAC Name | STF3a IC$_{50}$ μM |
|---|---|---|---|
| 126 | 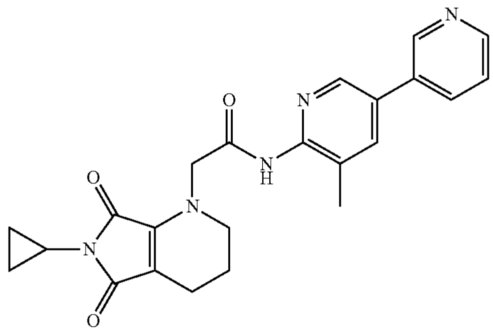 | 2-(6-cyclopropyl-5,7-dioxo-2,3,4,5,6,7-hexahydro-1H-pyrrolo[3,4-b]pyridin-1-yl)-N-(2-methyl-[3,3'-bipyridin]-6-yl)acetamide | >10 |
| 127 | 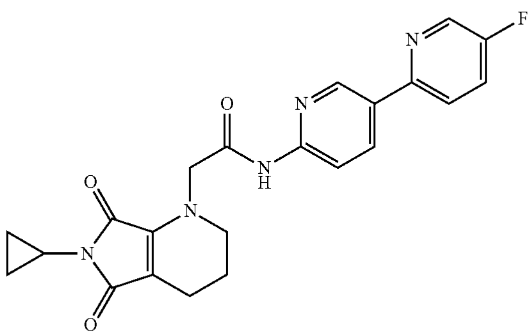 [SMILES: O=C(CN1CCCC2=C1C(=O)N(C1CC1)C2=O)Nc1ccc(-c2ccc(F)cn2)cn1] | 2-(6-cyclopropyl-5,7-dioxo-2,3,4,5,6,7-hexahydro-1H-pyrrolo[3,4-b]pyridin-1-yl)-N-(5-fluoro-[2,3'-bipyridin]-6'-yl)acetamide | <0.1 |
| 128 | 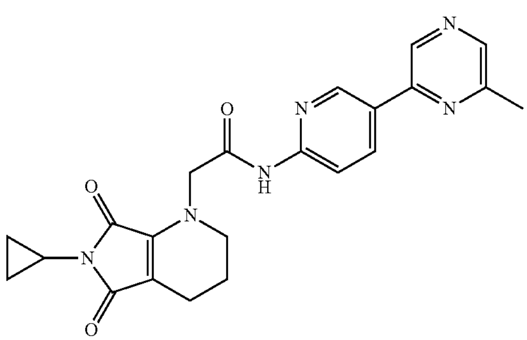 [SMILES: Cc1cncc(-c2ccc(NC(=O)CN3CCCC4=C3C(=O)N(C3CC3)C4=O)nc2)n1] | 2-(6-cyclopropyl-5,7-dioxo-2,3,4,5,6,7-hexahydro-1H-pyrrolo[3,4-b]pyridin-1-yl)-N-(5-(6-methylpyrazin-2-yl)pyridin-2-yl)acetamide | <0.1 |
| 129 | 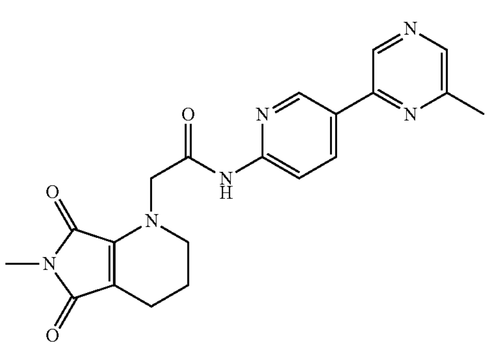 | 2-(6-methyl-5,7-dioxo-2,3,4,5,6,7-hexahydro-1H-pyrrolo[3,4-b]pyridin-1-yl)-N-(5-(6-methylpyrazin-2-yl)pyridin-2-yl)acetamide | <0.1 |

| Cpd ID | Structure | IUPAC Name | STF3a IC$_{50}$ μM |
|---|---|---|---|
| 130 | 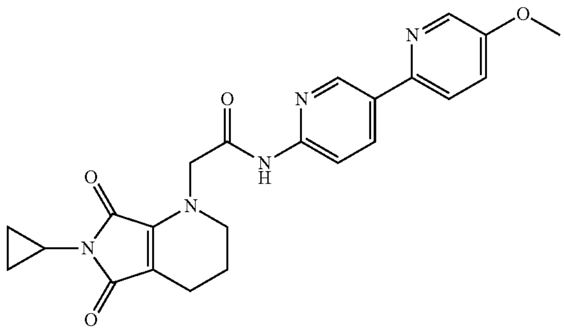 [SMILES: COc1ccc(-c2ccc(NC(=O)CN3CCCC4=C3C(=O)N(C3CC3)C4=O)nc2)nc1] | 2-(6-cyclopropyl-5,7-dioxo-2,3,4,5,6,7-hexahydro-1H-pyrrolo[3,4-b]pyridin-1-yl)-N-(5-methoxy-[2,3'-bipyridin]-6'-yl)acetamide | <0.1 |
| 131 | 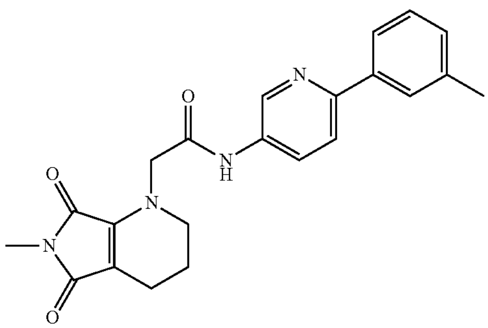 | 2-(6-methyl-5,7-dioxo-2,3,4,5,6,7-hexahydro-1H-pyrrolo[3,4-b]pyridin-1-yl)-N-(6-(m-tolyl)pyridin-3-yl)acetamide | <0.1 |
| 132 | 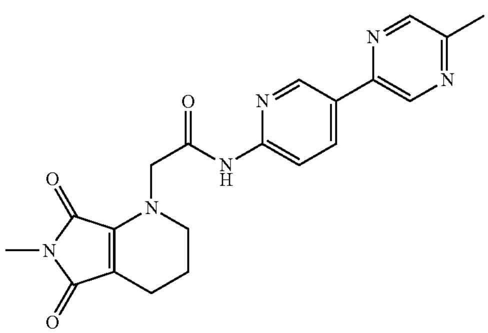 | 2-(6-methyl-5,7-dioxo-2,3,4,5,6,7-hexahydro-1H-pyrrolo[3,4-b]pyridin-1-yl)-N-(5-(5-methylpyrazin-2-yl)pyridin-2-yl)acetamide | <0.1 |
| 133 | 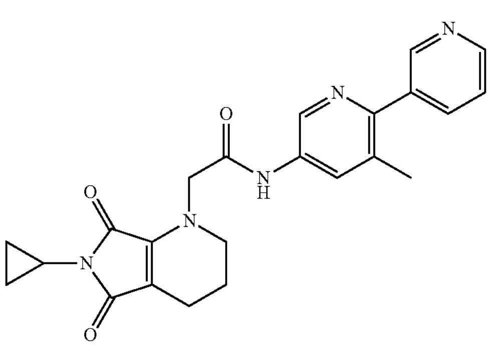 [SMILES: Cc1cc(NC(=O)CN2CCCC3=C2C(=O)N(C2CC2)C3=O)cnc1-c1cccnc1] | 2-(6-cyclopropyl-5,7-dioxo-2,3,4,5,6,7-hexahydro-1H-pyrrolo[3,4-b]pyridin-1-yl)-N-(3-methyl-2,3'-bipyridin-5-yl)acetamide | <1 |

-continued

| Cpd ID | Structure | IUPAC Name | STF3a IC$_{50}$ μM |
|---|---|---|---|
| 134 | 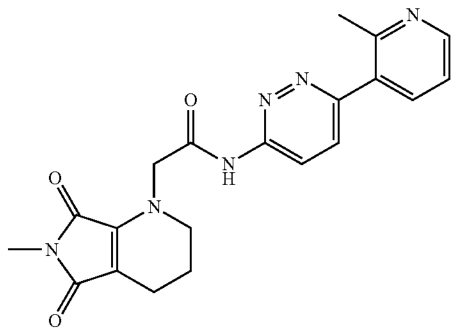 [SMILES: Cc1ncccc1-c1ccc(NC(=O)CN2CCCC3=C2C(=O)N(C)C3=O)nn1] | 2-(6-methyl-5,7-dioxo-2,3,4,5,6,7-hexahydro-1H-pyrrolo[3,4-b]pyridin-1-yl)-N-(6-(2-methylpyridin-3-yl)pyridazin-3-yl)acetamide | <5 |
| 135 | 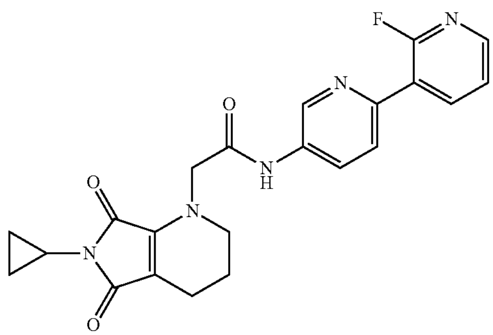 [SMILES: O=C(CN1CCCC2=C1C(=O)N(C1CC1)C2=O)Nc1ccc(-c2cccnc2F)nc1] | 2-(6-cyclopropyl-5,7-dioxo-2,3,4,5,6,7-hexahydro-1H-pyrrolo[3,4-b]pyridin-1-yl)-N-(2'-fluoro-2,3'-bipyridin-5-yl)acetamide | <0.1 |
| 136 | 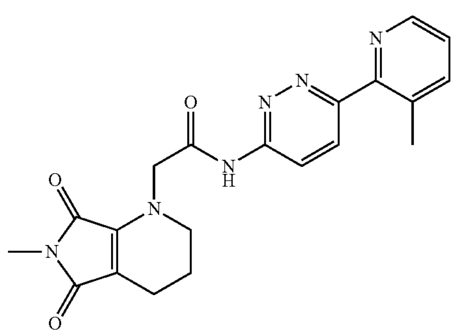 [SMILES: Cc1cccnc1-c1ccc(NC(=O)CN2CCCC3=C2C(=O)N(C)C3=O)nn1] | 2-(6-methyl-5,7-dioxo-2,3,4,5,6,7-hexahydro-1H-pyrrolo[3,4-b]pyridin-1-yl)-N-(6-(4-methylpyridin-3-yl)pyridazin-3-yl)acetamide | <5 |
| 137 | 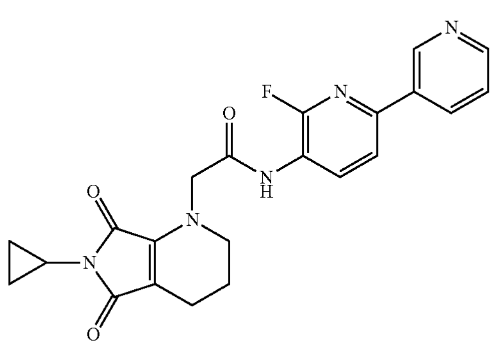 [SMILES: O=C(CN1CCCC2=C1C(=O)N(C1CC1)C2=O)Nc1ccc(-c2cccnc2)nc1F] | N-(6-fluoro-2,3'-bipyridin-5-yl)-2-(6-methyl-5,7-dioxo-2,3,4,5,6,7-hexahydro-1H-pyrrolo[3,4-b]pyridin-1-yl)acetamide | <0.1 |

| Cpd ID | Structure | IUPAC Name | STF3a IC$_{50}$ μM |
|---|---|---|---|
| 138 | 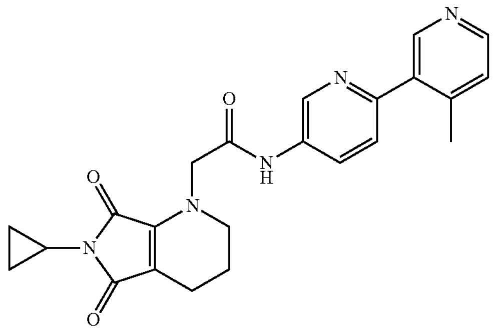 [SMILES: Cc1ccncc1-c1ccc(NC(=O)CN2CCCC3=C2C(=O)N(C2CC2)C3=O)cn1] | 2-(6-cyclopropyl-5,7-dioxo-2,3,4,5,6,7-hexahydro-1H-pyrrolo[3,4-b]pyridin-1-yl)-N-(4'-methyl-2,3'-bipyridin-5-yl)acetamide | <1 |
| 139 | 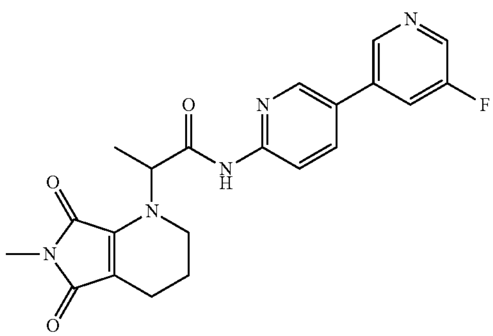 [SMILES: CC(C(=O)Nc1ccc(-c2cncc(F)c2)cn1)N1CCCC2=C1C(=O)N(C)C2=O] | N-(5'-fluoro-3,3'-bipyridin-6-yl)-2-(6-methyl-5,7-dioxo-2,3,4,5,6,7-hexahydro-1H-pyrrolo[3,4-b]pyridin-1-yl)propanamide | <0.1 |
| 140 | 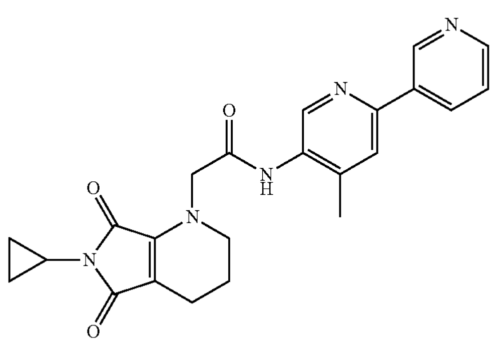 [SMILES: Cc1cc(-c2cccnc2)ncc1NC(=O)CN1CCCC2=C1C(=O)N(C1CC1)C2=O] | 2-(6-cyclopropyl-5,7-dioxo-2,3,4,5,6,7-hexahydro-1H-pyrrolo[3,4-b]pyridin-1-yl)-N-(4-methyl-2,3'-bipyridin-5-yl)acetamide | <10 |
| 141 | 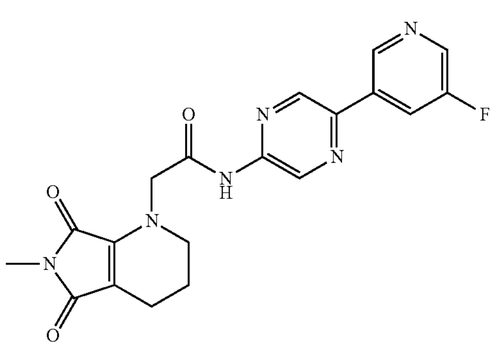 [SMILES: CN1C(=O)C2=C(C1=O)N(CC(=O)Nc1cnc(-c3cncc(F)c3)cn1)CCC2] | N-(5-(5-fluoropyridin-3-yl)pyrazin-2-yl)-2-(6-methyl-5,7-dioxo-2,3,4,5,6,7-hexahydro-1H-pyrrolo[3,4-b]pyridin-1-yl)acetamide | <0.1 |

-continued

| Cpd ID | Structure | IUPAC Name | STF3a IC$_{50}$ μM |
|---|---|---|---|
| 142 | 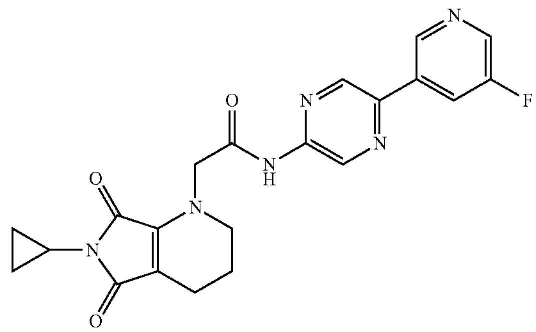 [SMILES: O=C(CN1CCCC2=C1C(=O)N(C1CC1)C2=O)Nc1cnc(-c2cncc(F)c2)cn1] | 2-(6-cyclopropyl-5,7-dioxo-2,3,4,5,6,7-hexahydro-1H-pyrrolo[3,4-b]pyridin-1-yl)-N-(5-(5-fluoropyridin-3-yl)pyrazin-2-yl)acetamide | <0.1 |
| 143 | 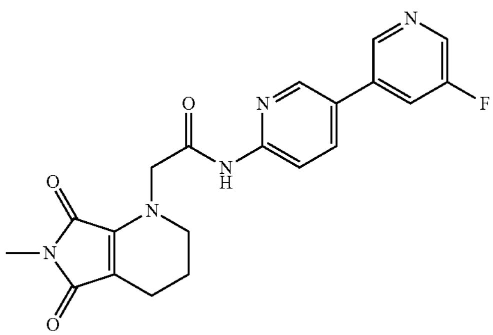 [SMILES: CN1C(=O)C2=C(C1=O)N(CC(=O)Nc1ccc(-c3cncc(F)c3)cn1)CCC2] | N-(5'-fluoro-3,3'-bipyridin-6-yl)-2-(6-methyl-5,7-dioxo-2,3,4,5,6,7-hexahydro-1H-pyrrolo[3,4-b]pyridin-1-yl)acetamide | <0.1 |
| 144 | 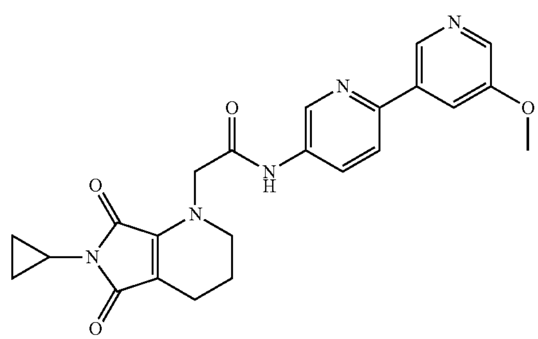 [SMILES: COc1cncc(-c2ccc(NC(=O)CN3CCCC4=C3C(=O)N(C3CC3)C4=O)cn2)c1] | 2-(6-cyclopropyl-5,7-dioxo-2,3,4,5,6,7-hexahydro-1H-pyrrolo[3,4-b]pyridin-1-yl)-N-(5'-methoxy-2,3'-bipyridin-5-yl)acetamide | <0.1 |
| 145 | 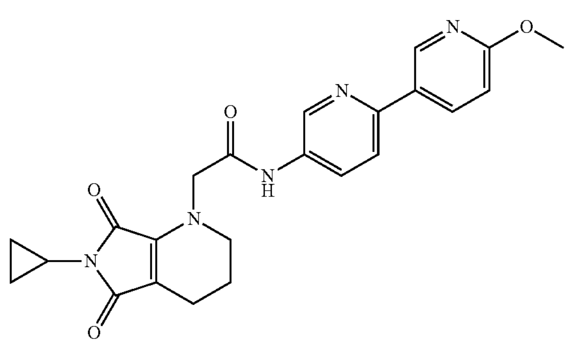 [SMILES: COc1ccc(-c2ccc(NC(=O)CN3CCCC4=C3C(=O)N(C3CC3)C4=O)cn2)cn1] | 2-(6-cyclopropyl-5,7-dioxo-2,3,4,5,6,7-hexahydro-1H-pyrrolo[3,4-b]pyridin-1-yl)-N-(6'-methoxy-2,3'-bipyridin-5-yl)acetamide | <0.1 |

| Cpd ID | Structure | IUPAC Name | STF3a IC$_{50}$ μM |
|---|---|---|---|
| 146 | 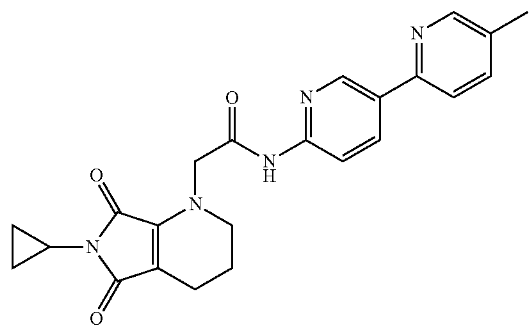 [SMILES: Cc1ccc(-c2ccc(NC(=O)CN3CCCC4=C3C(=O)N(C3CC3)C4=O)nc2)nc1] | 2-(6-cyclopropyl-5,7-dioxo-2,3,4,5,6,7-hexahydro-1H-pyrrolo[3,4-b]pyridin-1-yl)-N-(5-methyl-2,3'-bipyridin-6'-yl)acetamide | <1 |
| 147 | 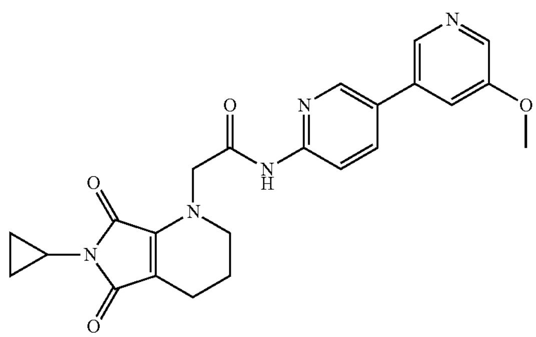 [SMILES: COc1cncc(-c2ccc(NC(=O)CN3CCCC4=C3C(=O)N(C3CC3)C4=O)nc2)c1] | 2-(6-cyclopropyl-5,7-dioxo-2,3,4,5,6,7-hexahydro-1H-pyrrolo[3,4-b]pyridin-1-yl)-N-(5'-methoxy-3,3'-bipyridin-6-yl)acetamide | <0.1 |
| 148 | 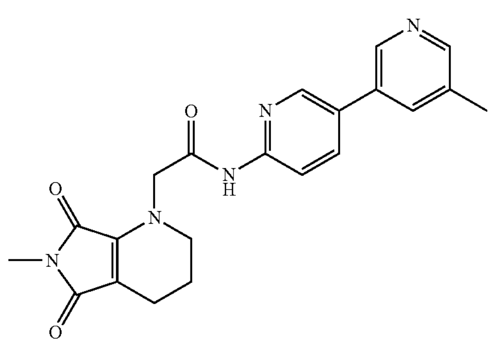 | 2-(6-methyl-5,7-dioxo-2,3,4,5,6,7-hexahydro-1H-pyrrolo[3,4-b]pyridin-1-yl)-N-(5'-methyl-[3,3'-bipyridin]-6-yl)acetamide | <0.1 |
| 149 | 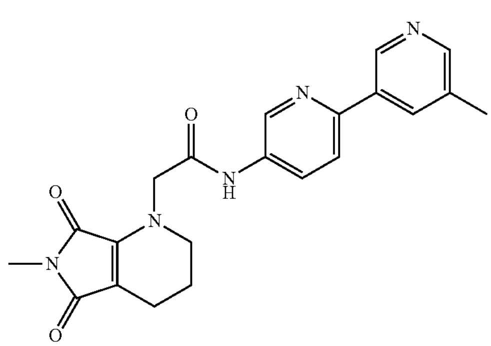 | 2-(6-methyl-5,7-dioxo-2,3,4,5,6,7-hexahydro-1H-pyrrolo[3,4-b]pyridin-1-yl)-N-(5'-methyl-[2,3'-bipyridin]-5-yl)acetamide | <0.1 |

| Cpd ID | Structure | IUPAC Name | STF3a IC$_{50}$ μM |
|---|---|---|---|
| 150 | 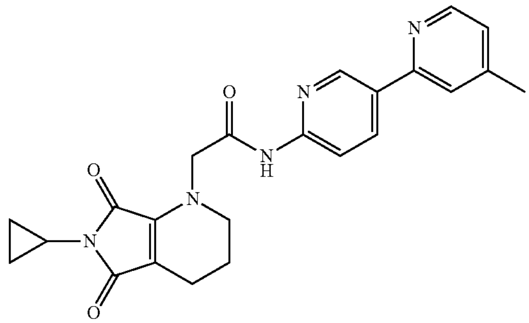 [SMILES: Cc1ccnc(-c2ccc(NC(=O)CN3CCCC4=C3C(=O)N(C3CC3)C4=O)nc2)c1] | 2-(6-cyclopropyl-5,7-dioxo-2,3,4,5,6,7-hexahydro-1H-pyrrolo[3,4-b]pyridin-1-yl)-N-(4-methyl-[2,3'-bipyridin]-6'-yl)acetamide | <0.1 |
| 151 | 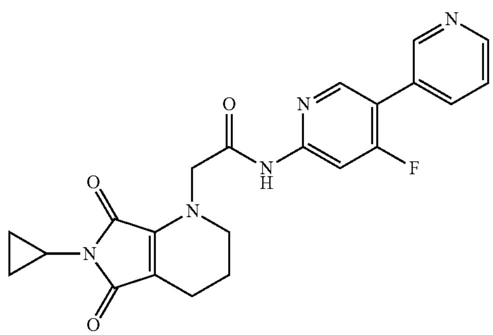 | 2-(6-cyclopropyl-5,7-dioxo-2,3,4,5,6,7-hexahydro-1H-pyrrolo[3,4-b]pyridin-1-yl)-N-(4-fluoro-3,3'-bipyridin-6-yl)acetamide | <0.1 |
| 152 | 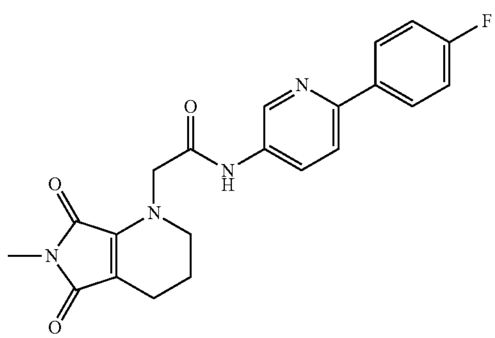 [SMILES: CN1C(=O)C2=C(C1=O)N(CC(=O)Nc1ccc(-c3ccc(F)cc3)nc1)CCC2] | N-(6-(4-fluorophenyl)pyridin-3-yl)-2-(6-methyl-5,7-dioxo-2,3,4,5,6,7-hexahydro-1H-pyrrolo[3,4-b]pyridin-1-yl)acetamide | <0.1 |
| 153 | 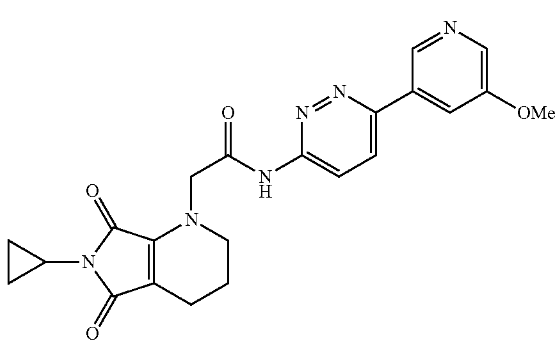 [SMILES: COc1cncc(-c2ccc(NC(=O)CN3CCCC4=C3C(=O)N(C3CC3)C4=O)nn2)c1] | 2-(6-cyclopropyl-5,7-dioxo-2,3,4,5,6,7-hexahydro-1H-pyrrolo[3,4-b]pyridin-1-yl)-N-(6-(5-methoxypyridin-3-yl)pyridazin-3-yl)acetamide | <0.1 |

-continued

| Cpd ID | Structure | IUPAC Name | STF3a IC$_{50}$ μM |
|---|---|---|---|
| 154 | 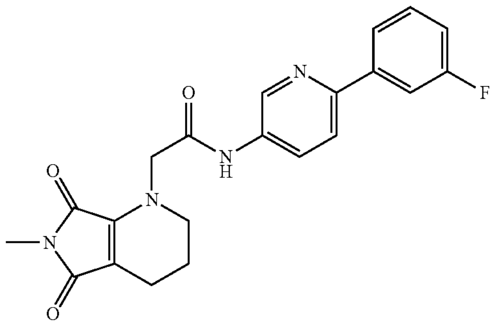 [SMILES: CN1C(=O)C2=C(C1=O)N(CC(=O)Nc1ccc(-c3cccc(F)c3)nc1)CCC2] | N-(6-(3-fluorophenyl)pyridin-3-yl)-2-(6-methyl-5,7-dioxo-2,3,4,5,6,7-hexahydro-1H-pyrrolo[3,4-b]pyridin-1-yl)acetamide | <0.1 |
| 155 | 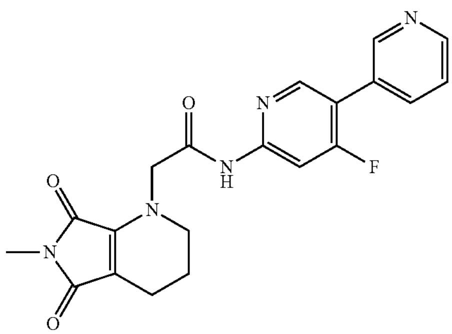 [SMILES: CN1C(=O)C2=C(C1=O)N(CC(=O)Nc1cc(F)c(-c3cccnc3)cn1)CCC2] | N-(4-fluoro-3,3'-bipyridin-6-yl)-2-(6-methyl-5,7-dioxo-2,3,4,5,6,7-hexahydro-1H-pyrrolo[3,4-b]pyridin-1-yl)acetamide | <0.1 |
| 156 | 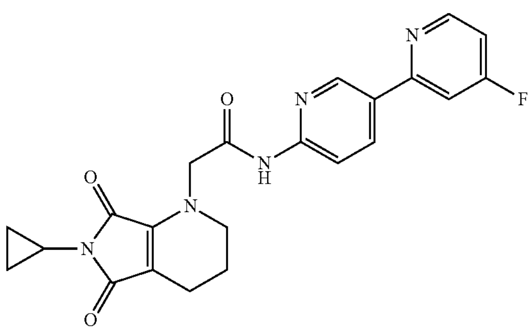 [SMILES: O=C(CN1CCCC2=C1C(=O)N(C1CC1)C2=O)Nc1ccc(-c2cc(F)ccn2)cn1] | 2-(6-cyclopropyl-5,7-dioxo-2,3,4,5,6,7-hexahydro-1H-pyrrolo[3,4-b]pyridin-1-yl)-N-(4-fluoro-[2,3'-bipyridin]-6'-yl)acetamide | <0.1 |
| 157 | 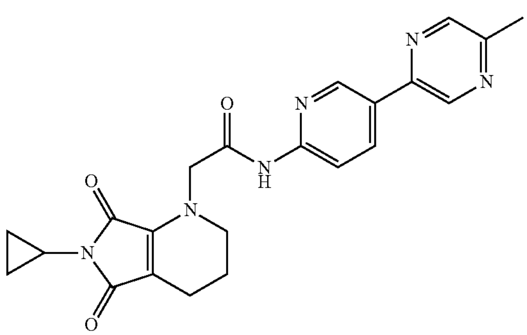 [SMILES: Cc1cnc(-c2ccc(NC(=O)CN3CCCC4=C3C(=O)N(C3CC3)C4=O)nc2)cn1] | 2-(6-cyclopropyl-5,7-dioxo-2,3,4,5,6,7-hexahydro-1H-pyrrolo[3,4-b]pyridin-1-yl)-N-(5-(5-methylpyrazin-2-yl)pyridin-2-yl)acetamide | <0.1 |

| Cpd ID | Structure | IUPAC Name | STF3a IC$_{50}$ μM |
|---|---|---|---|
| 158 | 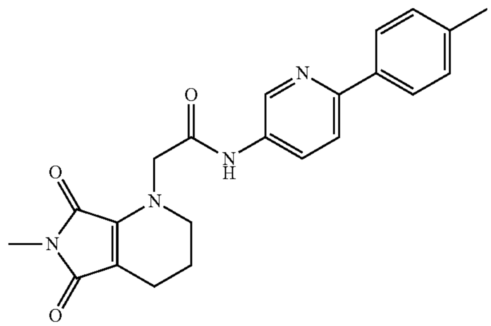 | 2-(6-methyl-5,7-dioxo-2,3,4,5,6,7-hexahydro-1H-pyrrolo[3,4-b]pyridin-1-yl)-N-(6-(p-tolyl)pyridin-3-yl)acetamide | <0.1 |

In one embodiment, compounds selected from Examples 1 to 158 having an IC$_{50}$ against STF3A cells of 10 micromolar or more are excluded.

Synthesis of the Examples

The compounds of formula (I) were synthesized according to the general synthesis scheme 1:

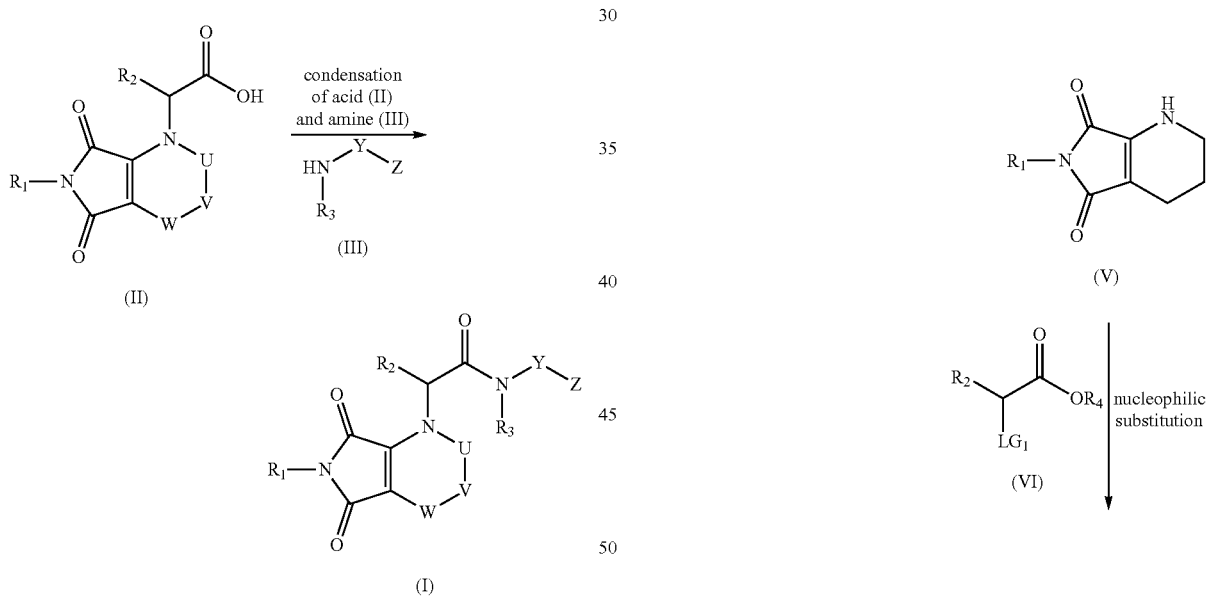

When U, V and W are each —CH$_2$—, compounds of formula (II) can be synthesised according to synthesis scheme 2:

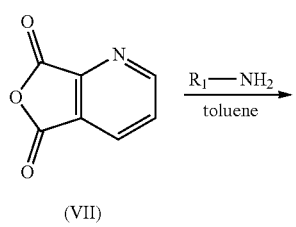

(VII)

When U and V together represent —CH=CH— and W represents C=O, compounds of formula (II) can be synthesised according to synthesis scheme 3:

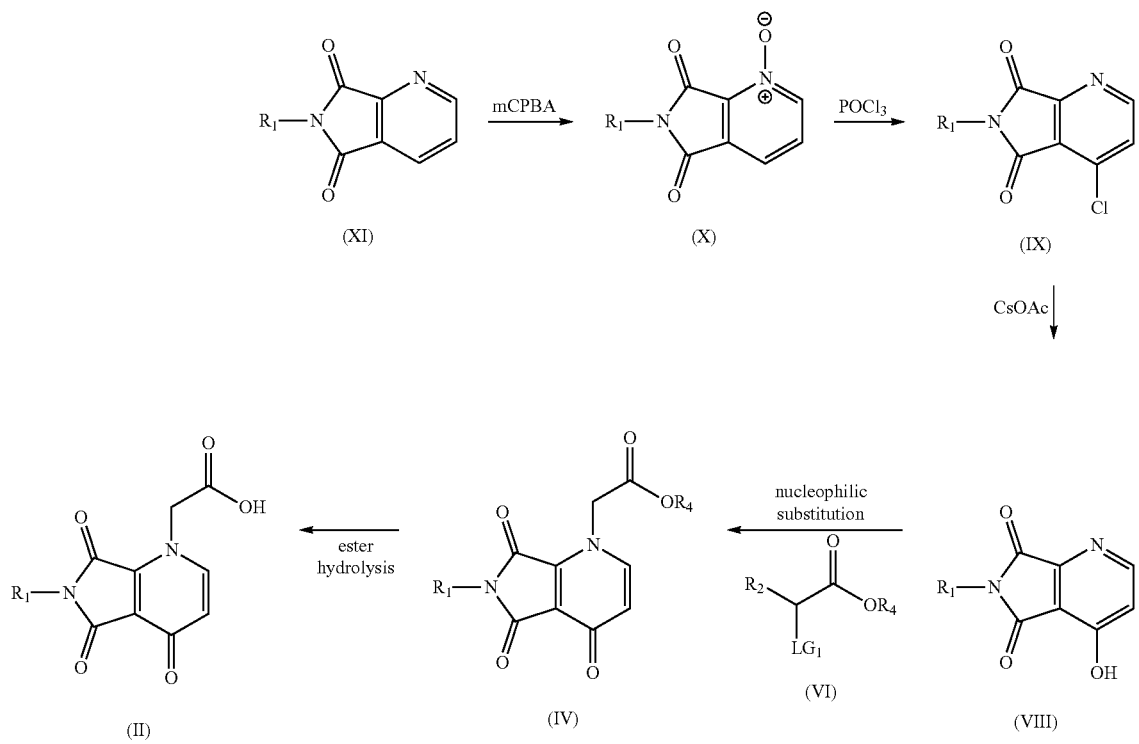

(XI)        (X)        (IX)

(II)        (IV)        (VI)        (VIII)

Compounds of formula (III) can be synthesized according to synthesis scheme 4:

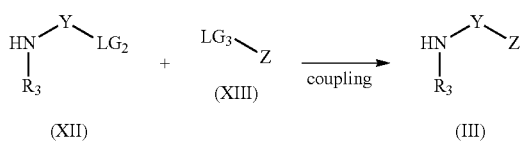

(XII)     (XIII)     (III)

Synthesis of Acids

Synthesis of acid-intermediate, 2-(6-methyl-5,7-dioxo-2,3,4,5,6,7-hexahydro-1H-pyrrolo[3,4-b]pyridin-1-yl)acetic acid Step 1: Preparation of 6-methyl-5H-pyrrolo[3,4-b]pyridine-5,7(6H)-dione

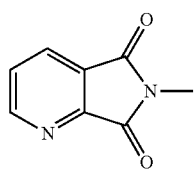

To a solution of furo[3,4-b]pyridine-5,7-dione, (5 g, 33.55 mmol) in toluene (100 mL) was added methyl amine (33.5 mL, 67.11, 2M solution in THF) and fitted with dean stark setup and heated at 130° C. for 16 h. After completion, the reaction mixture was cooled to room temperature and toluene was decanted and solid was washed with toluene, the combined toluene layers were concentrated, purified by column chromatography to afford 2.5 g (46%) of desired compound as a white solid.

$^1$H NMR (400 MHz, CDCl3) δ (ppm): 8.98-8.96 (m, 1H); 8.19-8.17 (m, 1H), 7.65-7.62 (m, 1H), 3.26 (s, 3H).

LC-MS: m/z 163 [M+H$^+$] with a purity of 99.35%.

Step 2: Preparation of 6-methyl-3,4-dihydro-1H-pyrrolo[3,4-b]pyridine-5,7(2H,6H)-dione

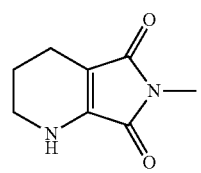

To a solution of Compound 6-methyl-5H-pyrrolo[3,4-b]pyridine-5,7(6H)-dione, (3 g, 18.51 mmol) in THF (60 mL) was added 300 mg of 10% Pd/C and reaction was stirred at room temperature under hydrogen balloon for 16 h. After completion, the reaction mixture was filtered through celite bed and filtrate was concentrated under vacuum. The crude compound was purified by column chromatography to afford 900 mg (29%) of desired compound as a yellow solid.

$^1$H NMR (400 MHz, DMSO-d$_6$) δ (ppm): 7.69 (brs, 1H), 3.22 (t, J=6 Hz, 2H), 2.77 (s, 3H), 2.17 (t, J=6.4 Hz, 2H), 1.73-1.67 (m, 2H).

LC-MS: m/z 167 [M+H$^+$] with a purity of 86.4%.

Step 3: Preparation of ethyl 2-(6-methyl-5,7-dioxo-2,3,4,5,6,7-hexahydro-1H-pyrrolo[3,4-b]pyridin-1-yl)acetate

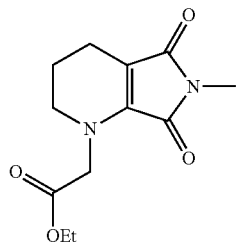 [SMILES: CCOC(=O)CN1CCCC2=C1C(=O)N(C)C2=O]

To a solution of Compound 6-methyl-3,4-dihydro-1H-pyrrolo[3,4-b]pyridine-5,7(2H,6H)-dione, (500 mg, 3.012 mmol) in acetonitrile (25 mL) was added K$_2$CO$_3$ (623 mg, 4.518 mmol) and methyl bromoacetate (817 mg, 4.89 mmol) and resulting reaction mixture was heated at 70° C. for 16 h. After completion the reaction mixture was concentrated, water (30 mL) was added and extracted with EtOAc (2×30 mL). The combined EtOAc layers were washed with brine solution (30 mL) and dried over Na$_2$SO$_4$ and concentrated under vacuum. The crude compound was purified by column chromatography to afford 280 mg (35%) of desired compound as a yellow solid.

$^1$H NMR (400 MHz, CDCl$_3$) δ (ppm): 5.83 (q, J=7.6 Hz, 1H), 4.18 (t, J 7.6 Hz, 2H), 3.25-3.24 (m, 2H), 2.92 (s, 3H), 2.35-2.29 (m, 2H), 1.90-1.85 (m, 2H), 1.27 (t, J=7.2 Hz, 3H).

LC-MS: m/z 267.10 [M+H$^+$] with a purity of 93.53%.

Step 4: Preparation of 2-(6-methyl-5,7-dioxo-2,3,4,5,6,7-hexahydro-1H-pyrrolo[3,4-b]pyridin-1-yl)acetic acid

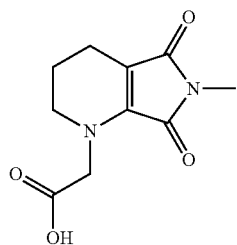 [SMILES: CN1C(=O)C2=C(C1=O)N(CC(=O)O)CCC2]

A solution of ethyl 2-(6-methyl-5,7-dioxo-2,3,4,5,6,7-hexahydro-1H-pyrrolo[3,4-b]pyridin-1-yl)acetate in 2:1 THF and water (0.1 M) was treated with LiOH.H$_2$O and 3-5 drops of methanol. The reaction was stirred at room temperature under ambient atmosphere for 16 hours. After completion of starting material, the reaction mixture was acidified with 1N HCl (pH 1) and purified by reversed phase chromatography to afford 280 mg (35%) of the purified acid.

$^1$H NMR (400 MHz, DMSO-d$_6$) δ (ppm): 4.38 (s, 2H), 3.39 (t, J=6.0 Hz, 2H), 2.77 (s, 3H), 2.18 (t, J=6.0 Hz, 2H), 1.80 (q, J=6.0 Hz, 2H).

Synthesis of acid-intermediate, 2-(6-methyl-5,7-dioxo-2,3,4,5,6,7-hexahydro-1H-pyrrolo[3,4-b]pyridin-1-yl)propanoic acid

Step 1: Preparation of ethyl 2-(6-methyl-5,7-dioxo-2,3,4,5,6,7-hexahydro-1H-pyrrolo[3,4-b]pyridin-1-yl)propanoate

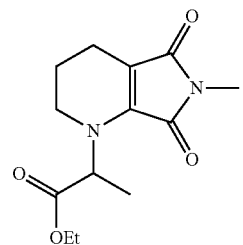 [SMILES: CCOC(=O)C(C)N1CCCC2=C1C(=O)N(C)C2=O]

To a solution of compound 6-methyl-3,4-dihydro-1H-pyrrolo[3,4-b]pyridine-5,7(2H,6H)-dione, (500 mg, 3.012 mmol) in acetonitrile (25 mL) was added K$_2$CO$_3$ (623 mg, 4.518 mmol) and ethyl bromoacetate (817 mg, 4.518 mmol) and resulting reaction mixture was heated at 70° C. for 16 h. After completion the reaction mixture was concentrated, water (30 mL) was added and extracted with EtOAc (2×30 mL). The combined EtOAc layers were washed with brine solution (30 mL) and dried over Na$_2$SO$_4$ and concentrated under vacuum. The crude compound was purified by column chromatography to afford 280 mg (35%) of desired compound as a yellow solid.

$^1$H NMR (400 MHz, CDCl$_3$) δ (ppm): 5.83 (q, J=7.6 Hz, 1H), 4.18 (t, J=7.6 Hz, 2H), 3.25-3.24 (m, 2H), 2.92 (s, 3H), 2.35-2.29 (m, 2H), 1.90-1.85 (m, 2H), 1.47 (d, J=6.8 Hz, 3H), 1.27 (t, J=7.2 Hz, 3H).

LC-MS: m/z 267.10 [M+H$^+$] with a purity of 93.53%.

Step 2: Preparation of 2-(6-methyl-5,7-dioxo-2,3,4,5,6,7-hexahydro-1H-pyrrolo[3,4-b]pyridin-1-yl)propanoic acid

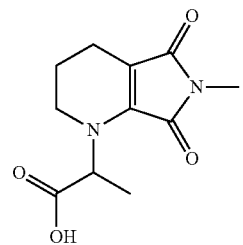 [SMILES: CC(C(=O)O)N1CCCC2=C1C(=O)N(C)C2=O]

To a stirred solution of ethyl 2-(6-methyl-5,7-dioxo-2,3,4,5,6,7-hexahydro-1H-pyrrolo[3,4-b]pyridin-1-yl)propanoate (280 mg, 1.052 mmol) in THF (20 mL), MeOH (10 mL) and water (5 mL) was added LiOH.H$_2$O (66 mg, 1.578 mmol) and stirred at r.t for 2 h. After completion of S.M, the reaction mixture was concentrated, the residue was dissolved in water (30 mL), washed with EtOAc (30 ml), acidified with aq.KHSO$_4$ and the aqueous layer was concentrated under vacuum and product was recovered by THF washings of residue. The THF was concentrated and gave 150 mg of desired compound (60%) as yellow solid.

¹H NMR (400 MHz, DMSO-d₆): δ 5.57 (q, J=7.2 Hz, 1H), 3.32-3.26 (m, 1H), 3.25-3.16 (m, 1H), 2.81 (s, 3H), 2.23-2.12 (m, 2H), 1.80-1.74 (m, 2H), 1.38 (d, J=7.6 Hz, 3H).

LC-MS: m/z 239.0 [M+H⁺] with a purity of 92.34%.

Synthesis of acid-intermediate, 2-(6-cyclopropyl-5, 7-dioxo-2,3,4,5,6,7-hexahydro-1H-pyrrolo[3,4-b]pyridin-1-yl)acetic acid Step 1: Preparation of 6-cyclopropyl-5H-pyrrolo[3, 4-b]pyridine-5,7(6H)-dione

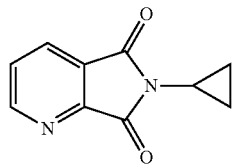 [SMILES: O=C1c2cccnc2C(=O)N1C1CC1]

To compound furo[3,4-b]pyridine-5,7-dione (5 g, 33.55 mmol) in toluene (100 mL) was added cyclopropyl amine (3.82 g, 67.11) and fitted with dean stark setup and heated at 130° C. for 16 h. After completion, the reaction mixture was cooled to r.t and toluene was decanted and solid was washed with toluene, the combined toluene layers were concentrated, purified by column chromatography to afford 1.7 g (27%) of desired compound as a white solid.

¹H NMR (400 MHz, CDCl3) δ (ppm): 8.97 (dd, J₁=1.2 Hz, J₂=3.6 Hz, 1H), 8.15 (dd, J₁=1.2 Hz, J₂=6.4 Hz, 1H), 7.63-7.60 (m, 1H), 2.80-2.75 (m, 1H), 1.12-1.01 (m, 4H).

LC-MS: m/z 189.10 [M+H⁺] with a purity of 97.22%.

Step 2: Preparation of 6-cyclopropyl-3,4-dihydro-1H-pyrrolo[3,4-b]pyridine-5,7(2H,6H)-dione

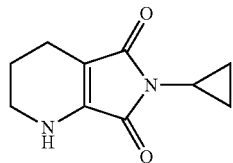 [SMILES: O=C1C2=C(NCCC2)C(=O)N1C1CC1]

To a solution of compound 6-cyclopropyl-5H-pyrrolo[3,4-b]pyridine-5,7(6H)-dione (1.6 g, 8.510 mmol) in THF (40 mL) was added 200 mg of 10% Pd/C and reaction was stirred room temperature for 16 h under hydrogen balloon. After completion, the reaction mixture was filtered through celite bed and filtrate was concentrated under vacuum. The crude compound was purified by column chromatography to afford 400 mg (24.5%) of desired compound as a yellow solid.

¹H NMR (400 MHz, CDCl3) δ (ppm): 4.94 (brs, 1H), 3.38-3.35 (m, 2H), 2.45-2.42 (m, 1H), 2.31 (t, J=6.0 Hz, 2H), 1.89-1.83 (m, 2H), 0.91-0.80 (m, 4H).

LC-MS: m/z 193.3 [M+H⁺] with a purity of 98.14%.

Step 3: Preparation of ethyl 2-(6-cyclopropyl-5,7-dioxo-2,3,4,5,6,7-hexahydro-1H-pyrrolo[3,4-b]pyridin-1-yl)acetate

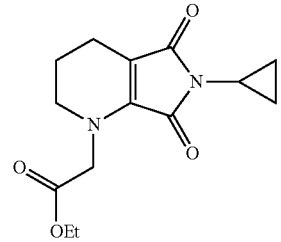

To a solution of Compound 6-cyclopropyl-3,4-dihydro-1H-pyrrolo[3,4-b]pyridine-5,7(2H,6H)-dione, (400 mg, 2.083 mmol) in acetonitrile (40 mL) was added K₂CO₃ (431 mg, 3.124 mmol) and ethyl bromoacetate (522 mg, 3.124 mmol) and resulting reaction mixture was heated at 70° C. for 16 h. After completion the reaction mixture concentrated, water (30 mL) was added and extracted with EtOAc (2×30 mL). The combined EtOAc layers were washed with brine solution (30 mL) and dried over Na₂SO₄ and concentrated under vacuum. The crude compound was purified by column chromatography to afford 400 mg (69%) of desired compound as a yellow solid.

¹H NMR (400 MHz, CDCl3) δ (ppm): 4.45 (s, 2H), 4.27-4.19 (m, 2H), 3.27 (t, J=5.6 Hz, 2H), 2.42-2.39 (m, 1H), 2.30 (t, J=6 Hz, 2H), 1.95-1.89 (m, 2H), 1.31-1.26 (m, 3H) 0.89-0.78 (m, 4H).

LC-MS: m/z 279.1 [M+H⁺] with a purity of 95.44%.

Step 4: Preparation of 2-(6-cyclopropyl-5,7-dioxo-2,3,4,5,6,7-hexahydro-1H-pyrrolo[3,4-b]pyridin-1-yl)acetic acid

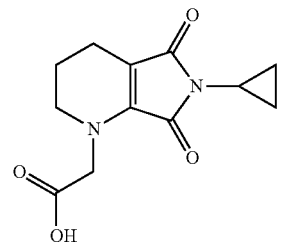 [SMILES: O=C(O)CN1CCCC2=C1C(=O)N(C1CC1)C2=O]

To a stirred solution of 2-(6-cyclopropyl-5,7-dioxo-2,3,4,5,6,7-hexahydro-1H-pyrrolo[3,4-b]pyridin-1-yl)acetate (400 mg, 1.438 mmol) in THF (20 mL), MeOH (20 mL) and water (10 mL) was added LiOH.H₂O (91 mg, 2.158 mmol) and stirred at r.t for 2 h. After completion of S.M, the reaction mixture was concentrated, the residue was dissolved in water (30 mL), washed with EtOAc (30 ml), acidified with aq.KHSO₄ and the product was extracted with EtOAc (2×50 mL). The combined organic layers were dried (Na₂SO₄), concentrated gave 210 mg of desired compound (58%) as yellow solid.

¹H NMR (400 MHz, DMSO-d₆) δ (ppm): 12.60 (brs, 1H), 4.36 (s, 2H), 3.26 (t, J=5.2 Hz, 2H), 2.39-2.35 (m, 1H), 2.15 (t, J=6 Hz, 2H), 1.82-1.76 (m, 2H), 0.78-0.73 (m, 2H), 0.68-0.64 (m, 2H).

LC-MS: m/z 251.00 [M+H⁺] with a purity of 99.14%.

Synthesis of acid-intermediate, 2-(6-cyclobutyl-5,7-dioxo-2,3,4,5,6,7-hexahydro-1H-pyrrolo[3,4-b]pyridin-1-yl)acetic acid

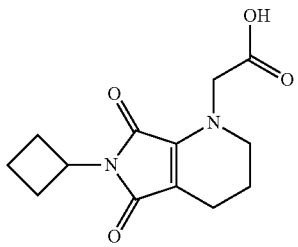 [SMILES: O=C(O)CN1CCCC2=C1C(=O)N(C1CCC1)C2=O]

$^1$H NMR (400 MHz, DMSO-d$_6$) δ 4.31-4.40 (m, 3H), 3.16 (s, 2H), 2.56-2.66 (m, 2H), 2.14-2.18 (m, 2H), 2.02-2.09 (m, 2H), 1.76-1.82 (m, 2H), 1.60-1.71 (m, 2H).
LC-MS: m/z 265 (M+H).

Synthesis of acid-intermediate, 2-(6-methyl-4,5,7-trioxo-4,5,6,7-tetrahydro-1H-pyrrolo[3,4-b]pyridin-1-yl)acetic acid Step 1: 6-methyl-5,7-dioxo-6,7-dihydro-5H-pyrrolo[3,4-b]pyridine 1-oxide

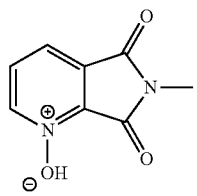

To a solution of Compound 6-methyl-5H-pyrrolo[3,4-b]pyridine-5,7(6H)-dione (300 mg, 1.85 mmol) in DCM (30 mL) was added MCPBA (638 mg, 3.70 mmol) at 0° C. and reaction was stirred at r.t for 16 h. after completion, the reaction mixture was concentrated under vacuum. The residue was purified by column chromatography to afford 200 mg (61%) of the desired compound as a light brown solid.
$^1$H NMR (400 MHz, DMSO-d$_6$): 8.47-8.45 (t, J=3.6 Hz, 1H), 7.71-7.70 (d, J=3.2 Hz, 2H), 3.00 (s, 3H).
LC-MS: m/z 178.97 (M+H$^+$) with a purity of 99.64%.

Step 2: 4-chloro-6-methyl-5H-pyrrolo[3,4-b]pyridine-5,7(6H)-dione

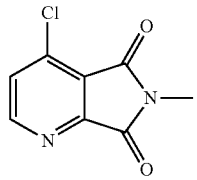

Compound 6-methyl-5,7-dioxo-6,7-dihydro-5H-pyrrolo[3,4-b]pyridine 1-oxide (100 mg, 0.56 m mol) in POCl$_3$ (1 mL) was heated at 100° C. for 3 h. After completion of S.M, the reaction mixture was concentrated; the residue was quenched with aq. NaHCO$_3$ solution and extracted with EtOAc (2×20 mL). The combined EtOAc layers were washed with brine solution (20 mL) and dried over Na$_2$SO$_4$ and concentrated under vacuum. The crude compound was purified by column chromatography to afford 40 mg (36%) of the desired compound as a pale pink solid.
$^1$H NMR (400 MHz, CDCl3): 8.11-8.09 (d, J=8 Hz, 1H), 7.64-7.62 (d, J 8 Hz, 1H), 3.25 (s, 3H).
LC-MS: m/z 197.05 (M+H$^+$), 199.06 (M+3H) with a purity of 95.21%.

Step 3: 4-hydroxy-6-methyl-5H-pyrrolo[3,4-b]pyridine-5,7(6H)-dione

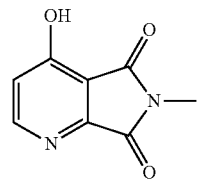

To a stirred solution of 4-chloro-6-methyl-5H-pyrrolo[3,4-b]pyridine-5,7(6H)-dione (50 mg, 0.253 mmol) in DMF (2 mL) was added CsOAc (122 mg, 0.634 mmol) was heated at 80° C. for 6 h. After completion of S.M, the reaction mixture was added aq. NH$_4$Cl solution compound was extracted with EtOAc (2×20 mL). The combined EtOAc layers were washed with brine solution (10 mL) and dried over Na$_2$SO$_4$ and concentrated under vacuum. The crude compound was purified by column chromatography to afford 25 mg (55%) of the desired compound as an off white solid.
$^1$H NMR (400 MHz, DMSO): 12.76 (brs, 1H), 7.96-7.94 (m, 1H), 6.79 (m, 1H), 2.98 (s, 3H).
LC-MS: m/z 179.09 (M+H$^+$) with a purity of 98.45%.

Step 4: ethyl 2-(6-methyl-4,5,7-trioxo-4,5,6,7-tetrahydro-1H-pyrrolo[3,4-b]pyridin-1-yl)acetate

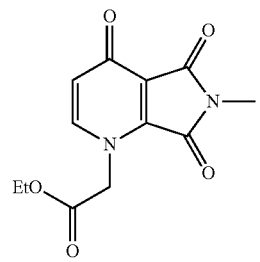 [SMILES: CCOC(=O)Cn1ccc(=O)c2c1C(=O)N(C)C2=O]

A stirred solution of 4-hydroxy-6-methyl-5H-pyrrolo[3,4-b]pyridine-5,7(6H)-dione (150 mg, 0.842 mmol) in DMF (3 mL) was treated with K$_2$CO$_3$ (140 mg, 1.011 mmol) followed by ethyl bromo acetate (163 mg, 1.011 mmol) at r.t and resulting reaction mixture was heated at 60° C. for 2 h. After completion of S.M, water (20 mL) was added to the reaction mixture and extracted with EtOAc (2×20 mL). The combined EtOAc layers were washed with brine solution (10 mL), dried over Na$_2$SO$_4$ and concentrated under vacuum. The crude compound was purified by column chromatography to afford 60 mg (27%) of the desired compound as a white solid.

¹H NMR (400 MHz, CDCl3): 7.69-7.67 (d, J=9.2 Hz, 1H), 6.80-6.77 (d, J=9.2 Hz, 1H), 5.23 (s, 2H), 4.29-4.23 (q, J=7.2 Hz, 2H), 1.31-1.28 (t, J=7.2 Hz, 3H).

LC-MS: m/z 265.14 (M+H⁺) with a purity of 94.10%.

Step 5: 2-(6-methyl-4,5,7-trioxo-4,5,6,7-tetrahydro-1H-pyrrolo[3,4-b]pyridin-1-yl)acetic acid

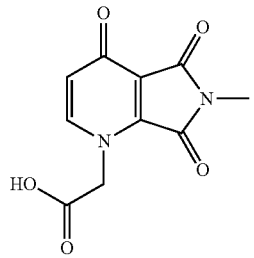 [SMILES: CN1C(=O)c2c(n(CC(=O)O)ccc2=O)C1=O]

Compound ethyl 2-(6-methyl-4,5,7-trioxo-4,5,6,7-tetrahydro-1H-pyrrolo[3,4-b]pyridin-1-yl)acetate in aq. 4N HCl was heated at 50° C. for 6 h. After completion of S.M, The reaction mixture was concentrated and dried under vacuum to give 40 mg of the desired compound as an off white solid.

¹H NMR (400 MHz, DMSO-d₆): 13.0 (brs, 1H), 8.20-8.18 (d, J=7.6 Hz, 1H), 7.25-7.23 (d, J=7.2 Hz, 1H), 5.00 (s, 2H), 2.02 (s, 3H).

LC-MS: m/z 237.13 (M+H⁺) with a purity of 93.29%.

Synthesis of Amines

General Procedure for Suzuki Reactions
Method A:

A stirred solution of the arylhalide (1 equiv.), boronic acid (1.5 equiv.) and 2 M potassium carbonate (2.5 equiv.) in 4:1 1,4-Dioxane and water was degassed for 15 min with argon. Tetrakis(triphenylphosphine)palladium(0) (0.05 equiv.) was added to reaction mixture and the reaction mixture was heated to reflux for 3-18 h. After completion of starting material, the reaction mixture was concentrated and water was added to reaction mixture and extracted with ethyl acetate. The combined organic layers were washed with brine, dried with Na₂SO₄ and concentrated under vacuum. The crude compound was purified by column chromatography to afford the purified product.

Preparation of [2,3'-bipyridin]-6'-amine

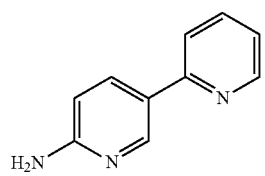 [SMILES: Nc1ccc(-c2ccccn2)cn1]

¹H NMR (400 MHz, METHANOL-d₄) δ (ppm): 8.55-8.56 (m, 1H), 8.50-8.51 (m, 1H), 8.14-8.16 (m, 1H), 7.83-7.87 (m, 1H), 7.75-7.77 (m, 1H), 7.28-7.32 (m, 1H), 6.75-6.77 (m, 1H).

LC-MS: m/z 172.0 [M+H⁺].

Preparation of 6-(p-tolyl)pyridazin-3-amine

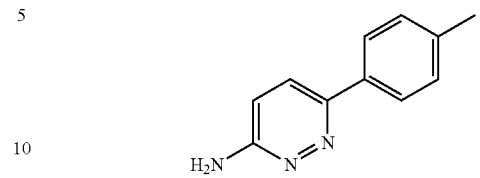

¹H NMR (400 MHz, Chloroform-d) δ (ppm): 7.84 (d, J=8.0 Hz, 2H), 7.61 (d, J=9.2 Hz, 1H), 7.27 (d, J=8.0 Hz, 2H), 6.81 (d, J=9.2 Hz, 1H), 4.73 (brs, 2H), 2.40 (s, 3H).

Preparation of 6-(4-fluorophenyl) pyridazin-3-amine

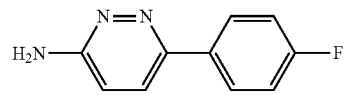 [SMILES: Nc1ccc(-c2ccc(F)cc2)nn1]

¹H-NMR (400 MHz; DMSO-d₆) δ (ppm): 8.02-7.98 (m, 2H), 7.82 (d, J=9.2 Hz, 1H), 7.29 (t, J=9.2 Hz, 2H), 6.84 (d, J=9.6 Hz, 1H), 6.5 (s, 2H).

LC-MS: m/z 190 [M+H⁺].

Preparation of 5-phenylpyridin-2-amine

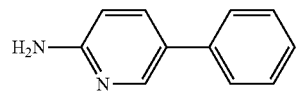

¹H NMR (400 MHz, DMSO-d₆) δ (ppm): 8.23 (s, 1H), 7.69 (d, J=8.0 Hz, 1H), 7.55 (d, J=8.0 Hz, 2H), 7.39 (t, J=8.0 Hz, 2H), 7.26 (t, J=8.0 Hz, 1H), 6.52 (d, J=8.0 Hz, 2H), 6.0 (brs, 2H).

LC-MS: m/z 171.12 [M+H⁺].

Preparation of 5-(thiazol-2-yl)pyridin-2-amine

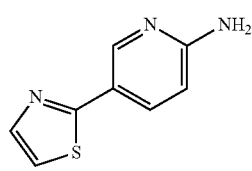 [SMILES: Nc1ccc(-c2nccs2)cn1]

¹H NMR (400 MHz, Methanol-d₄) δ (ppm): 8.48 (s, 1H), 7.95-7.98 (m, 1H), 7.77 (d, J=3.6 Hz, 1H), 7.48 (d, J=3.6 Hz, 1H), 6.64-6.66 (m, 1H).

LC-MS: m/z 178 [M+H⁺].

Preparation of 5-(4-fluorophenyl)pyridin-2-amine

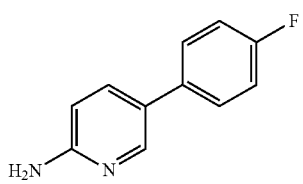 [SMILES: Nc1ccc(-c2ccc(F)cc2)cn1]

¹H NMR (400 MHz, Methanol-d₄) δ (ppm): 8.20 (s, 1H), 8.09-8.10 (m, 1H), 7.87-7.90 (m, 1H), 7.54-7.57 (m, 2H), 7.14-7.18 (m, 2H), 6.80-6.82 (m, 1H).

Preparation of 6-(o-tolyl)pyridazin-3-amine

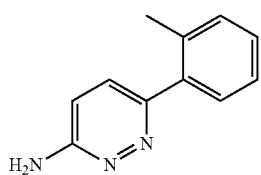

¹H NMR (400 MHz, Methanol-d₄) δ (ppm): 8.19 (s, 1H), 7.53 (d, J=9.2 Hz, 1H), 7.27-7.36 (m, 4H), 7.13 (d, J=9.2 Hz, 1H), 2.31 (s, 3H).

Preparation of 6-(2-methoxyphenyl)pyridazin-3-amine

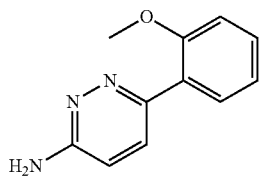

¹H NMR (400 MHz, DMSO-d₆) δ (ppm): 8.14 (s, 1H), 7.62-7.58 (m, 2H), 7.40-7.35 (m, 1H), 7.11 (d, J=8.0 Hz, 1H), 7.04 (t, J=7.6 Hz, 1H), 6.77 (d, J=9.2 Hz, 1H) 6.35 (s, 2H), 3.79 (s, 3H).

Preparation of 6-(4-methoxyphenyl)pyridazin-3-amine

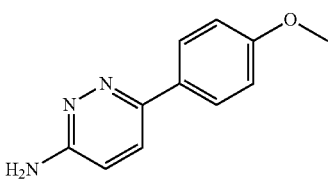

¹H NMR (400 MHz, CDCl₃) δ (ppm): 8.17 (s, 1H), 7.87 (d, J=8.0 Hz, 2H), 7.67 (d, J=9.6 Hz, 1H), 6.99 (d, J=8.8 Hz, 2H), 6.90 (d, J=9.2 Hz, 1H), 5.85 (br s, 1H), 3.86 (s, 3H)
LC-MS: m/z 202 [M+H⁺].

Preparation of 6-(3-methoxyphenyl)pyridazin-3-amine

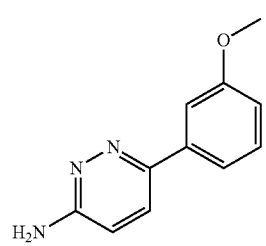

¹H NMR (400 MHz, DMSO-d₆) δ (ppm): 8.14 (s, 1H), 7.80 (d, J=9.2 Hz, 1H), 7.52-7.50 (m, 2H), 7.37 (t, J=8.0 Hz, 1H), 6.97-6.94 (m, 1H), 6.84 (d, J=9.6 Hz, 1H), 6.46 (s, 2H) 3.79 (s, 3H).
LC-MS: m/z 202 [M+H⁺].

Preparation of 5-(6-methylpyridin-3-yl)pyrazin-2-amine

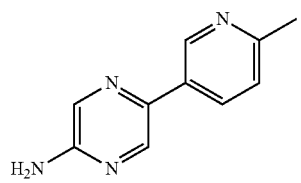

¹H NMR (400 MHz, DMSO-d₆) δ (ppm): 8.96 (d, J=2.0 Hz, 1H), 8.52 (d, J=1.6 Hz, 1H), 7.96 (d, J=1.6 Hz, 1H), 7.28 (d, J=8.0 Hz, 1H), 6.61 (s, 2H), 2.48 (s, 3H).
LC-MS: m/z 187 [M+H⁺].

Preparation of 6-(5-methylpyridin-3-yl)pyridazin-3-amine

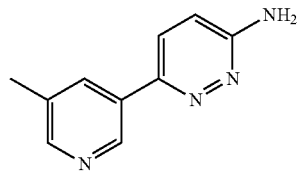

¹H NMR (400 MHz, DMSO-d₆) δ (ppm): 8.93 (d, J=2.0 Hz, 1H), 8.42 (d, J=1.6 Hz, 1H), 8.15-8.13 (m, 1H), 7.86 (d, J=9.2 Hz, 1H), 6.86 (d, J=9.2 Hz, 1H), 6.56 (s, 2H), 2.37 (s, 3H).

Preparation of 6-(3-fluorophenyl)pyridazin-3-amine

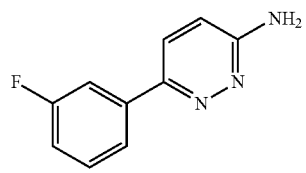 [SMILES: Nc1ccc(-c2cccc(F)c2)nn1]

$^1$H NMR (400 MHz, DMSO-d$_6$) δ (ppm): 7.86-7.76 (m, 3H), 7.53-7.47 (m, 1H), 7.23-7.18 (m, 1H), 6.85 (d, J=9.6 Hz, 1H), 6.55 (s, 2H).
LC-MS: m/z 190 [M+H$^+$].

Preparation of 3,5'-dimethyl-[2,3'-bipyridin]-5-amine

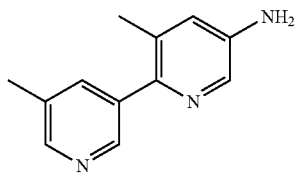

$^1$H NMR (400 MHz, DMSO-d$_6$) δ (ppm): 8.45 (d, J=2.0 Hz, 1H), 8.33 (d, J=1.2 Hz, 1H), 7.87 (d, J=2.8 Hz, 1H), 7.67 (d, J=0.4 Hz, 1H), 6.83 (d, J=2.0 Hz, 1H), 6.38 (s, 2H), 2.33 (s, 3H), 2.22 (s, 3H).
LC-MS: m/z 200 [M+H$^+$].

Preparation of 5-(pyrimidin-5-yl) pyridin-2-amine

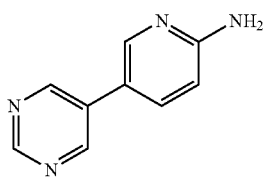 [SMILES: Nc1ccc(-c2cncnc2)cn1]

$^1$H NMR (400 MHz, CDCl$_3$) δ (ppm): 9.16 (s, 1H), 8.88 (s, 2H), 8.32 (d, J=2.0 Hz, 1H), 7.67-7.64 (m, 1H), 6.63 (d, J=8.4 Hz, 1H), 4.65 (s, 2H).

Preparation of 6-(pyrimidin-5-yl)pyridin-3-amine

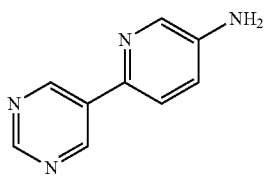 [SMILES: Nc1ccc(-c2cncnc2)nc1]

$^1$H NMR (400 MHz, CDCl$_3$) δ (ppm): 9.26 (s, 2H), 9.19 (s, 1H), 8.24 (d, J=2.8 Hz, 1H), 7.58 (d, J=8.4 Hz, 1H), 7.12-7.09 (m, 1H), 3.92 (s, 2H).

Preparation of 6-(m-tolyl)pyridazin-3-amine

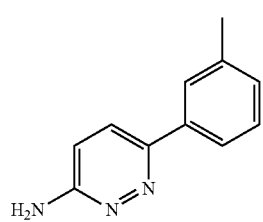

$^1$H NMR (400 MHz, Methanol-d$_4$) δ (ppm): 8.20 (s, 1H), 7.89-7.91 (m, 1H), 7.72 (s, 1H), 7.66-7.68 (m 1H), 7.35-7.38 (m, 1H), 7.26-7.28 (m, 1H), 7.14-7.16 (m, 1H), 2.42 (s, 3H).
LC-MS: m/z 186 [M+H$^+$].

Preparation of 6'-methyl-[3,3'-bipyridin]-6-amine

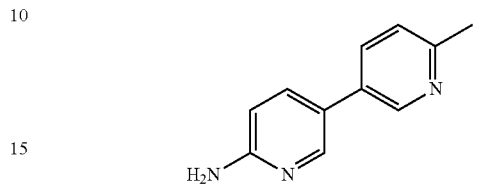

$^1$H NMR (400 MHz, DMSO-d$_6$) δ (ppm): 8.64 (s, 1H), 8.24 (s, 1H), 7.83-7.85 (m, 1H), 7.70-7.72 (m, 1H), 7.25-7.27 (m, 1H), 6.52-6.54 (m, 1H), 6.09 (bs, 2H), 2.33 (s, 3H).
LC-MS: m/z 186 [M+H$^+$].

Preparation of 6-(6-methylpyridin-3-yl)pyridazin-3-amine

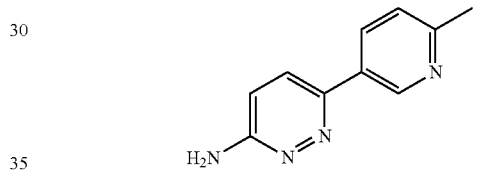

$^1$H NMR (400 MHz, DMSO-d$_6$) δ (ppm): 8.99-9.00 (m, 1H), 8.19-8.21 (m, 1H), 7.83-7.85 (m, 1H), 7.32-7.34 (m, 1H), 6.84-6.87 (m, 1H), 6.52 (brs, 2H), 2.32 (s, 3H).
LC-MS: m/z 187 [M+H$^+$].

Preparation of 4-(pyridazin-3-yl) aniline

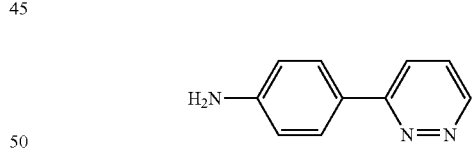

$^1$H NMR (400 MHz, CDCl$_3$) δ 9.00 (d, J=4.4 Hz, 1H), 8.00 (d, J=8.8 Hz, 1H), 7.87 (d, J=7.9 Hz, 2H), 7.62-7.60 (m, 1H), 6.67 (d, J=8.0 Hz, 2H), 5.61 (s, 2H).
Method B:

A stirred solution of the arylhalide (1 equiv.), boronic acid (1.11 equiv.) and sodium carbonate (3.33 equiv., pre-dissolved in 2 mL of water) in 3 mL of 1,4-dioxane and water was degassed for 15 min with nitrogen. Bis(triphenylphosphine)palladium(II) dichloride, Pd(dppf)Cl$_2$.DCM (0.06 equiv.) was added to reaction mixture and the reaction mixture was heated to reflux at 100° C. for 3-18 h. After completion of starting material, the reaction mixture was concentrated and water was added to reaction mixture and extracted with ethyl acetate. The combined organic layers were washed with brine, dried with Na$_2$SO$_4$ and concentrated under vacuum. The crude compound was purified by reversed phase chromatography to afford the purified amine.

Preparation of 6-phenylpyridazin-3-amine (3, Compound 3, 9, 13, 33, 38, 94 and 95 Amine)

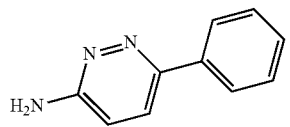 [SMILES: Nc1ccc(-c2ccccc2)nn1]

¹H NMR (400 MHz, DMSO-d₆) δ (ppm): 7.95 (d, J=8.4 Hz, 2H), 7.80 (d, J=10 Hz, 1H), 7.47 (m, 2H), 7.40-7.36 (m, 1H), 6.85 (d, J=9.2 Hz, 1H), 6.46 (br s, 2H).
LC-MS: m/z 172.08 [M+H⁺].

Preparation of 2,3'-bipyridin-5-amine

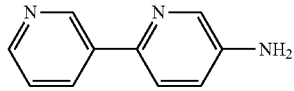 [SMILES: Nc1ccc(-c2cccnc2)nc1]

¹H NMR (400 MHz, DMSO-d₆) δ (ppm): 9.11 (s, 1H), 8.47 (d, J=4.8 Hz, 1H), 8.24 (d, J=8 Hz, 1H), 8.07 (s, 1H), 7.71 (d, J=8.8 Hz, 1H), 7.41-7.38 (m, 1H), 7.04-7.01 (m, 1H), 5.57 (brs, 2H).
LC-MS: m/z 172.15 [M+H⁺].

Preparation of 6'-methyl-[2,3'-bipyridin]-5-amine

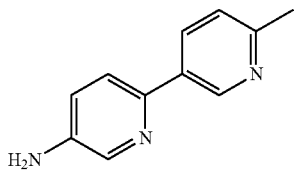

Step 1: Preparation of 6'-methyl-5-nitro-2,3'-bipyridine

¹H NMR (400 MHz, Methanol-d₄) δ (ppm): 9.46-9.47 (m, 1H), 9.19-9.20 (m, 1H), 8.65-8.68 (m, 1H), 8.47-8.50 (m, 1H), 8.18-8.21 (m, 1H), 7.47-7.49 (m, 1H), 2.62 (s, 3H).
LC-MS: m/z 216 [M+H⁺].

Step 2: Preparation of 6'-methyl-[2,3'-bipyridin]-5-amine

To a solution of 6'-methyl-5-nitro-2,3'-bipyridine in 2:1 ethanol and water (0.1M) was added iron powder (5 equiv.) and acetic acid (5 equiv.). The reaction was stirred vigorously at room temperature under ambient atmosphere for 1 hour. After completion of starting material, the reaction mixture was basified with 1N NaOH (pH 8-10) and extracted with ethyl acetate. The combined organic layers were washed with brine, dried with Na₂SO₄ and concentrated under vacuum. The crude compound was purified by reversed phase chromatography to afford the purified amine.

¹H NMR (400 MHz, Methanol-d₄) δ (ppm): 8.84 (s, 1H), 8.11-8.14 (m, 1H), 8.06-8.07 (m, 1H), 7.57-7.59 (m, 1H), 7.33-7.35 (m, 1H), 7.14-7.16 (m, 1H), 2.55 (s, 3H).

Preparation of ethyl 5-(2-methylthiazol-4-yl)pyridin-2-amine

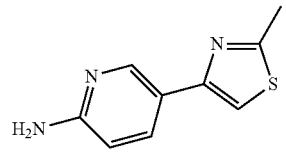

¹H NMR (400 MHz, DMSO-d₆) δ (ppm): 8.49 (d, J=1.6 Hz, 1H), 7.86 (dd, J₁=2 Hz, J₂=8.4 Hz, 1H), 7.60 (s, 1H), 6.48 (d, J=8.4 Hz, 1H), 6.08 (brs, 2H), 2.68 (s, 3H).
LC-MS: m/z 192.13 [M+H⁺].

Preparation of 6-(pyridin-3-yl)pyridazin-3-amine

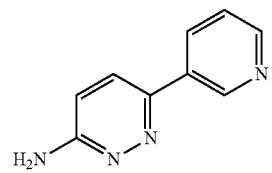 [SMILES: Nc1ccc(-c2cccnc2)nn1]

¹H NMR (400 MHz, DMSO-d₆) δ (ppm): 9.13 (d, J=1.6 Hz, 1H), 8.58 (dd, J=4.8 Hz, 1.6 Hz, 1H), 8.33-8.30 (m, 1H), 7.88 (d, J=9.2 Hz, 1H), 7.47 (dd, J=8.4 Hz, 8.0 Hz 1H), 6.87 (d, J=9.2 Hz, 1H), 6.57 (brs, 2H).
LC-MS: m/z 173 [M+H⁺].

Preparation of 6-(6-fluoropyridin-3-yl)pyridazin-3-amine

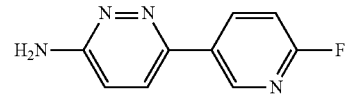

¹H NMR (400 MHz, DMSO-d₆) δ (ppm): 8.78 (s, 1H), 8.55-8.50 (m, 1H), 7.88 (d, J=9.2 Hz, 1H), 7.29-7.26 (m, 1H), 6.87 (d, J=9.2 Hz, 1H), 6.58 (brs, 2H).
LC-MS: m/z 191.13 [M+H⁺].

Preparation of 6-(5-fluoropyridin-3-yl)pyridazin-3-amine

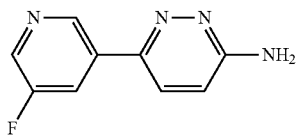

¹H NMR (400 MHz, DMSO-d₆): 9.04 (s, 1H), 8.59-8.58 (d, J=2.8 Hz, 1H), 8.24-8.21 (m, 1H), 7.95-7.93 (d, J=9.6 Hz, 1H), 6.89-6.86 (d, J=9.2 Hz, 1H), 6.68 (brs, 2H).
LC-MS: m/z 191.04 (M+H⁺) with a purity of 88.20%.

Preparation of 6-(5-(trifluoromethyl)pyridin-3-yl)pyridazin-3-amine

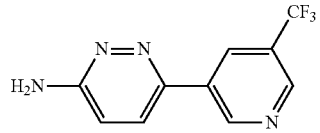

$^1$H NMR (400 MHz, DMSO-d$_6$) δ (ppm): 9.45 (s, 1H), 8.98 (s, 1H), 8.67 (s, 1H), 8.04 (d, J=9.2 Hz, 1H), 6.90 (d, J=9.2 Hz, 1H), 6.73 (br s, 2H).

LC-MS: m/z 241.15 [M+H$^+$].

Preparation of 3,3'-bipyridin-6-amine

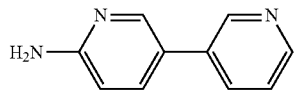

$^1$H NMR (400 MHz, DMSO-d$_6$) δ (ppm): 8.80 (d, J=2 Hz, 1H), 8.47-8.45 (m, 1H), 8.30 (d, J=2.4 Hz, 1H), 7.96 (t, J=8 Hz, 1H), 7.77-7.74 (m, 1H), 7.41 (t, J=7.6 Hz, 1H), 6.55 (d, J=8.4 Hz, 1H), 6.14 (brs, 2H).

LC-MS: m/z 172.0 [M+H$^+$] with a purity of 99.63%.

Preparation of 6-(6-(trifluoromethyl)pyridin-3-yl)pyridazin-3-amine

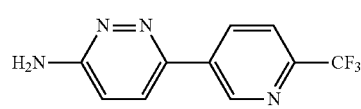

$^1$H NMR (400 MHz, DMSO-d$_6$): 9.33 (s, 1H), 8.61-8.59 (d, J=7.9 Hz, 1H), 8.00-7.97 (dd, J=3.5 Hz, J=2.6 Hz, 2H), 6.91-6.89 (d, J=9.2 Hz, 1H), 6.75 (brs, 2H).

LC-MS: m/z 241.13 (M+H$^+$) with a purity of 99.50%.

Preparation of 6-(4-(trifluoromethyl)phenyl)pyridazin-3-amine (3, Compound 49 Amine)

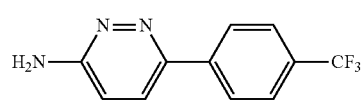 [SMILES: Nc1ccc(-c2ccc(C(F)(F)F)cc2)nn1]

$^1$H NMR (400 MHz, DMSO-d$_6$) δ (ppm): δ 8.19 (d, J=8.4 Hz, 2H), 7.90 (d, J=9.2 Hz, 1H), 7.81 (d, J=7.6 Hz, 2H), 6.88 (d, J=10 Hz, 1H), 6.63 (brs, 2H).

LC-MS: m/z 240.15 [M+H$^+$] with a purity of 99.94%.

Preparation of 6-(3-(trifluoromethyl)phenyl)pyridazin-3-amine

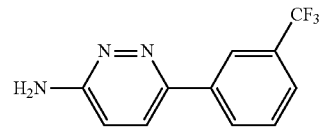 [SMILES: Nc1ccc(-c2cccc(C(F)(F)F)c2)nn1]

$^1$H NMR (400 MHz, DMSO-d$_6$) δ (ppm): δ 8.30 (s, 1H), 8.25 (d, J=7.2 Hz, 1H), 7.94 (d, J=9.2 Hz, 1H), 7.75-7.68 (m, 2H), 6.87 (d, J=9.2 Hz, 1H), 6.60 (brs, 2H).

LC-MS: m/z 240.15 [M+H$^+$] with a purity of 99.68%.

Preparation of 6-(3-(trifluoromethoxy)phenyl)pyridazin-3-amine

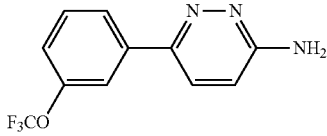

$^1$H NMR (400 MHz, DMSO-d$_6$) δ (ppm): 7.99-7.95 (m, 2H), 7.88 (d, J=9.2 Hz, 1H), 7.6 (t, J=7.6 Hz, 1H), 7.37 (d, J=8.3 Hz, 1H), 7.86 (d, J=9.6 Hz, 1H), 6.59 (s, 2H), LC-MS: m/z 254.05 [M+H$^+$] with a purity of 95.07%.

Preparation of 6-(4-(trifluoromethoxy) phenyl)pyridazin-3-amine

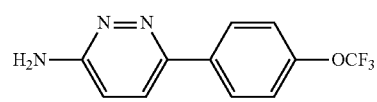

$^1$H NMR (400 MHz, DMSO-d$_6$) δ (ppm): 8.08 (dd, J$_1$=2 Hz, J$_2$=$_2$ 4.8 Hz, 2H), 7.83 (d, J=9.6 Hz, 1H), 7.44 (d, J=8.4 Hz, 2H), 6.86 (d, J=9.2 Hz, 1H), 6.53 (brs, 2H).

LC-MS: m/z 256.21 [M+H$^+$] with a purity of 95.19%.

Preparation of 6-(5-chloropyridin-3-yl)pyridazin-3-amine

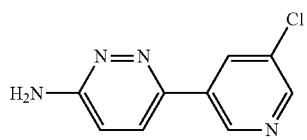 [SMILES: Nc1ccc(-c2cncc(Cl)c2)nn1]

$^1$H NMR (400 MHz, DMSO-d$_6$) δ (ppm): 9.11 (s, 1H), 8.63 (d, J=2 Hz, 1H), 8.42 (s, 1H), 7.94 (d, J=9.2 Hz, 1H), 6.89-6.86 (dd, J$_1$=9.2 Hz, J$_2$=0.8 Hz, 1H), 6.66 (brs, 2H).

LC-MS: m/z 207.11 [M+2H$^+$] with a purity of 98.58%.

Preparation of 6-(5-(difluoromethoxy) pyridin-3-yl) pyridazin-3-amine

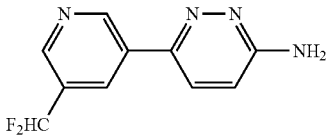

$^1$H NMR (400 MHz, DMSO-$d_6$) δ (ppm): 9.29 (s, 1H), 8.80 (d, J=1.2 Hz, 1H), 8.54 (s, 1H), 7.98 (d, J=9.2 Hz, 1H), 7.37-7.09 (m, 1H), 6.89 (d, J=9.2 Hz, 1H), 6.67 (brs, 2H).

Preparation of 5-methyl-6-(pyridin-3-yl) pyridazin-3-amine

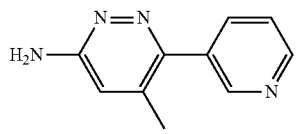

$^1$H NMR (400 MHz, DMSO-$d_6$) δ (ppm): 8.71 (s, 1H), 8.60 (d, J=4.8 Hz, 1H), 7.93 (d, J=7.6 Hz, 1H), 7.49-7.46 (m, 1H), 6.68 (s, 1H), 6.36 (brs, 2H), 2.18 (s, 3H).
LC-MS: m/z 187.0 [M+H$^+$] with a purity of 96.33%.

Preparation of 4-(pyridin-2-yl) aniline

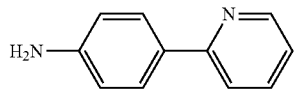

$^1$H NMR (400 MHz, DMSO-$d_6$) δ (ppm): 8.51 (d, J=4.4 Hz, 1H), 7.79 (d, J=8 Hz, 2H), 7.73 (d, J=3.2 Hz, 2H), 7.15-7.12 (m, 1H), 6.63 (d, J=8.4 Hz, 2H), 5.38 (brs, 2H).
LC-MS: m/z 171.0 [M+H$^+$] with a purity of 97.74%.

Preparation of 4-(pyridin-3-yl)aniline

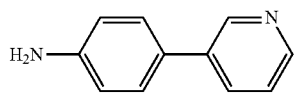

$^1$H NMR (400 MHz, DMSO-$d_6$) δ (ppm): 8.77 (d, J=1.6 Hz, 1H), 8.40 (dd, J=1.6 Hz, J=4.4 Hz, 1H), 7.92-7.89 (m, 1H), 7.42-7.35 (m, 3H), 6.68-6.65 (m, 2H), 5.31 (brs, 2H).
LC-MS: m/z 171.0. [M+H$^+$] with a purity of 99.37%.

Preparation of 4-(pyridin-3-yl) aniline

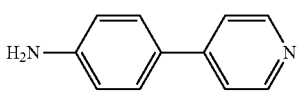

$^1$H NMR (400 MHz, DMSO-$d_6$) δ (ppm): 8.47 (dd, J=1.6 Hz, J=4.8 Hz, 2H), 7.55-7.51 (m, 4H), 6.66 (d, J=8.8 Hz, 2H), 5.48 (brs, 2H).
LC-MS: m/z 171.0 [M+H$^+$] with a purity of 99.79%.

Preparation of 5'-methyl-[3,3'-bipyridin]-6-amine

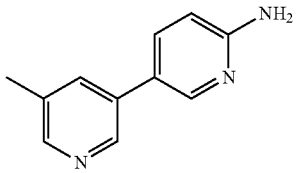

$^1$H NMR (400 MHz, DMSO-$d_6$) δ ppm: 8.58 (s, 1H), 8.30-8.29 (m, 1H), 8.27-8.26 (m, 1H), 7.78 (br s, 1H), 7.74 (dd, J=9.2 Hz, J=2.6 Hz, 1H), 6.54 (d, J=8.4 Hz, 1H), 6.12 (s, 2H), 2.33 (s, 3H).
LC-MS: m/z 186 [M+H$^+$].

Preparation of 6-(5-methylpyridin-3-yl) pyridazin-3-amine

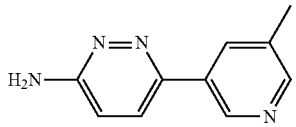

$^1$H NMR (400 MHz, DMSO-$d_6$) δ ppm: 8.93 (s, 1H), 8.42 (s, 1H), 8.15 (s, 1H), 7.87-7.85 (d, J=9.2 Hz, 1H), 6.88-6.86 (d, J=9.2 Hz, 1H), 6.56 (brs, 2H), 2.37 (s, 3H).
LC-MS: m/z 240.15 [M+H$^+$] with a purity of 98.49%.

Preparation of 6-(pyridin-4-yl) pyridazin-3-amine

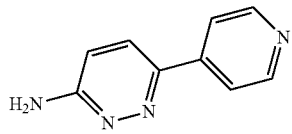 [SMILES: Nc1ccc(-c2ccncc2)nn1]

$^1$H NMR (400 MHz, DMSO-$d_6$) δ (ppm): 7.96-7.94 (d, J=8 Hz, 2H), 7.82-7.80 (d, J=9.2 Hz, 1H), 7.48-7.35 (m, 3H), 6.86-6.84 (m, 1H), 6.64 (br s, 2H).
LC-MS: m/z 172.0 [M+H$^+$].

Preparation of 3-fluorobiphenyl-4-amine

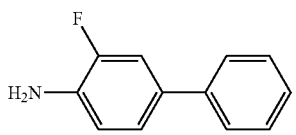

$^1$H NMR (400 MHz, DMSO-$d_6$): 7.57-7.55 (d, J=7.6 Hz, 2H), 7.39-7.31 (m, 3H), 7.26-7.22 (m, 2H), 6.86-6.82 (t, J=8.8 Hz, 1H), 5.25 (brs, 2H).
LC-MS: m/z 187.94 (M+H) with a purity of 99.96%.

Preparation of 6-(2-fluorophenyl)pyridazin-3-amine

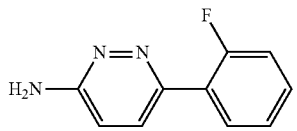 [SMILES: Nc1ccc(-c2ccccc2F)nn1]

¹H NMR (400 MHz, DMSO-d₆): 7.87-7.83 (m, 1H), 7.61-7.58 (dd, J₁=2.4 Hz, J₂=9.2 Hz, 1H), 7.48-7.42 (m, 1H), 7.33-7.28 (m, 2H), 6.86-6.84 (d, J=9.2 Hz, 1H), 6.54 (brs, 2H).

LC-MS: m/z 190.22 (M+H) with a purity of 99.74%.

Preparation of 5'-fluoro-2,3'-bipyridin-5-amine

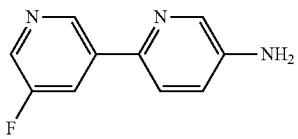

¹H NMR (400 MHz, DMSO-d₆): 9.0 (s, 1H), 8.45-8.44 (d, J=2.8 Hz, 1H), 8.12-8.10 (m, 1H), 8.06-8.05 (d, J=2.8, 1H), 7.79-7.77 (d, J=8.8 Hz, 1H), 7.03-7.0 (dd, J₁=2.4 Hz, J₂=6.4 Hz, 1H), 5.68 (brs, 2H).

LC-MS: m/z 189.98 (M+H⁺) with a purity of 99.73%.

Preparation of 5'-methyl-3,3'-bipyridin-6-amine (Compound 91 Amine)

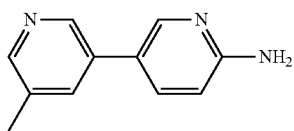

¹H NMR (400 MHz, DMSO-d₆): 8.59 (s, 1H), 8.30-8.28 (d, J=9.6 Hz, 2H), 7.78-7.72 (m, 2H), 6.55.6.52 (d, J=8.8 Hz, 1H), 6.13 (brs, 2H), 2.33 (s, 3H).

LC-MS: m/z 185.9 (M+H) with a purity of 93.09%.

Preparation of 6'-fluoro-3,3'-bipyridin-6-amine

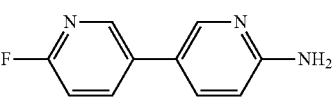

¹H NMR (400 MHz, DMSO-d₆): 8.436-8.432 (d, J=1.6 Hz, 1H), 8.28-8.27 (d, J=2 Hz, 1H), 8.19-8.14 (m, 1H), 7.75-7.72 (dd, J₁=2.8 Hz, J₂=8.4 Hz, 1H), 7.21-7.18 (dd, J₁=2.8 Hz, J₂=8.4 Hz, 1H), 6.55-6.52 (d, J=8.8 Hz, 1H), 6.15 (brs, 2H).

LC-MS: m/z 190.0 (M+H) with a purity of 99.71%.

Preparation of 2'-fluoro-3,3'-bipyridin-6-amine

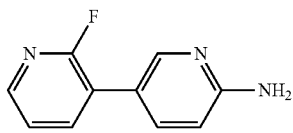 [SMILES: Nc1ccc(-c2cccnc2F)cn1]

¹H NMR (400 MHz, DMSO-d₆): 8.17 (s, 1H), 8.14-8.13 (m, 1H), 8.07-8.02 (m, 1H), 7.65-7.62 (m, 1H), 7.42-7.38 (m, 1H), 6.55-6.53 (d, J=8.8 Hz, 1H), 6.23 (brs, 2H).

LC-MS: m/z 190.0 (M+H) with a purity of 98.07%.

Preparation of 5'-fluoro-3,3'-bipyridin-6-amine

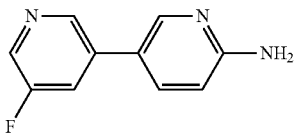 [SMILES: Nc1ccc(-c2cncc(F)c2)cn1]

¹H NMR (400 MHz, DMSO-d₆): 8.71 (s, 1H), 8.50-8.44 (d, J=2.8 Hz, 1H), 8.376-8.37 (d, J=2.4 Hz, 1H), 7.97-7.93 (m, 1H), 7.83-7.80 (m, 1H), 6.55-6.53 (d, J=8.4 Hz, 1H), 6.25 (brs, 2H).

LC-MS: m/z 189.97 (M+H) with a purity of 99.66%.

Preparation of 4-(pyrazin-2-yl)aniline

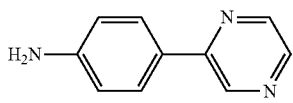

¹H NMR (400 MHz, DMSO-d₆): 9.401-9.037 (d, J=1.6 Hz, 1H), 8.53-8.52 (m, 1H), 8.376-8.37 (d, J=2.4 Hz, 1H), 7.85-7.83 (m, 2H), 6.67-6.65 (dd, J₁=2 Hz, J₂=6.8 Hz, 2H), 5.57 (brs, 2H).

LC-MS: m/z 171.94 (M+H) with a purity of 96.58%.

Preparation of 4-fluoro-3,3'-bipyridin-6-amine

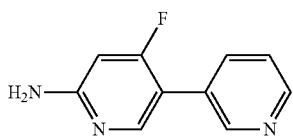

¹H NMR (400 MHz, DMSO-d₆): 8.67 (s, 1H), 8.52-8.51 (m, 1H), 8.13-8.10 (d, J=12 Hz, 1H), 7.89-7.86 (m, 1H), 7.46-7.43 (m, 1H), 6.46 (brs, 2H), 6.33-6.30 (d, J=12.8 Hz, 1H).

HPLC: at 254 nm with a purity of 99.59%.

Preparation of 2'-methyl-2,3'-bipyridin-5-amine

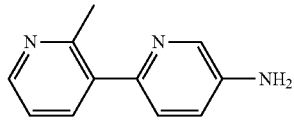

Step 1: Preparation of
2'-methyl-5-nitro-2,3'-bipyridine

HPLC: At 254 nm with a purity of 83.07%

Step 2: Preparation of
2'-methyl-2,3'-bipyridin-5-amine

We have proceeded further without analytical data.

Preparation of 2, 4'-bipyridin-5-amine

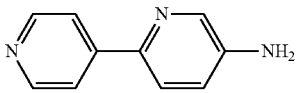 [SMILES: Nc1ccc(-c2ccncc2)nc1]

Step 1: Preparation of 5-nitro-2,4'-bipyridine $^1$H NMR (400 MHz, DMSO-d$_6$): 9.50-9.50 (d, J=2.4 Hz, 1H), 8.80-8.78 (m, 2H), 8.76-8.73 (m, 1H), 8.43-8.41 (d, J=8.8 Hz, 1H), 8.15-8.13 (dd, J$_1$=2 Hz, J$_2$=4.8 Hz, 2H).
LC-MS: m/z 202.03 [M+H$^+$] with a purity of 98.80%.

Step 2: Preparation of 2,4'-bipyridin-5-amine $^1$H NMR (400 MHz, DMSO-d$_6$): 8.54-8.53 (d, J=6 Hz, 2H), 8.07-8.06 (d, J=3.2 Hz, 1H), 7.88-7.86 (m, 2H), 7.80-7.88 (d, J=8.4 Hz, 1H), 7.02-6.99 (dd, J$_1$=2.8 Hz, J$_2$=8.4 Hz, 1H), 5.76 (brs, 2H).
LC-MS: m/z 172.03 [M+H$^+$] with a purity of 98.34%.

Preparation of 4'-methyl-3,3'-bipyridin-6-amine

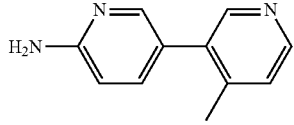

$^1$H NMR (400 MHz, DMSO-d$_6$): 8.37-8.35 (d, J=5.6 Hz, 1H), 8.32 (s, 1H), 7.92-7.91 (d, J=2 Hz, 1H), 7.46-7.43 (dd, J$_1$=2.4 Hz, J$_2$=8.4 Hz, 1H), 7.29-7.27 (d, J=4.8 Hz, 1H), 6.54-6.52 (d, J=8.4 Hz, 1H), 6.07 (brs, 2H), 2.27 (s, 3H).
HPLC: at 254 nm with a purity of 96.49%.

Preparation of 5-methyl-3,3'-bipyridin-6-amine

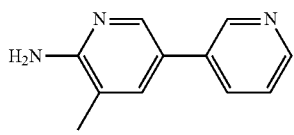

$^1$H NMR (400 MHz, DMSO-d$_6$): 8.80 (s, 1H), 8.46-8.45 (d, J=4.8 Hz, 1H), 8.18-8.175 (d, J=2 Hz, 1H), 7.97-7.95 (d, J=8 Hz, 1H), 7.63 (s, 1H), 7.41-7.38 (m, 1H), 5.93 (brs, 2H), 2.11 (s, 3H).
LC-MS: m/z 186.0 (M+H$^+$) with a purity of 98.13%.

Preparation of 4-methyl-3,3'-bipyridin-6-amine

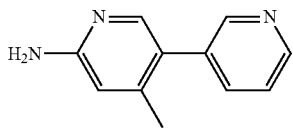

$^1$H NMR (400 MHz, DMSO-d$_6$): 8.52 (s, 2H), 7.76-7.73 (m, 2H), 7.43-7.40 (m, 1H), 6.38 (s, 1H), 5.38 (brs, 2H), 2.12 (s, 3H).
LC-MS: m/z 186.0 (M+H$^+$) with a purity of 98.01%.

Preparation of 2-methyl-3,3'-bipyridin-6-amine

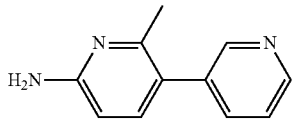

$^1$H NMR (400 MHz, DMSO-d$_6$): 8.51.8.48 (m, 2H), 7.73-7.71 (d, J=8 Hz, 1H), 7.43-7.39 (m, 1H), 7.29-7.26 (d, J=8.4 Hz, 1H), 6.39-6.37 (d, J=8.4 Hz, 1H), 5.99 (brs, 2H), 2.23 (s, 3H).
LC-MS: m/z 186.0 (M+H$^+$) with a purity of 99.44%.

Preparation of 6-methyl-2,3'-bipyridin-5-amine

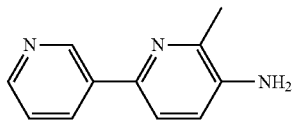

$^1$H NMR (400 MHz, DMSO-d$_6$): 9.11 (s, 1H), 8.458-8.45 (d, J=3.2 Hz, 1H), 8.25-8.23 (d, J=8 Hz, 1H), 7.60-7.58 (d, J=8 Hz, 1H), 7.40-7.37 (m, 1H), 7.01-6.99 (d, J=8.4 Hz, 1H), 5.29 (brs, 2H), 2.35 (s, 3H).
LC-MS: m/z 186.2[M+H$^+$] with a purity of 74.47%.

Preparation of 3-methyl-2,3'-bipyridin-5-amine

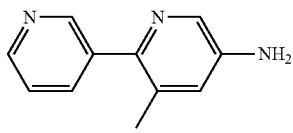

$^1$H NMR (400 MHz, CDCl3): 8.75 (s, 1H), 8.59-8.58 (d, J=2.8 Hz, 1H), 8.059-8.054 (d, J=2 Hz, 1H), 7.85-7.83 (d, J=8 Hz, 1H), 7.37-7.34 (m, 1H), 6.92-6.91 (d, J=2.8 Hz, 1H), 4.0 (brs, 2H), 2.30 (s, 3H).
LC-MS: m/z 186.0 [M+H$^+$] with a purity of 93.98%.

Preparation of 5'-methyl-2,3'-bipyridin-5-amine

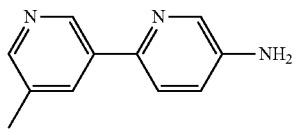

Step 2: Preparation of
5'-methyl-5-nitro-2,3'-bipyridine

¹H NMR (400 MHz, DMSO-d₆): 9.47-9.46 (d; J=2 Hz, 1H), 9.17 (s, 1H), 8.71-8.68 (dd, J₁=2.4 Hz, J₂=8.8 Hz, 1H), 8.58 (s, 1H), 8.39-8.34 (m, 2H), 2.42 (s, 3H).

LC-MS: m/z 216.03 (M+H⁺) with a purity of 90.92%.

Step 2: Preparation of
5'-methyl-2,3'-bipyridin-5-amine

¹H NMR (400 MHz, DMSO-d₆): 8.896-8.891 (d, J=1.6 Hz, 1H), 8.307-8.303 (d, J=1.6 Hz, 1H), 8.07 (s, 1H), 8.046-8.040 (d, J=2.4 Hz, 1H), 7.69-7.67 (d, J=8.4 Hz, 1H), 7.01-6.99 (dd, J₁=2.8 Hz, J₂=8.4 Hz, 1H), 5.54 (brs, 2H), 2.34 (s, 3H).

LC-MS: m/z 186.0 (M+H⁺) with a purity of 99.78%.

Preparation of 4-methyl-3,3'-bipyridin-6-amine

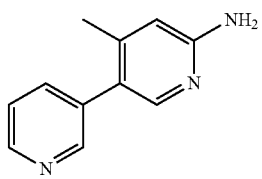

LC-MS: m/z 186.0 [M+H⁺].

Preparation of
5-(6-methylpyrazin-2-yl)pyridin-2-amine

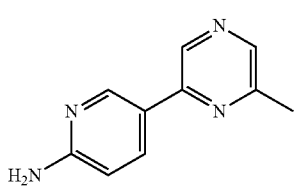

¹H NMR (400 MHz, CDCl3): 8.72 (s, 2H), 8.32 (s, 1H), 8.13-8.11 (dd, J₁=2 Hz, J₂=8 Hz, 1H), 6.62-6.60 (d, J=8.4 Hz, 1H), 4.67 (s, 2H), 2.59 (s, 3H).

LC-MS: m/z 187.0 (M+H⁺) with a purity of 99.39%.

Preparation of
6-(2-methylpyridin-3-yl)pyridazin-3-amine

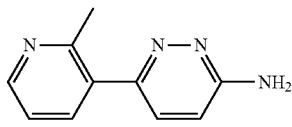

¹H NMR (400 MHz, CDCl3): 8.57-8.55 (dd, J₁=1.6 Hz, J₂=4.8 Hz, 1H), 7.76-7.73 (dd, J₁=2 Hz, J₂=8 Hz, 1H), 7.36-7.34 (d, J=8.8 Hz, 1H), 7.24-7.22 (m, 1H), 6.85-6.82 (d, J=8.8 Hz, 1H), 4.80 (brs, 2H), 2.60 (s, 3H).

LC-MS: m/z 187.0 (M+H⁺) with a purity of 73.36%.

Preparation of 2'-fluoro-2,3'-bipyridin-5-amine

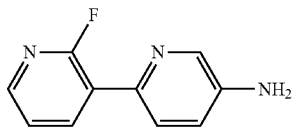 [SMILES: Nc1ccc(-c2cccnc2F)nc1]

Step 1: Preparation of
2'-fluoro-5-nitro-2,3'-bipyridine

¹H NMR (400 MHz, DMSO-d₆): 9.51-9.50 (d, J=2.4 Hz, 1H), 8.76-8.73 (dd, J₁=2 Hz, J₂=8 Hz 1H), 8.61-8.57 (m, 1H), 8.43-8.41 (d, J=4.8 Hz, 1H), 7.61-7.58 (m, 1H), 8.19-8.16 (dd, J₁=1.6 Hz, J₂=8.8 Hz 1H).

LC-MS: m/z 219.92 (M+H⁺) with a purity of 97.88%.

Step 2: Preparation of
2'-fluoro-2,3'-bipyridin-5-amine

¹H NMR (400 MHz, DMSO-d₆): 8.43-8.38 (m, 1H), 8.14-8.08 (m, 2H), 7.58-7.55 (dd, J₁=2.4 Hz, J₂=8.8 Hz, 1H), 7.43-7.39 (m, 1H), 7.02-6.99 (dd, J₁=2.8 Hz, J₂=7.6 Hz, 1H), 5.66 (brs, 2H).

LC-MS: m/z 189.97 (M+H⁺) with a purity of 92.44%.

Preparation of 3-fluoro-2,3'-bipyridin-5-amine

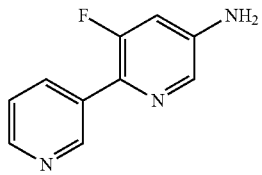 [SMILES: Nc1cnc(-c2cccnc2)c(F)c1]

¹H NMR (400 MHz, DMSO-d₆) δ (ppm): 8.96 (s, 1H), 8.51 (d, J=4.8 Hz, 1H), 8.14 (d, J=3.6 Hz, 1H), 7.95 (t, J=2.0 Hz, 1H), 7.46-7.43 (m, 1H), 6.85 (dd, J=2.4 Hz, 14.4 Hz, 1H) 5.95 (bs, 2H).

LC=MS: m/z 190.0 (M+H⁺).

Preparation of 6'-fluoro-2,3'-bipyridin-5-amine

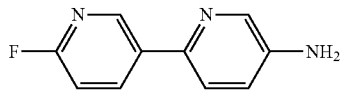 [SMILES: Nc1ccc(-c2ccc(F)nc2)nc1]

Step 1: Preparation of
6'-fluoro-5-nitro-2,3'-bipyridine $^1$H NMR (400 MHz, DMSO-d$_6$): 9.47-9.46 (d, J=2.4 Hz, 1H), 9.068-9.062 (d, J=2.4 Hz, 1H), 8.78-8.70 (m, 2H), 8.38-8.35 (d, J=8.8 Hz, 1H), 7.41-7.38 (dd, J$_1$=2.8 Hz, J$_2$=8.4 Hz, 1H).
LC-MS: m/z 219.94 (M+H$^+$) with a purity of 97.14%.

Step 2: Preparation of
6'-fluoro-2,3'-bipyridin-5-amine $^1$H NMR (400 MHz, DMSO-d$_6$): 8.72 (s, 1H), 8.46-8.41 (m, 1H), 8.04-8.03 (d, J=2.8 Hz, 1H), 7.70-7.68 (d, J=8.8 Hz, 1H), 7.20-7.17 (dd, J$_1$=2.8 Hz, J$_2$=8.4 Hz, 1H), 7.02-7.00 (dd, J$_1$=2.4 Hz, J$_2$=8.4 Hz, 1H), 5.56 (brs, 2H).
LC-MS: m/z 190.0 (M+H) with a purity of 98.88%.

Preparation of
6-(4-methylpyridin-3-yl)pyridazin-3-amine

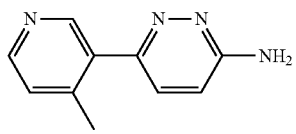

$^1$H NMR (400 MHz, DMSO-d$_6$): 8.50 (s, 1H), 8.45-8.43 (d, J=5.6 Hz, 1H), 7.50-7.48 (d, J=8.8 Hz, 1H), 7.33-7.32 (d, J=4.8 Hz, 1H), 6.87-6.85 (d, J=9.2 Hz, 1H), 6.49 (brs, 2H), 3.29 (s, 3H).
LC-MS: m/z 187.0 [M+H$^+$] with a purity of 99.69%.

Preparation of 6-fluoro-2,3'-bipyridin-5-amine

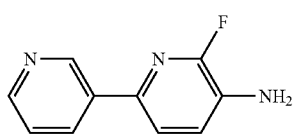 [SMILES: Nc1ccc(-c2cccnc2)nc1F]

$^1$H NMR (400 MHz, DMSO-d$_6$): 9.098-9.090 (d, J=2 Hz, 1H), 8.56-8.55 (d, J=4 Hz, 1H), 8.22-8.19 (m, 1H), 7.49-7.47 (d, J=8 Hz, 1H), 7.35-7.32 (m, 1H), 7.20-7.15 (m, 1H), 3.90 (brs, 2H).

Preparation of 6'-methyl-2,3'-bipyridin-5-amine

Step 1: Preparation of
6'-methyl-5-nitro-2,3'-bipyridine $^1$H NMR (400 MHz, CDCl3): 9.55-9.55 (d, J=2.4 Hz, 1H), 8.16 (s, 1H), 8.61-8.56 (m, 2H), 7.68-7.66 (d, J=7.6 Hz 1H), 7.27-7.26 (m, 1H), 2.46 (s, 3H).
LC-MS: m/z 216.03 (M+H$^+$) with a purity of 91.08%.

Step 2: Preparation of
6'-methyl-2,3'-bipyridin-5-amine $^1$H NMR (400 MHz, CDCl3): 8.56 (s, 1H), 8.44-8.43 (d, J=5.2 Hz, 1H), 8.21-8.20 (d, J=6.8 Hz, 1H), 7.26-7.20 (m, 2H), 7.10-7.07 (m, 1H), 3.81 (brs, 2H), 2.41 (s, 3H).
LC-MS: m/z 186.0 (M+H$^+$) with a purity of 90.22%.

Preparation of 2'-fluoro-3,3'-bipyridin-6-amine

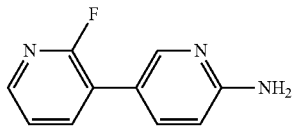

$^1$H NMR (400 MHz, DMSO-d$_6$): 8.17 (s, 1H), 8.14-8.13 (m, 1H), 8.07-8.02 (m, 1H), 7.65-7.62 (m, 1H), 7.42-7.38 (m, 1H), 6.55-6.53 (d, J=8.8 Hz, 1H), 6.23 (brs, 2H).
LC-MS: m/z 190.0 (M+H$^+$) with a purity of 98.07%.

Preparation of 5'-fluoro-3,3'-bipyridin-6-amine

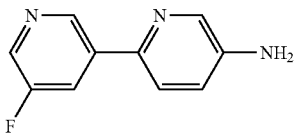 [SMILES: Nc1ccc(-c2cncc(F)c2)nc1]

$^1$H NMR (400 MHz, DMSO-d$_6$): 8.71 (s, 1H), 8.50-8.44 (d, J=2.8 Hz, 1H), 8.376-8.37 (d, J=2.4 Hz, 1H), 7.97-7.93 (m, 1H), 7.83-7.80 (m, 1H), 6.55-6.53 (d, J=8.4 Hz, 1H), 6.25 (brs, 2H).
LC-MS: m/z 189.97 (M+H$^+$) with a purity of 99.66%.

Preparation of 4-methyl-2,3'-bipyridin-5-amine

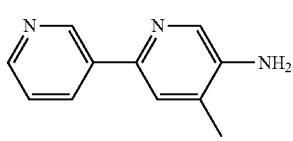

$^1$H NMR (400 MHz, DMSO-d$_6$): 9.11-9.10 (d, J=2 Hz, 1H), 8.46-8.44 (dd, J$_1$=1.6 Hz, J$_2$=4.8 Hz, 1H), 8.26-8.23 (m, 1H), 8.01 (s, 1H), 7.63 (s, 1H), 7.40-7.37 (m, 1H), 5.33 (brs, 2H), 2.14 (s, 3H).
LC-MS: m/z 186.0 [M+H$^+$] with a purity of 78.41%.

Preparation of
5-(5-fluoropyridin-3-yl)pyrazin-2-amine

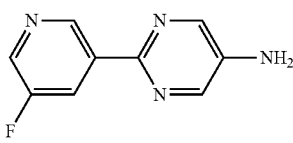 [SMILES: Nc1cnc(-c2cncc(F)c2)nc1]

¹H NMR (400 MHz, DMSO-d₆): 9.01 (s, 1H), 8.65 (s, 1H), 8.50-8.49 (d, J=2.4 Hz, 1H), 8.15-8.12 (m, 1H), 7.99 (s, 1H), 6.79 (brs, 2H).

LC-MS: m/z 191.0 (M+H$^+$) with a purity of 95.15%.

Preparation of 5'-methoxy-2,3'-bipyridin-5-amine

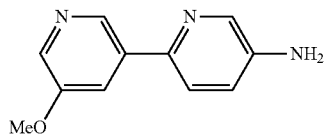

Step 1: Preparation of 5'-methoxy-5-nitro-2,3'-bipyridine

¹H NMR (400 MHz, DMSO-d₆): 9.52-9.51 (d, J=2.8 Hz, 1H), 8.855-8.551 (d, J=1.6 Hz, 1H), 8.59-8.56 (dd, J₁=2.4 Hz, J₂=8.8 Hz, 1H), 8.457-8.45 (d, J=2.8 Hz, 1H), 7.99-7.96 (m, 2H), 3.97 (s, 3H).

LC-MS: m/z 231.88 (M+H$^+$) with a purity of 96.05%.

Step 2: Preparation of 5'-methoxy-2,3'-bipyridin-5-amine

¹H NMR (400 MHz, DMSO-d₆): 8.705-8.701 (d, J=1.6 Hz, 1H), 8.18-8.17 (d, J=3.2 Hz, 1H), 8.05-8.04 (d, J=2.4 Hz, 1H), 7.81-7.80 (t, J=2 Hz, 1H), 7.74-7.72 (d, J=8.8 Hz, 1H), 7.02-6.99 (dd, J₁=2.8 Hz, J₂=8.4 Hz, 1H), 5.57 (brs, 2H), 3.88 (s, 3H).

LC-MS: m/z 201.90 (M+H$^+$) with a purity of 97.13%.

Preparation of 6'-methoxy-2,3'-bipyridin-5-amine

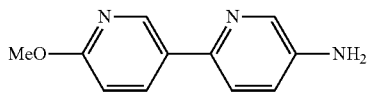

Step 1: Preparation of 6'-methoxy-5-nitro-2,3'-bipyridine

¹H NMR (400 MHz, DMSO-d₆): 9.47-9.47 (d, J=2.4 Hz, 1H), 8.889-8.883 (d, J=2.4 Hz, 1H), 8.53-8.50 (dd, J₁=2.8 Hz, J=8.8 Hz, 1H), 8.35-8.32 (dd, J₁=2.4 Hz, J=8.4 Hz, 1H), 7.85-7.83 (d, J=8.8 Hz, 1H), 6.90-6.87 (d, J=8.8 Hz, 1H), 4.02 (s, 3H).

LC-MS: m/z 231.91 (M+H$^+$) with a purity of 97.91%.

Step 2: Preparation of 6'-methoxy-2,3'-bipyridin-5-amine

¹H NMR (400 MHz, DMSO-d₆): 8.67-8.66 (d, J=2.4 Hz, 1H), 8.20-8.18 (d, J₁=2.4 Hz, J₂=8.8 Hz, 1H), 8.01-8.00 (d, J=2.4 Hz, 1H), 7.60-7.58 (d, J=5.2 Hz, 1H), 7.00-6.97 (dd, J₁=2.8 Hz, J₂=8.4 Hz, 1H), 6.84-6.82 (d, J=8.4 Hz, 1H), 5.41 (brs, 2H), 3.87 (s, 3H).

LC-MS: m/z 201.9 (M+H$^+$) with a purity of 98.28%.

Preparation of 5-methyl-2,3'-bipyridin-6'-amine

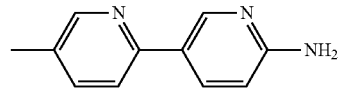

¹H NMR (400 MHz, DMSO-d₆): 8.65 (s, 1H), 8.46 (s, 1H), 8.12-8.09 (dd, J₁=3.2 Hz, J₂=8.4 Hz, 1H), 7.52-7.51 (d, J=1.6 Hz, 2H), 6.61-6.59 (d, J=8 Hz 1H), 4.63 (brs, 2H), 2.35 (s, 3H).

LC-MS: m/z 186.08 (M+H) with a purity of 83.26%.

Preparation of 5-fluoro-3,3'-bipyridin-6-amine

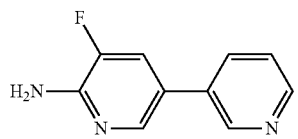

¹H NMR (400 MHz, DMSO-d₆): 8.857-8.85 (d, J=2.4 Hz, 1H), 8.49-8.48 (m, 1H), 8.19 (m, 1H), 8.04-8.01 (m, 1H), 7.83-7.79 (dd, J₁=1.6 Hz, J₂=10.8 Hz, 1H), 7.43-7.40 (m, 1H), 6.43 (brs, 2H).

HPLC: at 254 nm with a purity of 99.66%.

Preparation of 4-fluoro-3,3'-bipyridin-6-amine

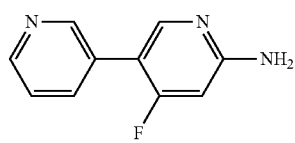 [SMILES: Nc1cc(F)c(-c2cccnc2)cn1]

¹H NMR (400 MHz, DMSO-d₆): 8.67 (s, 1H), 8.55-8.51 (dd, J₁=1.6 Hz, J₂=4.4 Hz, 1H), 8.14-8.11 (d, J=11.6 Hz, 1H), 7.89-7.86 (dd, J₁=1.6 Hz, J₂=8 Hz, 1H), 7.46-7.43 (m, 1H), 6.47 (brs, 2H). 6.34-6.31 (d, J=13.6 Hz, 1H).

LC-MS: m/z 189.93 (M+H$^+$) with a purity of 92.32%.

Preparation of 6-(4-fluorophenyl)pyridin-3-amine

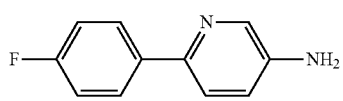 [SMILES: Nc1ccc(-c2ccc(F)cc2)nc1]

Step 1: Preparation of 2-(4-fluorophenyl)-5-nitropyridine

¹H NMR (400 MHz, CDCl3): 9.48-9.47 (d, J=2 Hz, 1H), 8.54-8.51 (dd, J₁=6.4 Hz, J₂=8.8 Hz, 1H), 8.12-8.09 (m, 2H), 7.87-7.85 (d, J=8.8 Hz, 1H), 7.25-7.19 (m, 2H).

LC-MS: m/z 218.88 (M+H$^+$) with a purity of 99.55%.

Step 2: Preparation of 6-(4-fluorophenyl)pyridin-3-amine

¹H NMR (400 MHz, DMSO-d₆): 8.008-8.001 (d, J=2.8 Hz, 1H), 7.95-7.91 (m, 2H), 7.61-7.59 (d, J=8.4 Hz, 1H), 7.21-7.17 (m, 2H), 7.08-6.98 (m, 1H), 5.43 (brs, 2H).
LC-MS: m/z 188.92 (M+H⁺) with a purity of 96.28%.

Preparation of 6-(5-methoxypyridin-3-yl)pyridazin-3-amine

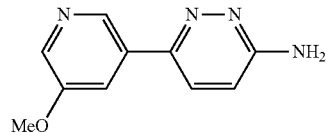 [SMILES: COc1cncc(-c2ccc(N)nn2)c1]

¹H NMR (400 MHz, DMSO-d₆): 8.74-8.73 (d, J=2 Hz, 1H), 8.31-8.30 (d, J=2.8 Hz, 1H), 7.92-7.85 (m, 2H), 6.88-6.86 (d, J=9.2 Hz 1H), 6.59 (brs, 2H), 3.91 (s, 3H).
LC-MS: m/z 202.96 (M+H⁺) with a purity of 83.80%.

Preparation of 6-(3-fluorophenyl)pyridin-3-amine

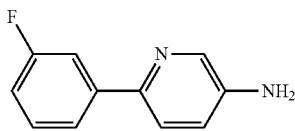 [SMILES: Nc1ccc(-c2cccc(F)c2)nc1]

Step 1: Preparation of 2-(3-fluorophenyl)-5-nitropyridine

¹H NMR (400 MHz, DMSO-d₆): 9.50-9.49 (d, J=2.4 Hz, 1H), 8.56-8.53 (dd, J₁=2.4 Hz, J₁=8.8 Hz, 1H), 7.91-7.82 (m, 3H), 7.53-7.47 (m, 1H), 7.25-7.19 (m, 1H).
LC-MS: m/z 218.88 (M+H⁺) with a purity of 99.25%.

Step 2: Preparation of 6-(3-fluorophenyl)pyridin-3-amine

¹H NMR (400 MHz, DMSO-d₆): 8.03-8.023 (d, J=2.8 Hz, 1H), 7.76-7.66 (m, 3H), 7.44-7.38 (m, 1H), 7.09-7.05 (m, 1H), 7.01-6.98 (m, 1H), 5.55 (brs, 2H).
LC-MS: m/z 189.22 (M+H⁺) with a purity of 95.86%.
Method C:
A stirred solution of the arylhalide (1 equiv.), boronic acid (1.11 equiv.) and sodium carbonate (3.33 equiv., pre-dissolved in 2 mL of water) in 3 mL of 1,4-dioxane and water was degassed for 15 min with nitrogen. Bis(triphenylphosphine)palladium(II) dichloride (0.06 equiv.) was added to reaction mixture and the reaction mixture was heated to reflux for 3-18 h. After completion of starting material, the reaction mixture was concentrated and water was added to reaction mixture and extracted with ethyl acetate. The combined organic layers were washed with brine, dried with Na₂SO₄ and concentrated under vacuum. The crude compound was purified by reversed phase chromatography to afford the purified amine.

Preparation of 5-(pyridin-3-yl)pyrazin-2-amine

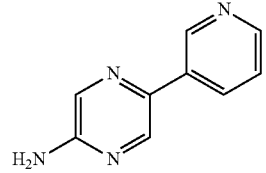

¹H NMR (400 MHz, DMSO-d₆) δ (ppm): 9.10 (s, 1H), 8.57 (s, 1H), 8.49-8.51 (m, 1H), 8.23-8.26 (m, 1H), 7.98 (s, 1H), 7.41-7.44 (m, 1H), 6.67 (brs, 2H).

Preparation of 6-methyl-[2,3'-bipyridin]-6'-amine

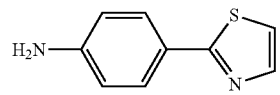

¹H NMR (400 MHz, Methanol-d₄) δ (ppm): 8.47 (s, 1H), 8.22 (brs, 1H), 8.15-8.18 (m, 1H), 7.72-7.76 (m, 1H), 7.52-7.54 (m, 1H), 7.18-7.20 (m, 1H), 6.78-6.81 (m, 1H), 2.56 (s, 3H).

Method D:
To a stirred solution of the boronic acid, (1 equiv.) in dioxane (0.02 M) and water (0.05 M) was added arylhalide (1.1 equiv.), PCy₃ (102 mg, 0.36 mmol) and K₃PO₄ (9 equiv.) and degassed for 15 min with nitrogen. Pd₂(dba)₃ (167 mg, 0.18 mmol) was added to the reaction mixture and degassed for another 15 min. The reaction mixture was heated to reflux at 100° C. for 10 h. After completion, reaction mixture was cooled to room temperature, added water (10 mL), extracted with ethyl acetate (3×10 mL). The combined ethyl acetate layers were washed with brine solution (1×10 mL), dried over anhydrous Na₂SO₄, filtered, rotary evaporated and dried under vacuum to afford crude product. The crude product was purified by column chromatography over silica gel (100-200 mesh).

Preparation of 4-(thiazol-2-yl) aniline

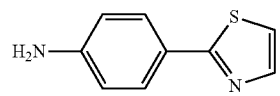

H-NMR (400 MHz; CDCl₃) δ (ppm): 7.77 (d, J=6.0 Hz, 1H), 7.19 (d, J=3.6 Hz, 1H), 6.71 (d, J=4.8 Hz, 2H), 3.8 (brs, 2H).
LC-MS: m/z 175 [M−H⁻] with a purity of 61.9%.

Synthesis of Final Targets

General Procedure for Amide Coupling Reactions
Amide Coupling Method A:
A solution of 2-(6-methyl-5, 7-dioxo-2,3,4,5,6, 7-hexahydro-1H-pyrrolo[3,4-b]pyridin-1-yl)acetic acid, 1 (1.3 equiv.) and anhydrous TEA (2.0 equiv.) in anhydrous DCM (0.05 M) was cooled to 0° C. under nitrogen atmosphere and treated with isobutyl chloroformate (1.5 equiv.). The reaction mixture stirred for 1 h, treated with biarylamine, 2 (1.0 equiv.) and gently brought up to room temperature for 2 h. After consumption of starting material, it was partitioned between DCM and saturated $NaHCO_3$. The organic phase was separated, washed with brine, dried over $Na_2SO_4$ and concentrated under vacuum. The residue was purified using reverse phase chromatography to afford desired product.

Synthesis of N-([2,3'-bipyridin]-6'-yl)-2-(6-methyl-5,7-dioxo-2,3,4,5,6,7-hexahydro-1H-pyrrolo[3,4-b]pyridin-1-yl)acetamide, (Compound 1)

Compound 1

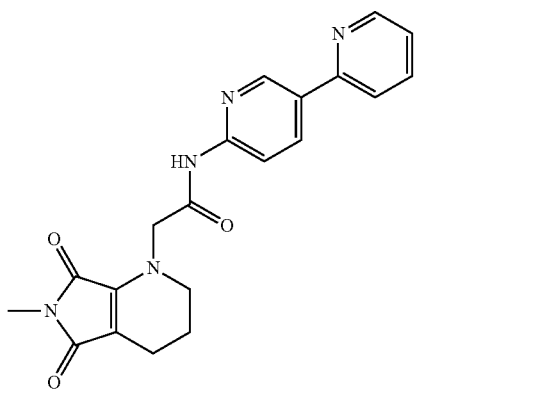

$^1$H NMR (400 MHz, DMSO-d$_6$) δ (ppm): 10.87 (s, 1H), 9.03-9.04 (m, 1H), 8.66-8.67 (m, 1H), 8.44-8.46 (m, 1H), 8.11-8.13 (m, 1H), 8.00-8.02 (m, 1H), 7.87-7.91 (m, 1H), 7.35-7.38 (m, 1H), 4.60 (s, 2H), 3.42 (t, J=6.0 Hz, 2H), 2.76 (s, 3H), 2.21 (t, J=6.0 Hz, 2H), 1.84 (q, J=6.0 Hz, 2H).

LC-MS: m/z 378 [M+H$^+$] with a purity of 95.85%.

Synthesis of 2-(6-methyl-5,7-dioxo-2,3,4,5,6,7-hexahydro-1H-pyrrolo[3,4-b]pyridin-1-yl)-N-(6-(6-methylpyridin-3-yl)pyridazin-3-yl)acetamide, (Compound 40)

Compound 40

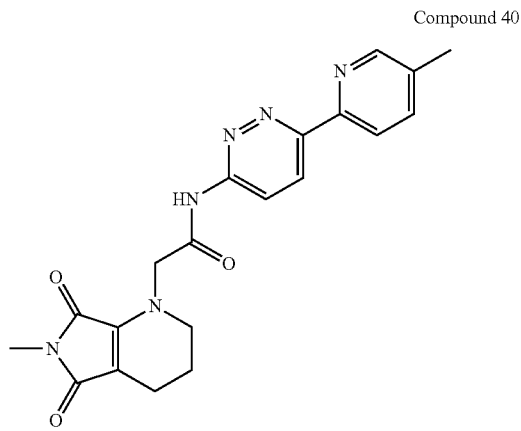

$^1$H NMR (400 MHz, DMSO-d$_6$) δ (ppm): 11.45 (s, 1H), 9.13-9.14 (m, 1H), 8.33-8.37 (m, 2H), 8.27-8.29 (m, 1H), 7.41-7.43 (m, 1H), 4.67 (s, 2H), 3.35 (t, J=6.0 Hz, 2H), 2.77 (s, 3H), 2.55 (s, 3H), 2.22 (t, J=6.0 Hz, 2H), 1.85 (q, J=6.0 Hz, 2H).

LC-MS: m/z 393 [M+H$^+$] with a purity of 98.68%.

Synthesis of 2-(6-methyl-5,7-dioxo-2,3,4,5,6,7-hexahydro-1H-pyrrolo[3,4-b]pyridin-1-yl)-N-(6-(5-methylpyridin-3-yl)pyridazin-3-yl)acetamide, (Compound 41)

Compound 41

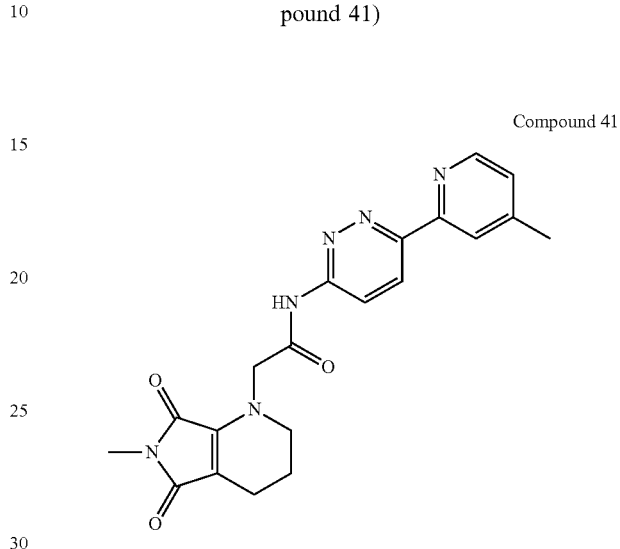

$^1$H NMR (400 MHz, DMSO-d$_6$) δ (ppm): 11.47 (s, 1H), 9.07 (d, J=2.0 Hz, 1H), 8.53 (d, J=1.2 Hz, 1H), 8.37-8.29 (m, 3H), 4.67 (s, 2H), 3.33-3-31 (brs, 2H), 2.77 (s, 3H), 2.22 (t, J=5.6 Hz, 2H), 1.88-1.84 (m, 2H).

LC-MS: m/z 393 [M+H$^+$] with a purity of 98.35%.

Synthesis of N-(6-(3-fluorophenyl)pyridazin-3-yl)-2-(6-methyl-5,7-dioxo-2,3,4,5,6,7-hexahydro-1H-pyrrolo[3,4-b]pyridin-1-yl)acetamide, (Compound 42)

Compound 42

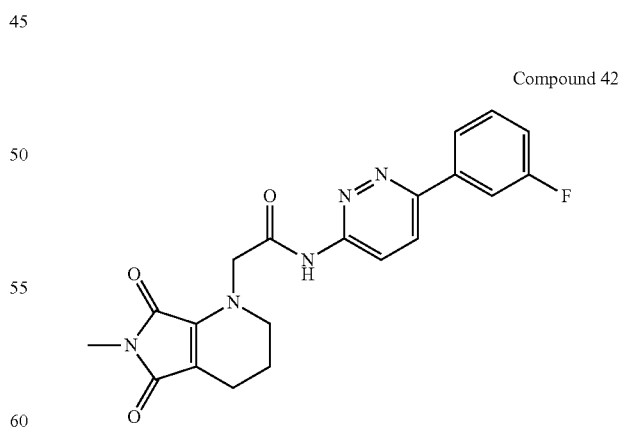

$^1$H NMR (400 MHz, DMSO-d$_6$) δ (ppm): 11.46 (s, 1H), 8.36-8.28 (m, 2H), 7.98-7.92 (m, 2H), 7.62-7.56 (m, 1H), 7.36-7.32 (m, 1H), 4.67 (s, 2H), 3.33-3-31 (brs, 2H), 2.77 (s, 3H), 2.22 (t, J=5.6 Hz, 2H), 1.88-1.82 (m, 2H).

LC-MS: m/z 396 [M+H$^+$] with a purity of 98.66%.

Synthesis of 2-(6-cyclopropyl-5,7-dioxo-2,3,4,5,6,7-hexahydro-1H-pyrrolo[3,4-b]pyridin-1-yl)-N-(6-(pyridin-3-yl)pyridazin-3-yl)acetamide, (Compound 43)

Synthesis of N-(6-(6-fluoropyridin-3-yl)pyridazin-3-yl)-2-(6-methyl-5,7-dioxo-2,3,4,5,6,7-hexahydro-1H-pyrrolo[3,4-b]pyridin-1-yl)acetamide, (Compound 46)

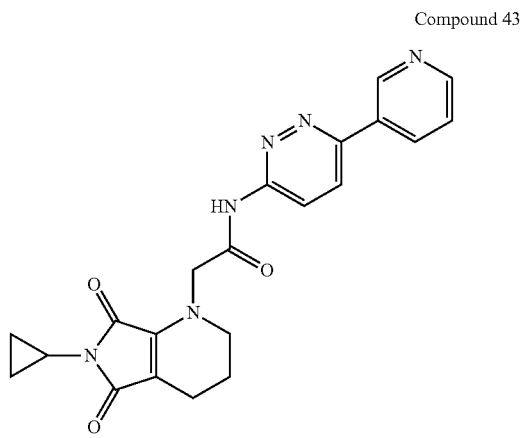 [SMILES: O=C(CN1CCCC2=C1C(=O)N(C1CC1)C2=O)Nc1ccc(-c2cccnc2)nn1]

Compound 43

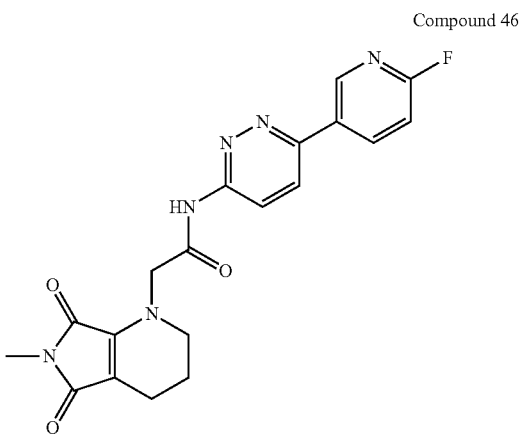 [SMILES: CN1C(=O)C2=C(C1=O)N(CC(=O)Nc1ccc(-c3ccc(F)nc3)nn1)CCC2]

Compound 46

$^1$H NMR (400 MHz, DMSO-d$_6$) δ (ppm): 11.45 (s, 1H), 9.27 (s, 1H), 8.68-8.70 (m, 1H), 8.46-8.49 (m, 1H), 8.31-8.38 (m, 2H), 7.55-7.58 (m, 1H), 4.65 (s, 2H), 3.33 (t, J=5.2 Hz, 2H), 2.35-2.40 (m, 1H), 2.19 (t, J=5.2 Hz, 2H), 1.83 (q, J=5.2 Hz, 2H), 0.66-0.77 (m, 4H).

LC-MS: m/z 405 [M+H$^+$] with a purity of 97.33%.

$^1$H NMR (400 MHz, DMSO-d$_6$) δ (ppm): 11.47 (s, 1H), 8.94 (d, J=2.4 Hz, 1H), 8.71-8.66 (m, 1H), 8.38-8.31 (m, 2H), 7.38-7.36 (m, 1H), 4.67 (s, 2H), 3.33-3-31 (brs, 2H), 2.77 (s, 3H), 2.22 (t, J=6.0 Hz, 2H), 1.88-1.82 (m, 2H).

LC-MS: m/z 397 [M+H$^+$] with a purity of 98.57%.

Synthesis of 2-(6-methyl-5,7-dioxo-2,3,4,5,6,7-hexahydro-1H-pyrrolo[3,4-b]pyridin-1-yl)-N-(6-(6-(trifluoromethyl)pyridin-3-yl)pyridazin-3-yl)acetamide, (Compound 45)

Synthesis of 2-(6-methyl-5,7-dioxo-2,3,4,5,6,7-hexahydro-1H-pyrrolo[3,4-b]pyridin-1-yl)-N-(6-(5-(trifluoromethyl)pyridin-3-yl)pyridazin-3-yl)acetamide, (Compound 48)

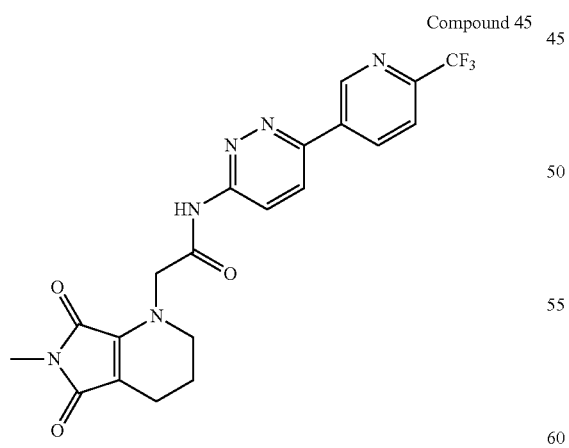

Compound 45

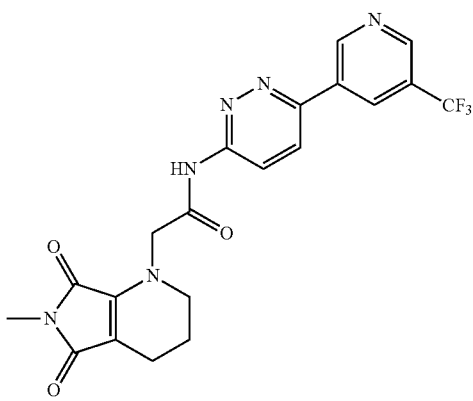

Compound 48

$^1$H NMR (400 MHz, DMSO-d$_6$) δ (ppm): 11.56 (br s, 1H), 9.46 (d, J=2.0 Hz, 1H), 8.77-8.75 (m, 1H), 8.45-8.40 (m, 2H), 8.08 (d, J=8.4 Hz, 2H), 4.68 (s, 2H), 3.37-3.31 (m, 2H), 2.77 (s, 3H), 2.22 (t, J=6.0 Hz, 2H), 1.88-1.84 (m, 2H).

LC-MS: m/z 447 [M+H$^+$] with a purity of 97.81%.

$^1$H NMR (400 MHz, DMSO-d$_6$) δ (ppm): 11.52 (br s, 1H), 9.58 (d, J=2.0 Hz, 1H), 9.10 (d, J=1.2 Hz, 1H), 8.83 (s, 1H), 8.51-8.48 (m, 1H), 8.42-8.39 (m, 1H), 4.68 (s, 2H), 3.37-3.34 (m, 2H), 2.77 (s, 3H), 2.22 (t, J=6.0 Hz, 2H), 1.87-1.84 (m, 2H)

LC-MS: m/z 447 [M+H$^+$] with a purity of 98.04%.

Synthesis of 2-(6-methyl-5,7-dioxo-2,3,4,5,6,7-hexahydro-1H-pyrrolo[3,4-b]pyridin-1-yl)-N-(6-(4-(trifluoromethyl)phenyl)pyridazin-3-yl)acetamide, (Compound 49)

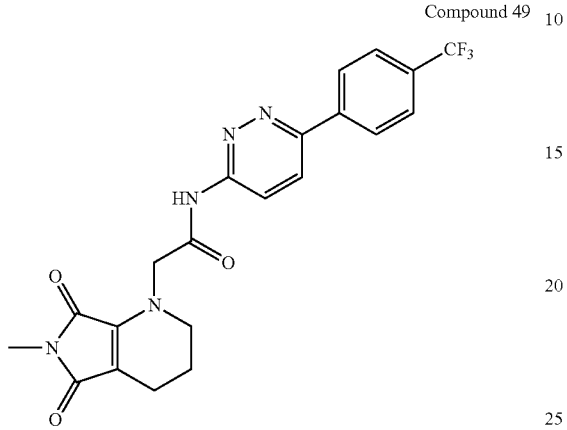

Compound 49

¹H NMR (400 MHz, DMSO-d₆) δ (ppm): 11.51 (br s, 1H), 8.40-8.33 (m, 4H), 7.92-7.89 (m, 1H), 4.67 (s, 2H), 3.37-3.34 (m, 2H), 2.77 (s, 3H), 2.22 (t, J=6.0 Hz, 2H), 1.87-1.84 (m, 2H)

LC-MS: m/z 446 [M+H⁺] with a purity of 98.25%.

Synthesis of 2-(6-methyl-5,7-dioxo-2,3,4,5,6,7-hexahydro-1H-pyrrolo[3,4-b]pyridin-1-yl)-N-(6-(3-(trifluoromethyl)phenyl)pyridazin-3-yl)acetamide, (Compound 50)

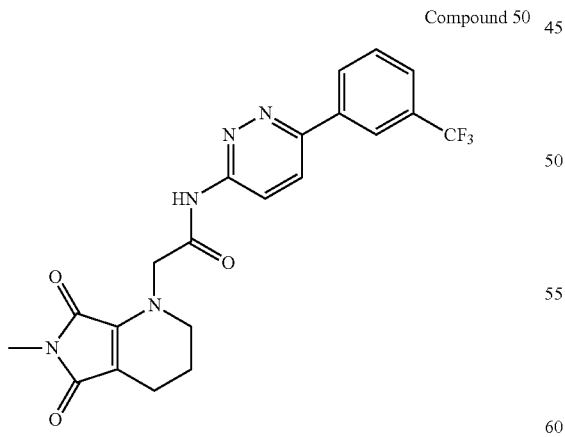

Compound 50

¹H NMR (400 MHz, DMSO-d₆) δ (ppm): 11.50 (br s, 1H), 8.45-8.38 (m, 4H), 7.88-7.86 (m, 1H), 7.81-7.77 (m, 1H), 4.67 (s, 2H), 3.37-3.34 (m, 2H), 2.77 (s, 3H), 2.22 (t, J=6.0 Hz, 2H), 1.87-1.84 (m, 2H).

LC-MS: m/z 446 [M+H⁺] with a purity of 97.15%.

Synthesis of N-(3,3'-bipyridin-6-yl)-2-(6-methyl-4,5,7-trioxo-4,5,6,7-tetrahydro-1H-pyrrolo[3,4-b]pyridin-1-yl)acetamide, (Compound 63)

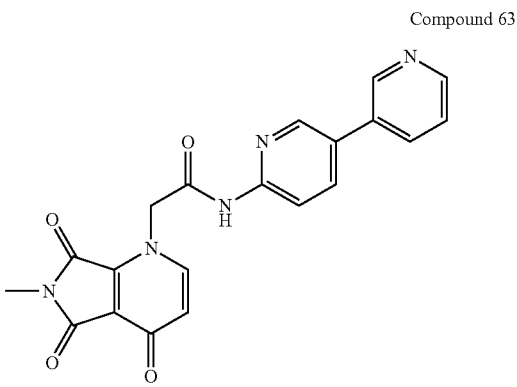 [SMILES: CN1C(=O)c2c(n(CC(=O)Nc3ccc(-c4cccnc4)cn3)ccc2=O)C1=O]

Compound 63

¹H NMR (400 MHz, DMSO-d₆) δ (ppm): 10.96 (s, 1H), 8.965-8.96 (d, J=2 Hz, 1H), 8.76-8.75 (d, J=2 Hz, 1H), 8.60-8.59 (d, J=3.6 Hz, 1H), 8.21-8.09 (m, 4H), 7.54-7.51 (m, 1H), 7.30-7.28 (d, J=8.4 Hz, 1H), 5.23 (s, 2H), 3.0 (s, 3H).

LC-MS: m/z 390.0 [M+H⁺] with a purity of 94.26%.

Synthesis of 2-(6-cyclopropyl-5,7-dioxo-2,3,4,5,6,7-hexahydro-1H-pyrrolo[3,4-b]pyridin-1-yl)-N-(6-(6-fluoropyridin-3-yl)pyridazin-3-yl)acetamide, (Compound 69)

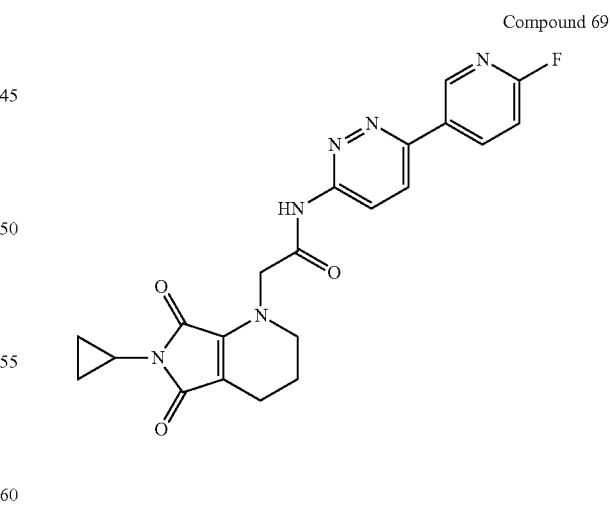

Compound 69

¹H NMR (400 MHz, DMSO-d₆) δ (ppm): 11.46 (s, 1H), 8.94 (s, 1H), 8.66-8.71 (m, 1H), 8.32-8.38 (m, 2H), 7.36-7.39 (m, 1H), 4.65 (s, 2H), 3.33 (t, J=5.2 Hz, 2H), 2.35-2.39 (m, 1H), 2.19 (t, J=5.2 Hz, 2H), 1.83 (q, J=5.2 Hz, 2H), 0.72-0.77 (m, 2H), 0.65-0.68 (m, 2H).

LC-MS: m/z 423 [M+H⁺] with a purity of 98.25%.

Synthesis of (S)-N-([2,3'-bipyridin]-5-yl)-2-(6-methyl-5,7-dioxo-2,3,4,5,6,7-hexahydro-1H-pyrrolo[3,4-b]pyridin-1-yl)propanamide, (Compound 116)

The two isomers was separated by chiral purification gave peak 1 (Compound 116) and peak 2 (Compound 117).

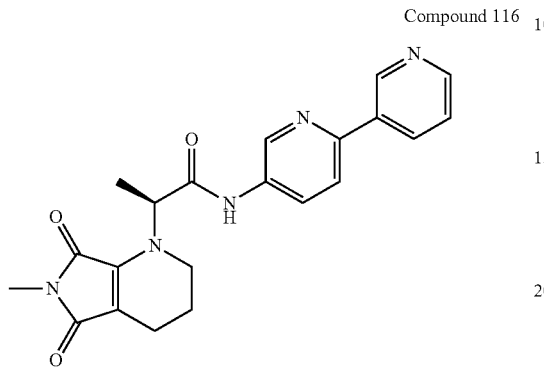

Compound 116

$^1$H NMR (400 MHz, DMSO-d$_6$): 10.27 (s, 1H), 9.22-9.21 (d, J=1.6 Hz, 1H), 8.88-8.87 (d, J=2.4 Hz, 1H), 8.59-8.58 (d, J=3.2 Hz, 1H), 8.39-8.37 (d, J=8.4 Hz, 1H), 8.18-8.15 (d, J$_1$=2 Hz, J$_2$=8.8 Hz, 1H), 8.04-8.02 (d, J=8 Hz, 1H), 7.50-7.47 (m, 1H), 5.72-5.70 (q, J=7.2 Hz, 1H), 3.33-3.29 (m, 2H), 2.81 (s, 3H), 2.23-2.18 (m, 2H), 1.83-1.79 (m, 2H), 1.47-1.45 (d, J=7.2 Hz, 3H).

LC-MS: m/z 391.95 (M+H) with a purity of 99.60%. ee: At 254 nm 98.9%.

Synthesis of (R)-N-([2,3'-bipyridin]-5-yl)-2-(6-methyl-5,7-dioxo-2,3,4,5,6,7-hexahydro-1H-pyrrolo[3,4-b]pyridin-1-yl)propanamide, (Compound 117)

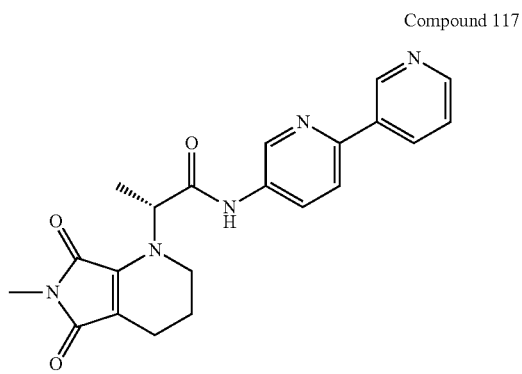 [SMILES: C[C@H](C(=O)Nc1ccc(-c2cccnc2)nc1)N1CCCC2=C1C(=O)N(C)C2=O]

Compound 117

$^1$H NMR (400 MHz, DMSO-d$_6$): 10.27 (s, 1H), 9.22-9.21 (d, J=1.6 Hz, 1H), 8.88-8.87 (d, J=2.4 Hz, 1H), 8.59-8.58 (d, J=3.2 Hz, 1H), 8.39-8.37 (d, J=8.4 Hz, 1H), 8.18-8.15 (d, J$_1$=2 Hz, J$_2$=8.8 Hz, 1H), 8.04-8.02 (d, J=8 Hz, 1H), 7.50-7.47 (m, 1H), 5.72-5.70 (q, J=7.2 Hz, 1H), 3.33-3.29 (m, 2H), 2.81 (s, 3H), 2.23-2.18 (m, 2H), 1.83-1.79 (m, 2H), 1.47-1.45 (d, J=7.2 Hz, 3H).

LC-MS: m/z 392.09 (M+H) with a purity of 99.38%. ee: At 254 nm 94.50%.

Synthesis of 2-(6-cyclopropyl-5,7-dioxo-2,3,4,5,6,7-hexahydro-1H-pyrrolo[3,4-b]pyridin-1-yl)-N-(6-methyl-2,3'-bipyridin-5-yl)acetamide, (Compound 123)

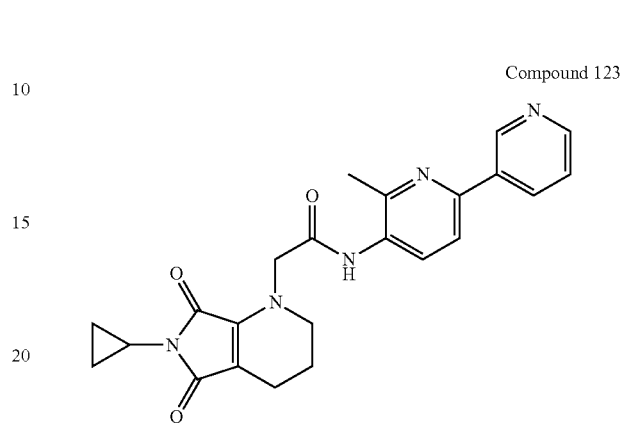

Compound 123

$^1$H NMR (400 MHz, DMSO-d$_6$): 9.69 (s, 1H), 9.22 (s, 1H), 8.60-8.59 (d, J=4 Hz, 1H), 8.40-7.38 (d, J=7.6 Hz, 1H), 7.96-7.94 (d, J=8.4 Hz, 1H), 7.89-7.87 (d, J=8 Hz, 1H), 7.51-7.48 (m, 1H), 4.58 (s, 2H), 3.36-3.29 (m, 2H), 2.52 (s, 3H), 2.49-2.39 (m, 1H), 2.19-2.16 (t, J=6.4 Hz, 2H), 1.85-1.82 (m, 2H), 0.79-0.66 (m, 4H).

LC-MS: m/z 418.14 (M+H) with a purity of 99.62%.

Synthesis of 2-(6-cyclopropyl-5,7-dioxo-2,3,4,5,6,7-hexahydro-1H-pyrrolo[3,4-b]pyridin-1-yl)-N-(3-methyl-2,3'-bipyridin-5-yl)acetamide, (Compound 133)

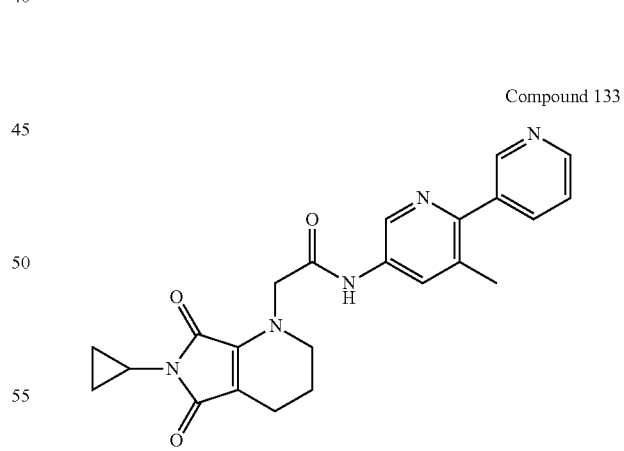

Compound 133

$^1$H NMR (400 MHz, DMSO-d$_6$): 10.37 (s, 1H), 8.73 (s, 1H), 8.65-8.645 (d, J=2 Hz, 1H), 8.60-8.58 (m, 1H), 8.03 (s, 1H), 7.96-7.94 (m, 1H), 7.49-7.46 (m, 1H), 4.55 (s, 2H), 3.34-3.31 (t, J=4.8 Hz, 2H), 2.39-2.36 (m, 1H), 2.34 (s, 3H), 1.85-1.82 (t, J=5.6 Hz, 2H), 1.85-1.82 (m, 2H), 0.76-0.73 (m, 2H), 0.69-0.66 (m, 2H).

LC-MS: m/z 418.14 (M+H) with a purity of 99.08%.

Synthesis of 2-(6-cyclopropyl-5,7-dioxo-2,3,4,5,6,7-hexahydro-1H-pyrrolo[3,4-b]pyridin-1-yl)-N-(2'-fluoro-2,3'-bipyridin-5-yl)acetamide, (Compound 135)

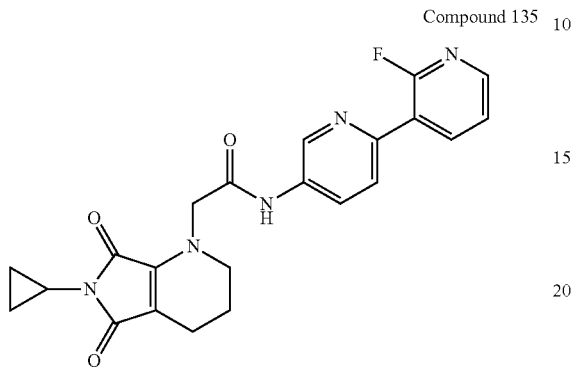

Compound 135

$^1$H NMR (400 MHz, DMSO-d$_6$): 8.758-8.752 (d, J=2.4 Hz, 1H), 8.54-8.49 (m, 1H), 8.26-8.18 (m, 3H), 7.90-7.88 (d, J=7.6 Hz, 1H), 7.34-7.26 (m, 1H), 4.41 (s, 2H), 3.48-3.45 (t, J=5.6 Hz, 2H), 2.49-2.44 (m, 1H), 2.36-2.33 (t, J=6 Hz, 2H), 1.98-1.92 (m, 2H), 0.93-0.84 (m, 4H).

LC-MS: m/z 421.90 (M+H) with a purity of 97.36%.

Synthesis of N-(6-fluoro-2,3'-bipyridin-5-yl)-2-(6-methyl-5,7-dioxo-2,3,4,5,6,7-hexahydro-1H-pyrrolo[3,4-b]pyridin-1-yl)acetamide, (Compound 137)

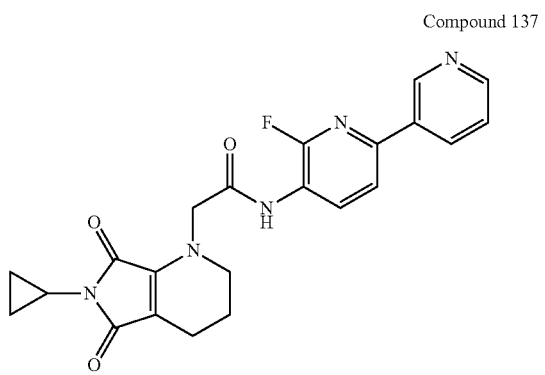 [SMILES: O=C(CN1CCCC2=C1C(=O)N(C1CC1)C2=O)Nc1ccc(-c2cccnc2)nc1F]

Compound 137

$^1$H NMR (400 MHz, CD$_3$OD): 9.16 (s, 1H), 8.67-8.63 (m, 1H), 8.56-8.55 (d, J=4.4 Hz, 1H), 8.44-8.42 (d, J=8 Hz, 1H), 7.88-7.86 (d, J=8.4 Hz, 1H), 7.55-7.52 (m, 1H), 4.79 (s, 2H), 3.34-3.33 (t, J=5.6 Hz, 2H), 2.41-2.36 (m, 1H), 2.30-2.27 (t, J=6.4 Hz, 2H), 1.98-1.92 (m, 2H), 0.91-074 (m, 4H).

LC-MS: m/z 422.18 (M+H) with a purity of 95.03%.

Synthesis of N-(5'-fluoro-3,3'-bipyridin-6-yl)-2-(6-methyl-5,7-dioxo-2,3,4,5,6,7-hexahydro-1H-pyrrolo[3,4-b]pyridin-1-yl)propanamide, (Compound 139)

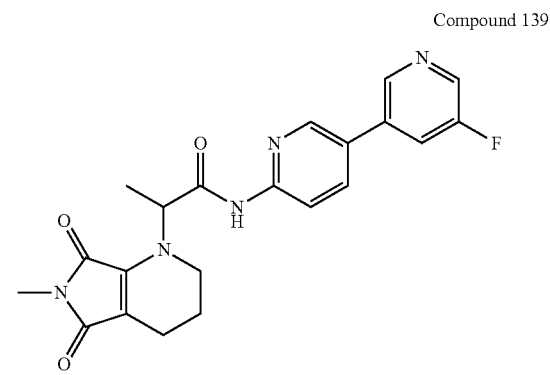 [SMILES: CC(C(=O)Nc1ccc(-c2cncc(F)c2)cn1)N1CCCC2=C1C(=O)N(C)C2=O]

Compound 139

$^1$H NMR (400 MHz, DMSO-d$_6$): 10.80 (s, 1H), 8.85 (s, 1H), 8.79-8.78 (d, J=2.4 Hz, 1H), 8.59-8.58 (d, J=2.8 Hz, 1H), 8.25-8.22 (dd, J$_1$=2 Hz, J$_2$=8.4 Hz, 1H), 8.16-8.13 (m, 2H), 5.73-5.68 (q, J=6.8 Hz, 1H), 3.32-3.31 (m, 2H), 2.76 (s, 3H), 2.22-2.14 (m, 2H), 1.81-1.80 (m, 2H), 1.47-1.45 (d, J=7.2 Hz, 3H).

LC-MS: m/z 410.12 (M+H) with a purity of 99.41%.

Synthesis of 2-(6-cyclopropyl-5,7-dioxo-2,3,4,5,6,7-hexahydro-1H-pyrrolo[3,4-b]pyridin-1-yl)-N-(4-methyl-2,3'-bipyridin-5-yl)acetamide, (Compound 140)

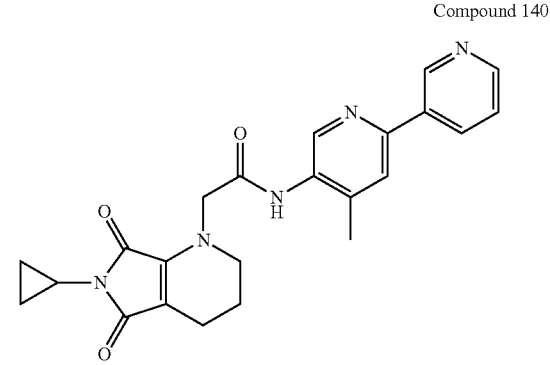 [SMILES: Cc1cc(-c2cccnc2)ncc1NC(=O)CN1CCCC2=C1C(=O)N(C1CC1)C2=O]

Compound 140

$^1$H NMR (400 MHz, DMSO-d$_6$): 9.75 (s, 1H), 9.23 (s, 1H), 8.63 (s, 1H), 8.61-8.60 (m, 1H), 8.41-8.39 (d, J=8 Hz, 1H), 7.97 (s, 1H), 7.51-7.48 (m, 1H), 4.58 (s, 2H), 3.34-3.32 (m, 2H), 2.41-2.37 (m, 1H), 2.31 (s, 3H), 2.19-2.16 (t, J=6 Hz, 2H), 1.84 (m, 2H), 0.80-0.75 (m, 2H), 0.70-0.68 (m, 2H).

LC-MS: m/z 418.14 (M+H) with a purity of 96.62%.

Synthesis of N-(5'-fluoro-3,3'-bipyridin-6-yl)-2-(6-methyl-5,7-dioxo-2,3,4,5,6,7-hexahydro-1H-pyrrolo[3,4-b]pyridin-1-yl)acetamide, (Compound 143)

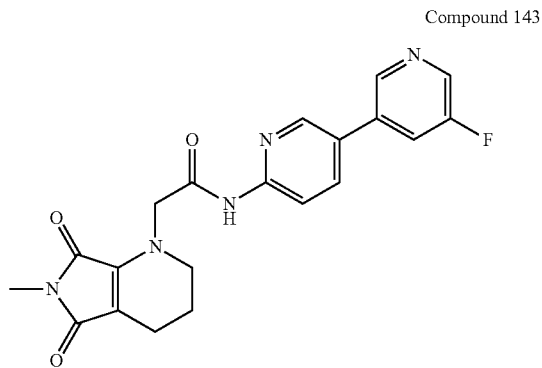 [SMILES: CN1C(=O)C2=C(C1=O)N(CC(=O)Nc1ccc(-c3cncc(F)c3)cn1)CCC2]

Compound 143

¹H NMR (400 MHz, DMSO-d$_6$): 10.87 (s, 1H), 8.86 (s, 1H), 8.80-8.79 (d, J=2 Hz, 1H), 8.59-8.58 (d, J=2.8 Hz, 1H), 8.25-8.22 (m, 1H), 8.17-8.11 (m, 2H), 4.61 (s, 2H), 3.36-3.32 (m, 2H), 2.77 (s, 3H), 2.23-2.20 (t, J=5.6 Hz, 2H), 1.86-1.83 (m, 2H).

LC-MS: m/z 396.11 (M+H) with a purity of 98.40%.

Synthesis of 2-(6-cyclopropyl-5,7-dioxo-2,3,4,5,6,7-hexahydro-1H-pyrrolo[3,4-b]pyridin-1-yl)-N-(5'-methoxy-2,3'-bipyridin-5-yl)acetamide, (Compound 144)

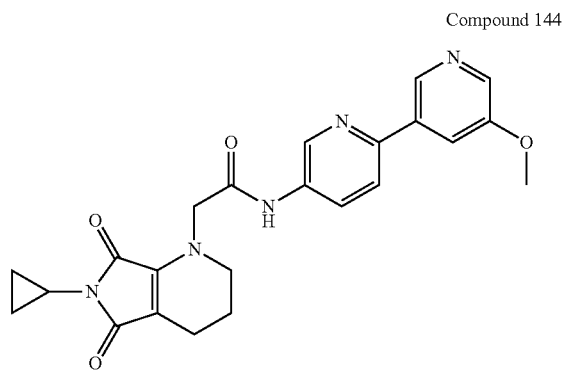 [SMILES: COc1cncc(-c2ccc(NC(=O)CN3CCCC4=C3C(=O)N(C3CC3)C4=O)cn2)c1]

Compound 144

¹H NMR (400 MHz, DMSO-d$_6$): 11.46 (s, 1H), 8.83-8.82 (d, J=2 Hz, 2H), 8.31-8.30 (d, J=2.8 Hz, 1H), 8.18-8.15 (m, 1H), 8.07-8.05 (d, J=8.8 Hz, 1H), 7.94-7.93 (m, 1H), 4.56 (s, 2H), 3.91 (s, 3H), 3.35-3.32 (t, J=5.2 Hz, 2H), 2.39-2.36 (m, 1H), 2.20-2.18 (t, J=6 Hz, 2H), 1.85-1.83 (m, 2H), 0.78-0.73 (m, 2H), 0.69-0.66 (m, 2H).

LC-MS: m/z 434.17 (M+H) with a purity of 97.21%.

Synthesis of 2-(6-cyclopropyl-5,7-dioxo-2,3,4,5,6,7-hexahydro-1H-pyrrolo[3,4-b]pyridin-1-yl)-N-(6'-methoxy-2,3'-bipyridin-5-yl)acetamide, (Compound 145)

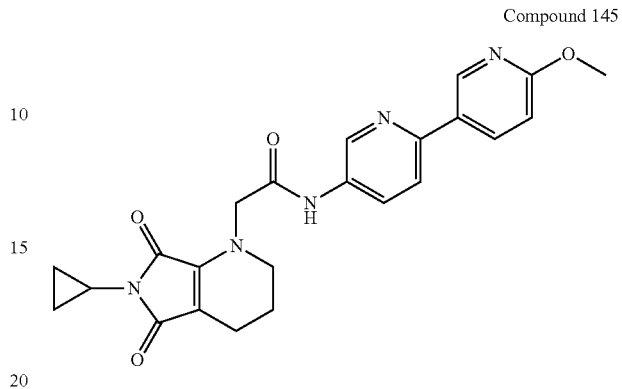

Compound 145

¹H NMR (400 MHz, DMSO-d$_6$): 10.39 (s, 1H), 8.82-8.81 (d, J=2 Hz, 1H), 8.786-8.780 (d, J=2.4 Hz, 1H), 8.34-8.31 (dd, J$_1$=2.4 Hz, J$_2$=8.4 Hz, 1H), 8.11-8.09 (dd, J$_1$=2.4 Hz, J$_2$=8.4 Hz, 1H), 7.93-7.91 (d, J=8.8 Hz, 1H), 6.92-6.89 (d, J=8.4 Hz, 1H), 4.55 (s, 2H), 3.90 (s, 3H), 3.34-3.31 (m, 2H), 2.40-2.35 (m, 1H), 2.20-2.17 (t, J=6 Hz, 2H), 1.85-1.82 (m, 2H), 0.76-0.71 (m, 2H), 0.69-0.65 (m, 2H).

LC-MS: m/z 434.13 (M+H) with a purity of 98.82%.

Synthesis of 2-(6-cyclopropyl-5,7-dioxo-2,3,4,5,6,7-hexahydro-1H-pyrrolo[3,4-b]pyridin-1-yl)-N-(5'-methoxy-3,3'-bipyridin-6-yl)acetamide, (Compound 147)

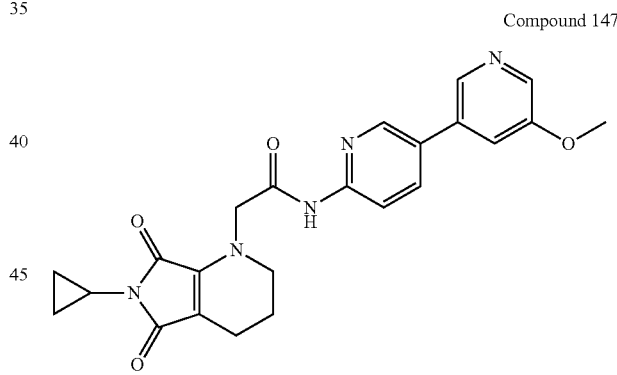

Compound 147

¹H NMR (400 MHz, DMSO-d$_6$): 10.82 (s, 1H), 8.76-8.75 (d, J=2 Hz, 1H), 8.538-8.534 (d, J=1.6 Hz, 1H), 8.30-8.29 (d, J=3.6 Hz 1H), 8.22-8.19 (m, 1H), 8.12-8.10 (d, J=8.8 Hz, 1H), 7.70 (s, 1H), 4.59 (s, 2H), 3.91 (s, 3H), 3.31-3.29 (m, 2H), 2.39-2.37 (m, 1H), 2.20-2.17 (t, J=6 Hz, 2H), 1.84-1.82 (m, 2H), 0.77-0.71 (m, 2H), 0.69-0.65 (m, 2H).

LC-MS: m/z 434.13 (M+H⁺) with a purity of 96.03%.

Amide Coupling Method B:

A solution of 2-(6-methyl-5, 7-dioxo-2,3,4,5,6,7-hexahydro-1H-pyrrolo[3,4-b]pyridin-1-yl)acetic acid, 1 (1.0 equiv.) and anhydrous N,N-Diisopropylethylamine (DIPEA) (1.5 equiv.), in anhydrous N,N-Dimethylformamide (DMF) (0.1 M) was treated with N-(3-Dimethylaminopropyl)-N'-ethylcarbodiimide hydrochloride (EDC)(1.5 equiv.), 1-Hydroxybenzotriazole hydrate (HOBt) (1.5 equiv.) and biarylamine, 2 (1.1 equiv.). The mixture was stirred for 18 h at room temperature under nitrogen atmosphere and partitioned between DCM and water. The organic phase was separated, washed with brine, dried over Na$_2$SO$_4$ and concentrated under vacuum. The residue was purified using reverse phase chromatography to afford desired product.

Synthesis of 2-(6-methyl-5,7-dioxo-2,3,4,5,6,7-hexahydro-1H-pyrrolo[3,4-b]pyridin-1-yl)-N-(4-(thiazol-2-yl)phenyl)acetamide, (Compound 2)

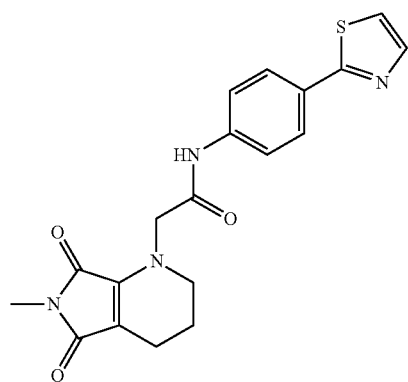

Compound 2

$^1$H NMR (400 MHz, METHANOL-d$_4$) δ (ppm): 7.90 (d, J=8.4 Hz, 2H), 7.83 (d, J=3.6 Hz, 2H), 7.69 (d, J=8.4 Hz, 2H), 7.55 (d, J=3.6 Hz, 2H), 4.60 (s, 2H), 4.55 (bs, 2H), 3.39 (t, J=5.6 Hz, 2H), 2.87 (s, 3H), 2.32 (t, J=5.6 Hz, 2H), 1.97 (q, J=5.6 Hz, 2H).
LC-MS: m/z 383 [M+H$^+$] with a purity of 95.50%.

Amide Coupling Method C:

A solution of biarylamine, 2 (1 equiv.) and 2-(6-methyl-5,7-dioxo-2,3,4,5,6,7-hexahydro-1H-pyrrolo[3,4-b]pyridin-1-yl)acetic acid, 1 (1.1 equiv.) in pyridine (0.1 M) was cooled to 0° C. under nitrogen atmosphere and treated with POCl$_3$ (3 equiv.). The reaction mixture stirred for 45 min. After consumption of starting material, the reaction mixture was quenched with saturated sodium bicarbonate and extracted with DCM. The combined organic layers were washed with brine, dried over Na$_2$SO$_4$ and concentrated under vacuum. The crude compound was purified by reversed phase chromatography to afford desired product.

Synthesis of 2-(6-methyl-5,7-dioxo-2,3,4,5,6,7-hexahydro-1H-pyrrolo[3,4-b]pyridin-1-yl)-N-(6-phenylpyridazin-3-yl)acetamide, (Compound 3)

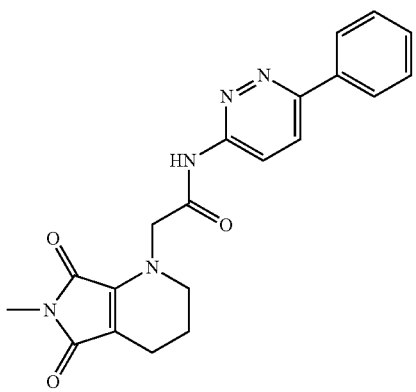

Compound 3

$^1$H NMR (400 MHz, METHANOL-d$_4$) δ (ppm): 8.47-8.49 (m, 1H), 8.10-8.13 (m, 1H), 8.00-8.02 (m, 2H), 7.49-7.55 (m, 3H), 4.70 (s, 2H), 4.55 (s, 1H), 3.42 (t, J=5.6 Hz, 2H), 2.86 (s, 3H), 2.32 (t, J=5.6 Hz, 2H), 1.98 (q, J=5.6 Hz, 2H).
LC-MS: m/z 378 [M+H$^+$] with a purity of 96.77%.

Synthesis of N-(6-(4-fluorophenyl)pyridazin-3-yl)-2-(6-methyl-5,7-dioxo-2,3,4,5,6,7-hexahydro-1H-pyrrolo[3,4-b]pyridin-1-yl)acetamide, (Compound 4)

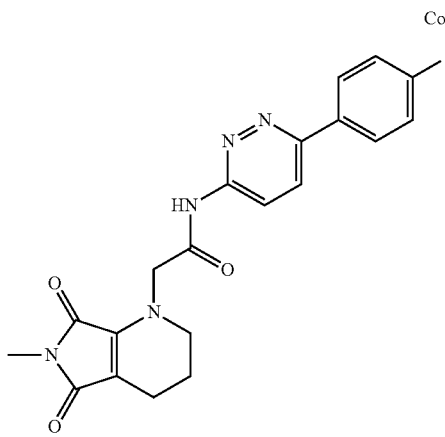

Compound 4

$^1$H NMR (400 MHz, METHANOL-d$_4$) δ (ppm): 8.46-8.48 (m, 1H), 8.09-8.11 (m, 1H), 8.05-8.08 (m, 2H), 7.24-7.29 (m, 2H), 4.70 (s, 2H), 4.55 (s, 1H), 3.41 (t, J=5.6 Hz, 2H), 2.86 (s, 3H), 2.32 (t, J=5.6 Hz, 2H), 1.98 (q, J=5.6 Hz, 2H).
LC-MS: m/z 396 [M+H$^+$] with a purity of 98.38%.

Synthesis of 2-(6-methyl-5,7-dioxo-2,3,4,5,6,7-hexahydro-1H-pyrrolo[3,4-b]pyridin-1-yl)-N-(5-phenylpyridin-2-yl)acetamide, (Compound 5)

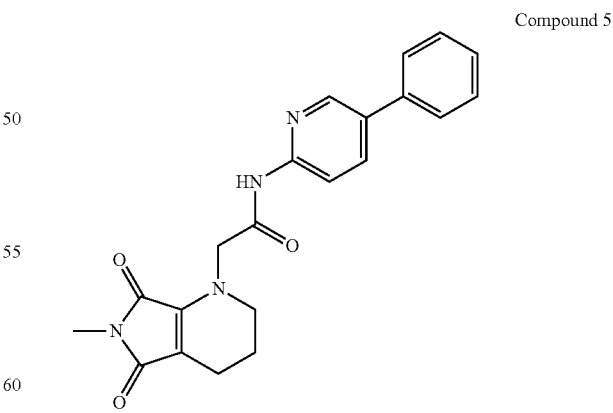

Compound 5

$^1$H NMR (400 MHz, DMSO-d$_6$) δ (ppm): 10.77 (s, 1H), 8.65 (s, 1H), 8.09 (bs, 2H), 7.69-7.71 (m, 2H), 7.46-7.49 (m, 2H), 7.36-7.40 (m, 1H), 4.60 (s, 2H), 3.42 (t, J=6.0 Hz, 2H), 2.76 (s, 3H), 2.21 (t, J=6.0 Hz, 2H), 1.84 (q, J=6.0 Hz, 2H).
LC-MS: m/z 377 [M+H$^+$] with a purity of 98.85%.

Synthesis of 2-(6-methyl-5,7-dioxo-2,3,4,5,6,7-hexahydro-1H-pyrrolo[3,4-b]pyridin-1-yl)-N-(5-(thiazol-2-yl)pyridin-2-yl)acetamide, (Compound 6)

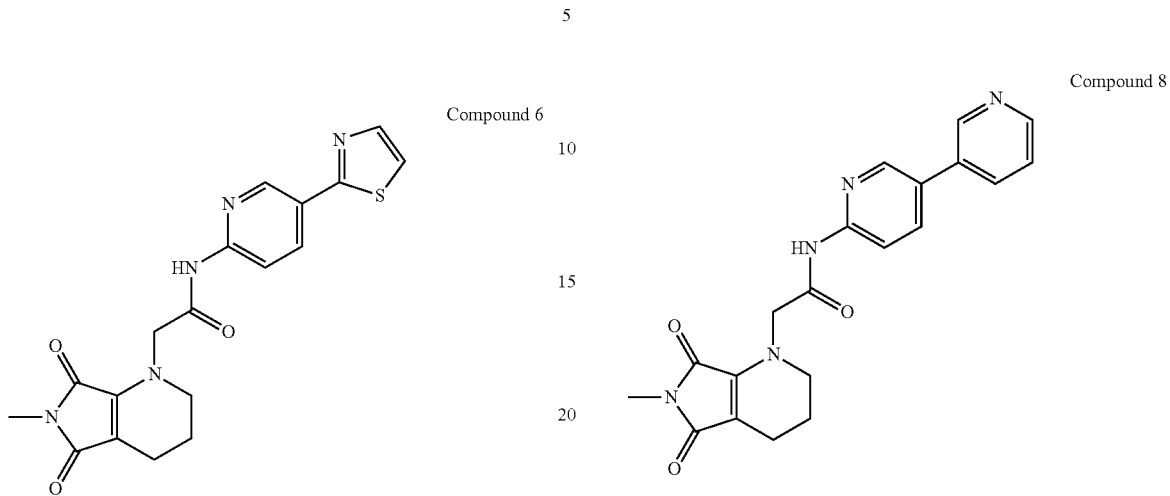

Compound 6

¹H NMR (400 MHz, METHANOL-d₄) δ (ppm): 8.88-8.89 (m, 1H), 8.27-8.29 (m, 1H), 8.18-8.20 (m, 1H), 7.89 (d, J=3.2 Hz, 1H), 7.63 (d, J=3.2 Hz, 1H), 4.64 (s, 2H), 3.40 (t, J=5.6 Hz, 2H), 2.86 (s, 3H), 2.32 (t, J=5.6 Hz, 2H), 1.97 (q, J=5.6 Hz, 2H).

LC-MS: m/z 384 [M+H⁺] with a purity of 98.65%.

Synthesis of N-(5-(4-fluorophenyl)pyridin-2-yl)-2-(6-methyl-5,7-dioxo-2,3,4,5,6,7-hexahydro-1H-pyrrolo[3,4-b]pyridin-1-yl)acetamide, (Compound 7)

Compound 7

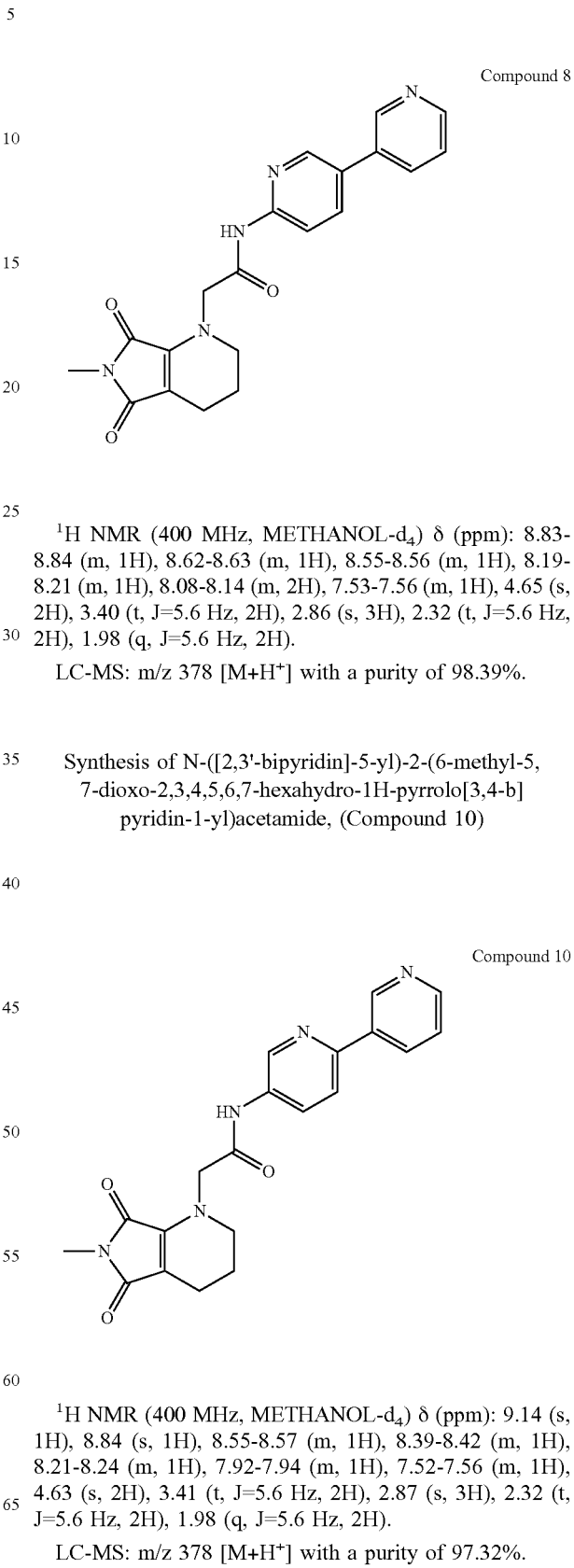

¹H NMR (400 MHz, METHANOL-d₄) δ (ppm): 8.53-8.54 (m, 1H), 8.11-8.14 (m, 1H), 7.98-8.01 (m, 1H), 7.63-7.66 (m, 2H), 7.18-7.22 (m, 2H), 4.64 (s, 2H), 3.40 (t, J=5.6 Hz, 2H), 2.86 (s, 3H), 2.32 (t, J=5.6 Hz, 2H), 1.97 (q, J=5.6 Hz, 2H).

LC-MS: m/z 395 [M+H⁺] with a purity of 98.05%.

Synthesis of N-([3,3'-bipyridin]-6-yl)-2-(6-methyl-5,7-dioxo-2,3,4,5,6,7-hexahydro-1H-pyrrolo[3,4-b]pyridin-1-yl)acetamide, (Compound 8)

Compound 8

¹H NMR (400 MHz, METHANOL-d₄) δ (ppm): 8.83-8.84 (m, 1H), 8.62-8.63 (m, 1H), 8.55-8.56 (m, 1H), 8.19-8.21 (m, 1H), 8.08-8.14 (m, 2H), 7.53-7.56 (m, 1H), 4.65 (s, 2H), 3.40 (t, J=5.6 Hz, 2H), 2.86 (s, 3H), 2.32 (t, J=5.6 Hz, 2H), 1.98 (q, J=5.6 Hz, 2H).

LC-MS: m/z 378 [M+H⁺] with a purity of 98.39%.

Synthesis of N-([2,3'-bipyridin]-5-yl)-2-(6-methyl-5,7-dioxo-2,3,4,5,6,7-hexahydro-1H-pyrrolo[3,4-b]pyridin-1-yl)acetamide, (Compound 10)

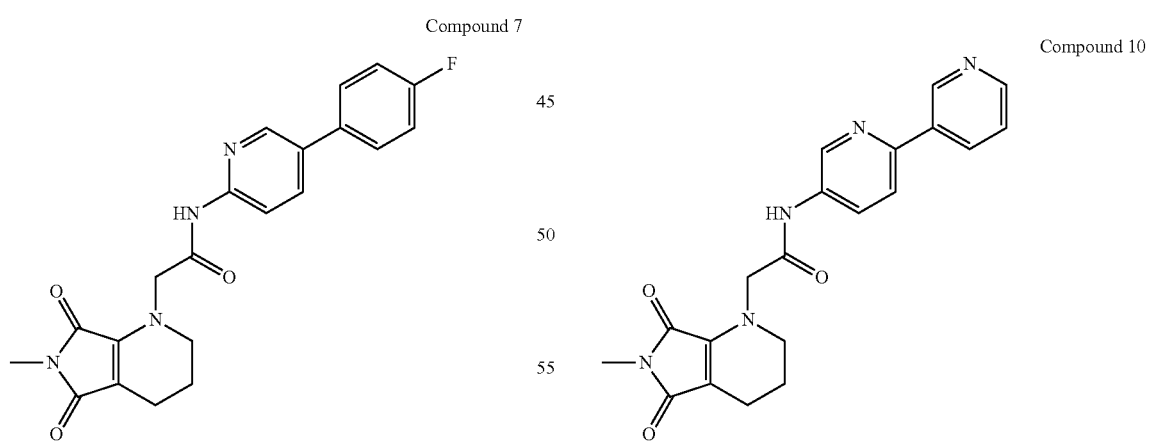

Compound 10

¹H NMR (400 MHz, METHANOL-d₄) δ (ppm): 9.14 (s, 1H), 8.84 (s, 1H), 8.55-8.57 (m, 1H), 8.39-8.42 (m, 1H), 8.21-8.24 (m, 1H), 7.92-7.94 (m, 1H), 7.52-7.56 (m, 1H), 4.63 (s, 2H), 3.41 (t, J=5.6 Hz, 2H), 2.87 (s, 3H), 2.32 (t, J=5.6 Hz, 2H), 1.98 (q, J=5.6 Hz, 2H).

LC-MS: m/z 378 [M+H⁺] with a purity of 97.32%.

Synthesis of 2-(6-methyl-5,7-dioxo-2,3,4,5,6,7-hexahydro-1H-pyrrolo[3,4-b]pyridin-1-yl)-N-(5-phenylpyrazin-2-yl)acetamide, (Compound 12)

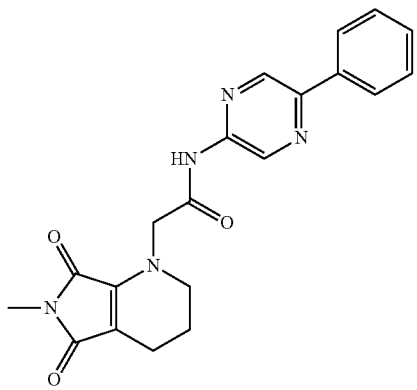

Comound 12

$^1$H NMR (400 MHz, METHANOL-d$_4$) δ (ppm): 9.37 (s, 1H), 8.83 (s, 1H), 8.00-8.02 (m, 2H), 7.42-7.52 (m, 3H), 4.67 (s, 2H), 3.41 (t, J=5.6 Hz, 2H), 2.87 (s, 3H), 2.33 (t, J=5.6 Hz, 2H), 1.98 (q, J=5.6 Hz, 2H).

LC-MS: m/z 378 [M+H$^+$] with a purity of 99.58%.

Synthesis of N-([3,3'-bipyridin]-6-yl)-2-(6-cyclopropyl-5,7-dioxo-2,3,4,5,6,7-hexahydro-1 H-pyrrolo[3,4-b]pyridin-1-yl)acetamide, (Compound 14)

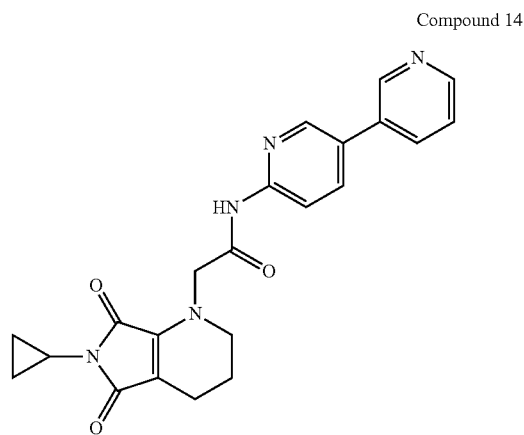 [SMILES: O=C(CN1CCCC2=C1C(=O)N(C1CC1)C2=O)Nc1ccc(-c2cccnc2)cn1]

Compound 14

$^1$H NMR (400 MHz, METHANOL-d$_4$) δ (ppm): 8.83 (s, 1H), 8.62 (s, 1H), 8.54-8.56 (m, 1H), 8.19-8.21 (m, 1H), 8.08-8.14 (m, 2H), 7.53-7.56 (m, 1H), 4.63 (s, 2H), 3.39 (t, J=5.6 Hz, 2H), 2.36-2.42 (m, 1H), 2.29 (t, J=5.6 Hz, 2H), 1.96 (q, J=5.6 Hz, 2H), 0.76-0.82 (m, 4H).

LC-MS: m/z 404 [M+H$^+$] with a purity of 98.50%.

Synthesis of 2-(6-cyclopropyl-5,7-dioxo-2,3,4,5,6,7-hexahydro-1H-pyrrolo[3,4-b]pyridin-1-yl)-N-(5-(2-methylthiazol-4-yl)pyridin-2-yl)acetamide, (Compound 15)

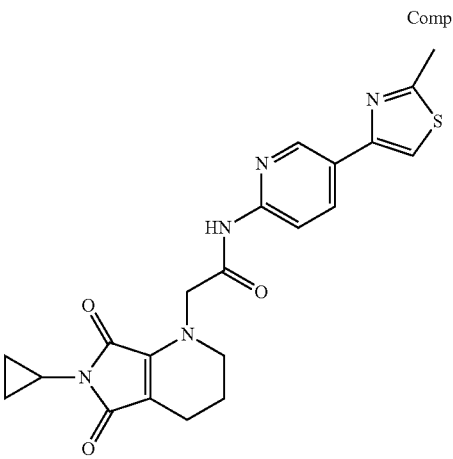

Compound 15

$^1$H NMR (400 MHz, METHANOL-d$_4$) δ (ppm): 8.83 (s, 1H), 8.21-8.24 (m, 1H), 8.10-8.12 (m, 1H), 7.70 (s, 1H), 4.62 (s, 2H), 3.38 (t, J=5.6 Hz, 2H), 2.76 (s, 3H), 2.36-2.42 (m, 1H), 2.29 (t, J=5.6 Hz, 2H), 1.96 (q, J=5.6 Hz, 2H), 0.77-0.81 (m, 4H).

LC-MS: m/z 424 [M+H$^+$] with a purity of 98.63%.

Synthesis of N-([2,3'-bipyridin]-6'-yl)-2-(6-cyclopropyl-5,7-dioxo-2,3,4,5,6,7-hexahydro-1H-pyrrolo[3,4-b]pyridin-1-yl)acetamide, (Compound 16)

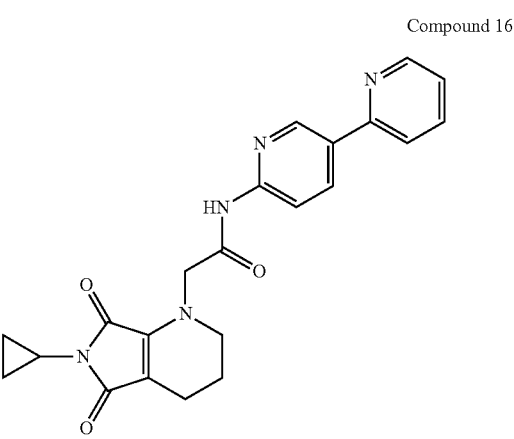 [SMILES: O=C(CN1CCCC2=C1C(=O)N(C1CC1)C2=O)Nc1ccc(-c2ccccn2)cn1]

Compound 16

$^1$H NMR (400 MHz, METHANOL-d$_4$) δ (ppm): 8.89-8.90 (m, 1H), 8.62-8.64 (m, 1H), 8.33-8.36 (m, 1H), 8.17-8.19 (m, 1H), 7.87-7.93 (m, 2H), 7.36-7.39 (m, 1H), 4.63 (s, 2H), 3.39 (t, J=5.6 Hz, 2H), 2.36-2.42 (m, 1H), 2.30 (t, J=5.6 Hz, 2H), 1.96 (q, J=5.6 Hz, 2H), 0.76-0.82 (m, 4H).

LC-MS: m/z 404 [M+H$^+$] with a purity of 98.81%.

Synthesis of N-(3-(3-chlorophenyl)isoxazol-5-yl)-2-(6-methyl-5,7-dioxo-2,3,4,5,6,7-hexahydro-1H-pyrrolo[3,4-b]pyridin-1-yl)propanamide, (Compound 18)

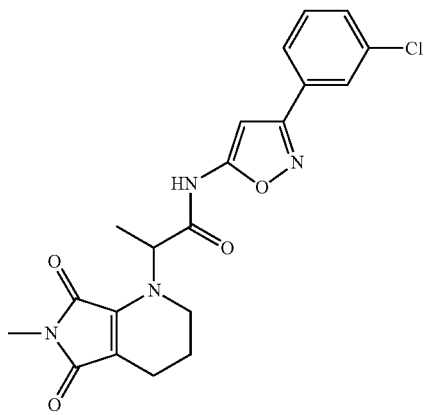

Compound 18

¹H NMR (400 MHz, METHANOL-d₄) δ (ppm): 7.83 (brs, 1H), 7.72-7.75 (m, 1H), 7.47-7.48 (m, 2H), 6.74 (s, 1H), 5.83 (q, J=7.2 Hz, 1H), 2.88 (s, 3H), 2.27-2.32 (m, 2H), 1.90-1.93 (m, 2H), 1.52 (d, J=7.2 Hz, 3H).

LC-MS: m/z 415 [M+H⁺] with a purity of 98.63%.

Synthesis of 2-(6-methyl-5,7-dioxo-2,3,4,5,6,7-hexahydro-1H-pyrrolo[3,4-b]pyridin-1-yl)-N-(5-phenylpyrazin-2-yl)propanamide, (Compound 19)

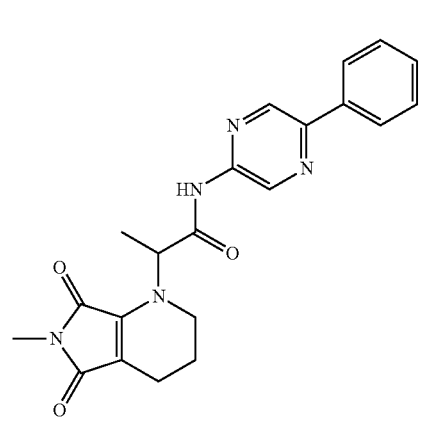

Compound 19

¹H NMR (400 MHz, METHANOL-d₄) δ (ppm): 9.38 (s, 1H), 8.83 (s, 1H), 8.00-8.02 (m, 2H), 7.44-7.52 (m, 3H), 5.83 (q, J=7.2 Hz, 1H), 3.43-3.48 (m, 2H), 2.89 (s, 3H), 2.23-2.38 (m, 2H), 1.89-1.97 (m, 2H), 1.55 (d, J=7.2 Hz, 3H).

LC-MS: m/z 392 [M+H⁺] with a purity of 98.60%.

Synthesis of N-([2,3'-bipyridin]-5-yl)-2-(6-methyl-5,7-dioxo-2,3,4,5,6,7-hexahydro-1H-pyrrolo[3,4-b]pyridin-1-yl)propanamide, (Compound 20)

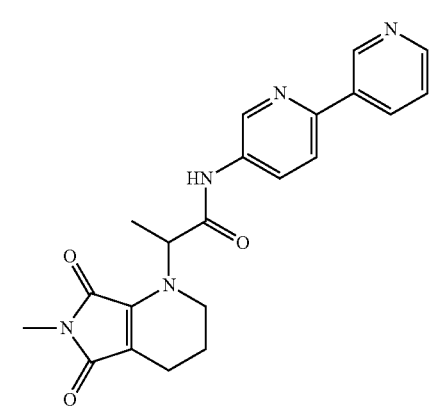

Compound 20

¹H NMR (400 MHz, METHANOL-d₄) δ (ppm): 9.13-9.14 (m, 1H), 8.86-8.87 (m, 1H), 8.55-8.57 (m, 1H), 8.39-8.42 (m, 1H), 8.22-8.25 (m, 1H), 7.91-7.94 (m, 1H), 7.52-7.56 (m, 1H), 5.82 (q, J=7.2 Hz, 1H), 3.41-3.44 (m, 2H), 2.89 (s, 3H), 2.25-2.37 (m, 2H), 1.89-1.94 (m, 2H), 1.53 (d, J=7.2 Hz, 3H).

LC-MS: m/z 392 [M+H⁺] with a purity of 98.21%.

Synthesis of 2-(6-methyl-5,7-dioxo-2,3,4,5,6,7-hexahydro-1H-pyrrolo[3,4-b]pyridin-1-yl)-N-(5-(pyridin-3-yl)pyrazin-2-yl)acetamide, (Compound 21)

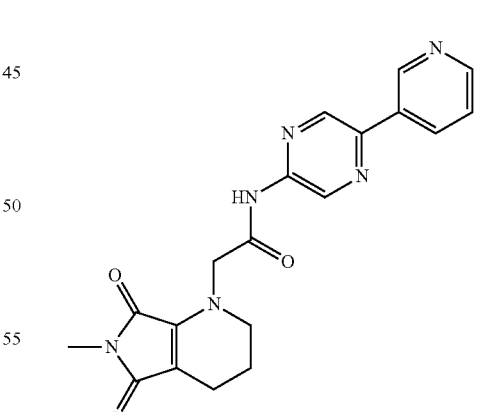

Compound 21

¹H NMR (400 MHz, DMSO-d₆) δ (ppm): 11.15 (brs, 1H), 9.35 (s, 1H), 9.26-9.27 (m, 1H), 9.09-9.10 (m, 1H), 8.64-8.65 (m, 1H), 8.42-8.45 (m, 1H), 7.52-7.55 (m, 1H), 4.65 (s, 2H), 3.31 (t, J=5.6 Hz, 2H), 2.77 (s, 3H), 2.22 (t, J=5.6 Hz, 2H), 1.85 (q, J=5.6 Hz, 2H).

LC-MS: m/z 379 [M+H⁺] with a purity of 98.20%.

Synthesis of 2-(6-methyl-5,7-dioxo-2,3,4,5,6,7-hexahydro-1H-pyrrolo[3,4-b]pyridin-1-yl)-N-(5-(pyridin-4-yl)pyrazin-2-yl)acetamide, (Compound 22)

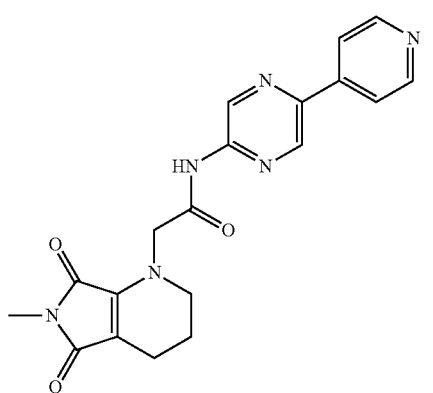

Compound 22

$^1$H NMR (400 MHz, DMSO-d$_6$) δ (ppm): 9.38 (s, 1H), 9.16 (s, 1H), 8.70 (d, J=6.4 Hz, 2H), 8.70 (d, J=6.4 Hz, 2H), 8.06 (d, J=6.4 Hz, 2H), 4.65 (s, 2H), 3.31 (t, J=5.6 Hz, 2H), 2.76 (s, 3H), 2.22 (t, J=5.6 Hz, 2H), 1.85 (q, J=5.6 Hz, 2H).

LC-MS: m/z 379 [M+H$^+$] with a purity of 97.74%.

Synthesis of 2-(6-methyl-5,7-dioxo-2,3,4,5,6,7-hexahydro-1H-pyrrolo[3,4-b]pyridin-1-yl)-N-(5-(pyridin-3-yl)pyrazin-2-yl)propanamide, (Compound 23)

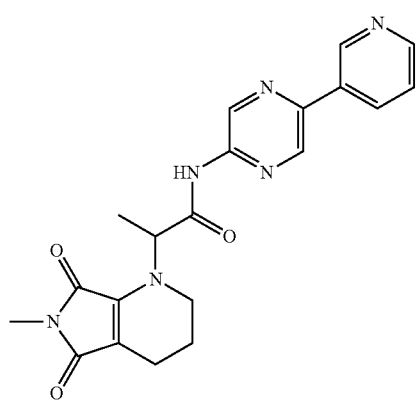

Compound 23

$^1$H NMR (400 MHz, METHANOL-d$_4$) δ (ppm): 9.45 (s, 1H), 9.20 (s, 1H), 8.92 (s, 1H), 8.59-8.61 (m, 1H), 8.47-8.50 (m, 1H), 7.55-7.59 (m, 1H), 5.83 (q, J=7.2 Hz, 1H), 3.44-3.48 (m, 2H), 2.89 (s, 3H), 2.23-2.36 (m, 2H), 1.90-1.97 (m, 2H), 1.56 (d, J=7.2 Hz, 3H).

LC-MS: m/z 393 [M+H$^+$] with a purity of 98.93%.

Synthesis of 2-(6-methyl-5,7-dioxo-2,3,4,5,6,7-hexahydro-1H-pyrrolo[3,4-b]pyridin-1-yl)-N-(6'-methyl-[2,3'-bipyridin]-5-yl)acetamide, (Compound 24)

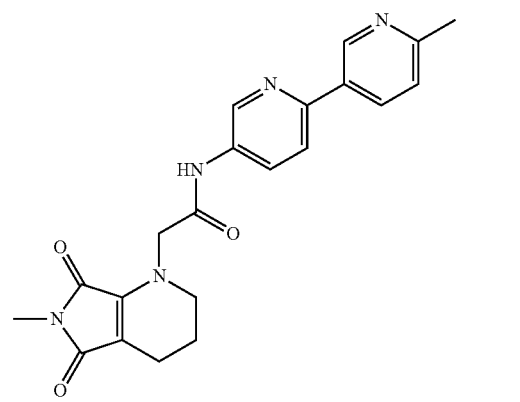

Compound 24

$^1$H NMR (400 MHz, DMSO-d$_6$) δ (ppm): 10.46 (s, 1H), 9.08 (s, 1H), 8.80 (s, 1H), 8.25-8.28 (m, 1H), 8.12-8.15 (m, 1H), 7.96-7.99 (m, 1H), 7.33-7.35 (m, 1H), 4.58 (s, 2H), 3.31 (t, J=5.6 Hz, 2H), 2.77 (s, 3H), 2.22 (t, J=5.6 Hz, 2H), 1.85 (q, J=5.6 Hz, 2H).

LC-MS: m/z 393 [M+H$^+$] with a purity of 96.99%.

Synthesis of 2-(6-methyl-5,7-dioxo-2,3,4,5,6,7-hexahydro-1H-pyrrolo[3,4-b]pyridin-1-yl)-N-(6-(pyridin-3-yl)pyridazin-3-yl)acetamide, (Compound 25)

Compound 25

$^1$H NMR (400 MHz, DMSO-d$_6$) δ (ppm): 11.47 (brs, 1H), 9.27 (s, 1H), 8.68-8.70 (m, 1H), 8.46-8.49 (m, 1H), 8.31-8.38 (m, 2H), 7.55-7.59 (m, 1H), 4.67 (s, 2H), 3.31 (t, J=5.6 Hz, 2H), 2.77 (s, 3H), 2.22 (t, J=5.6 Hz, 2H), 1.85 (q, J=5.6 Hz, 2H).

LC-MS: m/z 379 [M+H$^+$] with a purity of 96.37%.

Synthesis of 2-(6-cyclopropyl-5,7-dioxo-2,3,4,5,6,7-hexahydro-1H-pyrrolo[3,4-b]pyridin-1-yl)-N-(5-(pyridin-3-yl)pyrazin-2-yl)acetamide, (Compound 26)

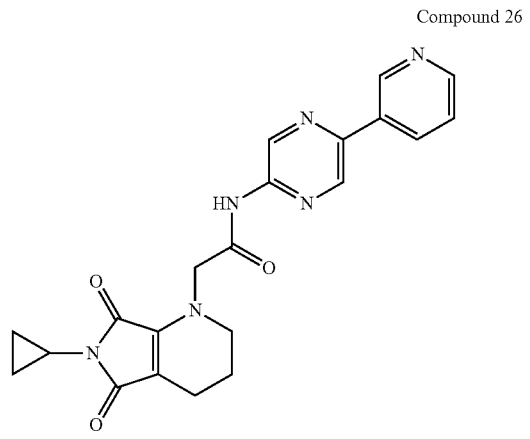 [SMILES: O=C(CN1CCCC2=C1C(=O)N(C1CC1)C2=O)Nc1cnc(-c2cccnc2)cn1]

Compound 26

¹H NMR (400 MHz, METHANOL-d₄) δ (ppm): 9.43 (s, 1H), 9.19-9.20 (m, 1H), 8.92 (s, 1H), 8.59-8.61 (m, 1H), 8.46-8.49 (m, 1H), 7.56-7.59 (m, 1H), 4.66 (s, 2H), 3.40 (t, J=5.6 Hz, 2H), 2.36-2.41 (m, 1H), 2.30 (t, J=5.6 Hz, 2H), 1.97 (q, J=5.6 Hz, 2H), 0.79-0.82 (m, 2H), 0.73-0.77 (m, 2H).

LC-MS: m/z 405 [M+H⁺] with a purity of 96.05%.

Synthesis of 2-(6-methyl-5,7-dioxo-2,3,4,5,6,7-hexahydro-1H-pyrrolo[3,4-b]pyridin-1-yl)-N-(6-(o-tolyl)pyridazin-3-yl)acetamide, (Compound 27)

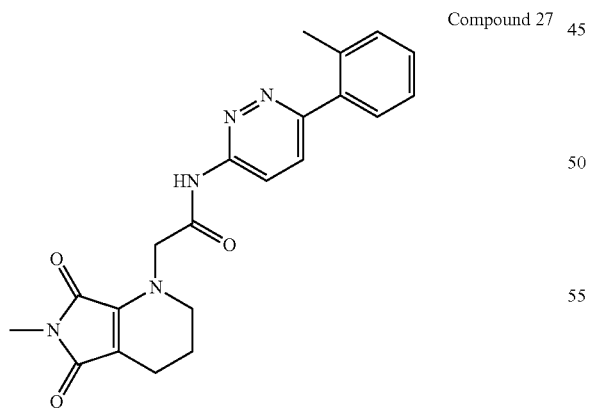

Compound 27

¹H NMR (400 MHz, METHANOL-d₄) δ (ppm): 8.48 (d, J=9.2 Hz, 1H), 7.78 (d, J=9.2 Hz, 1H), 7.30-7.40 (m, 4H), 4.70 (s, 2H), 3.42 (t, J=5.6 Hz, 2H), 2.87 (s, 3H), 2.32 (s, 3H), 2.32 (t, J=5.6 Hz, 2H), 1.98 (q, J=5.6 Hz, 2H).

LC-MS: m/z 393 [M+H⁺] with a purity of 96.06%.

Synthesis of N-(6-(2-methoxyphenyl)pyridazin-3-yl)-2-(6-methyl-5,7-dioxo-2,3,4,5,6,7-hexahydro-1H-pyrrolo[3,4-b]pyridin-1-yl)acetamide, (Compound 28)

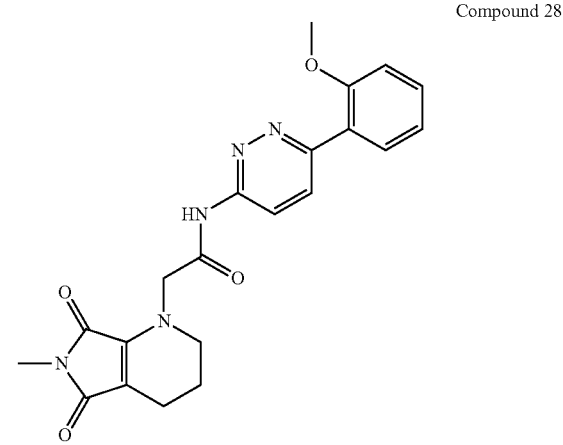 [SMILES: COc1ccccc1-c1ccc(NC(=O)CN2CCCC3=C2C(=O)N(C)C3=O)nn1]

Compound 28

¹H NMR (400 MHz, CDCl₃) δ (ppm): 10.06 (s, 1H), 8.48 (d, J=9.2 Hz, 1H), 8.06 (d, J=9.2 Hz, 1H), 7.89-7.87 (m, 1H), 7.46-7.42 (m, 1H), 7.10 (t, J=7.6 Hz, 1H), 7.03 (d, J=8.4 Hz, 1H) 4.78 (s, 2H), 3.87 (s, 3H), 3.39 (t, J=5.6 Hz, 2H), 2.93 (s, 3H), 2.38 (t, J=6.0 Hz, 2H), 1.97 (t, J=5.6 Hz, 2H)

LC-MS: m/z 408 [M+H⁺] with a purity of 95.60%.

Synthesis of 2-(6-methyl-5,7-dioxo-2,3,4,5,6,7-hexahydro-1H-pyrrolo[3,4-b]pyridin-1-yl)-N-(6-(m-tolyl)pyridazin-3-yl)acetamide, (Compound 29)

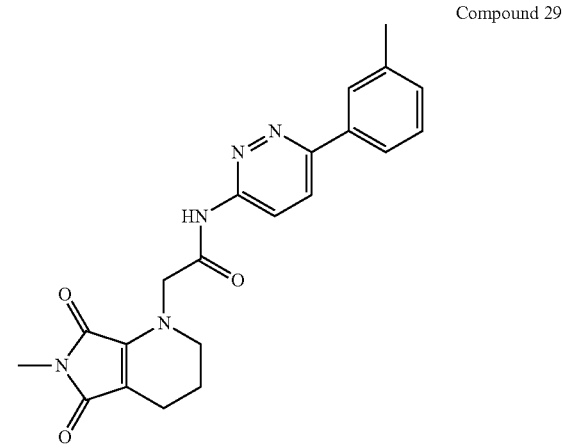 [SMILES: Cc1cccc(-c2ccc(NC(=O)CN3CCCC4=C3C(=O)N(C)C4=O)nn2)c1]

Compound 29

¹H NMR (400 MHz, METHANOL-d₄) δ (ppm): 8.45-8.47 (m, 1H), 8.09-8.11 (m, 1H), 7.83 (bs, 1H), 7.77-7:79 (m, 1H), 7.39-7.43 (m, 1H), 7.32-7.33 (m, 1H), 4.70 (s, 2H), 3.42 (t, J=5.6 Hz, 2H), 2.86 (s, 3H), 2.44 (s, 3H), 2.32 (t, J=5.6 Hz, 2H), 1.98 (q, J=5.6 Hz, 2H).

LC-MS: m/z 393 [M+H⁺] with a purity of 96.42%.

Synthesis of 2-(6-methyl-5,7-dioxo-2,3,4,5,6,7-hexahydro-1H-pyrrolo[3,4-b]pyridin-1-yl)-N-(6-(p-tolyl)pyridazin-3-yl)acetamide, (Compound 30)

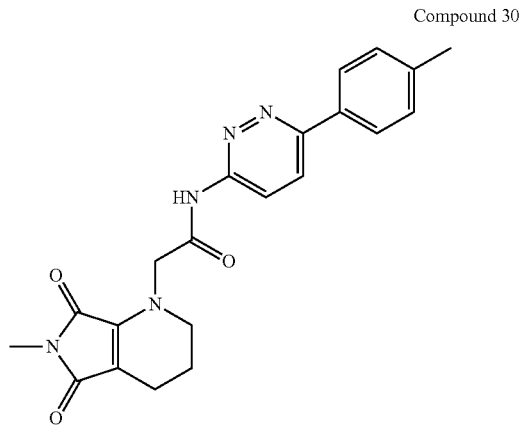

Compound 30

$^1$H NMR (400 MHz, METHANOL-d$_4$) δ (ppm): 8.44 (d, J=9.2 Hz, 1H), 8.09 (d, J=9.2 Hz, 1H), 7.90 (d, J=8.0 Hz, 2H), 7.35 (d, J=8.0 Hz, 2H), 4.69 (s, 2H), 3.41 (t, J=5.6 Hz, 2H), 2.86 (s, 3H), 2.41 (s, 3H), 2.32 (t, J=5.6 Hz, 2H), 1.98 (q, J=5.6 Hz, 2H).

LC-MS: m/z 393 [M+H$^+$] with a purity of 96.81%.

Synthesis of N-(6-(4-methoxyphenyl)pyridazin-3-yl)-2-(6-methyl-5,7-dioxo-2,3,4,5,6,7-hexahydro-1H-pyrrolo[3,4-b]pyridin-1-yl)acetamide, (Compound 31)

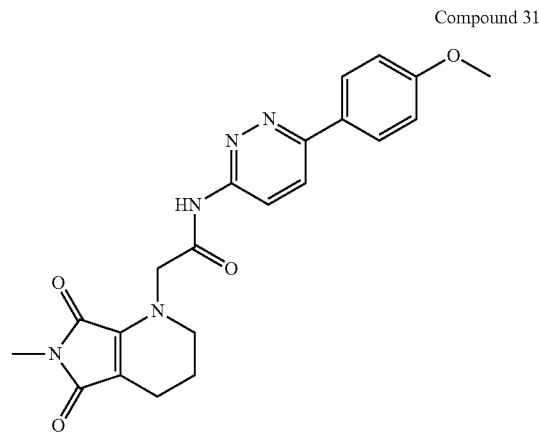

Compound 31

$^1$H NMR (400 MHz, DMSO-d$_6$) δ (ppm): 11.34 (s, 1H), 8.29-8.27 (m, 1H), 8.18-8.15 (m, 1H), 8.06 (d, J=8.8 Hz, 2H), 7.09 (d, J=8.8 Hz, 2H), 4.65 (s, 2H), 3.83 (s, 3H), 3.36-3.33 (m, 2H), 2.77 (s, 3H), 2.21 (t, J=6.4 Hz, 2H), 1.87-1.83 (m, 2H)

LC-MS: m/z 408 [M+H$^+$] with a purity of 97.22%.

Synthesis of N-(6-(3-methoxyphenyl)pyridazin-3-yl)-2-(6-methyl-5,7-dioxo-2,3,4,5,6,7-hexahydro-1H-pyrrolo[3,4-b]pyridin-1-yl)acetamide, (Compound 32)

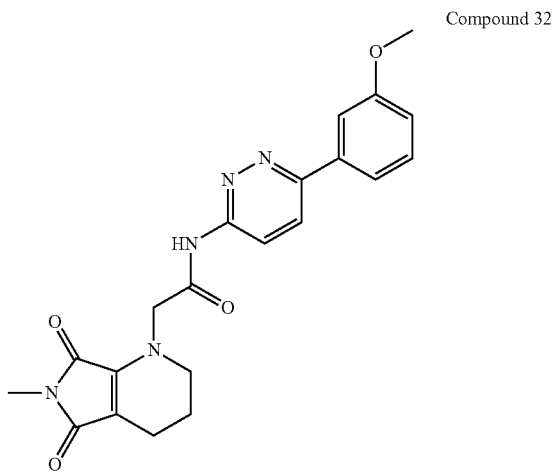

Compound 32

$^1$H NMR (400 MHz, DMSO-d$_6$) δ (ppm): 11.40 (s, 1H), 8.33-8.31 (m, 1H), 8.25-8.23 (m, 1H), 7.68-7.66 (m, 2H), 7.45 (t, J=8.0 Hz, 1H), 7.08-7.05 (m, 1H), 4.67 (s, 2H), 3.85 (s, 3H), 3.36-3.34 (m, 2H), 2.77 (s, 3H), 2.22 (t, J=6.0 Hz, 2H), 1.88-1.82 (m, 2H)

LC-MS: m/z 408 [M+H$^+$] with a purity of 97.23%.

Synthesis of 2-(6-isopropyl-5,7-dioxo-2,3,4,5,6,7-hexahydro-1H-pyrrolo[3,4-b]pyridin-1-yl)-N-(6-phenylpyridazin-3-yl)acetamide, (Compound 33)

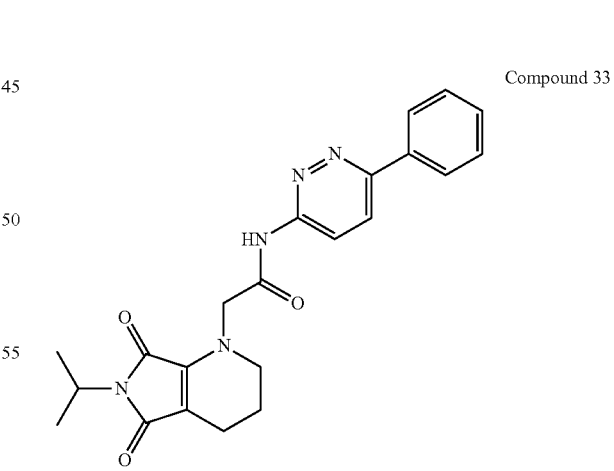

Compound 33

$^1$H NMR (400 MHz, METHANOL-d$_4$) δ (ppm): 8.49 (d, J=9.2 Hz, 1H), 8.12 (d, J=9.2 Hz, 1H), 8.00-8.02 (m, 2H), 7.49-7.55 (m, 3H), 4.69 (s, 2H), 4.21 (q, J=6.8 Hz, 1H), 3.40 (t, J=6.0 Hz, 2H), 2.30 (t, J=6.0 Hz, 2H), 1.97 (q, J=6.0 Hz, 2H), 1.32 (d, J=6.8 Hz, 6H).

LC-MS: m/z 407 [M+H$^+$] with a purity of 98.67%.

Synthesis of 2-(6-methyl-5,7-dioxo-2,3,4,5,6,7-hexahydro-1H-pyrrolo[3,4-b]pyridin-1-yl)-N-(6-methyl-[2,3'-bipyridin]-6'-yl)acetamide, (Compound 34)

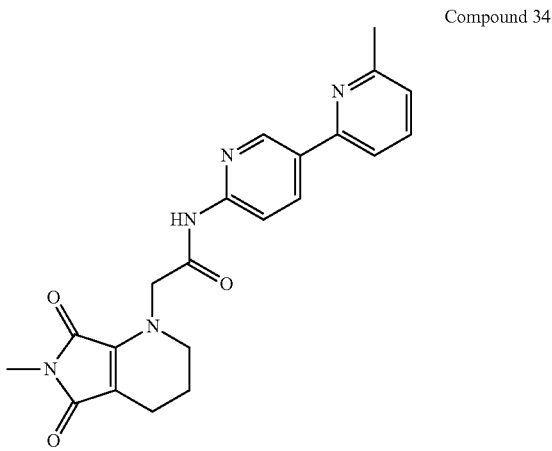 [SMILES: Cc1cccc(-c2ccc(NC(=O)CN3CCCC4=C3C(=O)N(C)C4=O)nc2)n1]

Compound 34

$^1$H NMR (400 MHz, METHANOL-d$_4$) δ (ppm): 8.86-8.87 (m, 1H), 8.30-8.33 (m, 1H), 8.14-8.16 (m, 1H), 7.76-7.80 (m, 1H), 7.63-7.65 (m, 1H), 7.24-7.26 (m, 1H), 4.65 (s, 2H), 3.41 (t, J=5.6 Hz, 2H), 2.87 (s, 3H), 2.59 (s, 3H), 2.32 (t, J=5.6 Hz, 2H), 1.98 (q, J=5.6 Hz, 2H).

LC-MS: m/z 392 [M+H$^+$] with a purity of 96.66%.

Synthesis of N-(6-(3-methoxyphenyl)pyridazin-3-yl)-2-(6-methyl-5,7-dioxo-2,3,4,5,6,7-hexahydro-1H-pyrrolo[3,4-b]pyridin-1-yl)acetamide, (Compound 35)

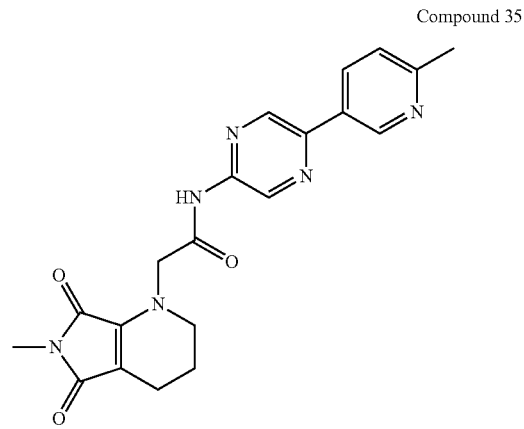

Compound 35

$^1$H NMR (400 MHz, DMSO-d$_6$) δ (ppm): 11.12 (s, 1H), 9.33 (s, 1H), 9.13 (d, J=2.4 Hz, 1H), 9.05 (d, J=1.6 Hz, 1H), 8.34-8.31 (m, 1H), 7.39 (d, J=8.0 Hz, 1H), 4.64 (s, 2H), 3.37-3.34 (m, 2H), 2.77 (s, 3H), 2.53 (s, 3H), 2.22 (t, J=6.0 Hz, 2H), 1.86-1.84 (m, 2H)

LC-MS: m/z 393 [M+H$^+$] with a purity of 95.59%.

Synthesis of 2-(6-methyl-5,7-dioxo-2,3,4,5,6,7-hexahydro-1H-pyrrolo[3,4-b]pyridin-1-yl)-N-(5-phenylpyrimidin-2-yl)acetamide, (Compound 36)

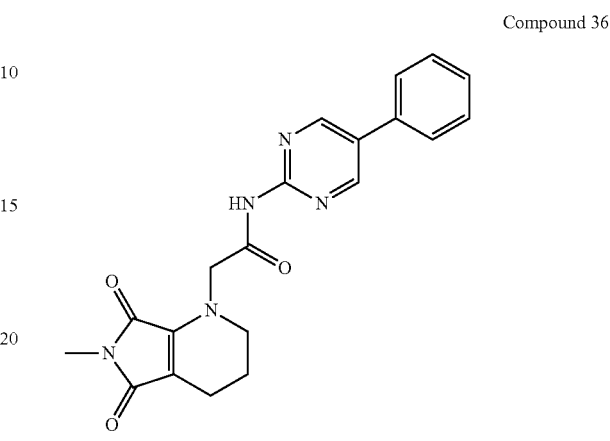

Compound 36

$^1$H NMR (400 MHz, DMSO-d$_6$) δ (ppm): 10.91 (s, 1H), 8.99 (s, 2H), 7.78-7.76 (m, 2H), 7.53-7.50 (m, 2H), 7.45-7.42 (m, 1H), 4.79 (s, 2H), 2.76 (s, 3H), 2.21 (t, J=5.6 Hz, 2H), 1.84 (t, J=5.2 Hz, 2H)

LC-MS: m/z 378 [M+H$^+$] with a purity of 97.25%.

Synthesis of 2-(6-methyl-5,7-dioxo-2,3,4,5,6,7-hexahydro-1H-pyrrolo[3,4-b]pyridin-1-yl)-N-(6-phenylpyridin-3-yl)acetamide, (Compound 37)

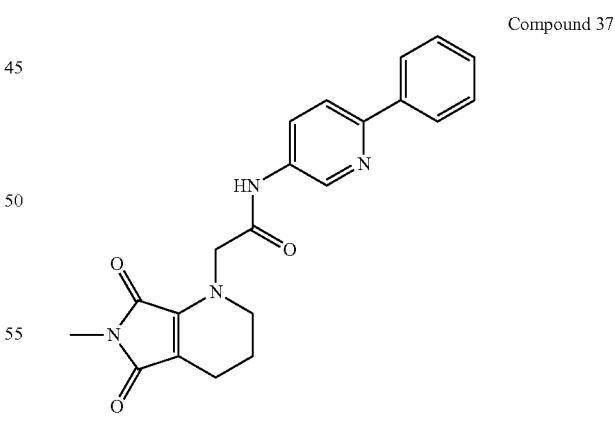

Compound 37

$^1$H NMR (400 MHz, DMSO-d$_6$) δ (ppm): 10.43 (s, 1H), 8.79 (d, J=2.4 Hz, 1H), 8.13-8.10 (m, 1H), 8.04-8.02 (m, 2H), 7.94-7.92 (m, 1H), 7.48-7.45 (m, 2H), 7.41-7.37 (m, 1H), 4.58 (s, 2H), 2.77 (s, 3H), 2.22 (t, J=6.4 Hz, 2H), 1.88-1.82 (m, 2H)

LC-MS: m/z 377 [M+H$^+$] with a purity of 97.41%.

Synthesis of 2-(6-cyclobutyl-5,7-dioxo-2,3,4,5,6,7-hexahydro-1H-pyrrolo[3,4-b]pyridin-1-yl)-N-(6-phenylpyridazin-3-yl)acetamide, (Compound 38)

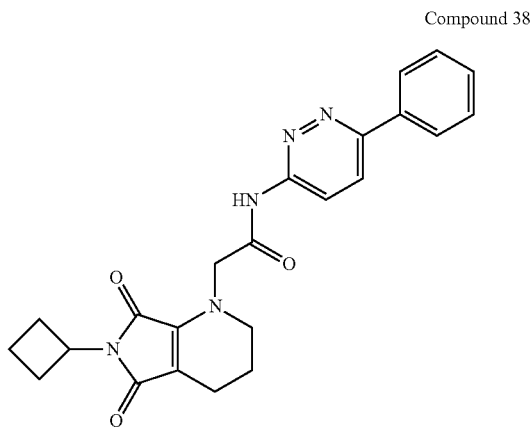 [SMILES: O=C(CN1CCCC2=C1C(=O)N(C1CCC1)C2=O)Nc1ccc(-c2ccccc2)nn1]

Compound 38

$^1$H NMR (400 MHz, METHANOL-$d_4$) δ (ppm): 8.49 (d, J=9.6 Hz, 1H), 8.12 (d, J=9.6 Hz, 1H), 8.00-8.03 (m, 2H), 7.49-7.55 (m, 3H), 4.69 (s, 2H), 4.41-4.50 (m, 1H), 3.40 (t, J=6.0 Hz, 2H), 2.70-2.81 (m, 2H), 2.30 (t, J=6.0 Hz, 2H), 2.09-2.15 (m, 2H), 1.97 (q, J=6.0 Hz, 2H), 1.65-1.79 (m, 2H).

LC-MS: m/z 418 [M+H$^+$] with a purity of 97.40%.

Synthesis of 2-(6-methyl-5,7-dioxo-2,3,4,5,6,7-hexahydro-1H-pyrrolo[3,4-b]pyridin-1-yl)-N-(6'-methyl-[3,3'-bipyridin]-6-yl)acetamide, (Compound 39)

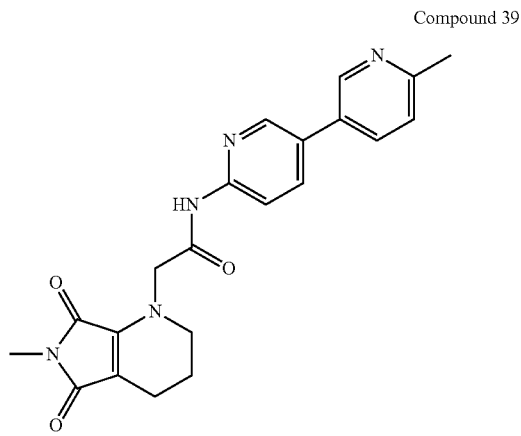

Compound 39

$^1$H NMR (400 MHz, DMSO-$d_6$) δ (ppm): 10.80 (s, 1H), 8.79 (s, 1H), 8.69 (s, 1H), 8.08-8.15 (m, 2H), 8.00-8.03 (m, 1H), 7.34-7.36 (m, 1H), 4.60 (s, 2H), 3.31 (t, J=5.6 Hz, 2H), 2.76 (s, 3H), 2.33 (s, 3H), 2.21 (t, J=5.6 Hz, 2H), 1.84 (q, J=5.6 Hz, 2H).

LC-MS: m/z 392 [M+H$^+$] with a purity of 95.03%.

Synthesis of 2-(6-cyclopropyl-5,7-dioxo-2,3,4,5,6,7-hexahydro-1H-pyrrolo[3,4-b]pyridin-1-yl)-N-(6'-methyl-[2,3'-bipyridin]-5-yl)acetamide, (Compound 44)

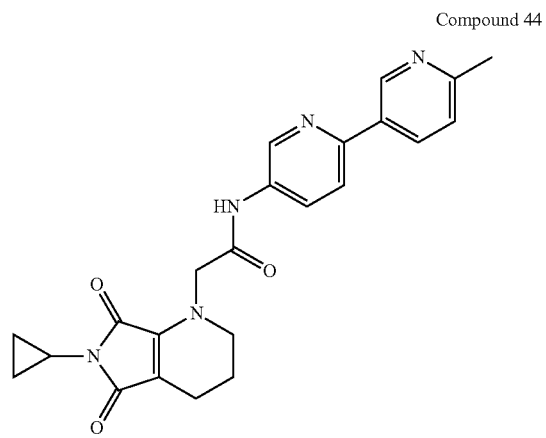 [SMILES: Cc1ccc(-c2ccc(NC(=O)CN3CCCC4=C3C(=O)N(C3CC3)C4=O)cn2)cn1]

Compound 44

$^1$H NMR (400 MHz, METHANOL-$d_4$) δ (ppm): 8.99 (bs, 1H), 8.81-8.82 (m, 1H), 8.27-8.29 (m, 1H), 8.18-8.21 (m, 1H), 7.87-7.89 (m, 1H), 7.39-7.41 (m, 1H), 4.60 (s, 2H), 3.39 (t, J=5.6 Hz, 2H), 2.58 (s, 3H), 2.36-2.42 (m, 1H), 2.29 (t, J=5.6 Hz, 2H), 1.96 (q, J=5.6 Hz, 2H), 0.76-0.82 (m, 4H).

LC-MS: m/z 418 [M+H$^+$] with a purity of 97.43%.

Synthesis of 2-(6-methyl-5,7-dioxo-2,3,4,5,6,7-hexahydro-1H-pyrrolo[3,4-b]pyridin-1-yl)-N-(4-(pyridazin-3-yl)phenyl)acetamide, (Compound 47)

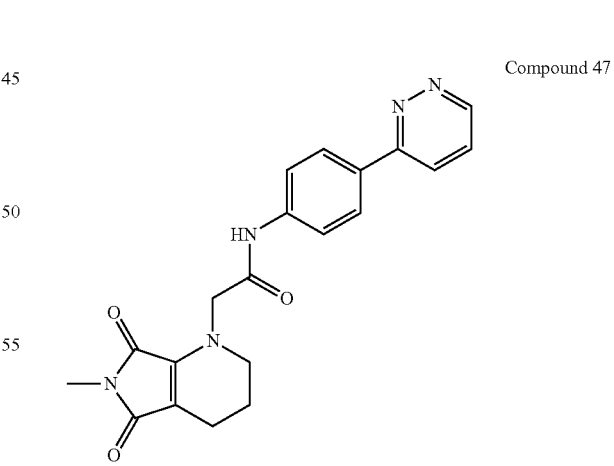

Compound 47

$^1$H NMR (400 MHz, DMSO-$d_6$) δ (ppm): 10.34 (s, 1H), 9.17-9.15 (m, 1H), 8.19-8.12 (m, 3H), 7.77-7.72 (m, 3H), 4.57 (s, 2H), 3.36-3.33 (m, 2H), 2.78 (s, 3H), 2.22 (t, J=6.0 Hz, 2H), 1.88-1.84 (m, 2H).

LC-MS: m/z 378 [M+H$^+$] with a purity of 97.86%.

Synthesis of 2-(6-cyclopropyl-5,7-dioxo-2,3,4,5,6,7-hexahydro-1H-pyrrolo[3,4-b]pyridin-1-yl)-N-(6-(5-fluoropyridin-3-yl)pyridazin-3-yl)acetamide, (Compound 52)

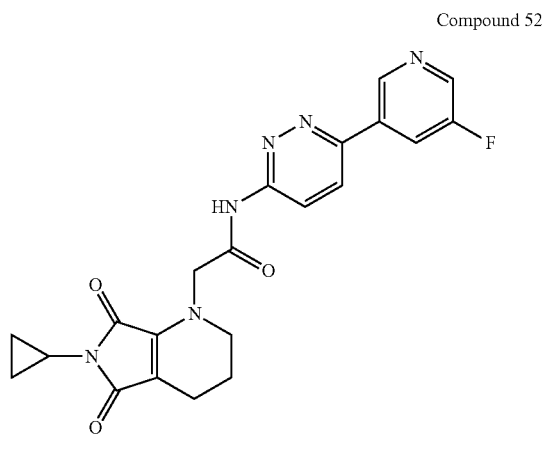 [SMILES: O=C(CN1CCCC2=C1C(=O)N(C1CC1)C2=O)Nc1ccc(-c2cncc(F)c2)nn1]

Compound 52

¹H NMR (400 MHz, DMSO-d₆) δ (ppm): 11.50 (br s, 1H), 9.18 (t, J=2.4 Hz, 1H), 8.71 (d, J=2.8 Hz, 1H), 8.42-8.38 (m, 3H), 4.65 (s, 2H), 3.31-3.30 (m, 2H), 2.40-2.34 (m, 1H), 2.19 (t, J=5.6 Hz, 2H), 1.85-1.82 (m, 2H), 0.75-0.72 (m, 2H), 0.67-0.66 (m, 2H).

LC-MS: m/z 423 [M+H⁺] with a purity of 95.22%.

Synthesis of 2-(6-cyclopropyl-5,7-dioxo-2,3,4,5,6,7-hexahydro-1H-pyrrolo[3,4-b]pyridin-1-yl)-N-(6-(4-(trifluoromethoxy)phenyl)pyridazin-3-yl)acetamide, (Compound 57)

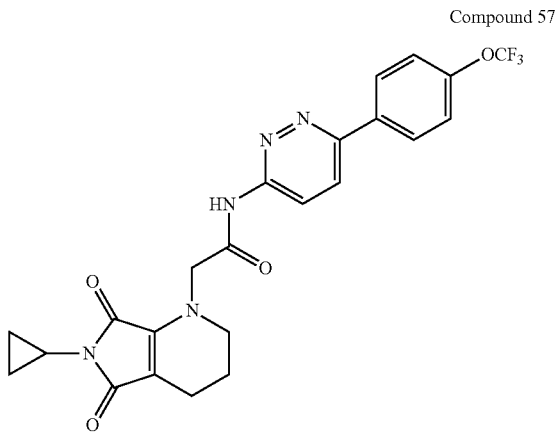 [SMILES: O=C(CN1CCCC2=C1C(=O)N(C1CC1)C2=O)Nc1ccc(-c2ccc(OC(F)(F)F)cc2)nn1]

Compound 57

¹H NMR (400 MHz, DMSO-d₆) δ (ppm): 11.43 (s, 1H), 8.34-8.36 (m, 1H), 8.23-8.29 (m, 3H), 7.52-7.54 (m, 2H), 4.65 (s, 2H), 3.33 (t, J=5.2 Hz, 2H), 2.34-2.40 (m, 1H), 2.19 (t, J=5.2 Hz, 2H), 1.83 (q, J=5.2 Hz, 2H), 0.72-0.77 (m, 2H), 0.66-0.68 (m, 2H).

LC-MS: m/z 488 [M+H⁺] with a purity of 96.93%.

Synthesis of N-(6-(5-chloropyridin-3-yl)pyridazin-3-yl)-2-(6-cyclopropyl-5,7-dioxo-2,3,4,5,6,7-hexahydro-1H-pyrrolo[3,4-b]pyridin-1-yl)acetamide, (Compound 58)

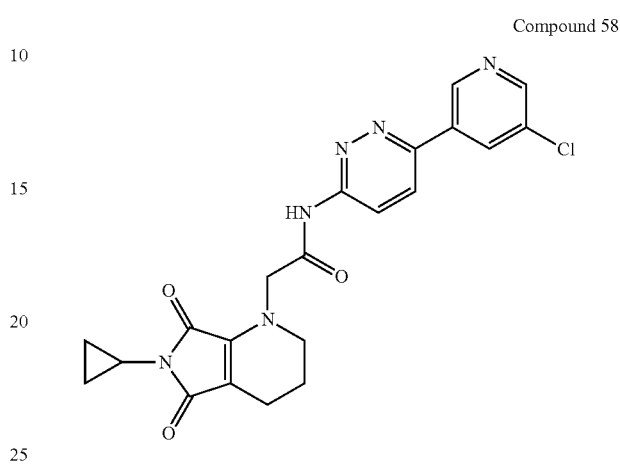

Compound 58

¹H NMR (400 MHz, DMSO-d₆) δ (ppm): 11.51 (br s, 1H), 9.25 (d, J=1.6 Hz, 1H), 8.76 (d, J=2.4 Hz, 1H), 8.60 (t, J=2.4 Hz, 1H), 8.42-8.36 (m, 2H), 4.65 (s, 2H), 3.31-3.30 (m, 2H), 2.40-2.34 (m, 1H), 2.19 (t, J=6.0 Hz, 2H), 1.85-1.82 (m, 2H), 0.77-0.72 (m, 2H), 0.67-0.64 (m, 2H).

LC-MS: m/z 439 [M+H⁺] with a purity of 97.76%.

Synthesis of 2-(6-methyl-5,7-dioxo-2,3,4,5,6,7-hexahydro-1H-pyrrolo[3,4-b]pyridin-1-yl)-N-(6-(pyridin-3-yl)pyridazin-3-yl)propanamide, (Compound 60)

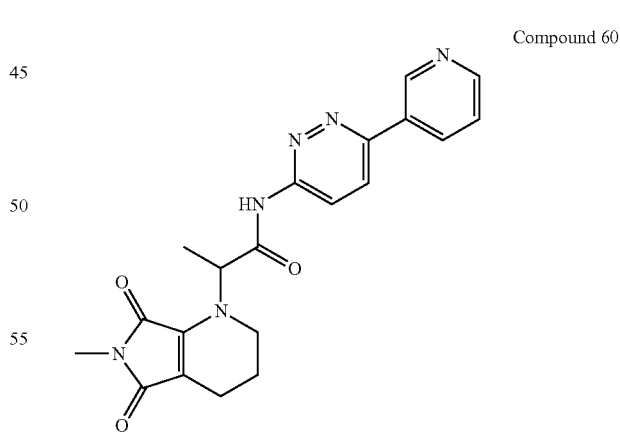

Compound 60

¹H NMR (400 MHz, METHANOL-d₄) δ (ppm): 9.21-9.22 (m, 1H), 8.65-8.67 (m, 1H), 8.53-8.55 (m, 1H), 8.47-8.50 (m, 1H), 8.20-8.23 (m, 1H), 7.59-7.62 (m, 1H), 5.85 (q, J=7.2 Hz, 1H), 3.45-3.47 (m, 2H), 2.89 (s, 3H), 2.23-2.38 (m, 2H), 1.88-2.00 (m, 2H), 1.57 (d, J=7.2 Hz, 3H).

LC-MS: m/z 393 [M+H⁺] with a purity of 92.47%.

Synthesis of 2-(6-cyclopropyl-5,7-dioxo-2,3,4,5,6,7-hexahydro-1H-pyrrolo[3,4-b]pyridin-1-yl)-N-(5-methyl-6-(pyridin-3-yl)pyridazin-3-yl)acetamide, (Compound 62)

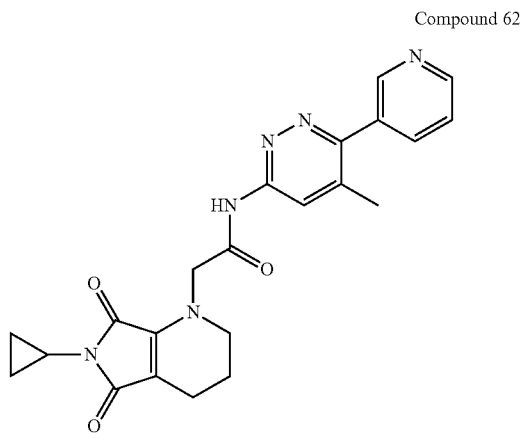 [SMILES: Cc1cc(NC(=O)CN2CCCC3=C2C(=O)N(C2CC2)C3=O)nnc1-c1cccnc1]

Compound 62

$^1$H NMR (400 MHz, DMSO-d$_6$) δ (ppm): 11.36 (br s, 1H), 8.80 (d, J=1.6 Hz, 1H), 8.69-8.68 (m, 1H), 8.27 (s, 1H), 8.06-8.04 (m, 1H), 7.57-7.54 (m, 1H), 4.63 (s, 2H), 3.31-3.30 (m, 2H), 2.39-2.32 (m, 4H), 2.18 (t, J=5.6 Hz, 2H), 1.85-1.82 (m, 2H), 0.78-0.73 (m, 2H), 0.71-0.65 (m, 2H). LC-MS: m/z 419 [M+H$^+$] with a purity of 96.01%.

Synthesis of 2-(6-cyclopropyl-5,7-dioxo-2,3,4,5,6,7-hexahydro-1H-pyrrolo[3,4-b]pyridin-1-yl)-N-(6-(pyrazin-2-yl)pyridin-3-yl)acetamide, (Compound 65)

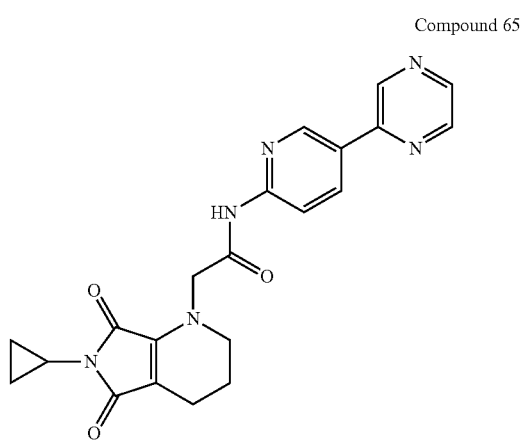 [SMILES: O=C(CN1CCCC2=C1C(=O)N(C1CC1)C2=O)Nc1ccc(-c2cnccn2)cn1]

Compound 65

$^1$H NMR (400 MHz, DMSO-d$_6$) δ (ppm): 10.93 (br s, 1H), 9.30 (d, J=1.2 Hz, 1H), 9.10 (d, J=1.6 Hz, 1H), 8.72-8.71 (m, 1H), 8.62 (d, J=2.4 Hz, 1H), 8.53-8.50 (m, 1H), 8.16 (d, J=8.8 Hz, 1H), 4.60 (s, 2H), 3.31-3.30 (m, 2H), 2.40-2.34 (m, 1H), 2.18 (t, J=6.4 Hz, 2H), 1.84-1.82 (m, 2H), 0.75-0.72 (m, 2H), 0.68-0.65 (m, 2H)
LC-MS: m/z 405 [M+H$^+$] with a purity of 96.75%.

Synthesis of 2-(6-methyl-5,7-dioxo-2,3,4,5,6,7-hexahydro-1H-pyrrolo[3,4-b]pyridin-1-yl)-N-(6-(pyrazin-2-yl)pyridin-3-yl)acetamide, (Compound 66)

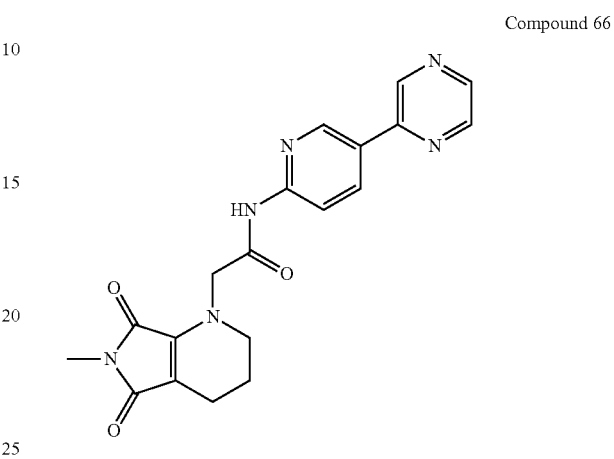

Compound 66

$^1$H NMR (400 MHz, DMSO-d$_6$) δ (ppm): 10.95 (br s, 1H), 9.30 (d, J=0.9 Hz, 1H), 9.10 (d, J=2.0 Hz, 1H), 8.72-8.71 (m, 1H), 8.62 (d, J=2.4 Hz, 1H), 8.53-8.50 (m, 1H), 8.16 (d, J=8.4 Hz, 1H), 4.62 (s, 2H), 3.31-3.30 (m, 2H), 2.77 (s, 3H), 2.22 (t, J=6.0 Hz, 2H), 1.86-1.83 (m, 2H).

LC-MS: m/z 379 [M+H$^+$] with a purity of 95.59%.

Synthesis of N-([1,1'-biphenyl]-4-yl)-2-(6-cyclopropyl-5,7-dioxo-2,3,4,5,6,7-hexahydro-1H-pyrrolo[3,4-b]pyridin-1-yl)acetamide, (Compound 67)

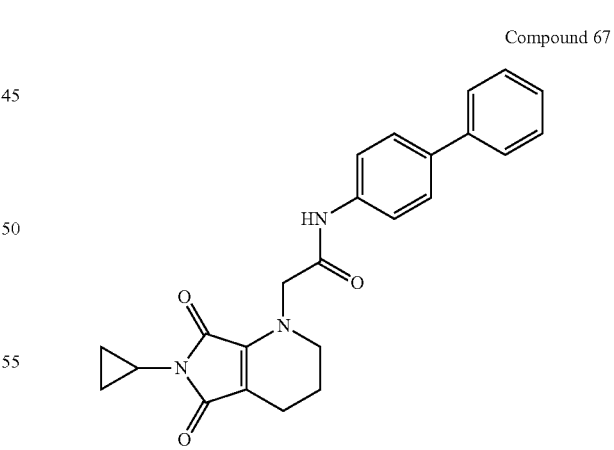

Compound 67

$^1$H NMR (400 MHz, DMSO-d$_6$) δ (ppm): 10.18 (s, 1H), 7.67-7.61 (m, 6H), 7.44 (t, J=7.2 Hz, 2H), 7.32 (t, J=7.2 Hz, 2H), 4.52 (s, 2H), 3.31-3.30 (m, 2H), 2.40-2.35 (m, 1H), 2.18 (t, J=6.0 Hz, 2H), 1.85-1.82 (m, 2H), 0.78-0.71 (m, 2H), 0.69-0.65 (m, 2H).

LC-MS: m/z 402 [M+H$^+$] with a purity of 98.05%.

Synthesis of 2-(6-cyclopropyl-5,7-dioxo-2,3,4,5,6,7-hexahydro-1H-pyrrolo[3,4-b]pyridin-1-yl)-N-(3,5'-dimethyl-[2,3'-bipyridin]-5-yl)acetamide, (Compound 68)

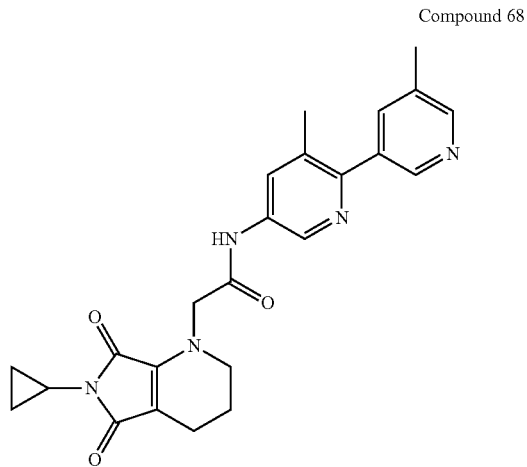 [SMILES: Cc1cncc(-c2ncc(NC(=O)CN3CCCC4=C3C(=O)N(C3CC3)C4=O)cc2C)c1]

Compound 68

$^1$H NMR (400 MHz, DMSO-d$_6$) δ (ppm): 10.39 (s, 1H), 8.63 (d, J=2.4 Hz, 1H), 8.52 (d, J=2.0 Hz, 1H), 8.43 (d, J=1.6 Hz, 1H), 8.02 (d, J=2.0 Hz, 1H), 7.576 (s, 1H), 4.55 (s, 2H), 3.31-3.30 (m, 2H), 2.40-2.33 (m, 7H), 2.19 (t, J=6.0 Hz, 2H), 1.85-1.82 (m, 2H), 0.78-0.73 (m, 2H), 0.69-0.67 (m, 2H).

LC-MS: m/z 432 [M+H$^+$] with a purity of 97.05%.

Synthesis of N-([1,1'-biphenyl]-4-yl)-2-(6-methyl-5,7-dioxo-2,3,4,5,6,7-hexahydro-1H-pyrrolo[3,4-b]pyridin-1-yl)acetamide, (Compound 70)

Compound 70

$^1$H NMR (400 MHz, DMSO-d$_6$) δ (ppm): 10.19 (s, 1H), 7.61-7.67 (m, 6H), 7.42-7.45 (m, 2H), 7.30-7.34 (m, 1H), 4.54 (s, 2H), 3.31 (t, J=5.6 Hz, 2H), 2.77 (s, 3H), 2.22 (t, J=5.6 Hz, 2H), 1.85 (q, J=5.6 Hz, 2H).

LC-MS: m/z 376 [M+H$^+$] with a purity of 96.59%.

Synthesis of 2-(6-methyl-5,7-dioxo-2,3,4,5,6,7-hexahydro-1H-pyrrolo[3,4-b]pyridin-1-yl)-N-(6-(pyridin-4-yl)pyridazin-3-yl)acetamide, (Compound 71)

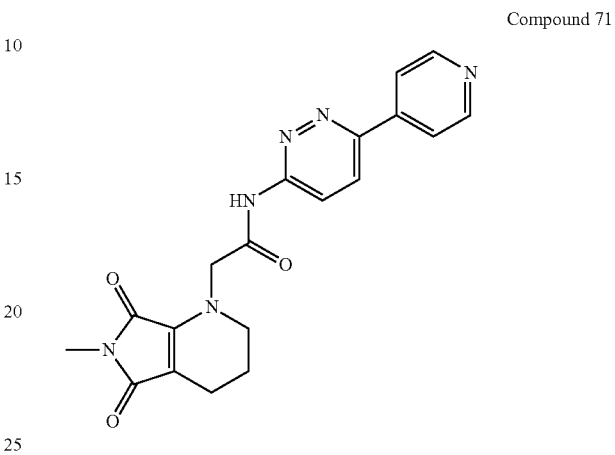

Compound 71

$^1$H NMR (400 MHz, DMSO-d$_6$) δ (ppm): 11.55 (s, 1H), 8.74-8.75 (m, 2H), 8.36-8.41 (m, 2H), 8.08-8.10 (m, 2H), 4.68 (s, 2H), 3.35 (t, J=5.6 Hz, 2H), 2.77 (s, 3H), 2.22 (t, J=5.6 Hz, 2H), 1.85 (q, J=5.6 Hz, 2H).

LC-MS: m/z 379 [M+H$^+$] with a purity of 95.91%.

Synthesis of N-(6-(5-fluoropyridin-3-yl)pyridazin-3-yl)-2-(6-methyl-5,7-dioxo-2,3,4,5,6,7-hexahydro-1H-pyrrolo[3,4-b]pyridin-1-yl)acetamide, (Compound 72)

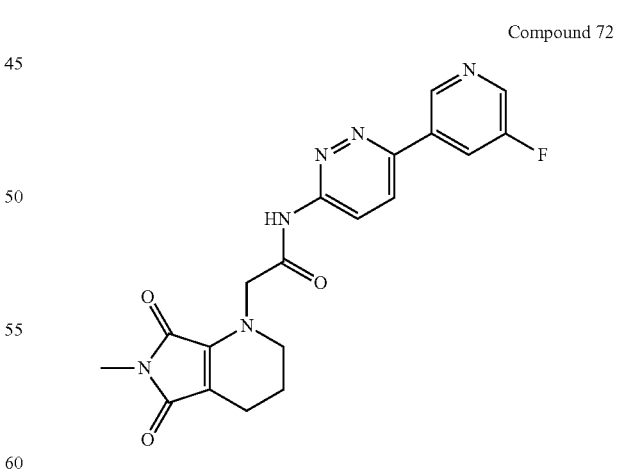

Compound 72

$^1$H NMR (400 MHz, DMSO-d$_6$) δ (ppm): 11.52 (s, 1H), 9.18-9.19 (m, 1H), 8.71-8.72 (m, 1H), 8.39-8.42 (m, 3H), 4.68 (s, 2H), 3.35 (t, J=5.6 Hz, 2H), 2.77 (s, 3H), 2.22 (t, J=5.6 Hz, 2H), 1.85 (q, J=5.6 Hz, 2H).

LC-MS: 397 m/z [M+H$^+$] with a purity of 96.15%.

Synthesis of 2-(6-methyl-5,7-dioxo-2,3,4,5,6,7-hexahydro-1H-pyrrolo[3,4-b]pyridin-1-yl)-N-(4-(pyrimidin-4-yl)phenyl)acetamide, (Compound 73)

Synthesis of 2-(6-methyl-5,7-dioxo-2,3,4,5,6,7-hexahydro-1H-pyrrolo[3,4-b]pyridin-1-yl)-N-(4-(pyrimidin-5-yl)phenyl)acetamide, (Compound 75)

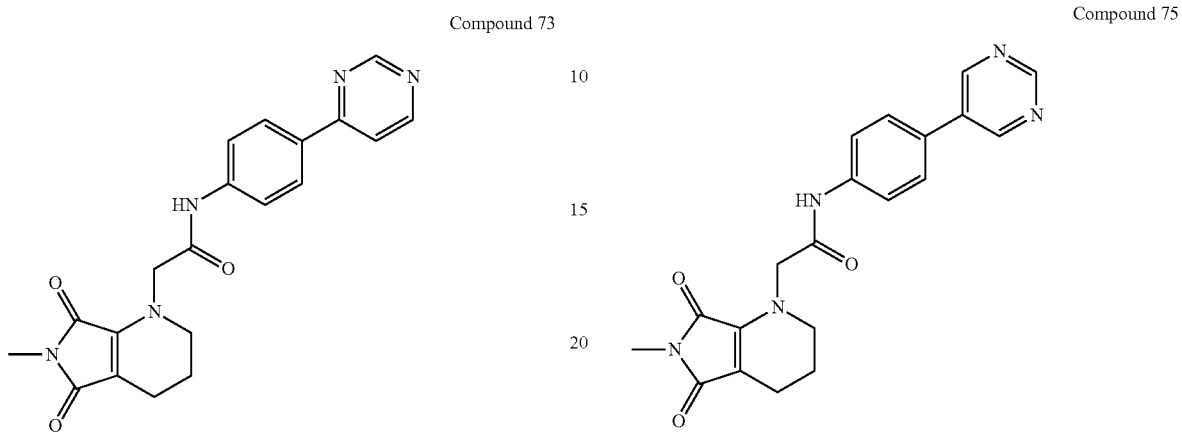

Compound 73

Compound 75

$^1$H NMR (400 MHz, DMSO-d$_6$) δ (ppm): 10.39 (s, 1H), 9.18 (d, J=1.2 Hz, 1H), 8.80 (d, J=5.6 Hz, 1H), 8.20 (d, J=8.8 Hz, 2H), 8.04-8.02 (m, 1H), 7.75 (d, J=8.8 Hz, 2H), 4.56 (s, 2H), 3.31-3.30 (m, 2H), 2.77 (s, 3H), 2.22 (t, J=6.0 Hz, 2H), 1.86-1.84 (m, 2H).

LC-MS: m/z 378 [M+H$^+$] with a purity of 98.60%.

$^1$H NMR (400 MHz, DMSO-d$_6$) δ (ppm): 10.30 (s, 1H), 9.14-9.12 (m, 3H), 7.80-7.72 (m, 4H), 4.56 (s, 2H), 3.31-3.30 (m, 2H), 2.77 (s, 3H), 2.22 (t, J=6.0 Hz, 2H), 1.88-1.82 (m, 2H).

LC-MS: m/z 378 [M+H$^+$] with a purity of 96.33%.

Synthesis of 2-(6-methyl-5,7-dioxo-2,3,4,5,6,7-hexahydro-1H-pyrrolo[3,4-b]pyridin-1-yl)-N-(4-(pyrimidin-2-yl)phenyl)acetamide, (Compound 74)

Synthesis of 2-(6-methyl-5,7-dioxo-2,3,4,5,6,7-hexahydro-1H-pyrrolo[3,4-b]pyridin-1-yl)-N-(4-(pyridin-2-yl)phenyl)acetamide, (Compound 76)

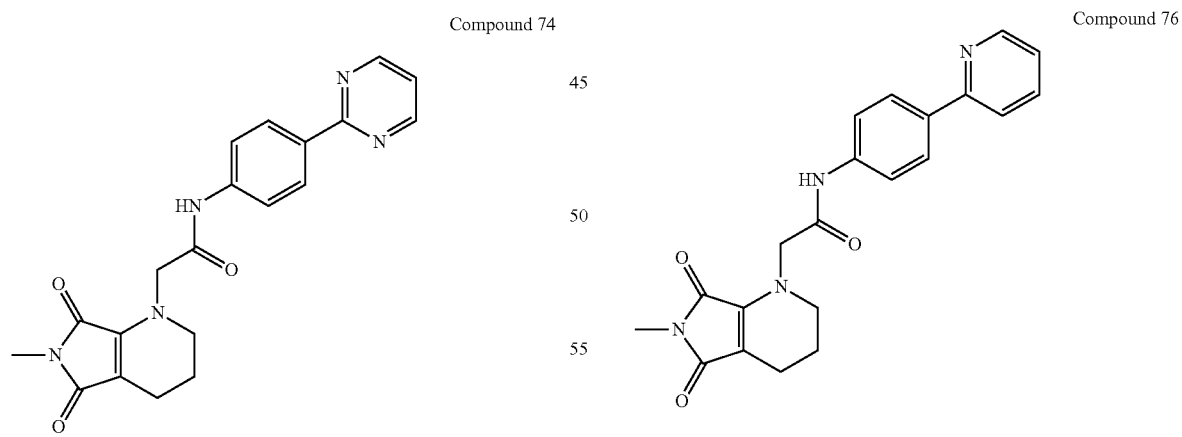

Compound 74

Compound 76

$^1$H NMR (400 MHz, DMSO-d$_6$) δ (ppm): 10.35 (s, 1H), 8.85 (d, J=5.2 Hz, 2H), 8.34 (d, J=8.8 Hz, 2H), 7.72 (d, J=8.8 Hz, 2H), 7.38 (d, J=4.8 Hz, 1H), 4.56 (s, 2H), 3.31-3.30 (m, 2H), 2.77 (s, 3H), 2.22 (t, J=6.0 Hz, 2H), 1.87-1.84 (m, 2H).

LC-MS: m/z 378 [M+H$^+$] with a purity of 95.40%.

$^1$H NMR (400 MHz, DMSO-d$_6$) δ (ppm): 10.26 (s, 1H), 8.62 (d, J=4.4 Hz, 1H), 8.05 (d, J=8.8 Hz, 2H), 7.92-7.90 (m, 1H), 7.86-7.82 (m, 1H), 7.69 (d, J=8.8 Hz, 2H), 7.31-7.28 (m, 4H), 4.55 (s, 2H), 3.31-3.30 (m, 2H), 2.77 (s, 3H), 2.22 (t, J=6.0 Hz, 2H), 1.86-1.84 (m, 2H).

LC-MS: m/z 377 [M+H$^+$] with a purity of 97.71%.

Synthesis of 2-(6-methyl-5,7-dioxo-2,3,4,5,6,7-hexahydro-1H-pyrrolo[3,4-b]pyridin-1-yl)-N-(4-(pyridin-3-yl)phenyl)acetamide, (Compound 77)

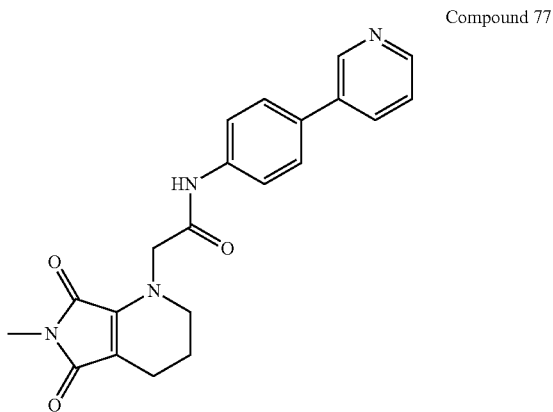 [SMILES: CN1C(=O)C2=C(C1=O)N(CC(=O)Nc1ccc(-c3cccnc3)cc1)CCC2]

Compound 77

¹H NMR (400 MHz, DMSO-d₆) δ (ppm): 10.25 (s, 1H), 8.87 (d, J=1.6 Hz, 1H), 8.53-8.52 (m, 1H), 8.06-8.03 (m, 1H), 7.70 (s, 4H), 7.47-7.44 (m, 1H), 4.55 (s, 2H), 3.35-3.31 (m, 2H), 2.77 (s, 3H), 2.22 (t, J=6.0 Hz, 2H), 1.88-1.84 (m, 2H).

LC-MS: m/z 377 [M+H⁺] with a purity of 97.57%.

Synthesis of 2-(6-methyl-5,7-dioxo-2,3,4,5,6,7-hexahydro-1H-pyrrolo[3,4-b]pyridin-1-yl)-N-(3-methyl-[1,1'-biphenyl]-4-yl)acetamide, (Compound 78)

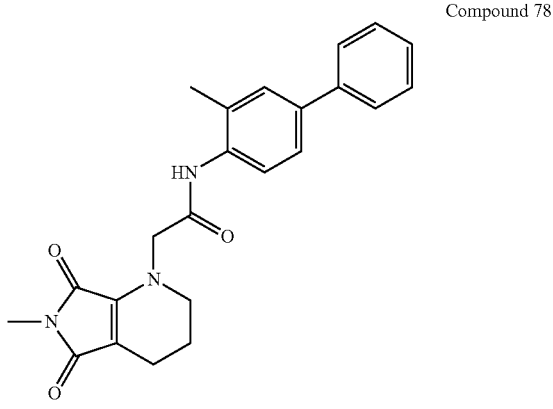 [SMILES: Cc1cc(-c2ccccc2)ccc1NC(=O)CN1CCCC2=C1C(=O)N(C)C2=O]

Compound 78

¹H NMR (400 MHz, DMSO-d₆) δ (ppm): 9.48 (brs, 1H), 7.63-7.65 (m, 2H), 7.42-7.52 (m, 5H), 7.32-7.35 (m, 1H), 4.57 (s, 2H), 3.35 (t, J=5.6 Hz, 2H), 2.78 (s, 3H), 2.28 (s, 3H), 2.19 (t, J=5.6 Hz, 2H), 1.85 (q, J=5.6 Hz, 2H).

LC-MS: m/z 390 [M+H⁺] with a purity of 99.13%.

Synthesis of 2-(6-methyl-5,7-dioxo-2,3,4,5,6,7-hexahydro-1H-pyrrolo[3,4-b]pyridin-1-yl)-N-(4-(pyridin-4-yl)phenyl)acetamide, (Compound 79)

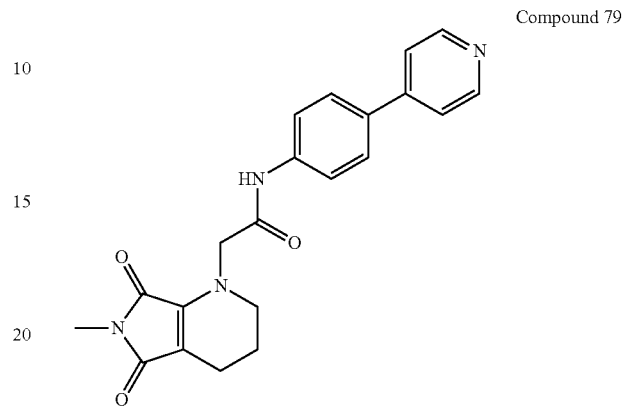

Compound 79

¹H NMR (400 MHz, DMSO-d₆) δ (ppm): 10.30 (s, 1H), 8.59 (d, J=6.0 Hz, 1H), 7.81-7.78 (m, 2H), 7.73-7.67 (m, 4H), 4.55 (s, 2H), 3.35-3.31 (m, 2H), 2.77 (s, 3H), 2.22 (t, J=6.0 Hz, 2H), 1.86-1.84 (m, 2H).

LC-MS: m/z 377 [M+H⁺] with a purity of 98.06%.

Synthesis of N-(2-fluoro-[1,1'-biphenyl]-4-yl)-2-(6-methyl-5,7-dioxo-2,3,4,5,6,7-hexahydro-1H-pyrrolo[3,4-b]pyridin-1-yl)acetamide, (Compound 80)

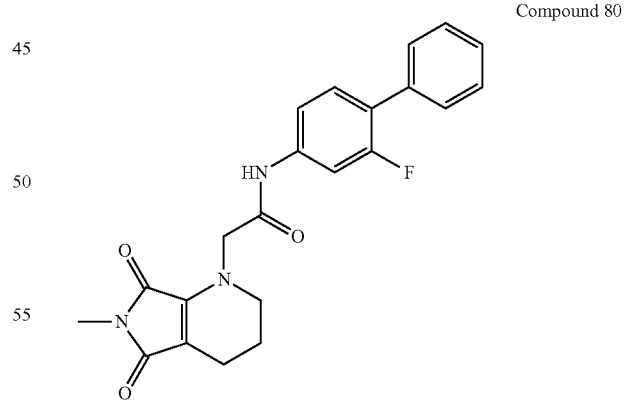

Compound 80

¹H NMR (400 MHz, DMSO-d₆) δ (ppm): 10.41 (s, 1H), 7.67-7.64 (m, 1H), 7.53-7.44 (m, 5H), 7.39-7.35 (m, 2H), 4.55 (s, 2H), 3.35-3.31 (m, 2H), 2.77 (s, 3H), 2.22 (t, J=6.0 Hz, 2H), 1.86-1.82 (m, 2H).

LC-MS: m/z 394 [M+H⁺] with a purity of 96.95%.

Synthesis of N-(3-methoxy-[1,1'-biphenyl]-4-yl)-2-(6-methyl-5,7-dioxo-2,3,4,5,6,7-hexahydro-1H-pyrrolo[3,4-b]pyridin-1-yl)acetamide, (Compound 81)

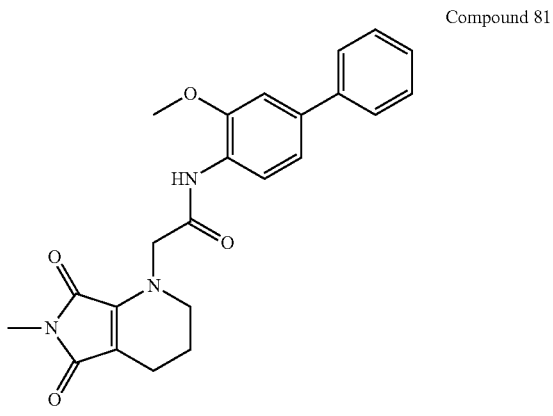 [SMILES: COc1cc(-c2ccccc2)ccc1NC(=O)CN1CCCC2=C1C(=O)N(C)C2=O]

Compound 81

¹H NMR (400 MHz, DMSO-d₆) δ (ppm): 9.38 (s, 1H), 8.06 (d, J=8.4 Hz, 1H), 7.69-7.67 (m, 2H), 7.44 (t, J=7.6 Hz, 2H), 7.36-7.30 (m, 2H), 7.22-7.19 (m, 1H), 4.59 (s, 2H), 3.95 (s, 3H), 3.29-3.27 (s, 2H), 2.77 (s, 3H), 2.21 (t, J=6.4 Hz, 2H), 1.86-1.83 (m, 2H).

LC-MS: m/z 406 [M+H⁺] with a purity of 96.93%.

Synthesis of 2-(6-methyl-5,7-dioxo-2,3,4,5,6,7-hexahydro-1H-pyrrolo[3,4-b]pyridin-1-yl)-N-(2-methyl-[1,1'-biphenyl]-4-yl)acetamide, (Compound 82)

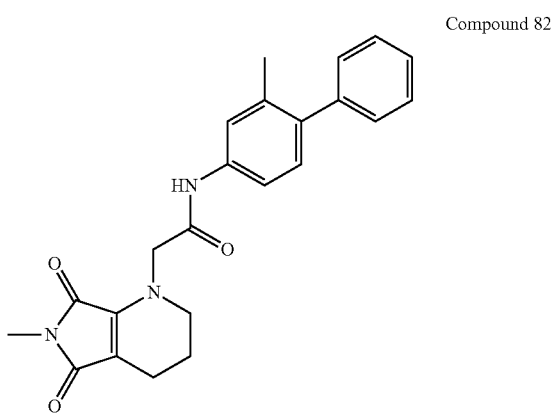 [SMILES: Cc1cc(NC(=O)CN2CCCC3=C2C(=O)N(C)C3=O)ccc1-c1ccccc1]

Compound 82

¹H NMR (400 MHz, DMSO-d₆) δ (ppm): 10.11 (s, 1H), 7.54 (s, 1H), 7.40-7.44 (m, 3H), 7.29-7.35 (m, 3H), 7.12-7.14 (m, 1H), 4.53 (s, 2H), 3.35 (t, J=5.6 Hz, 2H), 2.77 (s, 3H), 2.21 (t, J=5.6 Hz, 2H), 2.20 (s, 3H), 1.85 (q, J=5.6 Hz, 2H).

LC-MS: m/z 390 [M+H⁺] with a purity of 97.53%.

Synthesis of 2-(6-cyclopropyl-5,7-dioxo-2,3,4,5,6,7-hexahydro-1H-pyrrolo[3,4-b]pyridin-1-yl)-N-(6'-methyl-[3,3'-bipyridin]-6-yl)acetamide, (Compound 85)

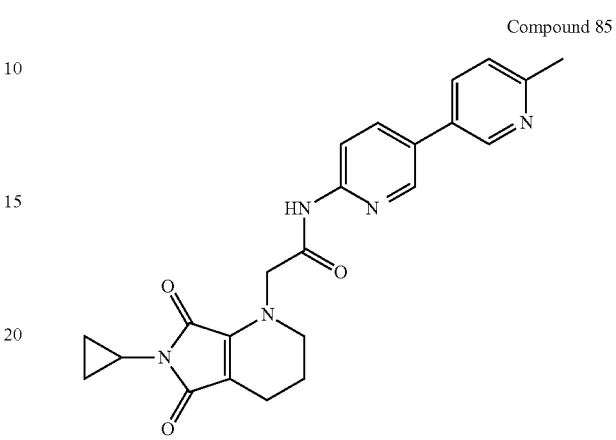

Compound 85

¹H NMR (400 MHz, CDCl₃) δ (ppm): 8.71 (d, J=2.0 Hz, 1H), 8.49 (d, J=2.0 Hz, 1H), 8.41 (s, 1H), 8.28 (d, J=8.8 Hz, 1H), 7.91-7.88 (m, 1H), 7.81 (d, J=6.4 Hz, 1H), 7.30 (d, J=8.0 Hz, 1H), 4.52 (s, 2H), 3.40 (t, J=5.2 Hz, 2H), 2.65 (s, 3H), 2.47-2.41 (m, 1H), 2.37 (t, J=6.0 Hz, 2H), 2.00-1.95 (m, 2H), 0.91-0.80 (m, 4H).

LC-MS: m/z 418 [M+H⁺] with a purity of 98.02%.

Synthesis of 2-(6-cyclopropyl-5,7-dioxo-2,3,4,5,6,7-hexahydro-1H-pyrrolo[3,4-b]pyridin-1-yl)-N-(6-(6-methylpyridin-3-yl)pyridazin-3-yl)acetamide, (Compound 86)

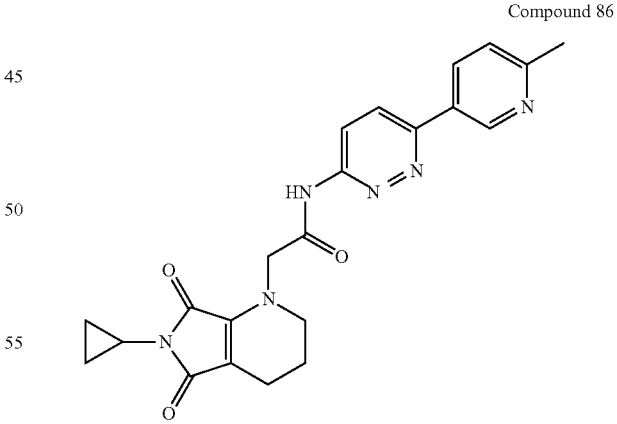

Compound 86

¹H NMR (400 MHz, CDCl₃) δ (ppm): 9.68 (s, 1H), 9.11 (d, J=2.0 Hz, 1H), 8.58 (d, J=9.6 Hz, 1H), 8.33 (d, J=8.4 Hz, 1H), 7.91 (d, J=9.2 Hz, 1H), 7.35 (d, J=8.0 Hz, 1H), 4.69 (s, 2H), 3.40 (t, J=5.2 Hz, 2H), 2.68 (s, 3H), 2.46-2.41 (m, 1H), 2.37 (t, J=6.0 Hz, 2H), 2.02-1.96 (m, 2H), 0.88-0.82 (m, 4H).

LC-MS: m/z 419 [M+H⁺] with a purity of 96.91%.

Synthesis of 2-(6-cyclopropyl-5,7-dioxo-2,3,4,5,6,7-hexahydro-1H-pyrrolo[3,4-b]pyridin-1-yl)-N-(5'-fluoro-[2,3'-bipyridin]-5-yl)acetamide, (Compound 87)

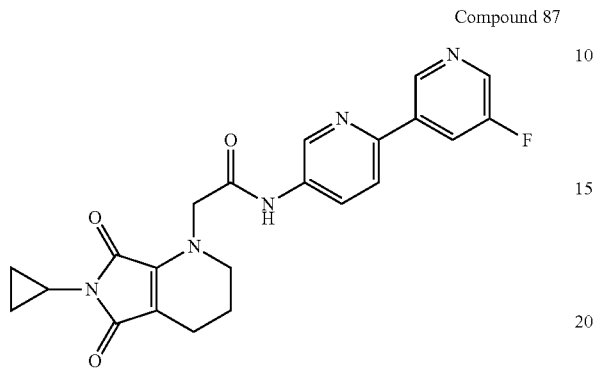

Compound 87

$^1$H NMR (400 MHz, DMSO-d$_6$) δ (ppm): 10.54 (s, 1H), 9.13 (s, 1H), 8.84-8.85 (m, 1H), 8.60 (s, 1H), 8.27-8.30 (m, 1H), 8.17-8.20 (m, 1H), 8.10-8.12 (m, 1H), 4.57 (s, 2H), 3.33 (t, J=5.2 Hz, 2H), 2.34-2.40 (m, 1H), 2.19 (t, J=5.2 Hz, 2H), 1.84 (q, J=5.2 Hz, 2H), 0.73-0.78 (m, 2H), 0.64-0.69 (m, 2H).

LC-MS: m/z 422 [M+H$^+$] with a purity of 98.01%.

Synthesis of N-([3,4'-bipyridin]-6-yl)-2-(6-methyl-5,7-dioxo-2,3,4,5,6,7-hexahydro-1H-pyrrolo[3,4-b]pyridin-1-yl)acetamide, (Compound 88)

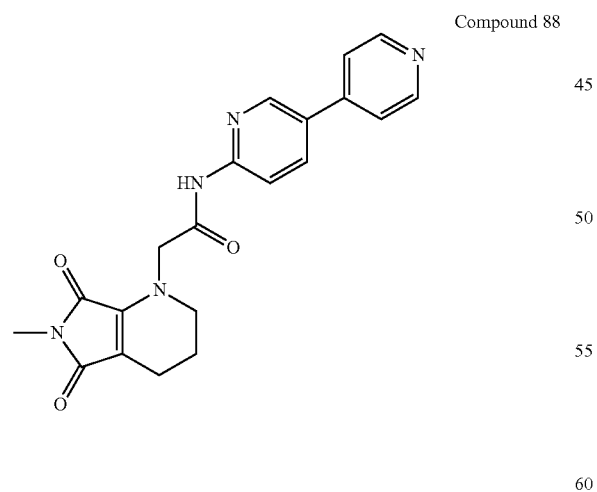

Compound 88

$^1$H NMR (400 MHz, CDCl$_3$) δ (ppm): 8.69 (d, J=6.0 Hz, 2H), 8.58-8.57 (m, 1H), 8.41 (s, 1H), 8.30 (d, J=8.4 Hz, 1H), 7.98-7.95 (m, 1H), 7.48-7.47 (m, 2H), 4.53 (s, 2H), 3.42 (t, J=5.6 Hz, 2H), 2.94 (s, 3H), 2.38 (t, J=6.0 Hz, 2H), 2.02-1.96 (m, 2H).

LC-MS: m/z 378 [M+H$^+$] with a purity of 97.34%.

Synthesis of 2-(6-cyclopropyl-5,7-dioxo-2,3,4,5,6,7-hexahydro-1H-pyrrolo[3,4-b]pyridin-1-yl)-N-(5-(pyrimidin-5-yl)pyridin-2-yl)acetamide, (Compound 89)

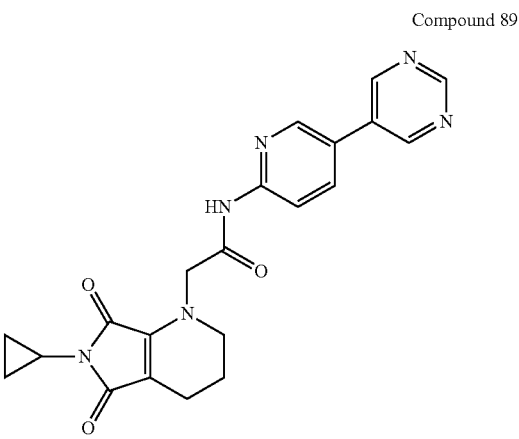 [SMILES: O=C(CN1CCCC2=C1C(=O)N(C1CC1)C2=O)Nc1ccc(-c2cncnc2)cn1]

Compound 89

$^1$H NMR (400 MHz, CDCl$_3$) δ (ppm): 9.24 (s, 1H), 8.94 (s, 2H), 8.52 (d, J=2.0 Hz, 1H), 8.40-8.33 (m, 2H), 7.94-7.91 (m, 1H), 4.52 (s, 2H), 3.40 (t, J=5.6 Hz, 2H), 2.47-2.42 (m, 1H), 2.36 (t, J=6.0 Hz, 2H), 2.01-1.95 (m, 2H), 0.91-0.81 (m, 4H).

LC-MS: m/z 405 [M+H$^+$] with a purity of 97.02%.

Synthesis of 2-(6-cyclopropyl-5,7-dioxo-2,3,4,5,6,7-hexahydro-1H-pyrrolo[3,4-b]pyridin-1-yl)-N-(4-(pyrimidin-5-yl)phenyl)acetamide, (Compound 90)

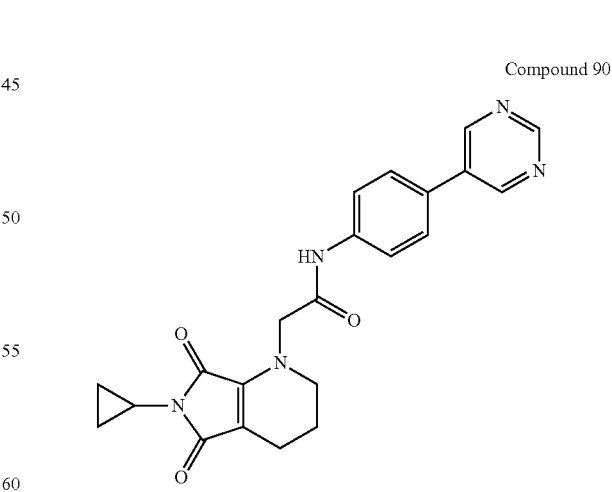

Compound 90

$^1$H NMR (400 MHz, CDCl$_3$) δ (ppm): 9.19 (s, 1H), 8.93 (s, 2H), 8.12 (s, 1H), 7.71-7.68 (m, 2H), 7.57-7.55 (m, 2H), 4.40 (s, 2H), 3.46 (t, J=5.2 Hz, 2H), 2.49-2.43 (m, 1H), 2.34 (t, J=6.0 Hz, 2H), 1.98-1.92 (m, 2H), 0.94-0.82 (m, 4H).

LC-MS: m/z 404 [M+H$^+$] with a purity of 97.97%.

Synthesis of N-(2-methoxy-[1,1'-biphenyl]-4-yl)-2-(6-methyl-5,7-dioxo-2,3,4,5,6,7-hexahydro-1H-pyrrolo[3,4-b]pyridin-1-yl)acetamide, (Compound 99)

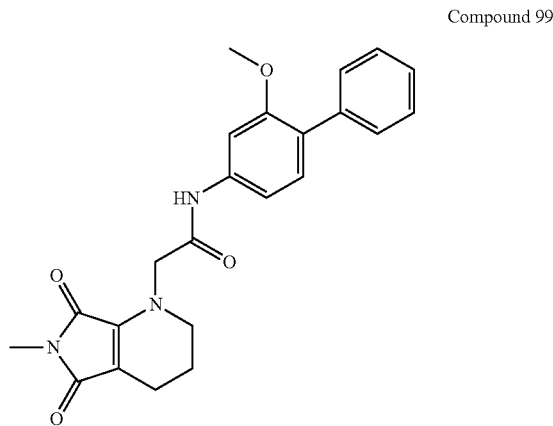 [SMILES: COc1cc(NC(=O)CN2CCCC3=C2C(=O)N(C)C3=O)ccc1-c1ccccc1]

Compound 99

¹H NMR (400 MHz, METHANOL-d₄) δ 7.44-7.48 (m, 3H), 7.32-7.36 (m, 2H), 7.21-7.27 (m, 2H), 7.09-7.12 (m, 1H), 4.60 (s, 2H), 4.56 (bs, 1H), 3.78 (s, 3H), 3.40 (t, J=5.6 Hz, 2H), 2.87 (s, 3H), 2.32 (t, J=5.6 Hz, 2H), 1.97 (q, J=5.6 Hz, 2H).

LC-MS: m/z 406 (M+H⁺) with a purity of 97.22%.

Synthesis of N-(5'-fluoro-[2,3'-bipyridin]-5-yl)-2-(6-methyl-5,7-dioxo-2,3,4,5,6,7-hexahydro-1H-pyrrolo[3,4-b]pyridin-1-yl)acetamide, (Compound 100)

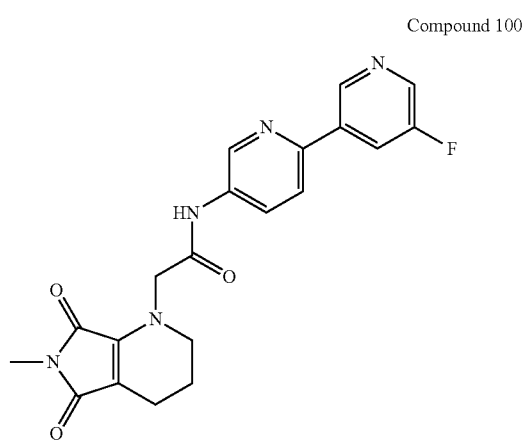 [SMILES: CN1C(=O)C2=C(C1=O)N(CC(=O)Nc1ccc(-c3cncc(F)c3)nc1)CCC2]

Compound 100

¹H NMR (400 MHz, METHANOL-d₄) δ 9.03 (s, 1H), 8.85 (s, 1H), 8.48-8.49 (m, 1H), 8.21-8.25 (m, 2H), 7.96-7.98 (m, 1H), 4.63 (s, 2H), 3.41 (t, J=5.6 Hz, 2H), 3.34 (s, 3H), 2.86 (s, 3H), 2.32 (t, J=5.6 Hz, 2H), 1.98 (q, J=5.6 Hz, 2H).

LC-MS: m/z 396 (M+H⁺) with a purity of 96.89%.

Synthesis of 2-(6-methyl-5,7-dioxo-2,3,4,5,6,7-hexahydro-1H-pyrrolo[3,4-b]pyridin-1-yl)-N-(5-(pyrimidin-5-yl)pyridin-2-yl)acetamide, (Compound 101)

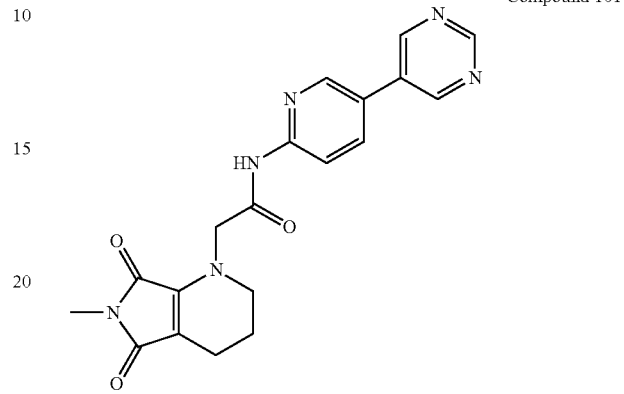

Compound 101

¹H NMR (400 MHz, CDCl₃) δ 9.24 (s, 1H), 8.94 (s, 2H), 8.52 (d, J=2.0 Hz, 1H), 8.44 (s, 1H), 8.34 (d, J=8.8 Hz, 1H), 7.94-7.91 (m, 1H), 4.53 (s, 2H), 3.42 (t, J=5.2 Hz, 2H), 2.95 (s, 3H), 2.39 (t, J=6.0 Hz, 2H), 2.02-1.96 (m, 2H).

LC-MS: m/z 379 [M+H⁺] with a purity of 96.17%.

Synthesis of 2-(6-cyclopropyl-5,7-dioxo-2,3,4,5,6,7-hexahydro-1H-pyrrolo[3,4-b]pyridin-1-yl)-N-(6-(pyrimidin-5-yl)pyridin-3-yl)acetamide, (Compound 102)

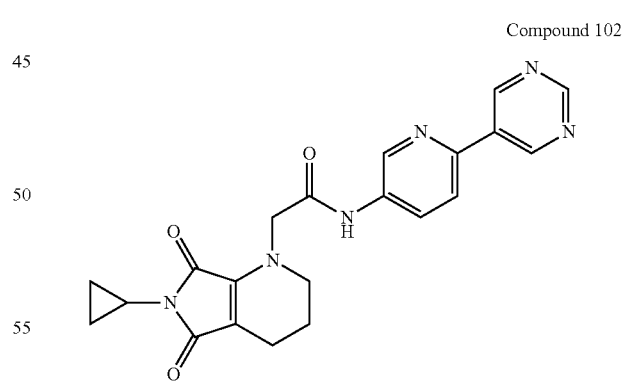

Compound 102

¹H NMR (400 MHz, CDCl₃) δ 9.30 (s, 2H), 9.23 (s, 1H), 8.70 (d, J=2.4 Hz, 1H), 8.34-8.31 (m, 2H), 7.75 (d, J=8.8 Hz, 1H), 4.41 (s, 2H), 3.47 (t, J=5.6 Hz, 2H), 2.49-2.44 (m, 1H), 2.35 (t, J=6.4 Hz, 2H), 1.99-1.93 (m, 2H), 0.94-0.82 (m, 4H).

LC-MS: m/z 405 [M+H⁺] with a purity of 95.90%.

Synthesis of 2-(6-methyl-5,7-dioxo-2,3,4,5,6,7-hexahydro-1H-pyrrolo[3,4-b]pyridin-1-yl)-N-(6-(pyrimidin-5-yl)pyridin-3-yl)acetamide, (Compound 103)

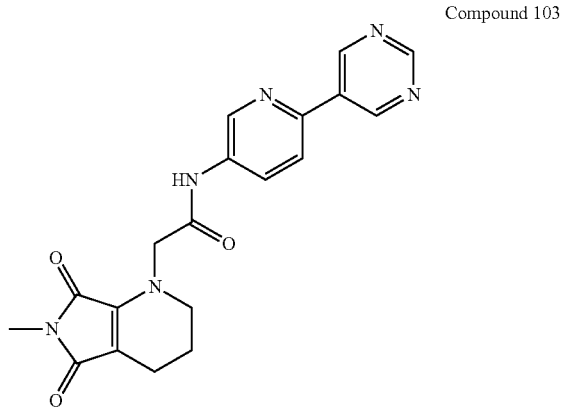 [SMILES: CN1C(=O)C2=C(C1=O)N(CC(=O)Nc1ccc(-c3cncnc3)nc1)CCC2]

Compound 103

$^1$H NMR (400 MHz, CDCl$_3$) δ 9.30 (s, 2H), 9.23 (s, 1H), 8.70 (d, J=2.4 Hz, 1H), 8.33-8.31 (m, 2H), 7.75 (d, J=8.8 Hz, 1H), 4.43 (s, 2H), 3.48 (t, J=5.2 Hz, 2H), 2.97 (s, 3H), 2.37 (t, J=6.0 Hz, 2H), 2.00-1.94 (m, 2H).

LC-MS: m/z 379 [M+H$^+$] with a purity of 97.77%.

Synthesis of 2-(6-cyclopropyl-5,7-dioxo-2,3,4,5,6,7-hexahydro-1H-pyrrolo[3,4-b]pyridin-1-yl)-N-(2'-fluoro-[3,3'-bipyridin]-6-yl)acetamide, (Compound 104)

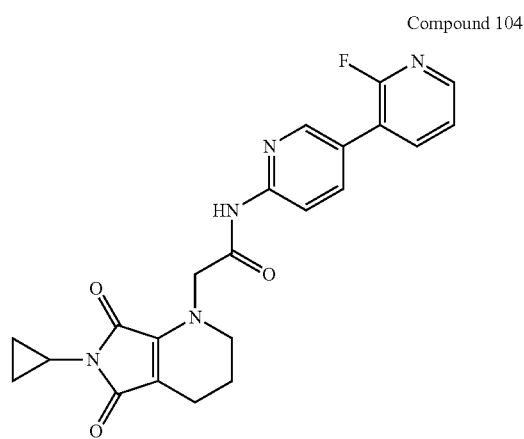

Compound 104

$^1$H NMR (400 MHz, CDCl$_3$) δ 8.50 (s, 1H), 8.35-8.23 (m, 3H), 7.94-7.84 (m, 2H), 7.33-7.29 (m, 1H), 4.51 (s, 2H), 3.40 (t, J=5.2 Hz, 2H), 2.47-2.42 (m, 1H), 2.36 (t, J=6.0 Hz, 2H), 2.00-1.95 (m, 2H), 0.91-0.81 (m, 4H).

LC-MS: m/z 422 [M+H$^+$] with a purity of 96.21%.

Synthesis of 2-(6-cyclopropyl-5,7-dioxo-2,3,4,5,6,7-hexahydro-1H-pyrrolo[3,4-b]pyridin-1-yl)-N-(6'-fluoro-[3,3'-bipyridin]-6-yl)acetamide, (Compound 105)

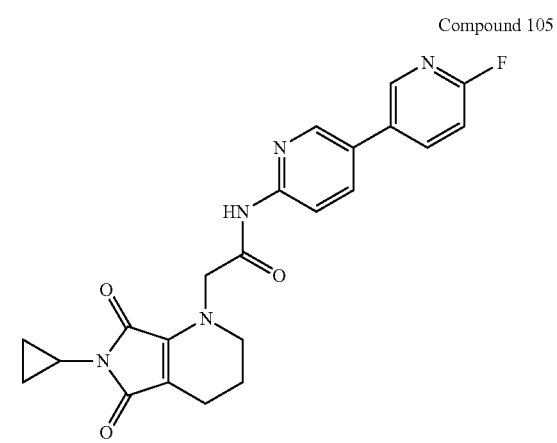 [SMILES: O=C(CN1CCCC2=C1C(=O)N(C1CC1)C2=O)Nc1ccc(-c2ccc(F)nc2)cn1]

Compound 105

$^1$H NMR (400 MHz, CDCl$_3$) δ 8.47-8.28 (m, 4H), 7.97-7.92 (m, 1H), 7.88-7.86 (m, 1H), 7.06-7.03 (m, 1H), 4.51 (s, 2H), 3.40 (t, J=5.2 Hz, 2H), 2.47-2.42 (m, 1H), 2.36 (t, J=6.4 Hz, 2H), 2.00-1.95 (m, 2H), 0.91-0.80 (m, 4H).

LC-MS: m/z 422 [M+H$^+$] with a purity of 96.14%.

Synthesis of 2-(6-cyclopropyl-5,7-dioxo-2,3,4,5,6,7-hexahydro-1H-pyrrolo[3,4-b]pyridin-1-yl)-N-(5'-fluoro-[3,3'-bipyridin]-6-yl)acetamide, (Compound 106)

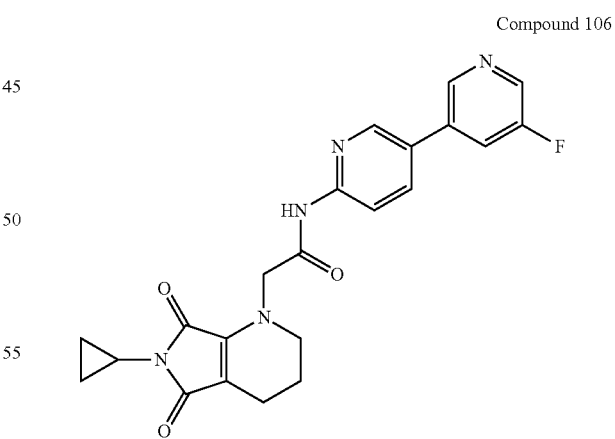

Compound 106

$^1$H NMR (400 MHz, CDCl$_3$) δ 8.65-8.64 (m, 1H), 8.52-8.49 (m, 2H), 8.39 (s, 1H), 8.31 (d, J=8.4 Hz, 1H), 7.93-7.90 (m, 1H), 7.59-7.55 (m, 1H), 4.51 (s, 2H), 3.40 (t, J=5.2 Hz, 2H), 2.47-2.42 (m, 1H), 2.36 (t, J=6.4 Hz, 2H), 2.01-1.95 (m, 2H), 0.91-0.81 (m, 4H).

LC-MS: m/z 422 [M+H$^+$] with a purity of 96.31%.

Synthesis of 2-(6-cyclopropyl-5,7-dioxo-2,3,4,5,6,7-hexahydro-1H-pyrrolo[3,4-b]pyridin-1-yl)-N-(5-fluoro-[3,3'-bipyridin]-6-yl)acetamide, (Compound 107)

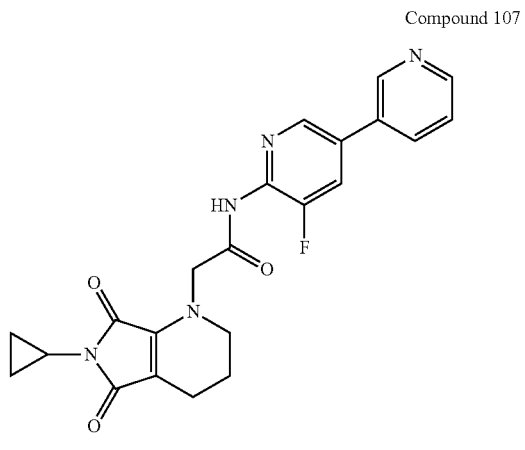 [SMILES: O=C(CN1CCCC2=C1C(=O)N(C1CC1)C2=O)Nc1ncc(-c2cccnc2)cc1F]

Compound 107

$^1$H NMR (400 MHz, CDCl$_3$) δ 8.82-8.81 (m, 1H), 8.68-8.66 (m, 1H), 8.41 (d, J=2.0 Hz, 1H), 8.06 (s, 1H), 7.85-7.82 (m, 1H), 7.67-7.64 (m, 1H), 7.44-7.40 (m, 1H), 4.85 (s, 2H), 3.42 (t, J=5.6 Hz, 2H), 2.45-2.40 (m, 1H), 2.35 (t, J=6.0 Hz, 2H), 1.99-1.93 (m, 2H), 0.87-0.81 (m, 4H).

LC-MS: m/z 422 [M+H$^+$] with a purity of 96.57%.

Synthesis of N-(6'-fluoro-[2,3'-bipyridin]-5-yl)-2-(6-methyl-5,7-dioxo-2,3,4,5,6,7-hexahydro-1H-pyrrolo[3,4-b]pyridin-1-yl)acetamide, (Compound 108)

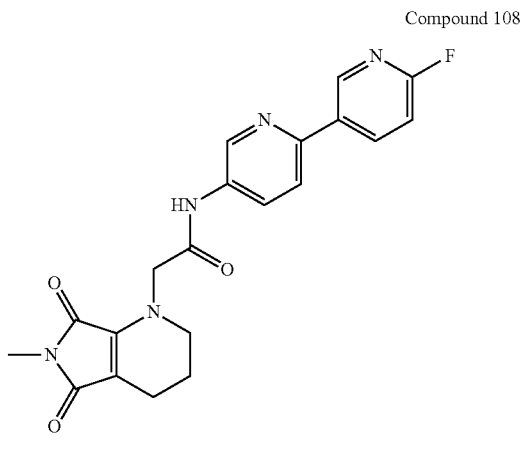 [SMILES: CN1C(=O)C2=C(C1=O)N(CC(=O)Nc1ccc(-c3ccc(F)nc3)nc1)CCC2]

Compound 108

$^1$H NMR (400 MHz, METHANOL-d$_4$) δ 8.78-8.82 (m, 2H), 8.49-8.54 (m, 1H), 8.19-8.22 (m, 1H), 7.88-7.90 (m, 1H), 7.16-7.18 (m, 1H), 4.62 (s, 2H), 3.41 (t, J=5.6 Hz, 2H), 2.87 (s, 3H), 2.32 (t, J=5.6 Hz, 2H), 1.97 (q, J=5.6 Hz, 2H).

LC-MS: m/z 396 (M+H$^+$) with a purity of 97.21%.

Synthesis of 2-(6-cyclopropyl-5,7-dioxo-2,3,4,5,6,7-hexahydro-1H-pyrrolo[3,4-b]pyridin-1-yl)-N-(4-fluoro-[3,3'-bipyridin]-6-yl)acetamide, (Compound 109)

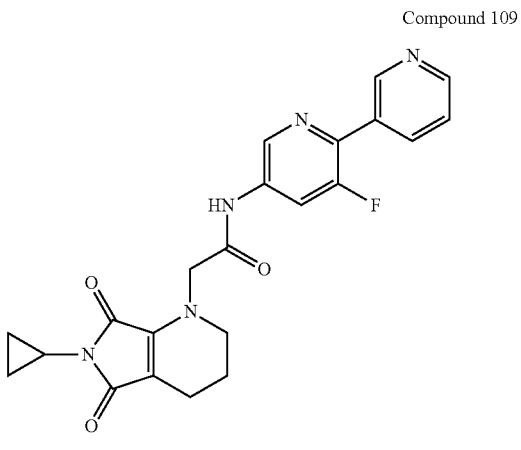 [SMILES: O=C(CN1CCCC2=C1C(=O)N(C1CC1)C2=O)Nc1cnc(-c2cccnc2)c(F)c1]

Compound 109

$^1$H NMR (400 MHz, CDCl$_3$) δ 9.19 (s, 1H), 8.65-8.63 (m, 1H), 8.50 (s, 1H), 8.44-8.43 (m, 1H), 8.27-8.24 (m, 1H), 7.41-7.38 (m, 1H), 4.40 (s, 2H), 3.46 (t, J=5.2 Hz, 2H), 2.49-2.44 (m, 1H), 2.35 (t, J=6.0 Hz, 2H), 1.99-1.93 (m, 2H), 0.94-0.82 (m, 4H).

LC-MS: m/z 422 [M+H$^+$] with a purity of 98.16%.

Synthesis of 2-(6-cyclopropyl-5,7-dioxo-2,3,4,5,6,7-hexahydro-1H-pyrrolo[3,4-b]pyridin-1-yl)-N-(2'-methyl-[3,3'-bipyridin]-6-yl)acetamide, (Compound 110)

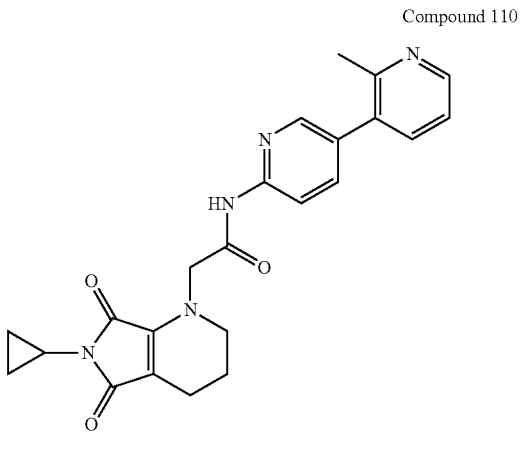 [SMILES: Cc1ncccc1-c1ccc(NC(=O)CN2CCCC3=C2C(=O)N(C2CC2)C3=O)nc1]

Compound 110

$^1$H NMR (400 MHz, CDCl$_3$) δ 8.55-8.53 (m, 1H), 8.36 (s, 1H), 8.27-8.26 (m, 2H), 7.71-7.68 (m, 1H), 7.51-7.49 (m, 1H), 7.23-7.20 (m, 1H), 4.52 (s, 2H), 3.40 (t, J=5.2 Hz, 2H), 2.51 (s, 3H), 2.47-2.42 (m, 1H), 2.36 (t, J=6.0 Hz, 2H), 2.01-1.95 (m, 2H), 0.91-0.81 (m, 4H).

LC-MS: m/z 418 [M+H$^+$] with a purity of 96.76%.

Synthesis of 2-(6-cyclopropyl-5,7-dioxo-2,3,4,5,6,7-hexahydro-1H-pyrrolo[3,4-b]pyridin-1-yl)-N-(4'-methyl-[3,3'-bipyridin]-6-yl)acetamide, (Compound 111)

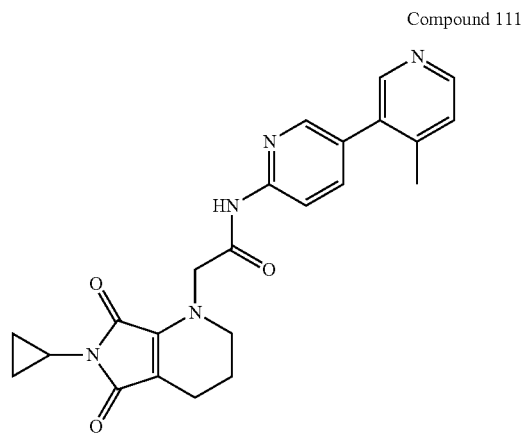 [SMILES: Cc1ccncc1-c1ccc(NC(=O)CN2CCCC3=C2C(=O)N(C2CC2)C3=O)nc1]

Compound 111

$^1$H NMR (400 MHz, CDCl$_3$) δ 8.49-8.48 (m, 1H), 8.42 (s, 1H), 8.36 (s, 1H), 8.28-8.26 (m, 2H), 7.71-7.68 (m, 1H), 7.22-7.21 (m, 1H), 7.23-7.20 (m, 1H), 4.52 (s, 2H), 3.40 (t, J=5.2 Hz, 2H), 2.47-2.42 (m, 1H), 2.36 (t, J=6.0 Hz, 2H), 2.01-1.95 (m, 2H), 1.56 (s, 3H), 0.91-0.81 (m, 4H)

LC-MS: m/z 418 [M+H$^+$] with a purity of 99.28%.

Synthesis of N-(6'-fluoro-[2,3'-bipyridin]-5-yl)-2-(6-methyl-5,7-dioxo-2,3,4,5,6,7-hexahydro-1H-pyrrolo[3,4-b]pyridin-1-yl)acetamide, (Compound 112)

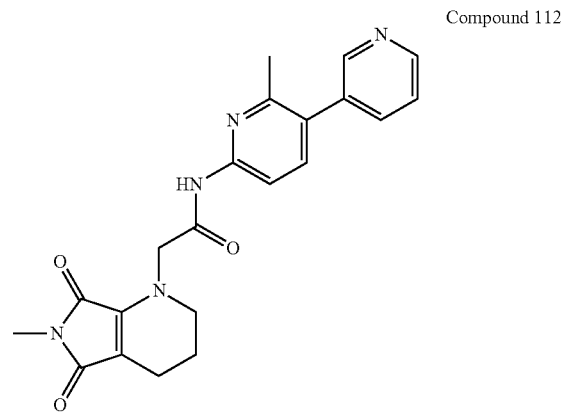 [SMILES: Cc1nc(NC(=O)CN2CCCC3=C2C(=O)N(C)C3=O)ccc1-c1cccnc1]

Compound 112

$^1$H NMR (400 MHz, METHANOL-d$_4$) δ 8.55 (bs, 2H), 7.99-8.01 (m, 1H), 7.86-7.89 (m, 1H), 7.63-7.65 (m, 1H), 7.52-7.55 (m, 1H), 4.63 (s, 2H), 3.40 (t, J=5.6 Hz, 2H), 2.87 (s, 3H), 2.42 (s, 3H), 2.32 (t, J=5.6 Hz, 2H), 1.98 (q, J=5.6 Hz, 2H).

LC-MS: m/z 392 (M+H$^+$) with a purity of 98.62%.

Synthesis of 2-(6-methyl-5,7-dioxo-2,3,4,5,6,7-hexahydro-1H-pyrrolo[3,4-b]pyridin-1-yl)-N-(5-methyl-[3,3'-bipyridin]-6-yl)acetamide, (Compound 113)

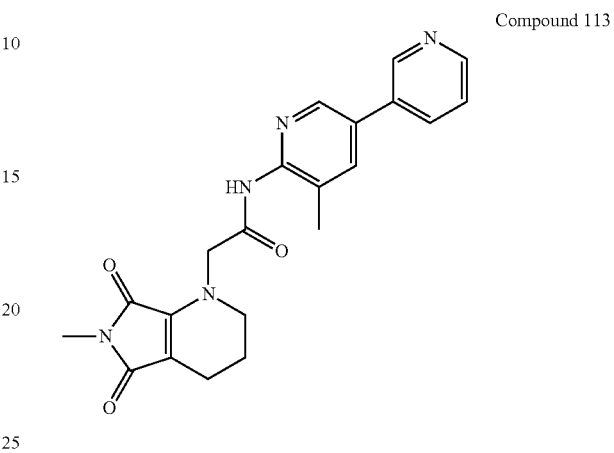

Compound 113

$^1$H NMR (400 MHz, METHANOL-d$_4$) δ 8.86 (bs, 1H), 8.55-8.58 (m, 2H), 8.14-8.17 (m, 1H), 8.04-8.05 (m, 1H), 7.54-7.57 (m, 1H), 4.69 (s, 2H), 3.43 (t, J=5.6 Hz, 2H), 2.87 (s, 3H), 2.36 (s, 3H), 2.31 (t, J=5.6 Hz, 2H), 1.97 (q, J=5.6 Hz, 2H).

LC-MS: m/z 392 (M+H$^+$) with a purity of 96.35%.

Synthesis of 2-(6-methyl-5,7-dioxo-2,3,4,5,6,7-hexahydro-1H-pyrrolo[3,4-b]pyridin-1-yl)-N-(4-methyl-[3,3'-bipyridin]-6-yl)acetamide, (Compound 114)

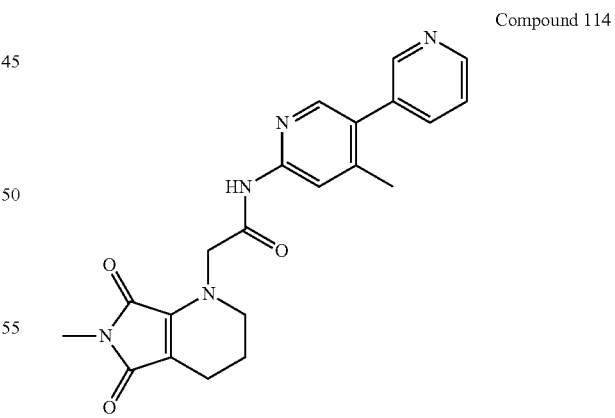

Compound 114

$^1$H NMR (400 MHz, METHANOL-d$_4$) δ 8.57-8.59 (m, 1H), 8.55 (s, 1H), 8.14 (s, 1H), 8.07 (bs, 1H), 7.87-7.90 (m, 1H), 7.53-7.56 (m, 1H), 4.64 (s, 2H), 3.40 (t, J=5.6 Hz, 2H), 2.87 (s, 3H), 2.32 (t, J=5.6 Hz, 2H), 2.31 (s, 3H), 1.98 (q, J=5.6 Hz, 2H).

LC-MS: m/z 392 (M+H$^+$) with a purity of 96.96%.

Synthesis of 2-(6-cyclopropyl-5,7-dioxo-2,3,4,5,6,7-hexahydro-1H-pyrrolo[3,4-b]pyridin-1-yl)-N-(5'-methyl-[3,3'-bipyridin]-6-yl)acetamide, (Compound 115)

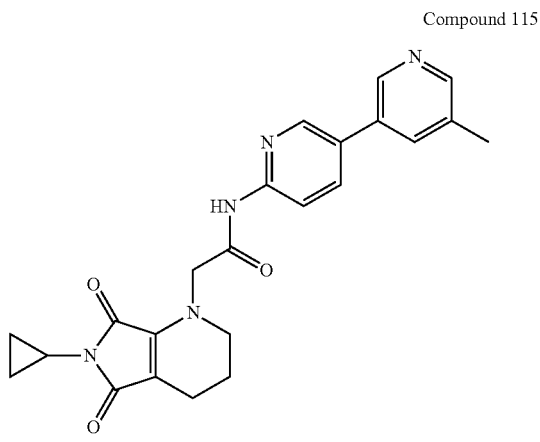 [SMILES: Cc1cncc(-c2ccc(NC(=O)CN3CCCC4=C3C(=O)N(C3CC3)C4=O)nc2)c1]

Compound 115

¹H NMR (400 MHz, CDCl₃) δ 8.97 (s, 1H), 8.69 (d, J=2.4 Hz, 1H), 8.49 (s, 1H), 8.29-8.26 (m, 2H), 8.13 (s, 1H), 7.76 (d, J=8.8 Hz, 1H), 4.44 (s, 2H), 3.49 (t, J=5.6 Hz, 2H), 2.51-2.46 (m, 1H), 2.44 (s, 3H), 2.37 (t, J=6.4 Hz, 2H), 2.01-1.95 (m, 2H), 1.56 (s, 3H), 0.96-0.84 (m, 4H).

LC-MS: m/z 418 [M+H⁺] with a purity of 98.20%.

Synthesis of 2-(6-cyclopropyl-5,7-dioxo-2,3,4,5,6,7-hexahydro-1H-pyrrolo[3,4-b]pyridin-1-yl)-N-(4-methyl-[3,3'-bipyridin]-6-yl)acetamide, (Compound 120)

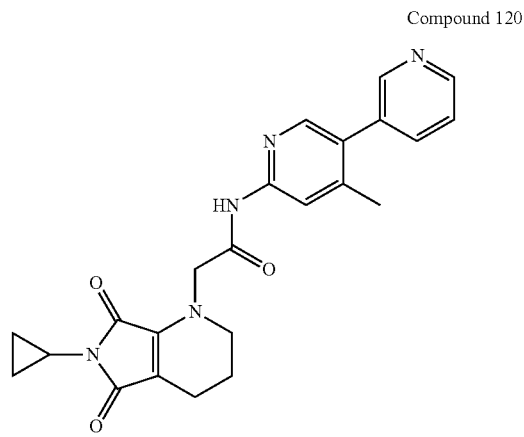 [SMILES: Cc1cc(NC(=O)CN2CCCC3=C2C(=O)N(C2CC2)C3=O)ncc1-c1cccnc1]

Compound 120

¹H NMR (400 MHz, CDCl₃) δ 8.65-8.63 (m, 1H), 8.58 (d, J=1.6 Hz, 1H), 8.28 (s, 1H), 8.15 (s, 1H), 8.11 (s, 1H), 7.65-7.62 (m, 1H), 7.40-7.37 (m, 1H), 4.51 (s, 2H), 3.39 (t, J=5.2 Hz, 2H), 2.47-2.41 (m, 1H), 2.35 (t, J=6.0 Hz, 2H), 2.31 (s, 3H), 2.00-1.95 (m, 2H), 0.90-0.80 (m, 4H)

LC-MS: m/z 418 [M+H⁺] with a purity of 98.51%.

Synthesis of 2-(6-cyclopropyl-5,7-dioxo-2,3,4,5,6,7-hexahydro-1H-pyrrolo[3,4-b]pyridin-1-yl)-N-(6'-fluoro-[2,3'-bipyridin]-5-yl)acetamide, (Compound 124)

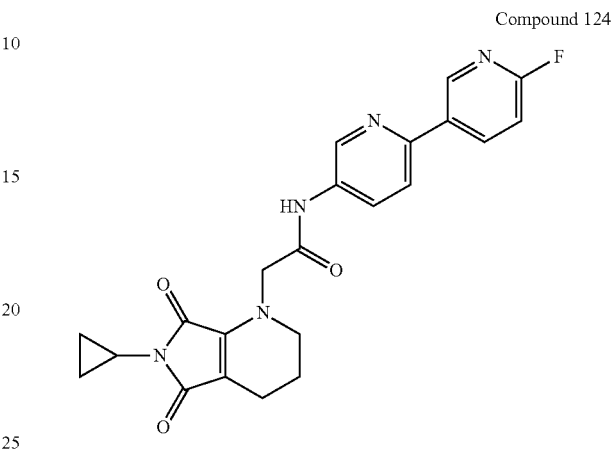

Compound 124

¹H NMR (400 MHz, METHANOL-d₄) δ 8.78-8.82 (m, 2H), 8.49-8.54 (m, 1H), 8.19-8.22 (m, 1H), 7.88-7.90 (m, 1H), 7.16-7.18 (m, 1H), 4.61 (s, 2H), 3.39 (t, J=5.6 Hz, 2H), 2.36-2.42 (m, 1H), 2.29 (t, J=5.6 Hz, 2H), 1.96 (q, J=5.6 Hz, 2H), 0.76-0.82 (m, 4H).

LC-MS: m/z 422 (M+H⁺) with a purity of 97.91%.

Synthesis of 2-(6-cyclopropyl-5,7-dioxo-2,3,4,5,6,7-hexahydro-1H-pyrrolo[3,4-b]pyridin-1-yl)-N-(2-methyl-[3,3'-bipyridin]-6-yl)acetamide, (Compound 125)

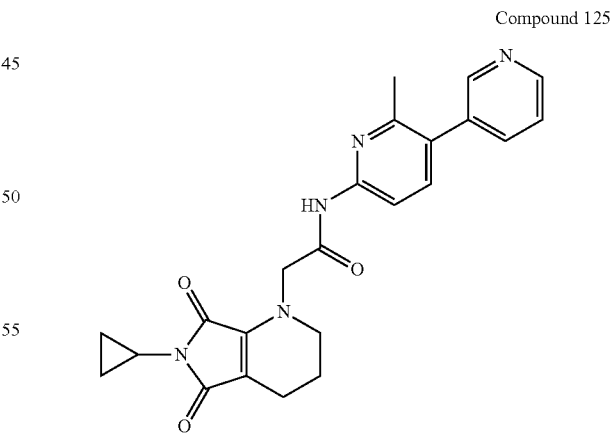

Compound 125

¹H NMR (400 MHz, METHANOL-d₄) δ 8.55-8.56 (m, 2H), 7.99-8.01 (bs, 1H), 7.86-7.89 (m, 1H), 7.64-7.66 (m, 1H), 7.52-7.55 (m, 1H), 4.61 (s, 2H), 3.38 (t, J=5.6 Hz, 2H), 2.42 (s, 3H), 2.36-2.41 (m, 1H), 2.29 (t, J=5.6 Hz, 2H), 1.96 (q, J=5.6 Hz, 2H), 0.76-0.82 (m, 4H).

LC-MS: m/z 418 (M+H⁺) with a purity of 96.20%.

Synthesis of 2-(6-cyclopropyl-5,7-dioxo-2,3,4,5,6,7-hexahydro-1H-pyrrolo[3,4-b]pyridin-1-yl)-N-(2-methyl-[3,3'-bipyridin]-6-yl)acetamide, (Compound 126)

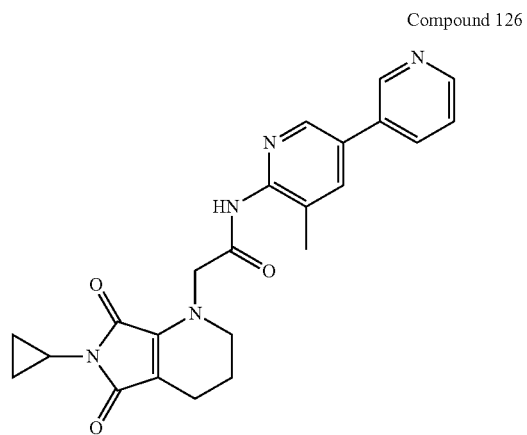 [SMILES: Cc1cc(-c2cccnc2)cnc1NC(=O)CN1CCCC2=C1C(=O)N(C1CC1)C2=O]

Compound 126

$^1$H NMR (400 MHz, METHANOL-d$_4$) δ 8.85-8.86 (m, 1H), 8.57-8.58 (m, 1H), 8.55-8.56 (m, 1H), 8.14-8.17 (m, 1H), 8.05 (bs, 1H), 7.54-7.57 (m, 1H), 4.67 (s, 2H), 3.41 (t, J=5.6 Hz, 2H), 2.38-2.42 (m, 1H), 2.36 (s, 3H), 2.28 (t, J=5.6 Hz, 2H), 1.96 (q, J=5.6 Hz, 2H), 0.74-0.83 (m, 4H).

LC-MS: m/z 418 (M+H$^+$) with a purity of 96.26%.

Synthesis of 2-(6-cyclopropyl-5,7-dioxo-2,3,4,5,6,7-hexahydro-1H-pyrrolo[3,4-b]pyridin-1-yl)-N-(5-(6-methylpyrazin-2-yl)pyridin-2-yl)acetamide, (Compound 128)

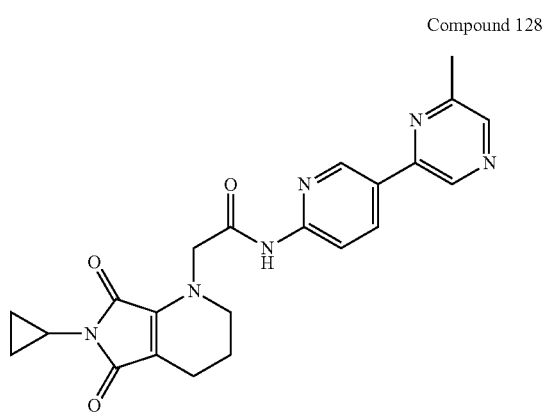 [SMILES: Cc1cncc(-c2ccc(NC(=O)CN3CCCC4=C3C(=O)N(C3CC3)C4=O)nc2)n1]

Compound 128

$^1$H NMR (400 MHz, CDCl$_3$) δ 8.93 (d, J=1.6 Hz, 1H), 8.80 (s, 1H), 8.42 (s, 1H), 8.37-8.34 (m, 2H), 8.31-8.29 (m, 1H), 4.52 (s, 2H), 3.40 (t, J=5.2 Hz, 2H), 2.63 (s, 3H), 2.47-2.42 (m, 1H), 2.36 (t, J=6.4 Hz, 2H), 2.01-1.95 (m, 2H), 0.91-0.82 (m, 4H).

LC-MS: m/z 419 [M+H$^+$] with a purity of 96.37%.

Synthesis of 2-(6-methyl-5,7-dioxo-2,3,4,5,6,7-hexahydro-1H-pyrrolo[3,4-b]pyridin-1-yl)-N-(5-(6-methylpyrazin-2-yl)pyridin-2-yl)acetamide, (Compound 129)

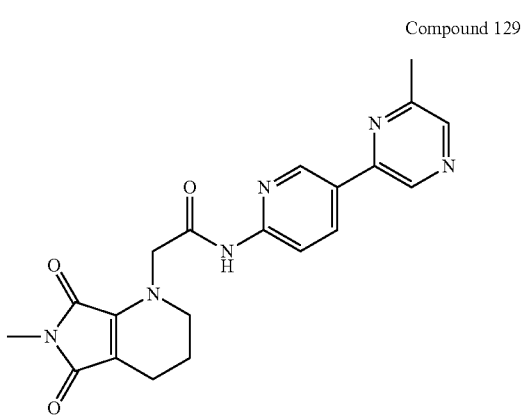 [SMILES: Cc1cncc(-c2ccc(NC(=O)CN3CCCC4=C3C(=O)N(C)C4=O)nc2)n1]

Compound 129

$^1$H NMR (400 MHz, CDCl$_3$) δ 8.93 (s, 1H), 8.80 (s, 1H), 8.42-8.29 (m, 4H), 4.54 (s, 2H), 3.41 (t, J=6.0 Hz, 2H), 2.94 (s, 3H), 2.63 (s, 3H), 2.39 (t, J=5.6 Hz, 2H), 2.00-1.98 (m, 2H).

LC-MS: m/z 393 [M+H$^+$] with a purity of 99.05%.

Synthesis of 2-(6-cyclopropyl-5,7-dioxo-2,3,4,5,6,7-hexahydro-1H-pyrrolo[3,4-b]pyridin-1-yl)-N-(5-methyl-2,3'-bipyridin-6'-yl)acetamide, (Compound 146)

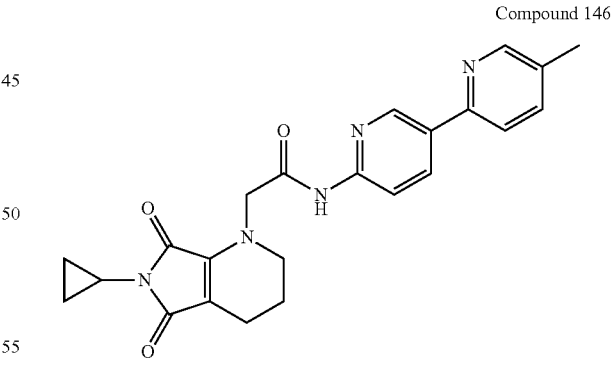

Compound 146

$^1$H NMR (400 MHz, DMSO-d$_6$): 10.82 (s, 1H), 9.015-9.01 (d, J=2 Hz, 1H), 8.50 (s, 1H), 8.43-8.40 (dd, J$_1$=2.4 Hz, J$_2$=8.8 Hz, 1H), 8.11-8.09 (d, J=9.2 Hz, 1H), 7.92-7.90 (d, J=8.4 Hz, 1H), 7.72-7.70 (m, 1H), 4.58 (s, 2H), 3.34-3.29 (m, 2H), 2.44-2.38 (m, 1H), 2.33 (s, 3H), 2.20-2.17 (t, J=6 Hz, 2H), 1.84-1.81 (m, 2H), 0.77-0.74 (m, 2H), 0.69-0.64 (m, 2H).

LC-MS: m/z 418.14 (M+H$^+$) with a purity of 99.06%.

Synthesis of 2-(6-cyclopropyl-5,7-dioxo-2,3,4,5,6,7-hexahydro-1H-pyrrolo[3,4-b]pyridin-1-yl)-N-(4-fluoro-3,3'-bipyridin-6-yl)acetamide, (Compound 151)

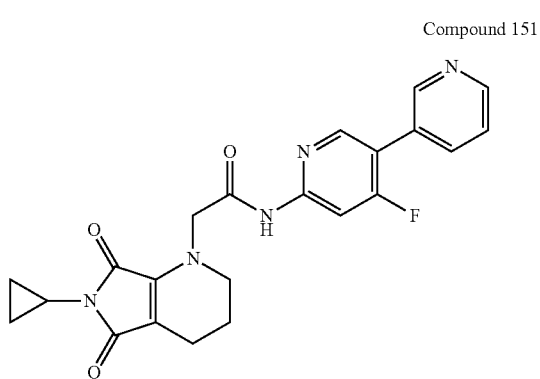 [SMILES: O=C(CN1CCCC2=C1C(=O)N(C1CC1)C2=O)Nc1cc(F)c(-c2cccnc2)cn1]

Compound 151

$^1$H NMR (400 MHz, DMSO-d$_6$): 11.11 (s, 1H), 8.80 (s, 1H), 8.63-8.58 (m, 2H), 8.04-7.95 (m, 2H), 7.55-7.51 (m, 1H), 4.60 (s, 2H), 3.33-3.29 (m, 2H), 2.40-2.34 (m, 1H), 2.20-2.14 (m, 2H), 1.86-1.82 (m, 2H), 0.75-0.71 (m, 2H), 0.69-0.64 (m, 2H).

LC-MS: m/z 422.07 (M+H$^+$) with a purity of 99.06%.

Synthesis of N-(6-(4-fluorophenyl)pyridin-3-yl)-2-(6-methyl-5,7-dioxo-2,3,4,5,6,7-hexahydro-1H-pyrrolo[3,4-b]pyridin-1-yl)acetamide, (Compound 152)

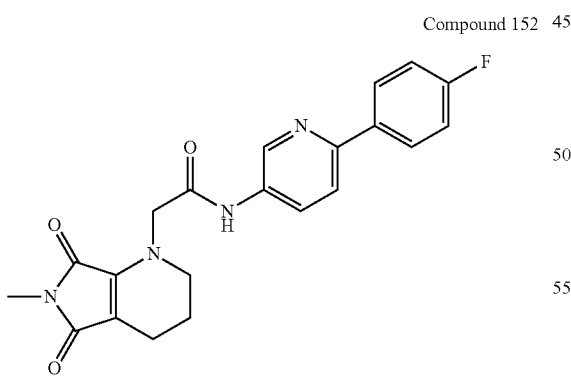

Compound 152

$^1$H NMR (400 MHz, DMSO-d$_6$): 10.40 (s, 1H), 8.788-8.782 (d, J=2.4 Hz, 1H), 8.12-8.06 (m, 3H), 7.93-7.91 (J=8.8 Hz, 1H), 7.30-7.26 (m, 2H), 4.57 (s, 2H), 3.34-3.33 (t, J=4.8 Hz, 2H), 2.77 (s, 3H), 2.23-2.20 (t, J=6 Hz, 2H), 1.87-1.84 (m, 2H).

LC-MS: m/z 395.07 (M+H$^+$) with a purity of 98.98%.

Synthesis of 2-(6-cyclopropyl-5,7-dioxo-2,3,4,5,6,7-hexahydro-1H-pyrrolo[3,4-b]pyridin-1-yl)-N-(6-(5-methoxypyridin-3-yl)pyridazin-3-yl)acetamide, (Compound 153)

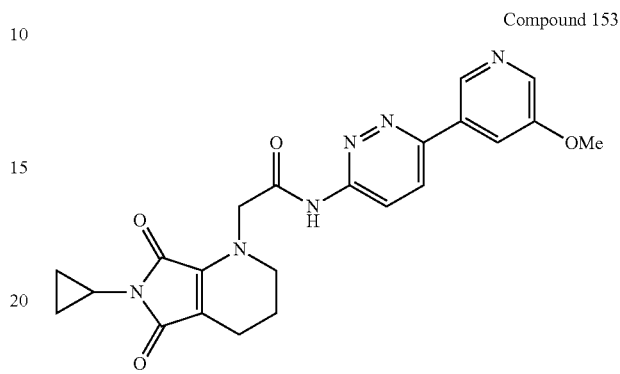

Compound 153

$^1$H NMR (400 MHz, DMSO-d$_6$): 11.44 (s, 1H), 8.879-8.875 (d, J=1.6 Hz, 1H), 8.417-8.410 (d, J=2 Hz, 1H), 8.36 (s, 2H), 8.03-8.02 (m, 1H), 4.66 (s, 2H), 3.94 (s, 3H), 3.35-3.33 (m, 2H), 2.40-2.34 (m, 1H), 2.20-2.17 (t, J=6 Hz, 2H), 1.85-1.82 (m, 2H), 0.77-0.71 (m, 2H), 0.69-0.65 (m, 2H).

LC-MS: m/z 435.10 (M+H$^+$) with a purity of 98.35%.

Synthesis of N-(6-(3-fluorophenyl)pyridin-3-yl)-2-(6-methyl-5,7-dioxo-2,3,4,5,6,7-hexahydro-1H-pyrrolo[3,4-b]pyridin-1-yl)acetamide, (Compound 154)

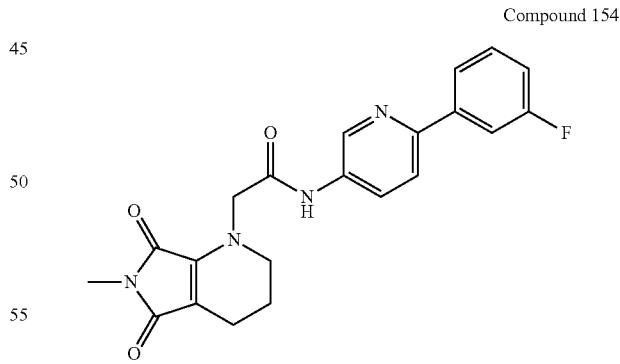

Compound 154

$^1$H NMR (400 MHz, DMSO-d$_6$): 10.43 (s, 1H), 8.81-8.80 (d, J=2.4 Hz, 1H), 8.15-8.12 (dd, J$_1$=2.4 Hz, J$_2$=8.8 Hz 1H), 8.00-7.98 (d, J=7.6 Hz, 1H), 7.90-7.82 (m, 2H), 7.53-7.48 (m, 1H), 7.24-7.19 (m, 1H), 4.58 (s, 2H), 3.36-3.34 (t, J=5.2 Hz, 2H), 2.77 (s, 3H), 2.23-2.20 (t, J=6 Hz, 2H), 1.87-1.84 (m, 2H).

LC-MS: m/z 395.10 (M+H$^+$) with a purity of 97.37%.

Synthesis of N-(4-fluoro-3,3'-bipyridin-6-yl)-2-(6-methyl-5,7-dioxo-2,3,4,5,6,7-hexahydro-1H-pyrrolo[3,4-b]pyridin-1-yl)acetamide, (Compound 155)

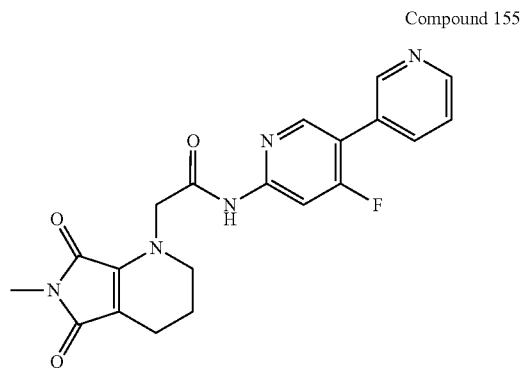 [SMILES: CN1C(=O)C2=C(C1=O)N(CC(=O)Nc1cc(F)c(-c3cccnc3)cn1)CCC2]

Compound 155

¹H NMR (400 MHz, DMSO-d₆): 11.12 (s, 1H), 8.79 (s, 1H), 8.63-8.58 (m, 2H), 8.03-7.95 (m, 2H), 7.55-7.51 (m, 1H), 4.62 (s, 2H), 3.35-3.32 (m, 2H), 2.77 (s, 3H), 2.23-2.20 (t, J=6.4 Hz, 2H), 1.86-1.83 (m, 2H).

LC-MS: m/z 396.08 (M+H⁺) with a purity of 98.79%.

Method D:

A stirred solution of 2-(6-methyl-5, 7-dioxo-2,3,4,5,6,7-hexahydro-1H-pyrrolo[3,4-b]pyridin-1-yl)propanoic acid, 1 (1.0 equiv.) in DCM (0.05 M) was treated with HATU (1.2 equiv.), TEA (2.0 equiv.) and biarylamine, 2 (1.0 equiv.) and stirred at room temperature for 16 h. After completion, water was added to the reaction mixture and extracted with DCM. The combined DCM layers were dried over Na₂SO₄ and concentrated under vacuum. The crude compound was purified by column chromatography to afford desired product.

Synthesis of N-(2,3'-bipyridin-6'-yl)-2-(6-cyclopropyl-5,7-dioxo-2,3,4,5,6,7-hexahydro-1H-pyrrolo[3,4-b]pyridin-1-yl)acetamide, (Compound 9)

Compound 9

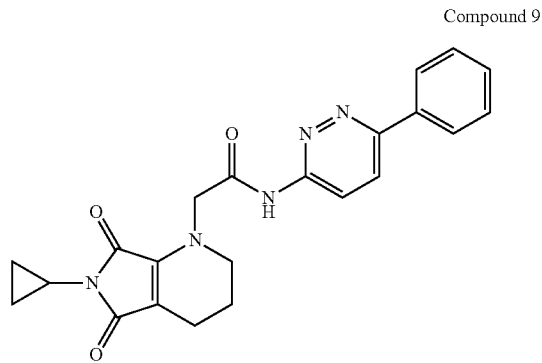 [SMILES: O=C(CN1CCCC2=C1C(=O)N(C1CC1)C2=O)Nc1ccc(-c2ccccc2)nn1]

¹H NMR (400 MHz, DMSO-d₆) δ (ppm): 10.84 (s, 1H), 9.05 (d, J=1.6 Hz, 1H), 8.67 (d, J=4.4 Hz, 1H), 8.45 (dd, J₁=2.4 Hz, J₂=6.4 Hz, 1H), 8.12 (d, J=8.8 Hz, 1H), 8.01 (d, J=8 Hz, 1H), 7.89 (t, J=6.4 Hz, 1H), 7.38-7.35 (m, 1H), 4.95 (s, 2H), 3.29 (m, 2H), 2.50-2.35 (m, 1H), 2.20-2.17 (m, 2H), 1.84-1.82 (m, 2H), 0.77-0.70 (m, 2H), 0.69-0.67 (m, 2H).

LC-MS: 404.07 [M+H⁺] with a purity of 97.02%.

Synthesis of N-([3,3'-bipyridin]-6-yl)-2-(6-methyl-5,7-dioxo-2,3,4,5,6,7-hexahydro-1H-pyrrolo[3,4-b]pyridin-1-yl)propanamide, (Compound 11)

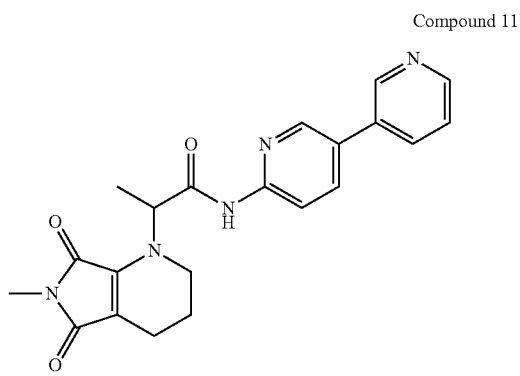

Compound 11

¹H NMR (400 MHz, DMSO-d₆) δ (ppm): 10.82 (s, 1H), 8.95 (d, J=2 Hz, 1H), 8.74 (d, J=2 Hz, 1H), 8.60-8.58 (m, 1H), 8.20-8.13 (m, 3H), 7.52-7.49 (m, 1H), 5.72 (q, J=6.8 Hz, 1H), 3.35-3.30 (m, 2H), 2.79 (s, 3H), 2.22-2.17 (m, 2H), 2.07 (m, 2H), 1.46 (d, J=7.2 Hz, 3H).

LC-MS: m/z 392.20 [M+H⁺] with a purity of 96.00%.

Synthesis of 2-(6-methyl-5,7-dioxo-2,3,4,5,6,7-hexahydro-1H-pyrrolo[3,4-b]pyridin-1-yl)-N-(6-phenylpyridazin-3-yl)propanamide, (Compound 13)

Compound 13

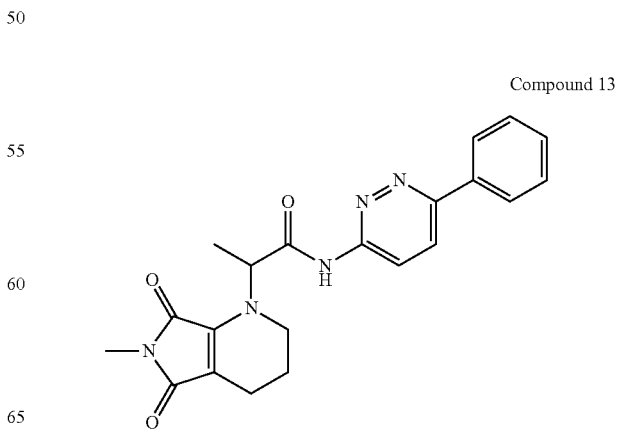

¹H NMR (400 MHz, DMSO-d₆) δ (ppm): 11.41 (s, 1H), 8.35 (d, J=9.6 Hz, 1H), 8.24 (d, J=9.6 Hz, 1H), 8.10 (d, J=7.2 Hz, 2H), 7.56-7.49 (m, 3H), 5.77 (q, J=7.2 Hz, 1H), 3.39-3.34 (m, 2H), 2.80 (s, 3H), 2.33-2.15 (m, 2H), 1.81-1.80 (m, 2H), 1.49 (d, J=7.2 Hz, 3H).

LC-MS: m/z 391.54 [M+H⁺] with a purity of 95.88%.

Synthesis of N-([2,3'-bipyridin]-6'-yl)-2-(6-methyl-5,7-dioxo-2,3,4,5,6,7-hexahydro-1H-pyrrolo[3,4-b]pyridin-1-yl)propanamide, (Compound 17)

Compound 17

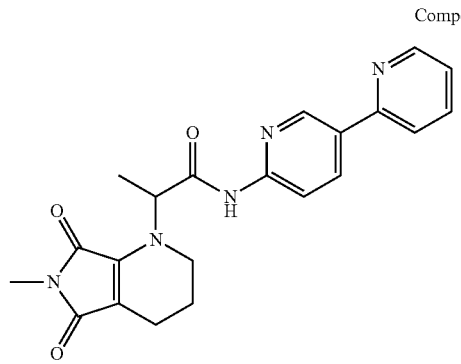

¹H NMR (400 MHz, DMSO-d₆) δ (ppm): 10.78 (s, 1H), 9.04 (s, 1H), 8.67 (d, J=4.4 Hz, 1H), 8.46 (d, J=8.4 Hz, 1H), 8.15 (d, J=8.4 Hz, 1H), 8.01 (d, J=7.6 Hz, 1H), 7.89 (t, J=6.8 Hz, 1H), 7.37 (t, J=4.8 Hz, 1H), 5.72 (q, J=7.2 Hz, 1H), 3.37 (m, 2H), 2.79 (s, 3H), 2.25-214 (m, 2H), 1.82-1.80 (m, 2H), 1.46 (d, J=7.2 Hz, 3H).

LC-MS: m/z 392.20 [M+H⁺] with a purity of 99.81%.

Synthesis of 2-(6-cyclopropyl-5,7-dioxo-2,3,4,5,6,7-hexahydro-1H-pyrrolo[3,4-b]pyridin-1-yl)-N-(6-(4-(trifluoromethyl)phenyl)pyridazin-3-yl)acetamide, (Compound 51)

Compound 51

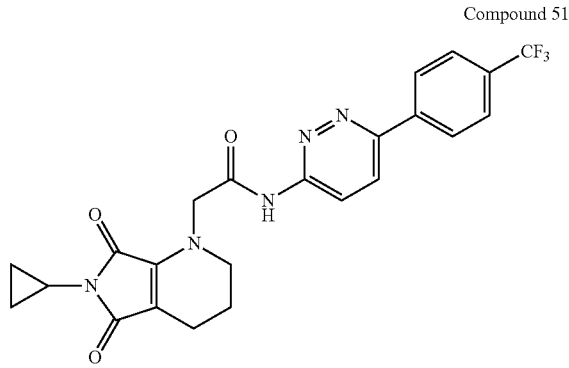 [SMILES: O=C(CN1CCCC2=C1C(=O)N(C1CC1)C2=O)Nc1ccc(-c2ccc(C(F)(F)F)cc2)nn1]

¹H NMR (400 MHz, DMSO-d₆) δ (ppm): 11.46 (s, 1H), 8.39-8.32 (m, 3H), 7.90 (d, J=7.6 Hz, 2H), 4.66 (s, 2H), 3.37-3.35 (m, 2H), 2.39-2.37 (m, 1H), 2.18 (t, J=5.6 Hz, 2H), 1.84 (m, 2H), 0.75-0.73 (m, 2H), 0.69-0.67 (m, 2H).

LC-MS: m/z 472.0 [M+H⁺] with a purity of 89.12%.

Synthesis of 2-(6-cyclopropyl-5,7-dioxo-2,3,4,5,6,7-hexahydro-1H-pyrrolo[3,4-b]pyridin-1-yl)-N-(6-(5-methylpyridin-3-yl)pyridazin-3-yl)acetamide, (Compound 53)

Compound 53

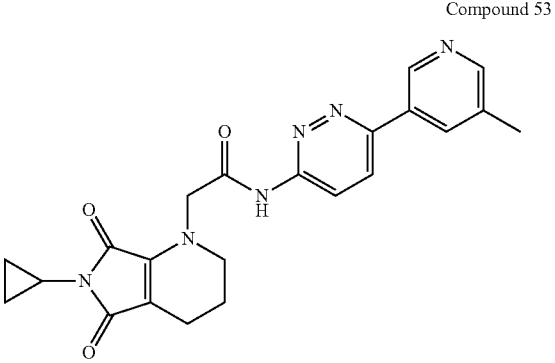 [SMILES: Cc1cncc(-c2ccc(NC(=O)CN3CCCC4=C3C(=O)N(C3CC3)C4=O)nn2)c1]

¹H NMR (400 MHz, DMSO-d₆) δ (ppm): 11.47(s, 1H), 9.08 (d, J=1.7 Hz, 1H), 8.53(s, 1H), 8.37-8.29 (m, 3H), 4.65 (s, 2H), 3.34-3.33 (m, 2H), 2.39-2.35 (m, 4H), 2.18 (t, J=6.1 Hz, 2H), 1.83 (t, J=5.2 Hz, 2H), 0.77-0.71 (m, 2H), 0.69-0.65 (m, 2H).

LC-MS: m/z 472.31 [M+H⁺] with a purity of 98.02%.

Synthesis of 2-(6-cyclopropyl-5,7-dioxo-2,3,4,5,6,7-hexahydro-1H-pyrrolo[3,4-b]pyridin-1-yl)-N-(6-(5-(trifluoromethyl)pyridin-3-yl)pyridazin-3-yl)acetamide, (Compound 54)

Compound 54

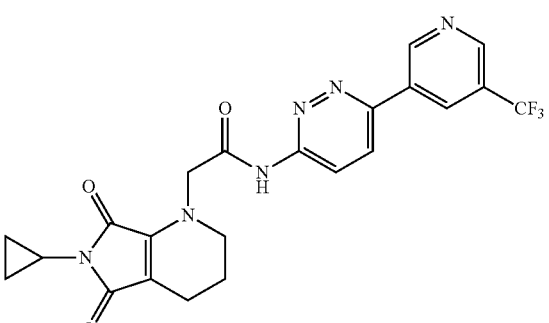

¹H NMR (400 MHz, DMSO-d₆) δ (ppm): 11.53 (s, 1H), 9.58 (s, 1H), 9.10 (s,1H), 8.83(s,1H), 8.51-8.39 (m, 2H), 4.66 (s, 2H), 3.34-3.24 (m, 2H), 2.37-2.32 (m, 1H), 2.19 (t, J=6.1 Hz, 2H), 1.83 (t, J=5.3 Hz, 2H), 0.75-0.67 (m, 4H).

LC-MS: m/z 473.39 [M+H⁺] with a purity of 96.44%.

Synthesis of 2-(6-cyclopropyl-5,7-dioxo-2,3,4,5,6,7-hexahydro-1H-pyrrolo[3,4-b]pyridin-1-yl)-N-(6-(3-(trifluoromethyl)phenyl)pyridazin-3-yl)acetamide, (Compound 55)

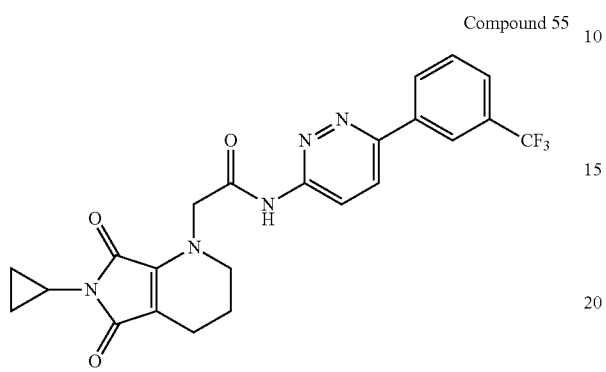

Compound 55

¹H NMR (400 MHz, DMSO-d₆) δ (ppm): 11.47 (s, 1H), 8.45-8.36 (m, 4H), 7.87 (d, J=8 Hz, 1H), 7.79 (t, J=7.2 Hz, 1H), 4.66 (s, 2H), 3.35-3.32 (m, 2H), 2.39-2.35 (m, 1H), 2.18 (t, J=6 Hz, 2H), 1.86-1.82 (m, 2H), 0.77-0.71 (m, 2H), 0.69-0.65 (m, 2H).

LC-MS: m/z 472.31 [M+H⁺] with a purity of 99.75%.

Synthesis of 2-(6-cyclopropyl-5,7-dioxo-2,3,4,5,6,7-hexahydro-1H-pyrrolo[3,4-b]pyridin-1-yl)-N-(6-(3-(trifluoromethoxy)phenyl)pyridazin-3-yl)acetamide, (Compound 56)

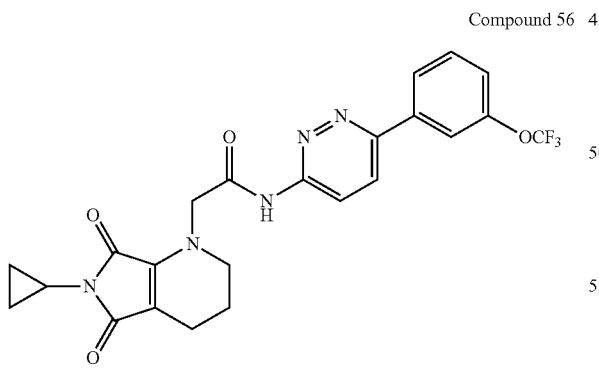

Compound 56

¹H NMR (400 MHz, DMSO-d₆) δ (ppm): 10.42 (s, 1H), 8.34 (d, J=9.2 Hz, 1H), 8.25 (d, J=9.2 Hz, 1H), 8.11 (d, J=6.8 Hz, 2H), 7.56-7.48 (m, 3H), 4.69 (s, 2H), 3.39-3.25 (m, 2H), 2.36-2.35 (m, 1H), 2.19 (t, J=5.6 Hz, 2H), 1.83 (m, 2H), 0.77-0.74 (m, 2H), 0.68-0.66 (m, 2H).

LC-MS: m/z 39.20 [M+H⁺] with a purity of 96.00%.

Synthesis of N-(2,3'-bipyridin-5-yl)-2-(6-cyclopropyl-5,7-dioxo-2,3,4,5,6,7-hexahydro-1H-pyrrolo[3,4-b]pyridin-1-yl)acetamide, (Compound 59)

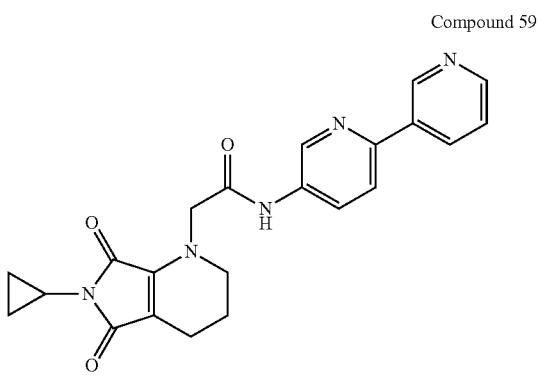 [SMILES: O=C(CN1CCCC2=C1C(=O)N(C1CC1)C2=O)Nc1ccc(-c2cccnc2)nc1]

Compound 59

¹H NMR (400 MHz, DMSO-d₆) δ (ppm): 10.45 (s, 1H), 9.22 (s, 1H), 8.84 (d, J=2 Hz, 1H), 8.59 (d, J=3.6 Hz, 1H), 8.39-8.37 (m, 1H), 8.17-8.14 (m, 1H), 8.03 (d, J=8.8 Hz, 1H), 7.51-7.47 (m, 1H), 4.57 (s, 2H), 3.33-3.29 (m, 2H), 2.38 (t, J=5.2 Hz, 1H), 2.19 (t, J=6.4 Hz, 2H), 1.857-1.83 (m, 2H), 0.76-0.69 (m, 2H), 0.68-0.65 (m, 2H).

LC-MS: m/z 404.1 [M+H⁺] with a purity of 99.52%.

Synthesis of 2-(6-cyclopropyl-5,7-dioxo-2,3,4,5,6,7-hexahydro-1H-pyrrolo[3,4-b]pyridin-1-yl)-N-(6-(5-(difluoromethoxy)pyridin-3-yl)pyridazin-3-yl)acetamide, (Compound 61)

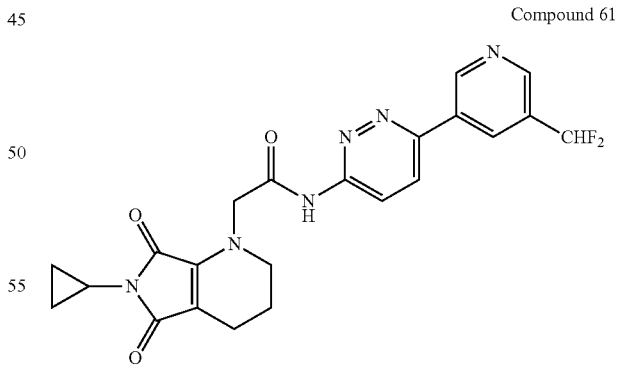

Compound 61

¹H NMR (400 MHz, DMSO-d₆) δ (ppm): 11.51 (s, 1H), 9.44 (s, 1H), 8.91 (s, 1H), 8.70 (s, 1H), 8.45-8.38 (m, 1H), 7.41-7.13 (m, 1H), 4.66 (s, 2H), 3.35-3.29 (m, 2H), 2.40-2.32 (m, 1H), 2.20-2.17 (m, 2H), 1.853-1.827 (m, 2H), 0.77-0.69 (m, 2H), 0.68-0.65 (m, 2H).

LC-MS: m/z 455.32 [M+H⁺] with a purity of 98.68%.

Synthesis of 2-(6-methyl-4,5,7-trioxo-4,5,6,7-tetrahydro-1H-pyrrolo[3,4-b]pyridin-1-yl)-N-(6-(pyridin-3-yl)pyridazin-3-yl)acetamide, (Compound 64)

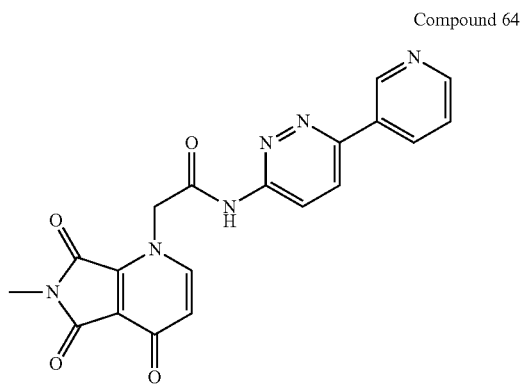 [SMILES: CN1C(=O)c2c(n(CC(=O)Nc3ccc(-c4cccnc4)nn3)ccc2=O)C1=O]

Compound 64

$^1$H NMR (400 MHz, DMSO-d$_6$) δ (ppm): 11.61 (s, 1H), 9.27 (s, 1H), 8.69 (s, 1H), 8.46-8.43 (m, 1H), 8.34-8.33 (m,2H), 8.21 (d, J=8.4 Hz, 1H), 7.58 (m, 1H), 7.30 (d, J=8.4 Hz, 1H), 5.29 (s, 2H), 3.0 (s, 3H).

LC-MS: m/z 391.0 [M+H$^+$] with a purity of 95.80%.

Synthesis of N-(3-fluorobiphenyl-4-yl)-2-(6-methyl-5,7-dioxo-2,3,4,5,6,7-hexahydro-1H-pyrrolo[3,4-b]pyridin-1-yl)acetamide, (Compound 83)

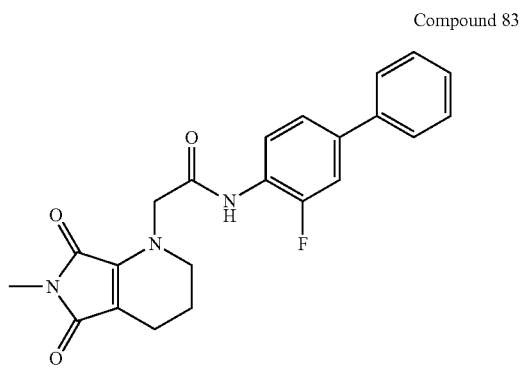 [SMILES: CN1C(=O)C2=C(C1=O)N(CC(=O)Nc1ccc(-c3ccccc3)cc1F)CCC2]

Compound 83

$^1$H NMR (400 MHz, DMSO-d$_6$): 10.0 (s, 1H), 8.02-7.98 (t, J=8.4 Hz, 1H), 7.69-7.68 (d, J=7.6 Hz, 2H), 7.62-7.58 (dd, J$_1$=2 Hz, J$_2$=10.4 Hz, 1H), 7.50-7.45 (m, 3H), 7.38-7.34 (t, J=7.2 Hz, 1H), 4.60 (s, 2H), 3.34-3.29 (m, 2H), 2.78 (s, 3H), 2.22-2.19 (t, J=5.6 Hz, 2H), 1.86-1.83 (m, 2H).

LC-MS: m/z 394.12 (M+H$^+$) with a purity of 99.93%.

Synthesis of N-(6-(2-fluorophenyl)pyridazin-3-yl)-2-(6-methyl-5,7-dioxo-2,3,4,5,6,7-hexahydro-1H-pyrrolo[3,4-b]pyridin-1-yl)acetamide, (Compound 84)

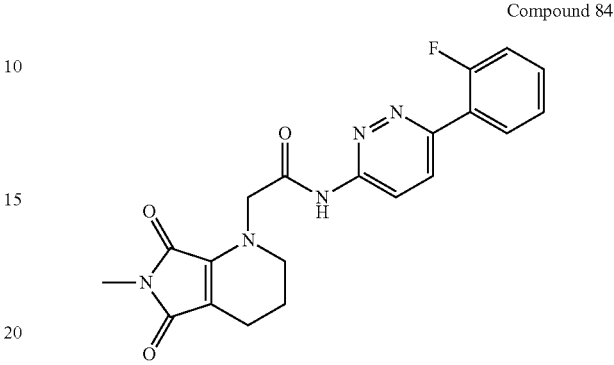

Compound 84

$^1$H NMR (400 MHz, DMSO-d$_6$): 11.45 (s, 1H), 8.37-8.34 (d, J=9.6 Hz, 1H), 8.04-8.02 (m, 1H), 7.97-7.94 (m, 1H), 7.57-7.55 (m, 1H), 7.41-7.37 (m, 2H), 4.67 (s, 2H), 3.36-3.34 (t, J=4.8 Hz, 2H), 2.77 (s, 3H), 2.23-2.20 (t, J=6 Hz, 2H), 1.86-1.84 (m, 2H).

LC-MS: m/z 396.10 (M+H$^+$) with a purity of 96.25%.

Synthesis of 2-(6-cyclopropyl-5,7-dioxo-2,3,4,5,6,7-hexahydro-1H-pyrrolo[3,4-b]pyridin-1-yl)-N-(5'-methyl-2,3'-bipyridin-5-yl)acetamide, (Compound 91)

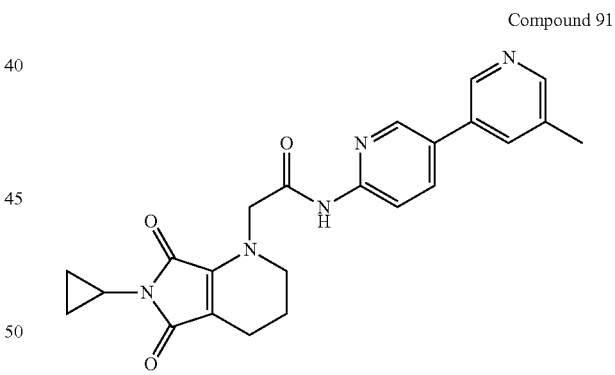

Compound 91

$^1$H NMR (400 MHz, DMSO-d$_6$): 10.81 (s, 1H), 8.74-8.72 (d, J=8.4 Hz, 2H), 8.42 (s, 1H), 8.17-8.12 (m, 2H), 7.97 (s, 1H), 4.59 (s, 2H), 3.29-3.27 (m, 2H), 2.37 (s, 3H), 2.33-2.32 (m, 1H), 2.21-2.18 (t, J=5.2 Hz, 2H), 1.84-1.82 (m, 2H), 0.76-0.74 (m, 2H), 0.69-0.67 (m, 2H).

LC-MS: m/z 418.41 (M+H$^+$) with a purity of 97.41%.

Synthesis of (S)-N-([3,3'-bipyridin]-6-yl)-2-(6-methyl-5,7-dioxo-2,3,4,5,6,7-hexahydro-1H-pyrrolo[3,4-b]pyridin-1-yl)propanamide, (Compound 92)

The two isomers of was separated by chiral purification gave peak 1 (compound 92) and peak 2 (compound 93).

Compound 92

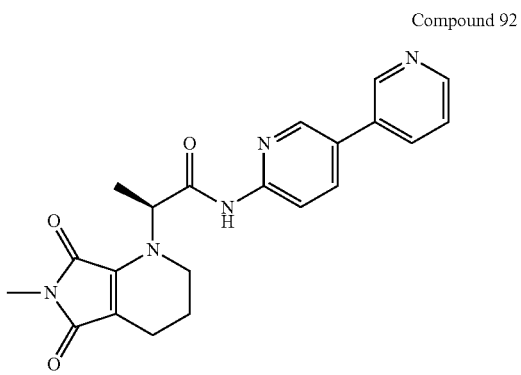 [SMILES: C[C@@H](C(=O)Nc1ccc(-c2cccnc2)cn1)N1CCCC2=C1C(=O)N(C)C2=O]

¹H NMR (400 MHz, DMSO-d₆): 10.82 (s, 1H), 8.95-8.94 (d, J=2 Hz, 1H), 8.74-8.73 (d, J=2 Hz, 1H), 8.60-=8.58 (m, 1H), 8.20-8.13 (m, 3H), 7.52-7.49 (m, 1H), 5.74-5.70 (q, J=6.8 Hz, 1H), 3.35-3.30 (m, 2H), 2.79 (s, 3H), 2.22-2.17 (m, 2H), 2.07 (m, 2H), 1.47-1.45 (d, J=7.2 Hz, 3H).

LC-MS: m/z 391.9 (M+H⁺) with a purity of 99.05%. ee: At 254 nm 100%.

Synthesis of (R)-N-([3,3'-bipyridin]-6-yl)-2-(6-methyl-5,7-dioxo-2,3,4,5,6,7-hexahydro-1H-pyrrolo[3,4-b]pyridin-1-yl)propanamide, (Compound 93)

Compound 93

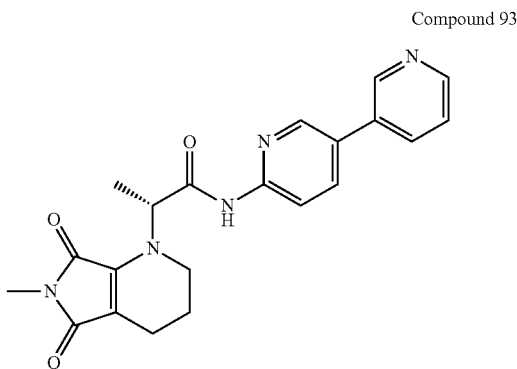 [SMILES: C[C@H](C(=O)Nc1ccc(-c2cccnc2)cn1)N1CCCC2=C1C(=O)N(C)C2=O]

¹H NMR (400 MHz, DMSO-d₆): 10.82 (s, 1H), 8.95-8.94 (d, J=2 Hz, 1H), 8.74-8.73 (d, J=2 Hz, 1H), 8.60-=8.58 (m, 1H), 8.20-8.13 (m, 3H), 7.52-7.49 (m, 1H), 5.74-5.70 (q, J=6.8 Hz, 1H), 3.35-3.30 (m, 2H), 2.79 (s, 3H), 2.22-2.17 (m, 2H), 2.07 (m, 2H), 1.47-1.45 (d, J=7.2 Hz, 3H).

LC-MS: m/z 391.9 (M+H⁺) with a purity of 99.45%. ee: At 254 nm 98.27%.

Synthesis of (S)-2-(6-methyl-5,7-dioxo-2,3,4,5,6,7-hexahydro-1H-pyrrolo[3,4-b]pyridin-1-yl)-N-(6-phenylpyridazin-3-yl)propanamide (Compound 94)

The two isomers of was separated by chiral purification gave peak 1 (compound 94) and peak 2 (compound 95).

Compound 94

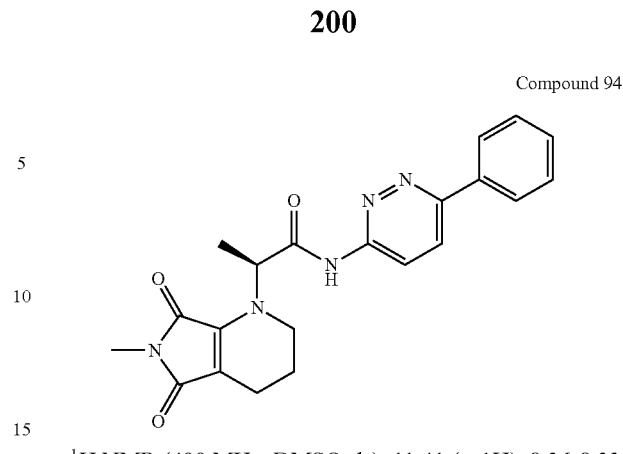

¹H NMR (400 MHz, DMSO-d₆): 11.41 (s, 1H), 8.36-8.33 (d, J=9.6 Hz, 1H), 8.26-8.23 (d, J=9.6 Hz, 1H), 8.11-8.09 (d, J=7.2 Hz, 2H), 7.56-7.49 (m, 3H), 5.79-5.74 (q, J=7.2 Hz, 1H), 3.39-3.34 (m, 2H), 2.80 (s, 3H), 2.33-2.15 (m, 2H), 1.81-1.80 (m, 2H), 1.50-1.48 (d, J=7.2 Hz, 3H).

LC-MS: m/z 391.9 (M+H⁺) with a purity of 99.12%. ee: at 254 nm 99.94%

Synthesis of (R)-2-(6-methyl-5,7-dioxo-2,3,4,5,6,7-hexahydro-1H-pyrrolo[3,4-b]pyridin-1-yl)-N-(6-phenylpyridazin-3-yl)propanamide (Compound 95)

Compound 95

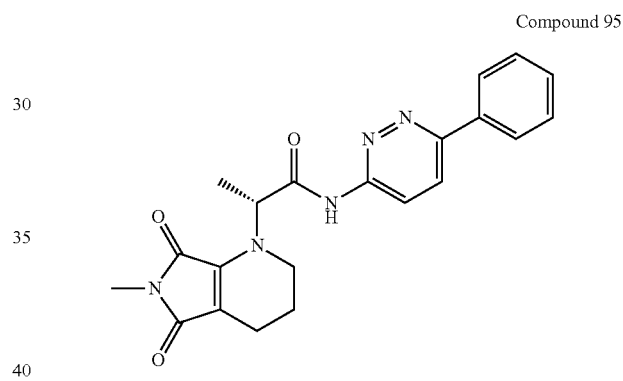

¹H NMR (400 MHz, DMSO-d₆): 11.41 (s, 1H), 8.36-8.33 (d, J=9.6 Hz, 1H), 8.26-8.23 (d, J=9.6 Hz; 1H), 8.11-8.09 (d, J=7.2 Hz, 2H), 7.56-7.49 (m, 3H), 5.79-5.74 (q, J=7.2 Hz, 1H), 3.39-3.34 (m, 2H), 2.80 (s, 3H), 2.33-2.15 (m, 2H), 1.81-1.80 (m, 2H), 1.50-1.48 (d, J=7.2 Hz, 3H).

LC-MS: m/z 391.9 (M+H⁺) with a purity of 99.70%. ee: at 254 nm 99.90%.

Synthesis of N-(6'-fluoro-3,3'-bipyridin-6-yl)-2-(6-methyl-5,7-dioxo-2,3,4,5,6,7-hexahydro-1H-pyrrolo[3,4-b]pyridin-1-yl)propanamide, (Compound 96)

Compound 96

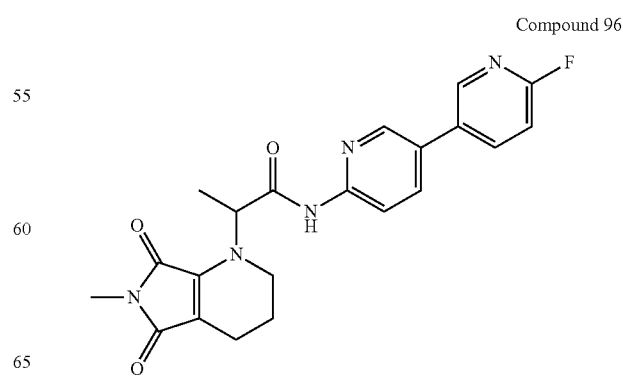

¹H NMR (400 MHz, CDCl3): 8.64 (s, 1H), 8.475-8.47 (d, J=2 Hz, 1H), 8.39 (s, 1H), 8.31-8.29 (d, J=8.8 Hz, 1H), 7.96-7.91 (m, 1H), 7.88-7.85 (dd, J$_1$=2.4 Hz, J$_2$=8.8 Hz, 1H), 7.05-7.02 (dd, J$_1$=2.4 Hz, J$_2$=8.4 Hz, 1H), 5.79-5.75 (m, 1H), 3.38-3.33 (m, 2H), 2.98 (s, 3H), 2.38-2.31 (m, 2H), 1.93-1.89 (m, 2H), 1.53-1.51 (d, J=9.2 Hz, 3H).

LC-MS: m/z 410.15 (M+H⁺) with a purity of 95.99%.

Synthesis of N-(2'-fluoro-3,3'-bipyridin-6-yl)-2-(6-methyl-5,7-dioxo-2,3,4,5,6,7-hexahydro-1H-pyrrolo[3,4-b]pyridin-1-yl)propanamide, (Compound 97)

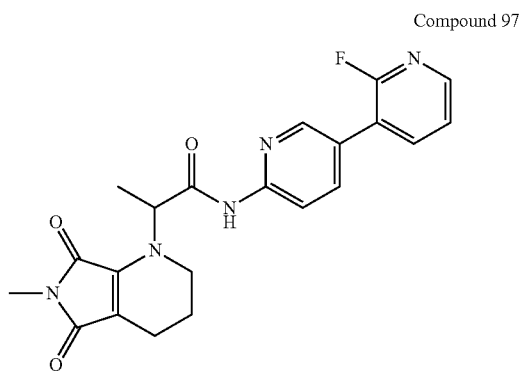 [SMILES: CC(C(=O)Nc1ccc(-c2cccnc2F)cn1)N1CCCC2=C1C(=O)N(C)C2=O]

Compound 97

¹H NMR (400 MHz, CDCl3): 8.64 (s, 1H), 8.49 (s, 1H), 8.31-8.29 (d, J=8.4 Hz, 1H), 8.24-8.22 (d, J=4.8 Hz, 1H), 7.94-7.92 (d, J=8.8 Hz, 1H), 7.88-7.83 (m, 1H), 7.32-7.29 (m, 1H), 5.79-5.74 (q, J=6.8 Hz, 1H), 3.37-3.30 (m, 2H), 2.98 (s, 3H), 2.41-2.31 (m, 2H), 1.93-1.87 (m, 2H), 1.52-1.50 (d, J=7.6 Hz, 3H).

LC-MS: m/z 410.22 (M+H⁺) with a purity of 97.89%.

Synthesis of 2-(6-methyl-5,7-dioxo-2,3,4,5,6,7-hexahydro-1H-pyrrolo[3,4-b]pyridin-1-yl)-N-(4-(pyrazin-2-yl)phenyl)acetamide, (Compound 118)

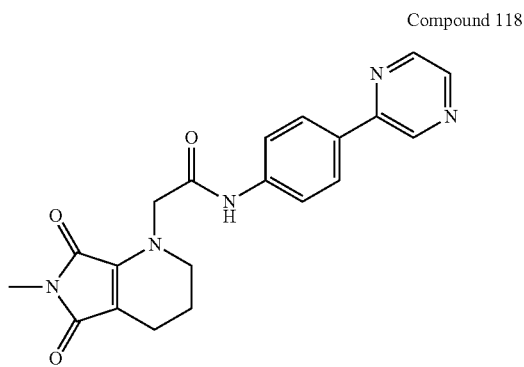 [SMILES: CN1C(=O)C2=C(C1=O)N(CC(=O)Nc1ccc(-c3cnccn3)cc1)CCC2]

Compound 118

¹H NMR (400 MHz, DMSO-d$_6$): 10.31 (s, 1H), 9.21 (s, 1H), 8.67 (s, 1H), 8.56-8.55 (d, J=2.8 Hz, 1H), 8.12-8.10 (d, J=8.4 Hz, 2H), 7.75-7.73 (d, J=8.8 Hz, 2H), 4.56 (s, 2H), 3.35-3.33 (t, J=5.6 Hz, 2H), 2.77 (s, 3H), 2.23-2.20 (t, J=6 Hz, 2H), 1.87-1.84 (m, 2H).

LC-MS: m/z 377.97 (M+H⁺) with a purity of 96.14%.

Synthesis of N-(4-fluoro-3,3'-bipyridin-6-yl)-2-(6-methyl-5,7-dioxo-2,3,4,5,6,7-hexahydro-1H-pyrrolo[3,4-b]pyridin-1-yl)propanamide, (Compound 119)

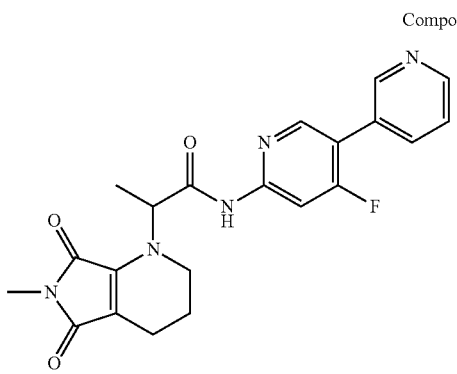

Compound 119

¹H NMR (400 MHz, DMSO-d$_6$): 11.09 (s, 1H), 8.79 (s, 1H), 8.63-8.57 (m, 2H), 8.03-7.98 (m, 2H), 7.55-7.52 (m, 1H), 5.71-5.68 (q, J=7.2 Hz, 1H), 3.32-3.29 (m, 2H), 2.79 (s, 3H), 2.22-2.17 (m, 2H), 1.80-1.79 (m, 2H), 1.47-1.45 (d, J=7.2 Hz, 3H).

LC-MS: m/z 410.12 (M+H⁺) with a purity of 99.36%.

Synthesis of 2-(6-cyclopropyl-5,7-dioxo-2,3,4,5,6,7-hexahydro-1H-pyrrolo[3,4-b]pyridin-1-yl)-N-(2'-methyl-2,3'-bipyridin-5-yl)acetamide, (Compound 121)

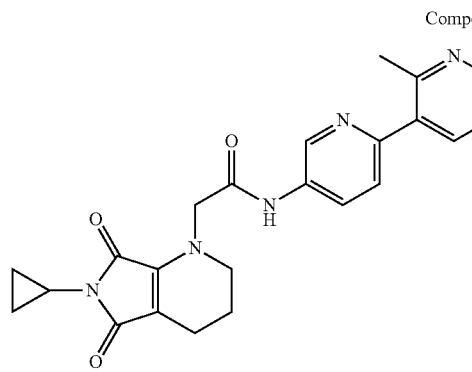

Compound 121

¹H NMR (400 MHz, CDCl3): 8.75-8.74 (d, J=2.8 Hz, 1H), 8.59-8.57 (d, J=4.8 Hz, 2H), 8.34-8.32 (m, 1H), 7.95 (m, 1H), 7.46-7.43 (d, J=8.4 Hz, 2H), 4.46 (s, 2H), 3.47-3.44 (t, J=5.2 Hz, 2H), 2.77 (s, 3H), 2.48-2.44 (m, 1H), 2.36-2.33 (t, J=6.4 Hz, 2H), 1.99-1.93 (m, 2H), 0.93-0.82 (m, 4H).

LC-MS: m/z 418.11 (M+H⁺) with a purity of 99.07%.

Synthesis of N-(2,4'-bipyridin-5-yl)-2-(6-methyl-5,7-dioxo-2,3,4,5,6,7-hexahydro-1H-pyrrolo[3,4-b]pyridin-1-yl)acetamide, (Compound 122)

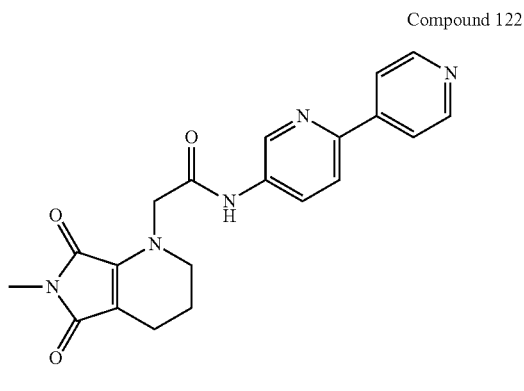 [SMILES: CN1C(=O)C2=C(C1=O)N(CC(=O)Nc1ccc(-c3ccncc3)nc1)CCC2]

Compound 122

¹H NMR (400 MHz, DMSO-d₆): 10.54 (s, 1H), 8.86-8.86 (d, J=2 Hz, 1H), 8.67-8.65 (d, J=5.6 Hz, 2H), 8.20-8.18 (m, 1H), 8.11-8.09 (d, J=8.8 Hz, 1H), 8.01-7.99 (d, J=6 Hz, 2H), 4.59 (s, 2H), 3.36-3.34 (t, J=4.8 Hz, 2H), 2.77 (s, 3H), 2.24-2.21 (t, J=6 Hz, 2H), 1.87-1.84 (m, 2H).

LC-MS: m/z 378.11 (M+H⁺) with a purity of 99.81%.

Synthesis of 2-(6-cyclopropyl-5,7-dioxo-2,3,4,5,6,7-hexahydro-1H-pyrrolo[3,4-b]pyridin-1-yl)-N-(5-fluoro-[2,3'-bipyridin]-6'-yl)acetamide, (Compound 127)

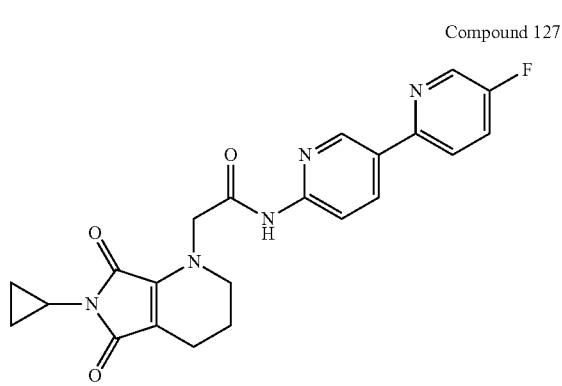 [SMILES: O=C(CN1CCCC2=C1C(=O)N(C1CC1)C2=O)Nc1ccc(-c2ccc(F)cn2)cn1]

Compound 127

¹H NMR (400 MHz, DMSO-d₆) δ 10.87 (s, 1H), 9.01 (d, J=1.6 Hz, 1H), 8.66 (d, J=3.2 Hz, 1H), 8.44-8.41 (dd, J₁=2 Hz, J₂=8.8 Hz, 1H), 8.12-8.09 (m, 2H), 7.87-7.82 (m, 1H), 4.59 (s, 2H), 3.41-3.26 (m, 2H), 2.38-2.35 (m, 1H), 2.20-2.17 (t, J=5.6 Hz, 2H), 1.90-1.83 (m, 2H), 0.77-0.66 (m, 4H).

LC-MS: m/z 422.11 [M+H⁺] with a purity of 98.69%.

Synthesis of 2-(6-cyclopropyl-5,7-dioxo-2,3,4,5,6,7-hexahydro-1H-pyrrolo[3,4-b]pyridin-1-yl)-N-(5-methoxy-[2,3'-bipyridin]-6'-yl)acetamide, (Compound 130)

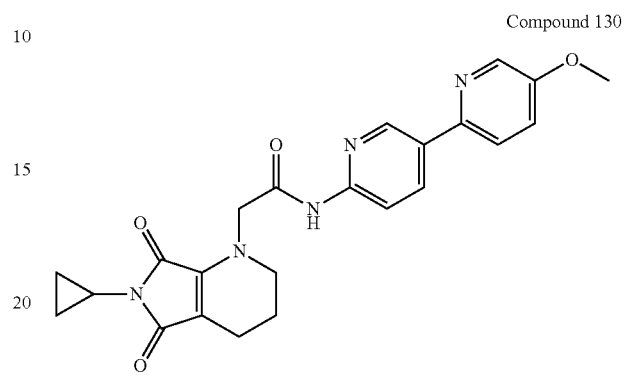

Compound 130

¹H NMR (400 MHz, DMSO-d₆) δ 10.80 (s, 1H), 8.97 (d, J=2.0 Hz, 1H), 8.39-8.36 (m, 2H), 8.10-8.08 (d, J=8.0 Hz, 1H), 7.98-7.96 (d, J=8.8 Hz, 1H), 7.51-7.48 (dd, J₁=3.2 Hz, J₂=8.8 Hz, 1H), 4.58 (s, 2H), 3.88 (s, 3H), 3.42-3.26 (m, 2H), 2.38-2.32 (m, 1H), 2.20-2.17 (t, J=6.4 Hz, 2H), 1.84-1.81 (m, 2H), 0.77-0.64 (m, 4H).

LC-MS: m/z 432.1 [M+H⁺] with a purity of 97.84%.

Synthesis of 2-(6-methyl-5,7-dioxo-2,3,4,5,6,7-hexahydro-1H-pyrrolo[3,4-b]pyridin-1-yl)-N-(6-(m-tolyl)pyridin-3-yl)acetamide, (Compound 131)

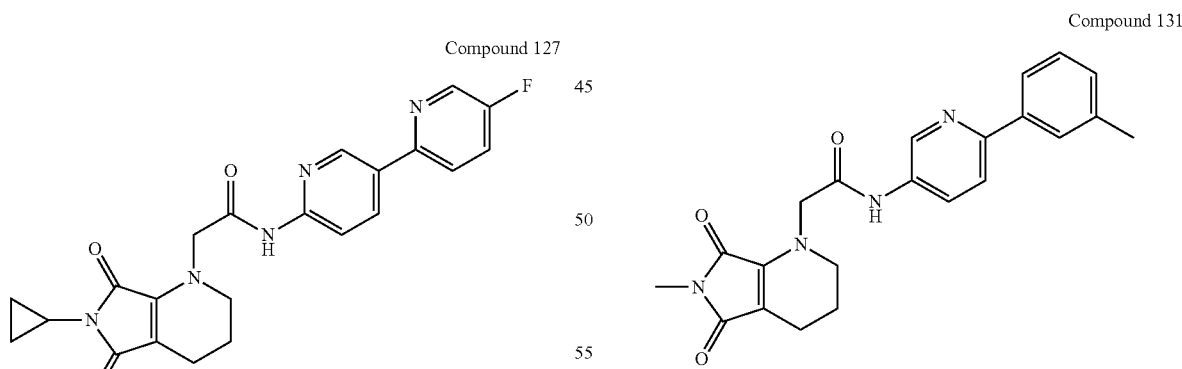

Compound 131

¹H NMR (400 MHz, DMSO-d₆) δ 10.42 (s, 1H), 8.78-8.77 (d, J=2.8 Hz, 1H), 8.12-8.10 (dd, J₁=2.4 Hz, J₂=8.8 Hz, 1H), 7.92-7.90 (d, J=8.8 Hz, 1H), 7.87 (s, 1H), 7.82-7.80 (d, J=7.6 Hz, 1H), 7.36-7.32 (t, J=7.2 Hz, 1H), 7.21-7.20 (d, J=7.2 Hz, 1H), 4.58 (s, 2H), 3.36-3.26 (m, 2H), H), 2.77 (s, 3H), 2.38 (s, 3H), 2.23-2.20 (t, J=5.6 Hz, 2H), 1.87-1.84 (m, 2H).

LC-MS: m/z 391.34 [M+H⁺] with a purity of 96.85%.

Synthesis of 2-(6-methyl-5,7-dioxo-2,3,4,5,6,7-hexahydro-1H-pyrrolo[3,4-b]pyridin-1-yl)-N-(5-(5-methylpyrazin-2-yl)pyridin-2-yl)acetamide, (Compound 132)

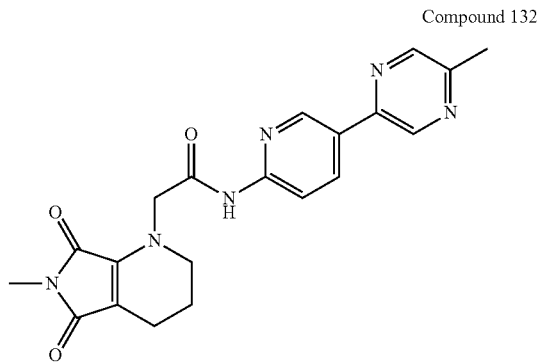

Compound 132

¹H NMR (400 MHz, DMSO-d$_6$): 10.90 (s, 1H), 9.15 (d, J=1.6 Hz, 1H), 9.06 (d, J=2.0 Hz, 1H), 8.60 (s, 1H), 8.48-8.46 (dd, J=2.4, J=8.8 Hz, 1H), 7.15-7.13 (d, J=8.8 Hz, 2H), 4.61 (s, 2H), 3.34-3.33 (m, 2H), 2.70 (s, 3H), 2.54 (s, 3H), 2.23-2.20 (t, J=6.0 Hz, 2H), 1.87-1.82 (m, 2H).

LC-MS: m/z 393.16 (M+H⁺) with a purity of 99.40%.

Synthesis of 2-(6-methyl-5,7-dioxo-2,3,4,5,6,7-hexahydro-1H-pyrrolo[3,4-b]pyridin-1-yl)-N-(6-(2-methylpyridin-3-yl)pyridazin-3-yl)acetamide, (Compound 134)

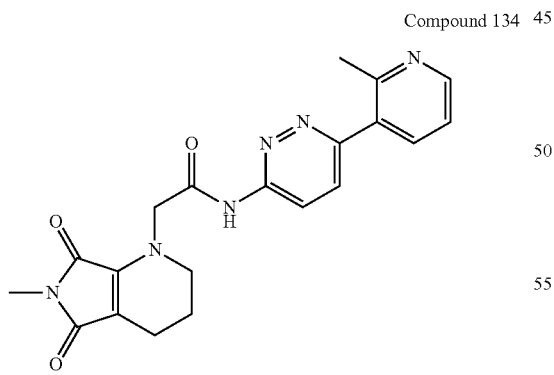

Compound 134

¹H NMR (400 MHz, DMSO-d$_6$): 11.44 (s, 1H), 8.57-8.56 (dd, J$_1$=2 Hz, J$_2$=4.8 Hz, 1H), 8.36-8.34 (d, J=9.2 Hz, 2H), 7.88-7.86 (m, 1H), 7.41-7.37 (m, 1H), 4.67 (s, 2H), 3.37-3.35 (m, 2H), 2.77 (s, 3H), 2.79 (s, 3H), 2.23-2.20 (t, J=6 Hz, 2H), 1.87-1.84 (m, 2H).

LC-MS: m/z 392.90 (M+H⁺) with a purity of 97.70%.

Synthesis of 2-(6-methyl-5,7-dioxo-2,3,4,5,6,7-hexahydro-1H-pyrrolo[3,4-b]pyridin-1-yl)-N-(6-(4-methylpyridin-3-yl)pyridazin-3-yl)acetamide, (Compound 136)

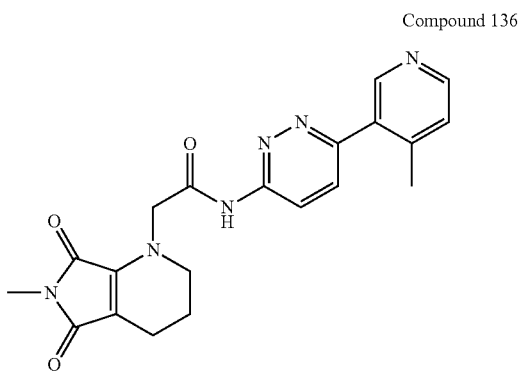 [SMILES: Cc1ccncc1-c1ccc(NC(=O)CN2CCCC3=C2C(=O)N(C)C3=O)nn1]

Compound 136

¹H NMR (400 MHz, DMSO-d$_6$): 10.09 (s, 1H), 8.59 (s, 1H), 8.53-8.52 (d, J=5.2 Hz, 1H), 8.37-8.34 (d, J=9.2 Hz 1H), 7.95-7.93 (d, J=9.2 Hz, 1H), 7.95-7.93 (d, J=4.8 Hz, 1H), 4.67 (s, 2H), 3.37-3.35 (t, J=5.2 Hz, 2H), 2.77 (s, 3H), 2.36 (s, 3H), 2.23-2.21 (t, J=5.6 Hz, 2H), 1.87-1.84 (m, 2H).

LC-MS: m/z 393.16 (M+H⁺) with a purity of 99.35%.

Synthesis of 2-(6-cyclopropyl-5,7-dioxo-2,3,4,5,6,7-hexahydro-1H-pyrrolo[3,4-b]pyridin-1-yl)-N-(4'-methyl-2,3'-bipyridin-5-yl)acetamide, (Compound 138)

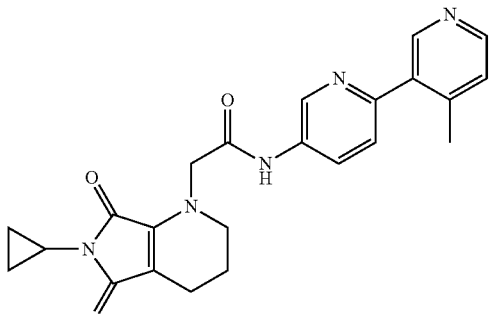

Compound 138

¹H NMR (400 MHz, DMSO-d$_6$): 10.43 (s, 1H), 8.85-8.84 (d, J=2.4 Hz, 1H), 8.53(s, 1H), 8.44-8.43 (d, J=4.8 Hz, 1H), 8.14-8.11 (dd, J$_1$=2 Hz, J$_2$=8.4 Hz, 1H), 7.60-7.58 (d, J=8.8 Hz, 1H), 7.33-7.31 (d, J=4.8 Hz, 1H), 4.56 (s, 2H), 3.35-3.28 (m, 2H), 2.39-2.38 (m, 1H), 2.36 (s, 3H), 2.20-2.17 (t, J=6.4 Hz, 2H), 1.85-1.83 (m, 2H), 0.76-0.73 (m, 2H), 0.69-0.67 (m, 2H).

LC-MS: m/z 418.14 (M+H⁺) with a purity of 99.47%.

Synthesis of N-(5-(5-fluoropyridin-3-yl)pyrazin-2-yl)-2-(6-methyl-5,7-dioxo-2,3,4,5,6,7-hexahydro-1H-pyrrolo[3,4-b]pyridin-1-yl)acetamide, (Compound 141)

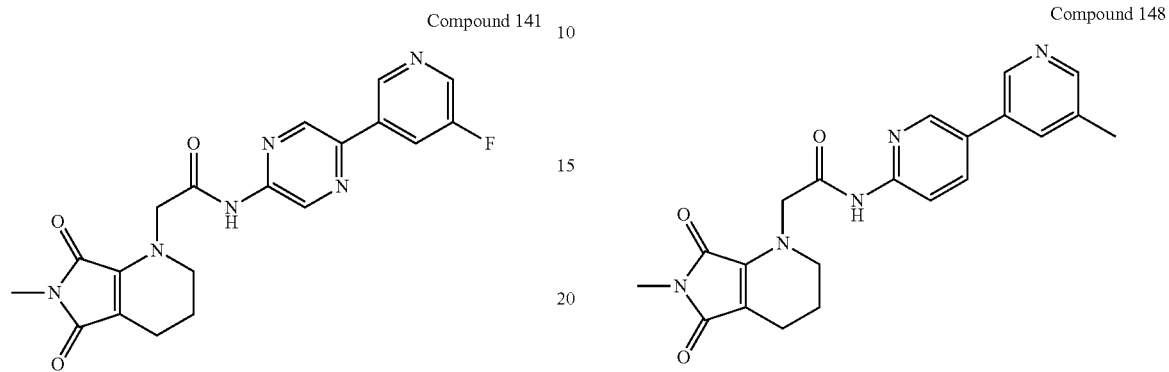

Compound 141

¹H NMR (400 MHz, DMSO-d₆): 11.20 (s, 1H), 9.36 (s, 1H), 9.17-9.15 (m, 2H), 8.66-8.65 (d, J=2.4 Hz, 1H), 8.37-8.34 (m, 1H), 4.66 (s, 2H), 3.37-3.34 (t, J=5.2 Hz, 2H), 2.77 (s, 3H), 2.24-2.21 (t, J=6 Hz, 2H), 1.87-1.84 (m, 2H).

LC-MS: m/z 397.08 (M+H⁺) with a purity of 99.05%.

Synthesis of 2-(6-cyclopropyl-5,7-dioxo-2,3,4,5,6,7-hexahydro-1H-pyrrolo[3,4-b]pyridin-1-yl)-N-(5-(5-fluoropyridin-3-yl)pyrazin-2-yl)acetamide, (Compound 142)

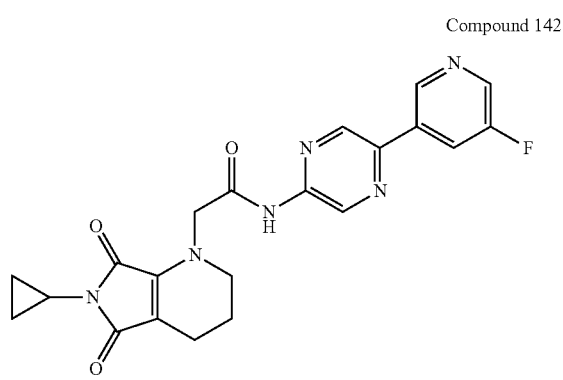 [SMILES: O=C(CN1CCCC2=C1C(=O)N(C1CC1)C2=O)Nc1cnc(-c2cncc(F)c2)cn1]

Compound 142

¹H NMR (400 MHz, DMSO-d₆): 11.19 (s, 1H), 9.37 (s, 1H), 9.17-9.16 (d, J=7.2 Hz, 2H), 8.66-8.66 (d, J=2.4 Hz, 1H), 8.37-8.34 (d, J=10.4 Hz, 1H), 4.64 (s, 2H), 3.34-3.33 (m, 2H), 2.39-2.36 (m, 1H), 2.21-2.18 (t, J=5.6 Hz, 2H), 1.85-1.82 (m, 2H), 0.77-0.71 (m, 2H), 0.69-0.67 (m, 2H).

LC-MS: m/z 423.11 (M+H⁺) with a purity of 96.44%.

Synthesis of 2-(6-methyl-5,7-dioxo-2,3,4,5,6,7-hexahydro-1H-pyrrolo[3,4-b]pyridin-1-yl)-N-(5'-methyl-[3,3'-bipyridin]-6-yl)acetamide, (Compound 148)

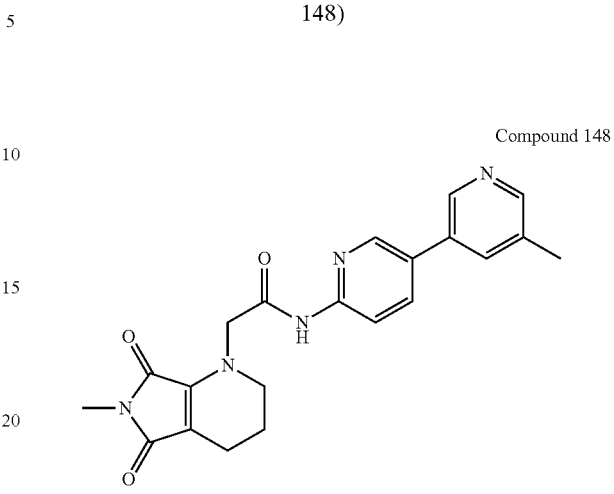

Compound 148

¹H NMR (400 MHz, DMSO-d₆): 10.82 (s, 1H), 8.74-8.71 (dd, J=1.6 Hz, J=9.2 Hz, 2H), 8.42 (s, 1H), 8.17-8.10 (m, 2H), 7.98 (s, 1H), 4.61 (s, 2H), 3.34-3.32 (m, 2H), 2.77 (s, 3H), 2.37 (s, 3H), 2.23-2.20 (t, J=5.6 Hz, 2H), 1.86-1.83 (m, 2H).

LC-MS: m/z 392.15 (M+H⁺) with a purity of 95.68%.

Synthesis of 2-(6-methyl-5,7-dioxo-2,3,4,5,6,7-hexahydro-1H-pyrrolo[3,4-b]pyridin-1-yl)-N-(5'-methyl-[2,3'-bipyridin]-5-yl)acetamide, (Compound 149)

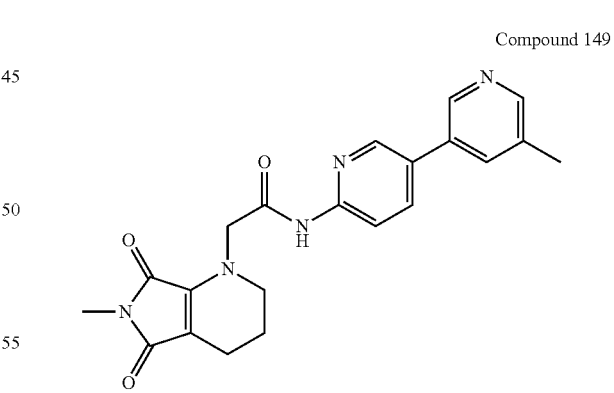

Compound 149

¹H NMR (400 MHz, DMSO-d₆): 10.46 (s, 1H), 9.01 (d, J=2 Hz, 1H), 8.82 (d, J=2.4 Hz, 1H), 8.43 (s, 1H), 8.21 (s, 1H), 8.16-8.13 (dd, J=2.4 Hz, J=8.8 Hz, 1H), 8.02-8.00 (d, J=8.4 Hz, 1H), 4.58 (s, 2H), 3.36-3.35 (m, 2H), 2.77 (s, 3H), 2.37 (s, 3H), 2.24-2.21 (t, J=6.0 Hz, 2H), 1.87-1.84 (m, 2H).

LC-MS: m/z 392.08 (M+H⁺) with a purity of 98.72%.

Synthesis of 2-(6-cyclopropyl-5,7-dioxo-2,3,4,5,6,7-hexahydro-1H-pyrrolo[3,4-b]pyridin-1-yl)-N-(4-methyl-[2,3'-bipyridin]-6'-yl)acetamide, (Compound 150)

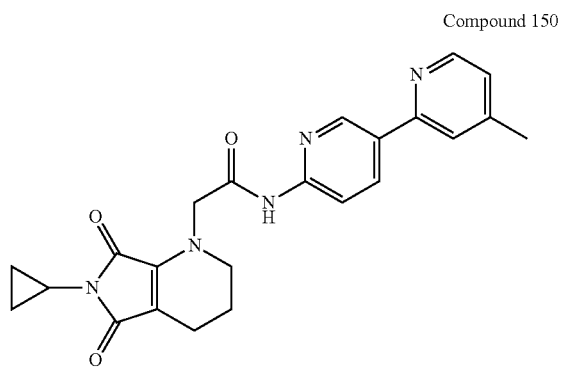 [SMILES: Cc1ccnc(-c2ccc(NC(=O)CN3CCCC4=C3C(=O)N(C3CC3)C4=O)nc2)c1]

Compound 150

¹H NMR (400 MHz, DMSO-d₆): 10.86 (s, 1H), 9.03 (d, J=2 Hz, 1H), 8.51 (d, J=5.2 Hz, 1H), 8.45-8.42 (dd, J=2.4 Hz, J=8.8 Hz, 1H), 8.12 (d, J=9.2 Hz, 1H), 7.86 (s, 1H), 7.20 (d, J=4.8 Hz, 1H), 4.58 (s, 2H), 3.32-3.28 (m, 2H), 2.39-2.35 (m, 5H), 2.20-2.17 (t, J=6.4 Hz, 2H), 1.84-1.81 (m, 2H), 0.77-0.65 (m, 4H).

LC-MS: m/z 418.11 (M+H⁺) with a purity of 97.21%.

Synthesis of 2-(6-cyclopropyl-5,7-dioxo-2,3,4,5,6,7-hexahydro-1H-pyrrolo[3,4-b]pyridin-1-yl)-N-(4-fluoro-[2,3'-bipyridin]-6'-yl)acetamide, (Compound 156)

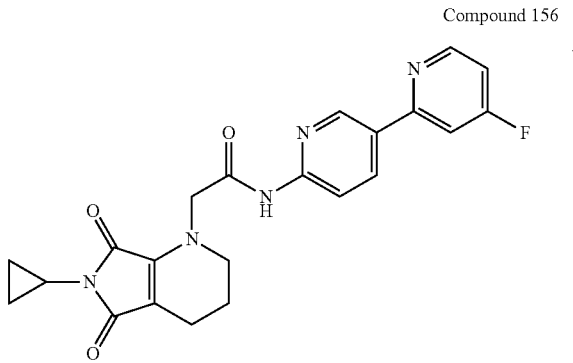

Compound 156

¹H NMR (400 MHz, DMSO-d₆): 10.94 (s, 1H), 9.09 (d, J=2 Hz, 1H), 8.71-8.69 (dd, J=5.6 Hz, J=9.2 Hz, 1H), 8.52-8.49 (dd, J=2.0 Hz, J=8.4 Hz, 1H), 8.23-8.20 (m, 1H), 8.03 (d, J=10.8 Hz, 1H), 7.31 (s, 1H), 4.59 (s, 2H), 3.33-3.30 (m, 2H), 2.19-2.17 (t, J=6.0 Hz, 2H), 1.83-1.82 (m, 2H), 0.75-0.66 (m, 4H).

LC-MS: m/z 421.80 (M+H⁺) with a purity of 95.01%.

Synthesis of 2-(6-cyclopropyl-5,7-dioxo-2,3,4,5,6,7-hexahydro-1H-pyrrolo[3,4-b]pyridin-1-yl)-N-(5-(5-methylpyrazin-2-yl)pyridin-2-yl)acetamide, Compound 157)

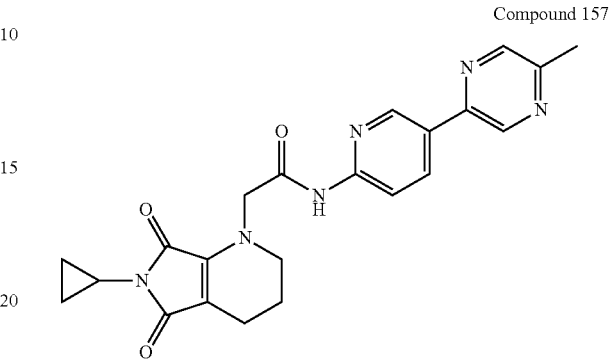

Compound 157

¹H NMR (400 MHz, DMSO-d₆): 10.89 (s, 1H), 9.15 (d, J=1.6 Hz, 1H), 9.06-9.05 (d, J=2.0 Hz, 1H), 8.60 (s, 1H), 8.49-8.46 (dd, J=2.4 Hz, J=8.4 Hz, 1H), 8.15-8.13 (d, J=8.8 Hz, 1H), 7.31 (s, 1H), 4.59 (s, 2H), 3.39-3.34 (m, 2H), 2.54 (s, 3H), 2.20-2.17 (t, J=6.0 Hz, 2H), 1.84-1.81 (m, 2H), 0.77-0.64 (m, 4H).

LC-MS: m/z 419.15 (M+H⁺) with a purity of 95.49%.

Synthesis of 2-(6-methyl-5,7-dioxo-2,3,4,5,6,7-hexahydro-1H-pyrrolo[3,4-b]pyridin-1-yl)-N-(6-(p-tolyl)pyridin-3-yl)acetamide, (Compound 158)

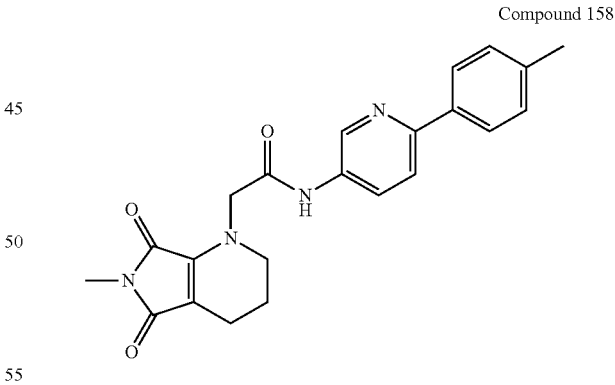

Compound 158

¹H NMR (400 MHz, DMSO-d₆): 10.38 (s, 1H), 8.76 (d, J=2.8 Hz, 1H), 8.10-8.07 (dd, J=2.8, J=8.8 Hz, 1H), 7.94-7.87 (m, 3H), 7.28-7.26 (d, J=8.0 Hz, 2H), 4.57 (s, 2H), 3.36-3.34 (m, 2H), 2.77 (s, 3H), 2.34 (s, 3H), 2.32-2.20 (t, J=6.4 Hz, 2H), 1.86-1.84 (m, 2H).

LC-MS: m/z 391.14 (M+H⁺) with a purity of 96.48%.

Materials and Methods

Cell Lines and Culture Conditions:

HEK293-STF cell line was modified from Human embryonic kidney cell line HEK293 transfected with the STF reporter. HEK293-STF3A cell line was further modified from HEK293-STF cell line to express Wnt3A. This cell line was used to identify compounds that regulate either early or late signaling components of the Wnt pathway. These two cell lines were obtained from David Virshup's laboratory, Duke-NUS. L-Wnt3A (ATCC, #CRL-2647) cell line was used for providing Wnt3A conditioned media. The three cell lines were grown in DMEM with 10% FBS incubated in 37° C. with 5% $CO_2$.

Cell Viability Assay:

5000 cells in 75 μl culture media were seeded in each well of black 96 well plates (Greiner #655090) and incubated overnight at 37° C. 25 μl of serially diluted compound was added to the cells giving final concentration of 50 μM to 1.5 nM. After 1 day of treatment, 100 μl of CellTiter-Glo Luminescent Cell Viability Assay reagent (#G7571, Promega) was added to each well and incubated for 10 minutes at room temperature. Luminescence was measured using Tecan Safire2 microplate reader.

STF3A Assay:

$2 \times 10^4$ HEK293-STF3A cells in 75 μl culture media were seeded in each well of white 96 well plates (Greiner #655098) and incubated overnight at 37° C. 25 μl serially diluted compound was added to the cells to give final concentration of 50 μM to 1.5 nM. After 1 day of treatment, 100 μl of Steady-Glo Luciferase Assay reagent (#E2520, Promega) was added to each well and incubated for 10 minutes at room temperature. Luminescence was measured using Tecan Safire2 plate reader.

STF/WNT3A conditioned medium (STF/WNT3A CM) assay:

L-Wnt3A cells were cultured in three T-175 flasks at $3 \times 10^4$ cells/ml in 30 ml culture medium per flask. After 4 days of incubation, the Wnt3A conditioned media were harvested and then centrifuged at 2000 rpm for 10 minutes to remove the debris. The Wnt3A conditioned media were stored at −20° C. if not used immediately.

$2 \times 10^4$ HEK293-STF cells in 25 μl culture media were added in each well of white 96 well plates (Greiner #655098). 25 μl serially diluted compound was added to the cells. After 4 hours of incubation, 100 μl Wnt-3A conditioned medium was added to the cells. The final concentration of compound ranged from 33 μM to 1 nM. After incubation for 1 day at 37° C., 100 μl of Steady-Glo® Luciferase Assay reagent (#E2520, Promega) was added to each well and incubated for 10 minutes at room temperature. Luminescence was measured using Tecan Safire2 microplate reader.

Western Blot:

$8.0 \times 10^5$ cells in 2.5 ml media were seeded in T-25 flasks. Compounds were diluted to 600 nM in 1 ml medium and 0.5 ml was added to the T-25 flask to give a final concentration of 100 nM. After incubation in 37° C. for two days, the culture media were collected and centrifuged at 2000 rpm for 10 min. The supernatants were collected and 32 μl from each sample was used for SDS PAGE gel electrophoresis. After transferring the separated proteins to the membrane it was incubated with the primary Wnt3A antibody (1:1000, #09-162, Millipore) overnight. After washing with Tris-Buffered Saline containing 0.05% Tween 20 (TBST), the membrane was incubated with polyclonal Goat anti-Rabbit IgG HRP-conjugated secondary antibody (1:3000, #P0448) for 1 hour at room temperature. After washing with TBST, the membrane was developed with Amersham™ ECL™ Select Western Blotting Detection Reagent (#RPN2235, GE Healthcare Life Sciences) and documented with Bio-Rad Molecular Imager VersaDoc MP.

MMTV-Wnt1 Mouse Model:

8-10 weeks old Female BALBc mice were anesthetised with 150 mg/kg Ketamine +75 mg/kg Xylazine. Under aseptic conditions, skin near the $4^{th}$ mammary fat pad was incised, Mammary fat pad was tweaked with forceps and tumor fragment ~2 mm³ was implanted. The incision was closed using a tissue adhesive. Animals were randomised into groups of eight and treated daily with the test compounds for 14 days. Tumors were measured in two dimensions using calipers, and volume was calculated using the formula: Tumor Volume (mm³)=$w^2 \times \frac{1}{2}$. Maximum tumor volume limit was 2000 mm³.

Wnt3A Palmitoylation Assay:

The assay used to determine the inhibition of the palmitoylation of Wnts by compound was described by Yap et al, (Yap M C, Kostiuk M A, Martin D D, Perinpanayagam M A, Hak P G, Siddam A, Majjigapu J R, Rajaiah G, Keller B O, Prescher J A, Wu P, Bertozzi C R, Falck J R, Berthiaume L G. 2010. Rapid and selective detection of fatty acylated proteins using omega-alkynyl-fatty acids and click chemistry. J Lipid Res. 51(6):1566-1580) with some modification. $3 \times 10^6$ HeLa cells were seeded in 10 cm culture dish and incubated at 37° C. overnight. The cells were transfected with 5 μg pCDNA3.2/V5-Wnt3a vector (Najdi R, Proffitt K, Sprowl S, Kaur S, Yu J, Covey T M, Virshup D M, Waterman M L. 2012. A uniform human Wnt expression library reveals a shared secretory pathway and unique signaling activities. Differentiation, 84(2), 203-213. doi:10.1016/j.diff.2012.06.004) to over-express V5-tagged Wnt3a. After six hours, the cells were washed with PBS and treated with 100 μM alkyne palmitate in medium with 5% BSA. 100 nM compound or DMSO was added and the cells were incubated overnight at 37° C. The cells were lyzed and 600 μg cell lysate was collected and incubated with anti-V5 antibody (Invitrogen) followed by the pull down of V5-Wnt3a with the addition of Protein A/G agarose beads (Thermo scientific). The pulled down lysates containing V5-Wnt3a was click-reacted with biotin-azide (Invitrogen). The biotin-labelled protein lysate was then separated on SDS-PAGE and transferred to a nitrocellulose membrane. The membrane was incubated with primary anti-V5 antibody, followed by secondary anti-mouse Dylight 680 (Thermo scientific) to detect V5-Wnt3a. The membrane was then incubated with streptavidin-Dylight 800 (Thermo scientific) to detect biotin labelled Wnt3a. The signals were captured on the Odyssey CLx Infrared Imaging System (LI-COR Bioscience).

Soft Agar Assay:

AsPC-1 cells were maintained in RPMI164 supplemented with 10% FBS, 2 mM L-glutamine and P/S (100 units/ml penicillin and 100 μg/ml streptomycin). HPAF-II cells were maintained in MEM (Eagles') supplemented with 10% FBS, 2 mM L-glutamine and P/S (100 units/ml penicillin and 100 μg/ml streptomycin). CFPAC-1 cells were maintained in Iscove MEM supplemented with 10% FBS, 2 mM L-glutamine and P/S (100 units/ml penicillin and 100 μg/ml streptomycin).

600 μl of 0.6% agar was added to 24-well plate to form the base layer. Then a middle layer of 0.36% agar (containing 5000 cells and serially diluted compound) was added on to the base layer. Finally 500 μl of fresh growth medium was added to the top of the middle layer. The plates were incubated at 37° C. with 5% carbon dioxide in a humidified incubator for 2 weeks. Formation of colonies was observed using a light microscope. When the colony size was larger than 500 μm, 70 μl MTT (5 mg/ml) was added to each well and the plates were incubated at 37° C. for at least 2 hours. Colonies were counted with GelCount® instrument. The colony counts were plotted against compound concentrations using the GraphPad Prism software. The software was also used to perform non-linear curve fitting and calculation of compound concentration that inhibited 50% colony formation.

Results:

Maleimide compounds specifically inhibit mammalian PORCN.

PORCN-null HT1080 cells were transfected with mammalian or Xenopus PORCN expression plasmids, along with WNT3A, STF reporter and mCherry as transfection control. 6 hours after transfection, cells were treated with the compounds or DMSO as indicated, and the following day assayed for luciferase. Xenopus PORCN was resistant to the inhibitory effects of compounds. The two compounds, Compound 14 and 43 inhibit the activity of mammalian porcupine (FIG. 1).

Figure 2:
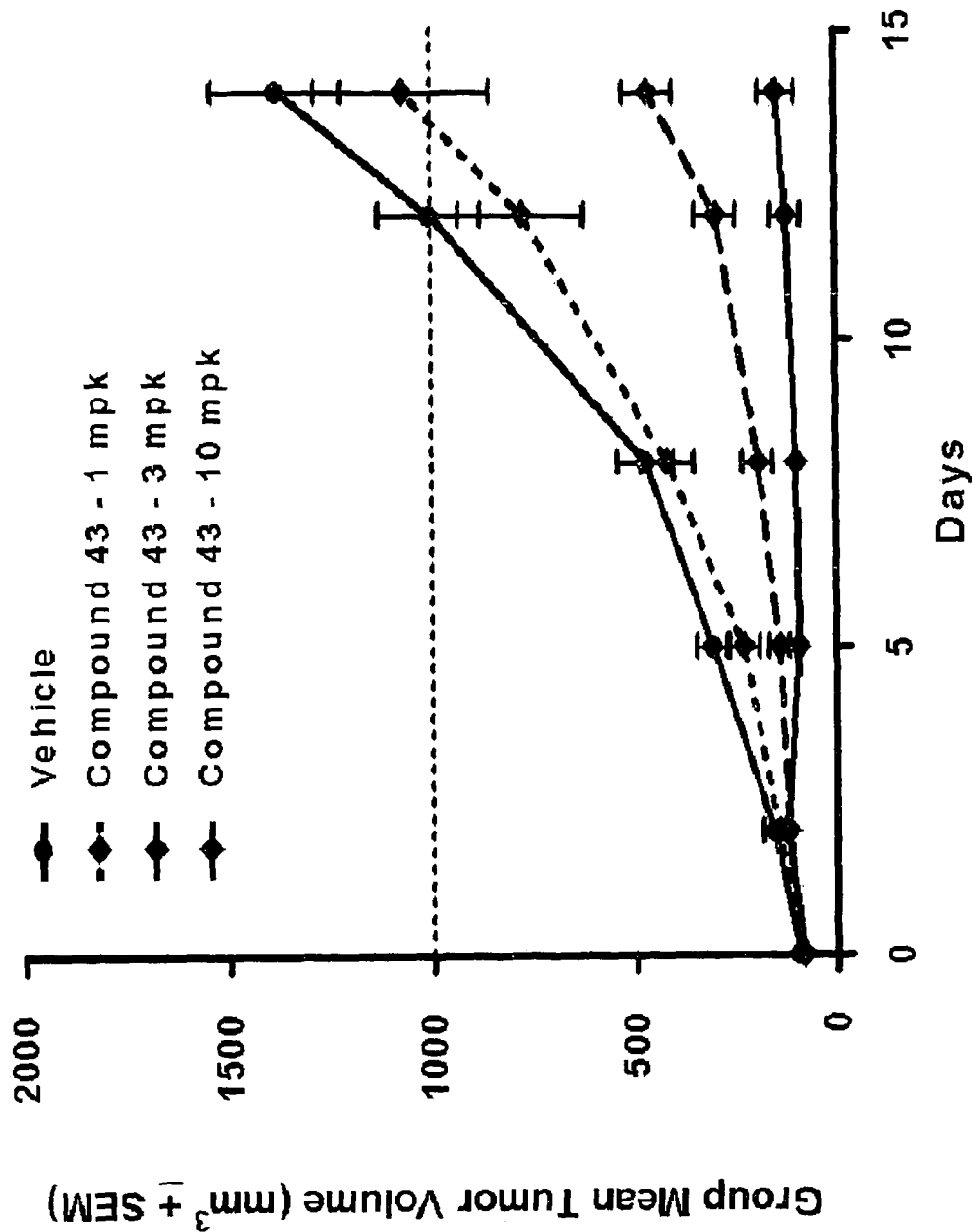
FIG. 2: A graph illustrating efficacy of Compound 43 on the MMTV-Wnt1 mouse model.
Figure 3:
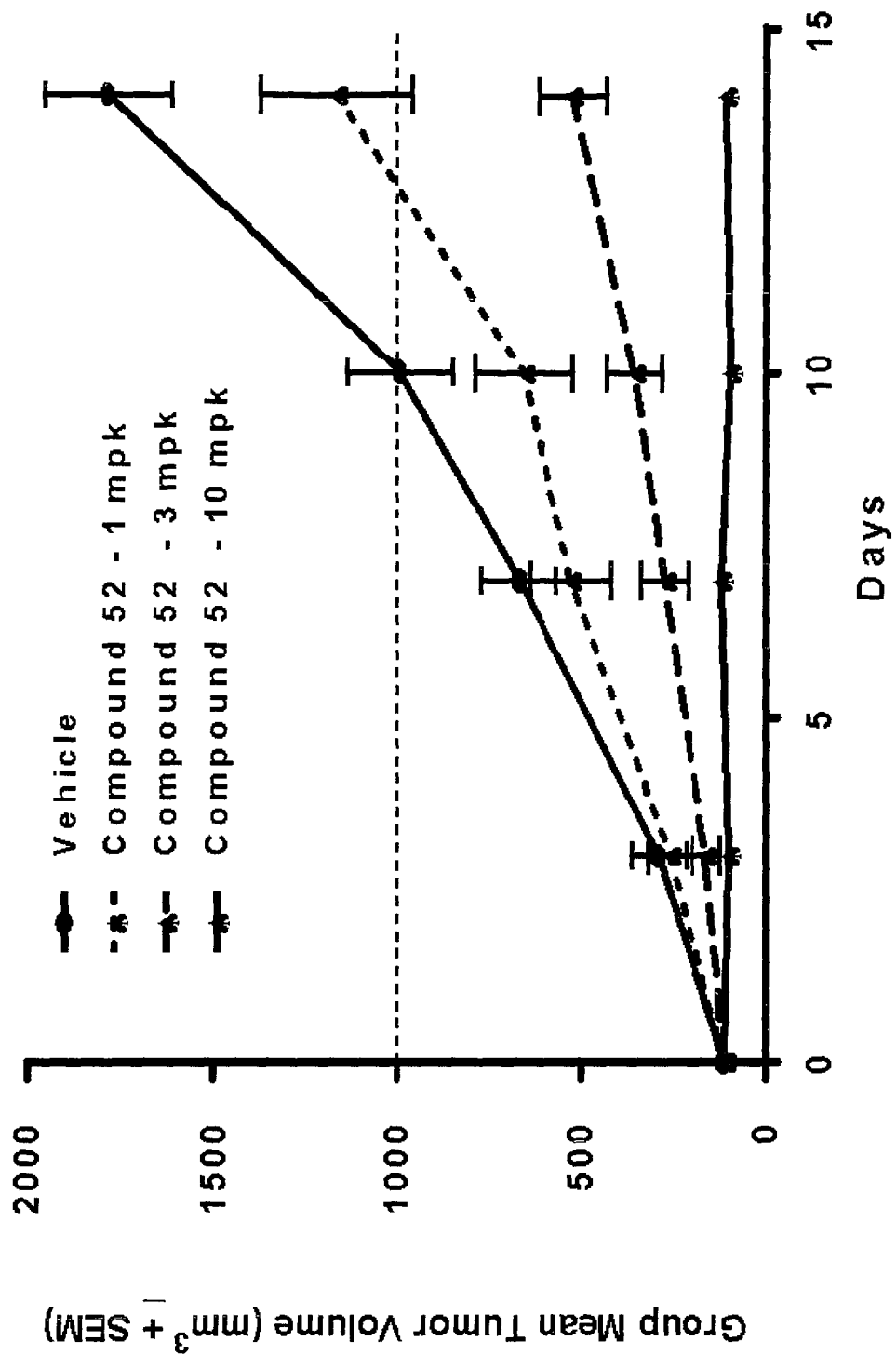
FIG. 3: A graph illustrating efficacy of Compound 52 on the MMTV-Wnt1 mouse model.
Figure 4:
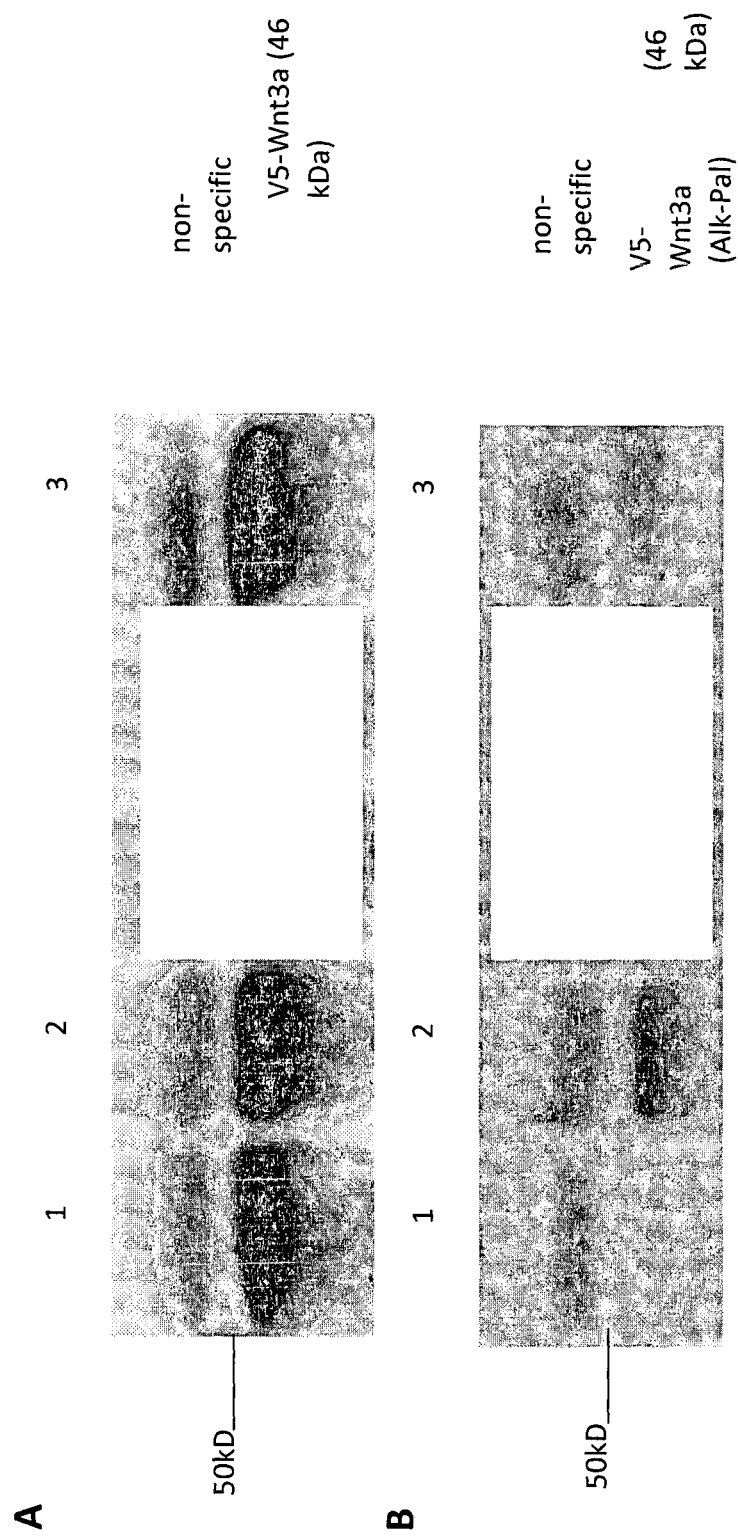
FIG. 4: Images illustrating inhibition of Palmitoylation of Wnt3a by Compound 43.

Treatment with Compounds 43 and 52 decreased tumor growth in all the treated mice (FIG. 2 and FIG. 3).

Figure 5:
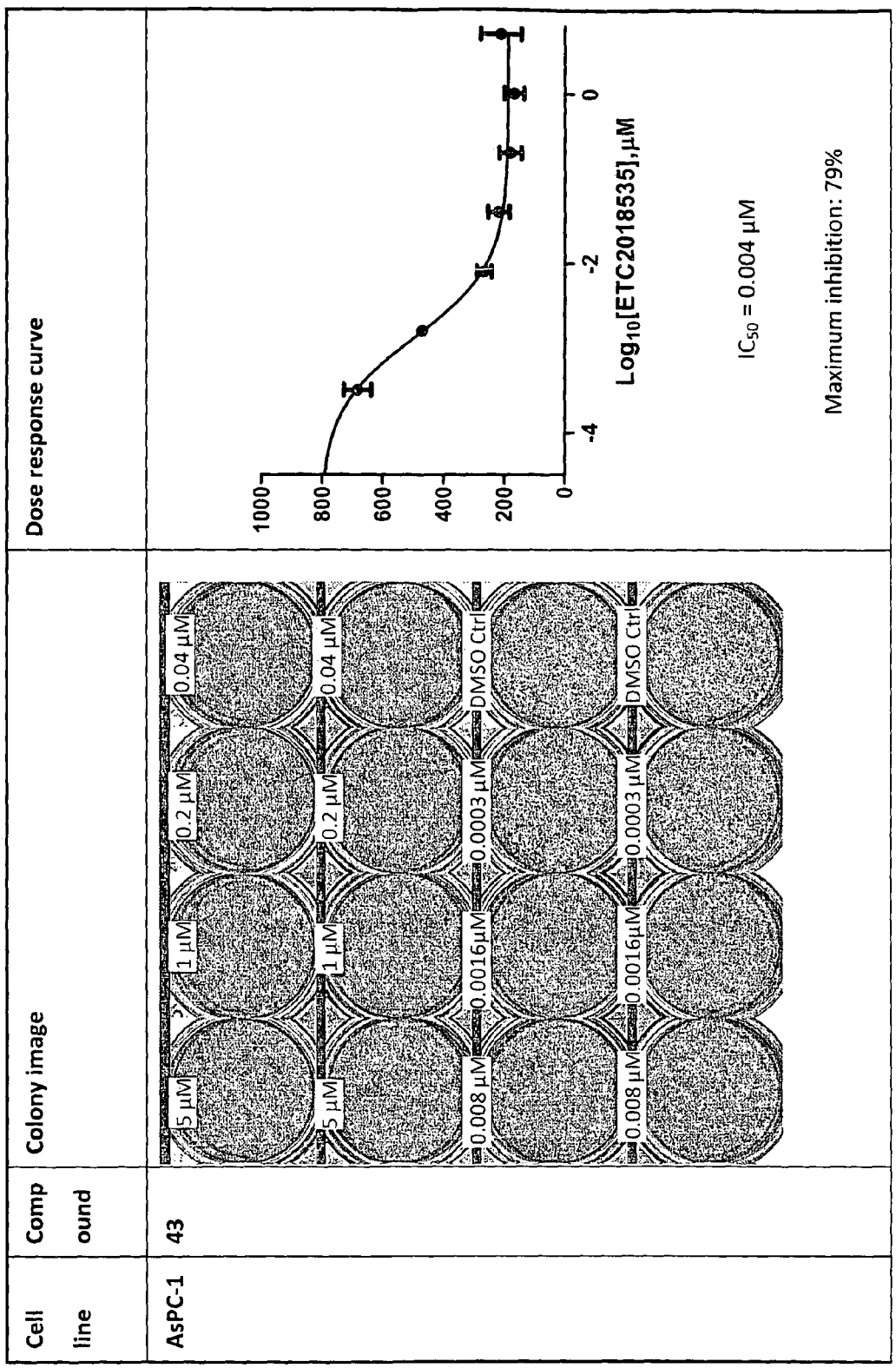
FIGS. 5 to 7: Images and graphs showing results of the Soft Agar Assay.

FIG. 5. Palmitoylation of Wnt3a is inhibited by Compound 43. A. The Wnt3a-V5 was visualized using anti-V5 antibody, followed by anti-mouse Dylight 680. B. Biotin-azide clicked palmitate in V5-Wnt3a was detected with streptavidin-Dylight 800. A non-specific band was observed above the Wnt3a-V5 protein. Biotin-azide clicked palmitate was detected with streptavidin-Dylight 800 (lower band). DMSO was used as negative control. Lane 1: Without Alkyne palmitate; Lane 2: untreated control, DMSO+ Alkyne palmitate; Lane 3: 100 nM Compound 43+Alkyne palmitate.

Figure 6:
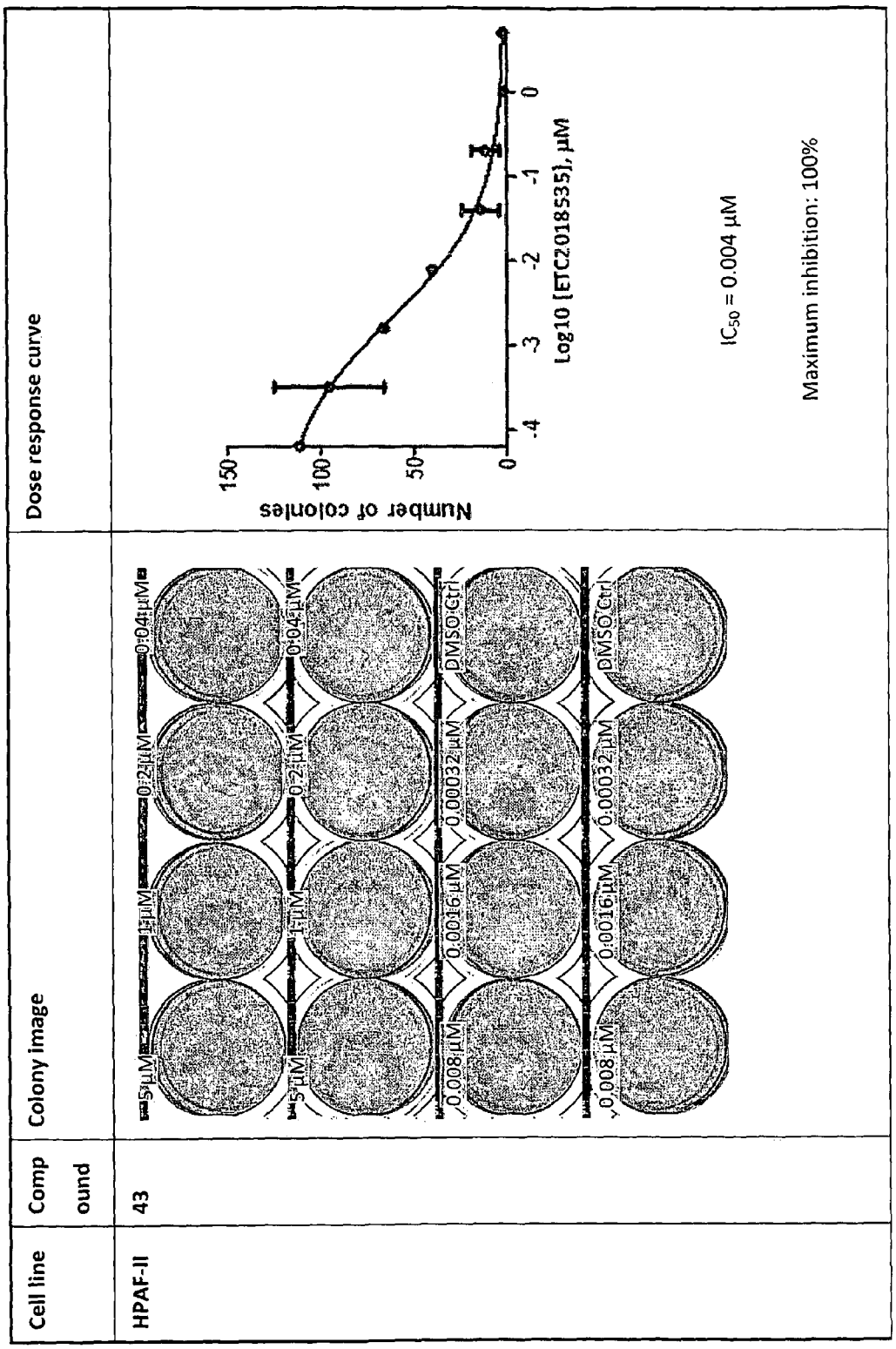
Figure 7:
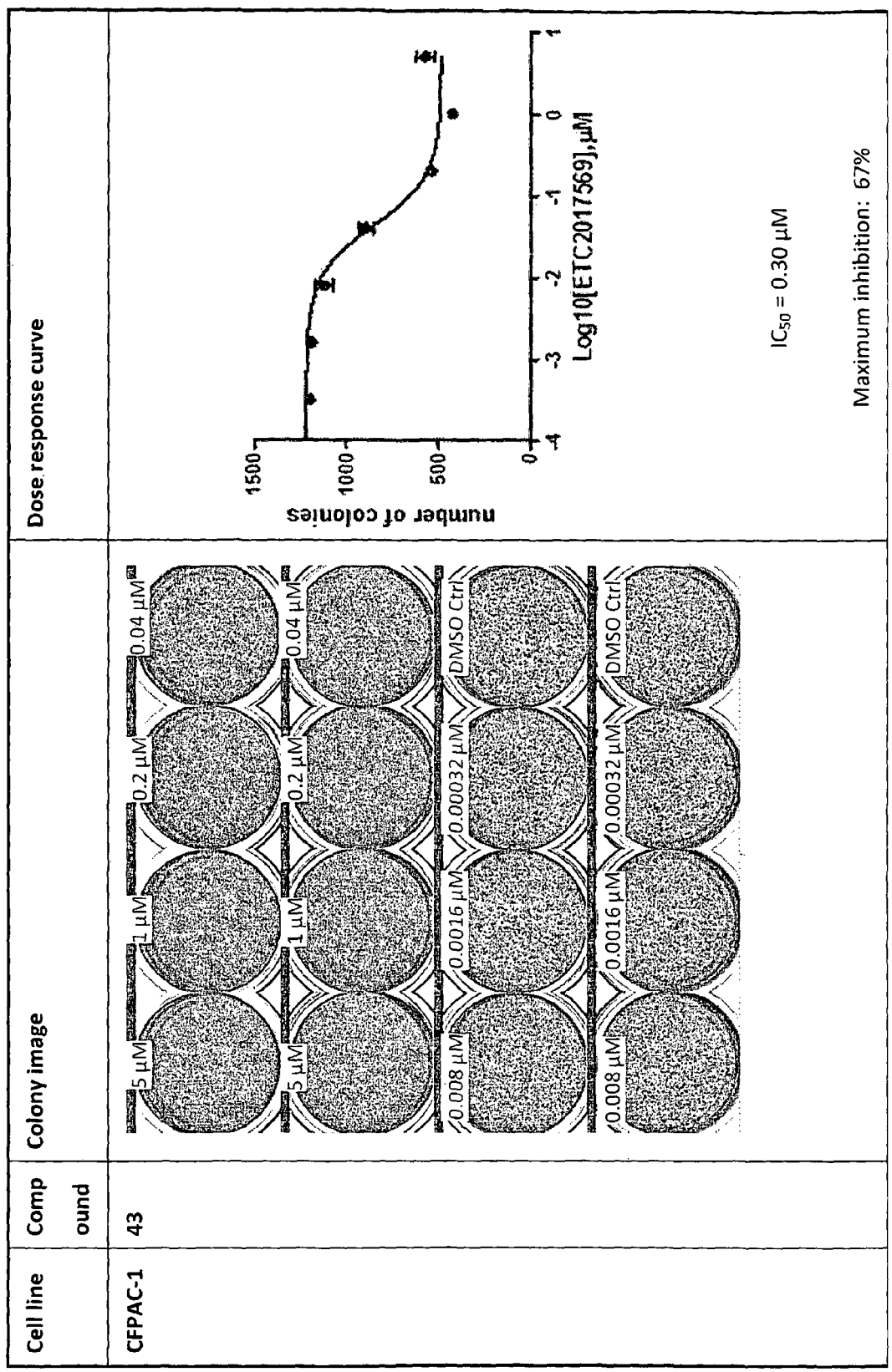

Results of the Soft Agar Assay are shown in FIGS. 5 to 7 and Table 1: Fifty percent colony growth inhibitory concentration ($IC_{50}$, μM) of Compound 43 on pancreatic cell lines AsPC-1 and HPAF-II. Results shown below are mean±standard deviation (SD) from two independent experiments.

| Compound | Cell line | Test 1 $IC_{50}$ (μM) | Test 2 $IC_{50}$ (μM) | Mean $IC_{50}$ (μM) | Standard deviation (SD) | Maximum inhibition |
|---|---|---|---|---|---|---|
| 43 | AsPC-1 | 0.004 | 0.005 | 0.005 | 0.001 | 79% |
| | HPAF-II | 0.004 | 0.002 | 0.003 | 0.001 | 100% |
| | CFPAC-1 | 0.30 | 0.14 | 0.220 | 0.113 | 67% |

The results of the MMTV-Wnt1 Mouse Model are shown in FIG. 2 and Table 2

TABLE 2

| Compound - dose | % TGI | T/C | % T/C | Significance | TRD | NTRD |
|---|---|---|---|---|---|---|
| Vehicle | — | — | — | — | 0/8 | 0/8 |
| Compound 43-1 mg/Kg | 24 | 0.775 | 77.5 | NS | 0/8 | 0/8 |
| Compound 43-3 mg/Kg | 72 | 0.337 | 33.7 | *** | 0/8 | 0/8 |
| Compound 43-10 mg/Kg | 97 | 0.185 | 18.5 | *** | 0/8 | 0/8 |

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications mentioned throughout the specification of the present invention are herein incorporated in their entirety by reference.

The invention embraces all combinations of preferred and more preferred groups and embodiments of groups recited above.

The invention claimed is:

1. A compound of Formula (I)

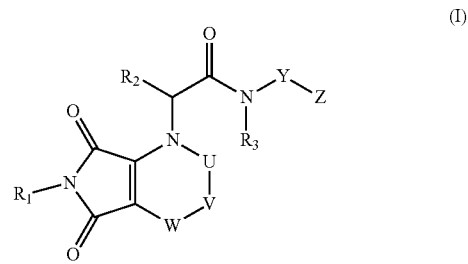

(I)

or a pharmaceutically acceptable salt thereof, including all tautomers and stereoisomers thereof wherein:

$R_1$ represents optionally substituted alkyl (wherein optional substituents include one or more substituents each independently selected from $C_{1-6}$alkoxy); optionally substituted carbocyclyl (wherein optional substituents include one or more substituents each independently selected from $C_{1-6}$alkyl, $C_{1-6}$alkoxy, $C_{1-6}$haloalkyl, $C_{1-6}$haloalkoxy and halo); or -alkylaryl;

$R_2$ represents H; or alkyl;

$R_3$ represents H; or alkyl;

U, V and W represent —($CH_2$)—; or U and V together represent —CH═CH— and W represents C═O;

Y represents aryl; heteroaryl; optionally substituted carbocyclyl (wherein optional substituents include one or more substituents each independently selected from $C_{1-6}$alkyl, $C_{1-6}$alkoxy, $C_{1-6}$haloalkyl, $C_{1-6}$haloalkoxy and halo); or optionally substituted heterocyclyl (wherein optional substituents include one or more substituents each independently selected from $C_{1-6}$alkyl, $C_{1-6}$alkoxy, —C(O)OC$_{1-6}$alkyl, —C(O)C$_{1-6}$alkyl and —C(O)NHC$_{1-6}$alkyl); and Z represents aryl; heteroaryl; optionally substituted carbocyclyl (wherein optional substituents include one or more substituents each independently selected from $C_{1-6}$alkyl, $C_{1-6}$alkoxy, $C_{1-6}$haloalkyl, $C_{1-6}$haloalkoxy and halo); or optionally substituted heterocyclyl (wherein optional substituents include one or more substituents each independently selected from $C_{1-6}$alkyl, $C_{1-6}$alkoxy, —C(O)OC$_{1-6}$alkyl, —C(O)C$_{1-6}$alkyl and —C(O)NHC$_{1-6}$alkyl).

2. The compound of claim 1, wherein the compounds is of Formula (I),

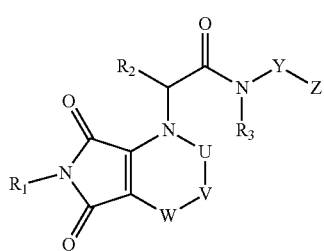

or a pharmaceutically acceptable salt thereof, including all tautomers and stereoisomers thereof, wherein:

$R_1$ represents alkyl which is optionally substituted by one or more substituents each independently selected from $C_{1-6}$alkoxy; carbocyclyl which is optionally substituted by one or more substituents each independently selected from $C_{1-6}$alkyl, $C_{1-6}$alkoxy, $C_{1-6}$haloalkyl, $C_{1-6}$haloalkoxy and halo; or -alkylaryl;

$R_2$ represents H; or alkyl;

$R_3$ represents H; or alkyl;

U, V and W each represent —(CH$_2$)—; or U and V together represent —CH=CH— and W represents C=O;

Y represents aryl; heteroaryl; carbocyclyl which is optionally substituted by one or more substituents each independently selected from $C_{1-6}$alkyl, $C_{1-6}$alkoxy, $C_{1-6}$haloalkyl (e.g. fluoromethyl), $C_{1-6}$haloalkoxy and halo; or heterocyclyl which is optionally substituted by one or more substituents each independently selected from $C_{1-6}$alkyl, $C_{1-6}$alkoxy, —C(O)OC$_{1-6}$alkyl, —C(O)C$_{1-6}$alkyl and —C(O)NHC$_{1-6}$alkyl; and Z represents aryl; heteroaryl; carbocyclyl which is optionally substituted by one or more substituents each independently selected from $C_{1-6}$alkyl, $C_{1-6}$alkoxy, $C_{1-6}$haloalkyl (e.g. fluoromethyl), $C_{1-6}$haloalkoxy and halo; or heterocyclyl which is optionally substituted by one or more substituents each independently selected from $C_{1-6}$alkyl, $C_{1-6}$alkoxy, —C(O)OC$_{1-6}$alkyl, —C(O)C$_{1-6}$alkyl and —C(O)NHC$_{1-6}$alkyl.

3. A compound according to claim 1 wherein $R_1$ represents $C_{1-3}$ alkyl or $C_{3-4}$ cycloalkyl.

4. A compound according to claim 1 wherein $R_2$ represents H.

5. A compound according to claim 1 wherein $R_3$ represents H.

6. A compound according to claim 1 wherein U, V and W each represent —(CH$_2$)—.

7. A compound according to claim 1 wherein Y represents phenyl or monocyclic heteroaryl comprising one or two nitrogen ring atoms or 6-membered heteroaryl.

8. A compound according to claim 7 wherein Z and —NR$_3$ are positioned on ring Y at the 1- and 4- positions relative to each other.

9. A compound according claim 1 wherein Y is unsubstituted or monosubstituted.

10. A compound according to claim 1 wherein Z is phenyl or monocyclic heteroaryl comprising one or two nitrogen atoms.

11. A compound as defined in any one of examples 1 to 158:

| Cpd ID | Structure | IUPAC Name |
|---|---|---|
| 1 | 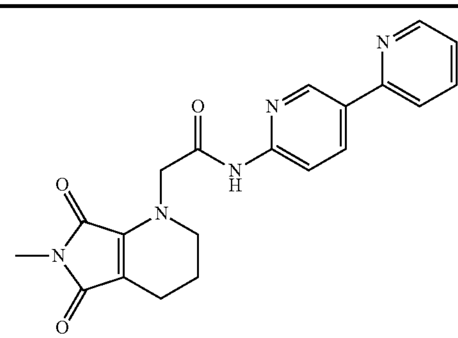 | N-([2,3'-bipyridin]-6'-yl)-2-(6-methyl-5,7-dioxo-2,3,4,5,6,7-hexahydro-1H-pyrrolo[3,4-b]pyridin-1-yl)acetamide |
| 2 | 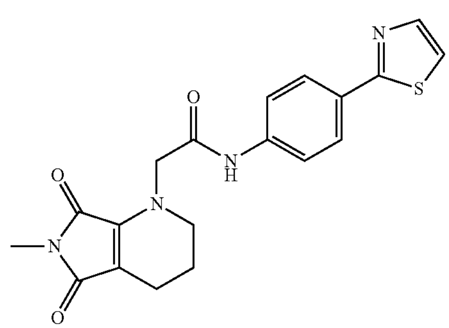 [SMILES: CN1C(=O)C2=C(C1=O)N(CC(=O)Nc1ccc(-c3nccs3)cc1)CCC2] | 2-(6-methyl-5,7-dioxo-2,3,4,5,6,7-hexahydro-1H-pyrrolo[3,4-b]pyridin-1-yl)-N-(4-(thiazol-2-yl)phenyl)acetamide |

-continued

| Cpd ID | Structure | IUPAC Name |
|---|---|---|
| 3 | 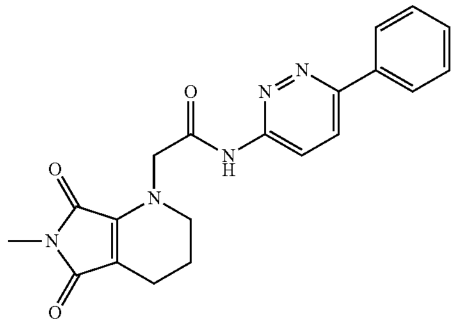 [SMILES: CN1C(=O)C2=C(C1=O)N(CC(=O)Nc1ccc(-c3ccccc3)nn1)CCC2] | 2-(6-methyl-5,7-dioxo-2,3,4,5,6,7-hexahydro-1H-pyrrolo[3,4-b]pyridin-1-yl)-N-(6-phenylpyridazin-3-yl)acetamide |
| 4 | 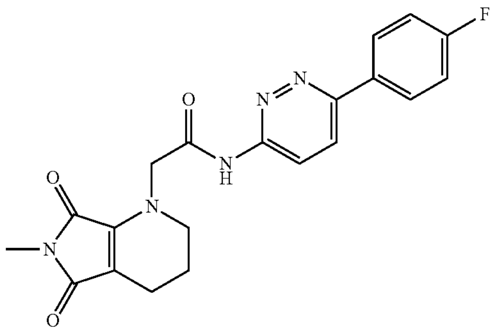 [SMILES: CN1C(=O)C2=C(C1=O)N(CC(=O)Nc1ccc(-c3ccc(F)cc3)nn1)CCC2] | N-(6-(4-fluorophenyl)pyridazin-3-yl)-2-(6-methyl-5,7-dioxo-2,3,4,5,6,7-hexahydro-1H-pyrrolo[3,4-b]pyridin-1-yl)acetamide |
| 5 | 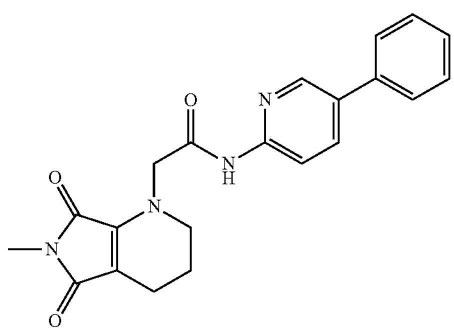 [SMILES: CN1C(=O)C2=C(C1=O)N(CC(=O)Nc1ccc(-c3ccccc3)cn1)CCC2] | 2-(6-methyl-5,7-dioxo-2,3,4,5,6,7-hexahydro-1H-pyrrolo[3,4-b]pyridin-1-yl)-N-(5-phenylpyridin-2-yl)acetamide |
| 6 | 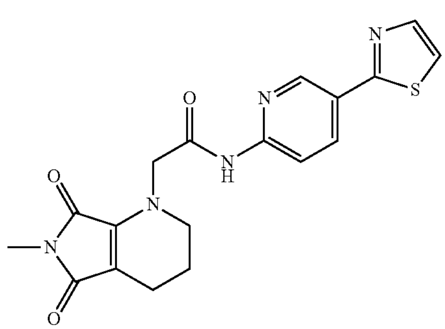 [SMILES: CN1C(=O)C2=C(C1=O)N(CC(=O)Nc1ccc(-c3nccs3)cn1)CCC2] | 2-(6-methyl-5,7-dioxo-2,3,4,5,6,7-hexahydro-1H-pyrrolo[3,4-b]pyridin-1-yl)-N-(5-(thiazol-2-yl)pyridin-2-yl)acetamide |

| Cpd ID | Structure | IUPAC Name |
|---|---|---|
| 7 | 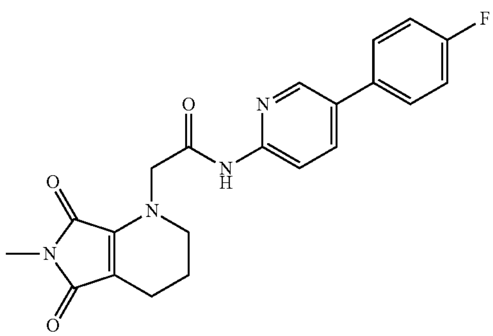 [SMILES: CN1C(=O)C2=C(C1=O)N(CC(=O)Nc1ccc(-c3ccc(F)cc3)cn1)CCC2] | N-(5-(4-fluorophenyl)pyridin-2-yl)-2-(6-methyl-5,7-dioxo-2,3,4,5,6,7-hexahydro-1H-pyrrolo[3,4-b]pyridin-1-yl)acetamide |
| 8 | 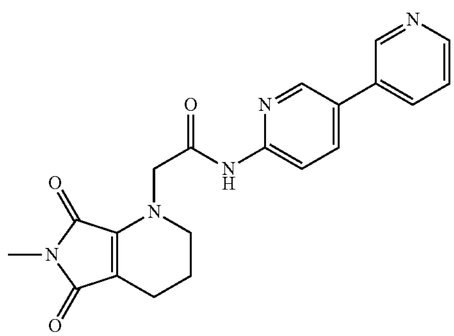 [SMILES: CN1C(=O)C2=C(C1=O)N(CC(=O)Nc1ccc(-c3cccnc3)cn1)CCC2] | N-([3,3'-bipyridin]-6-yl)-2-(6-methyl-5,7-dioxo-2,3,4,5,6,7-hexahydro-1H-pyrrolo[3,4-b]pyridin-1-yl)acetamide |
| 9 | 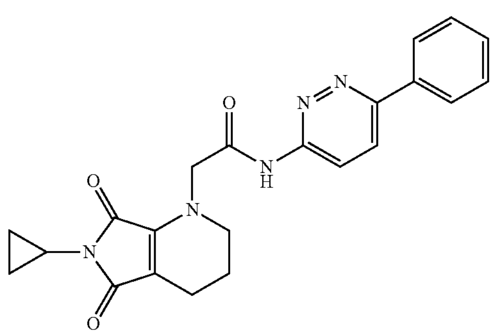 [SMILES: O=C(CN1CCCC2=C1C(=O)N(C1CC1)C2=O)Nc1ccc(-c2ccccc2)nn1] | N-(2,3'-bipyridin-6'-yl)-2-(6-cyclopropyl-5,7-dioxo-2,3,4,5,6,7-hexahydro-1H-pyrrolo[3,4-b]pyridin-1-yl)acetamide |
| 10 | 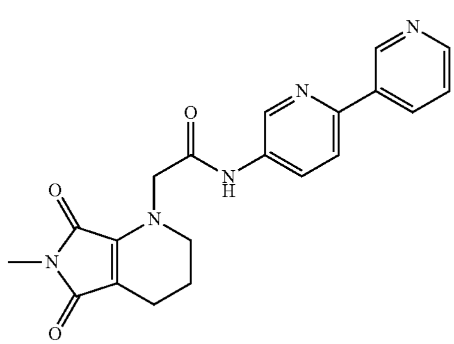 [SMILES: CN1C(=O)C2=C(C1=O)N(CC(=O)Nc1ccc(-c3cccnc3)nc1)CCC2] | N-([2,3'-bipyridin]-5-yl)-2-(6-methyl-5,7-dioxo-2,3,4,5,6,7-hexahydro-1H-pyrrolo[3,4-b]pyridin-1-yl)acetamide |

| Cpd ID | Structure | IUPAC Name |
|---|---|---|
| 11 | 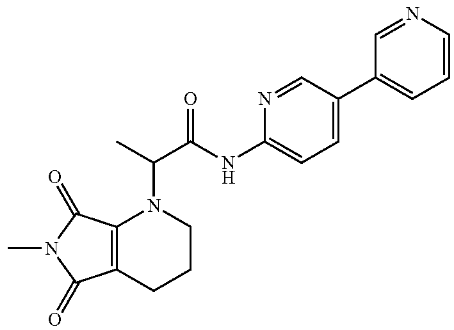 [SMILES: CC(C(=O)Nc1ccc(-c2cccnc2)cn1)N1CCCC2=C1C(=O)N(C)C2=O] | N-([3,3'-bipyridin]-6-yl)-2-(6-methyl-5,7-dioxo-2,3,4,5,6,7-hexahydro-1H-pyrrolo[3,4-b]pyridin-1-yl)propanamide |
| 12 | 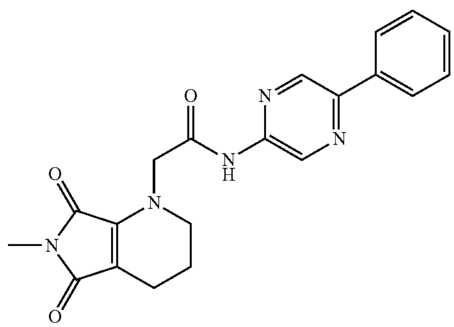 [SMILES: CN1C(=O)C2=C(C1=O)N(CC(=O)Nc1cnc(-c3ccccc3)cn1)CCC2] | 2-(6-methyl-5,7-dioxo-2,3,4,5,6,7-hexahydro-1H-pyrrolo[3,4-b]pyridin-1-yl)-N-(5-phenylpyrazin-2-yl)acetamide |
| 13 | 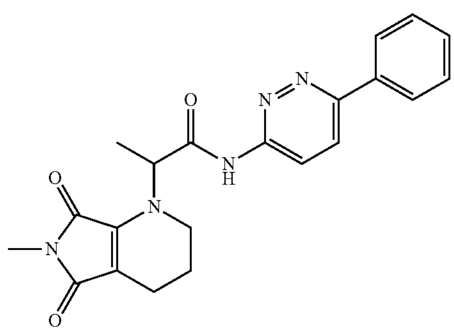 | 2-(6-methyl-5,7-dioxo-2,3,4,5,6,7-hexahydro-1H-pyrrolo[3,4-b]pyridin-1-yl)-N-(6-phenylpyridazin-3-yl)propanamide |
| 14 | 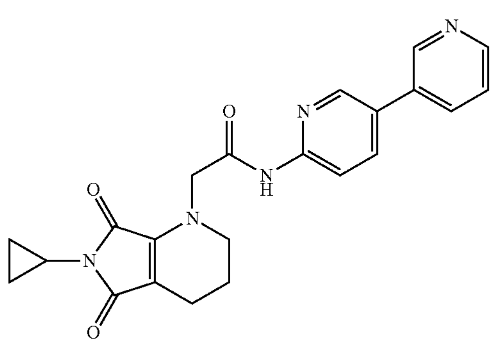 [SMILES: O=C(CN1CCCC2=C1C(=O)N(C1CC1)C2=O)Nc1ccc(-c2cccnc2)cn1] | N-([3,3'-bipyridin]-6-yl)-2-(6-cyclopropyl-5,7-dioxo-2,3,4,5,6,7-hexahydro-1H-pyrrolo[3,4-b]pyridin-1-yl)acetamide |

| Cpd ID | Structure | IUPAC Name |
|---|---|---|
| 15 | 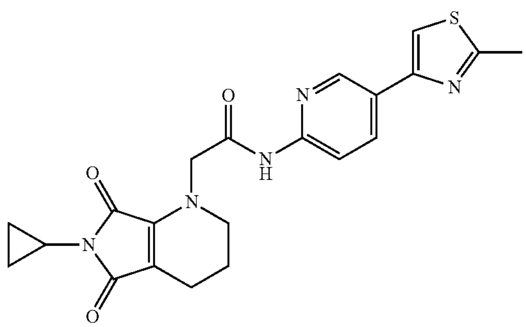 [SMILES: Cc1nc(-c2ccc(NC(=O)CN3CCCC4=C3C(=O)N(C3CC3)C4=O)nc2)cs1] | 2-(6-cyclopropyl-5,7-dioxo-2,3,4,5,6,7-hexahydro-1H-pyrrolo[3,4-b]pyridin-1-yl)-N-(5-(2-methylthiazol-4-yl)pyridin-2-yl)acetamide |
| 16 | 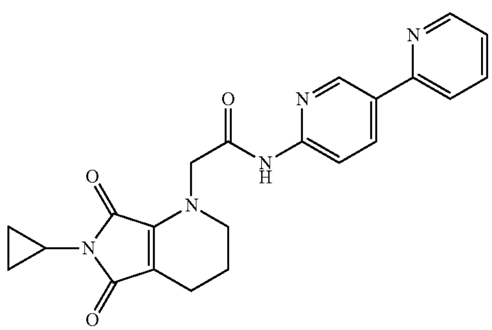 [SMILES: O=C(CN1CCCC2=C1C(=O)N(C1CC1)C2=O)Nc1ccc(-c2ccccn2)cn1] | N-([2,3'-bipyridin]-6'-yl)-2-(6-cyclopropyl-5,7-dioxo-2,3,4,5,6,7-hexahydro-1H-pyrrolo[3,4-b]pyridin-1-yl)acetamide |
| 17 | 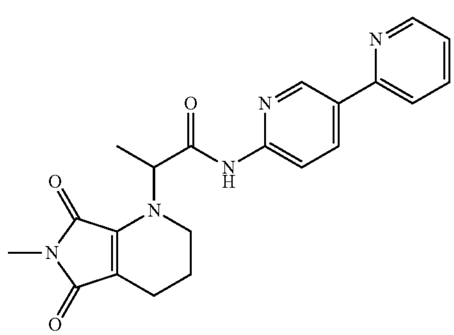 [SMILES: CC(C(=O)Nc1ccc(-c2ccccn2)cn1)N1CCCC2=C1C(=O)N(C)C2=O] | N-([2,3'-bipyridin]-6'-yl)-2-(6-methyl-5,7-dioxo-2,3,4,5,6,7-hexahydro-1H-pyrrolo[3,4-b]pyridin-1-yl)propanamide |
| 18 | 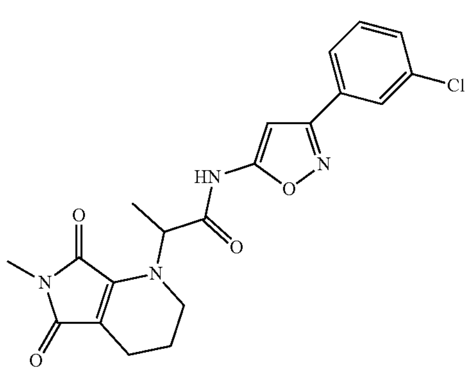 [SMILES: CC(C(=O)Nc1cc(-c2cccc(Cl)c2)no1)N1CCCC2=C1C(=O)N(C)C2=O] | N-(3-(3-chlorophenyl)isoxazol-5-yl)-2-(6-methyl-5,7-dioxo-2,3,4,5,6,7-hexahydro-1H-pyrrolo[3,4-b]pyridin-1-yl)propanamide |

-continued

| Cpd ID | Structure | IUPAC Name |
|---|---|---|
| 19 | 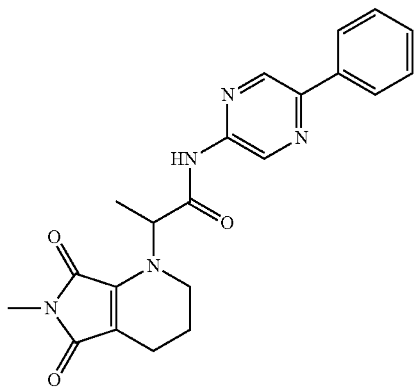 [SMILES: CC(C(=O)Nc1cnc(-c2ccccc2)cn1)N1CCCC2=C1C(=O)N(C)C2=O] | 2-(6-methyl-5,7-dioxo-2,3,4,5,6,7-hexahydro-1H-pyrrolo[3,4-b]pyridin-1-yl)-N-(5-phenylpyrazin-2-yl)propanamide |
| 20 | 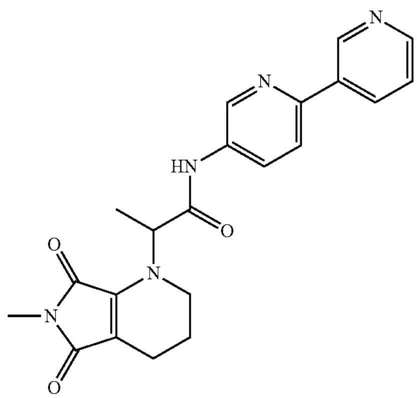 [SMILES: CC(C(=O)Nc1ccc(-c2cccnc2)nc1)N1CCCC2=C1C(=O)N(C)C2=O] | N-([2,3'-bipyridin]-5-yl)-2-(6-methyl-5,7-dioxo-2,3,4,5,6,7-hexahydro-1H-pyrrolo[3,4-b]pyridin-1-yl)propanamide |
| 21 | 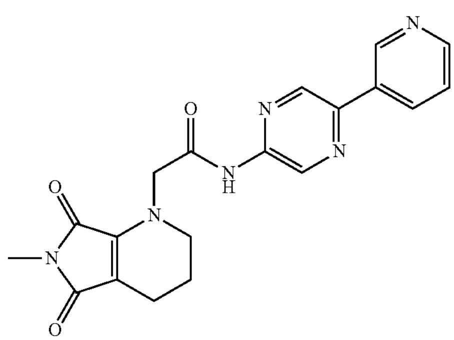 | 2-(6-methyl-5,7-dioxo-2,3,4,5,6,7-hexahydro-1H-pyrrolo[3,4-b]pyridin-1-yl)-N-(5-(pyridin-3-yl)pyrazin-2-yl)acetamide |
| 22 | 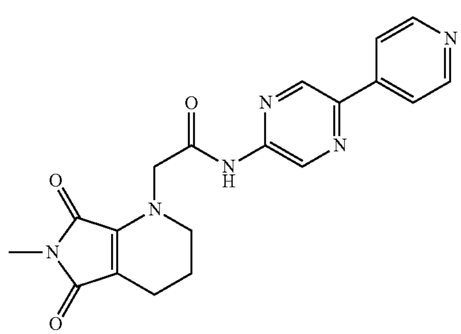 [SMILES: CN1C(=O)C2=C(C1=O)N(CC(=O)Nc1cnc(-c3ccncc3)cn1)CCC2] | 2-(6-methyl-5,7-dioxo-2,3,4,5,6,7-hexahydro-1H-pyrrolo[3,4-b]pyridin-1-yl)-N-(5-(pyridin-4-yl)pyrazin-2-yl)acetamide |

| Cpd ID | Structure | IUPAC Name |
|---|---|---|
| 23 | 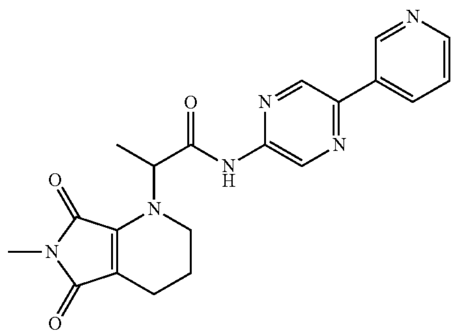 [SMILES: CC(C(=O)Nc1cnc(-c2cccnc2)cn1)N1CCCC2=C1C(=O)N(C)C2=O] | 2-(6-methyl-5,7-dioxo-2,3,4,5,6,7-hexahydro-1H-pyrrolo[3,4-b]pyridin-1-yl)-N-(5-(pyridin-3-yl)pyrazin-2-yl)propanamide |
| 24 | 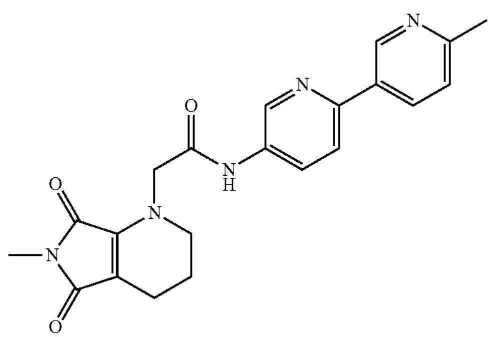 | 2-(6-methyl-5,7-dioxo-2,3,4,5,6,7-hexahydro-1H-pyrrolo[3,4-b]pyridin-1-yl)-N-(6'-methyl-[2,3'-bipyridin]-5-yl)acetamide |
| 25 | 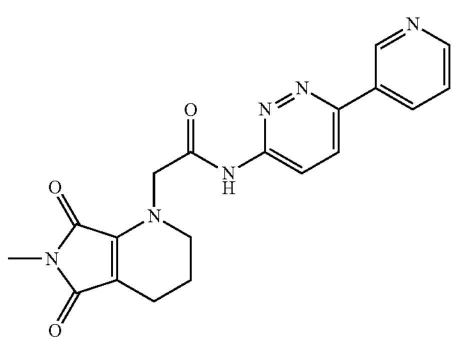 [SMILES: CN1C(=O)C2=C(C1=O)N(CC(=O)Nc1ccc(-c3cccnc3)nn1)CCC2] | 2-(6-methyl-5,7-dioxo-2,3,4,5,6,7-hexahydro-1H-pyrrolo[3,4-b]pyridin-1-yl)-N-(6-(pyridin-3-yl)pyridazin-3-yl)acetamide |
| 26 | 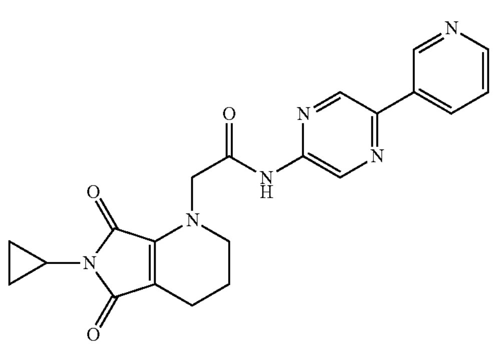 | 2-(6-cyclopropyl-5,7-dioxo-2,3,4,5,6,7-hexahydro-1H-pyrrolo[3,4-b]pyridin-1-yl)-N-(5-(pyridin-3-yl)pyrazin-2-yl)acetamide |

| Cpd ID | Structure | IUPAC Name |
|---|---|---|
| 27 | 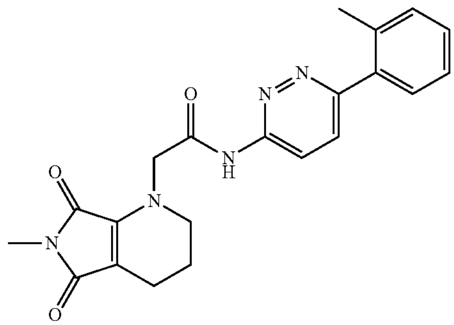 [SMILES: Cc1ccccc1-c1ccc(NC(=O)CN2CCCC3=C2C(=O)N(C)C3=O)nn1] | 2-(6-methyl-5,7-dioxo-2,3,4,5,6,7-hexahydro-1H-pyrrolo[3,4-b]pyridin-1-yl)-N-(6-(o-tolyl)pyridazin-3-yl)acetamide |
| 28 | 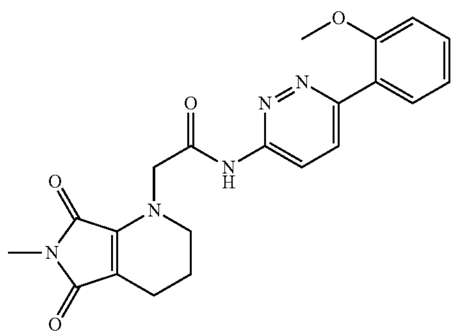 [SMILES: COc1ccccc1-c1ccc(NC(=O)CN2CCCC3=C2C(=O)N(C)C3=O)nn1] | N-(6-(2-methoxyphenyl)pyridazin-3-yl)-2-(6-methyl-5,7-dioxo-2,3,4,5,6,7-hexahydro-1H-pyrrolo[3,4-b]pyridin-1-yl)acetamide |
| 29 | 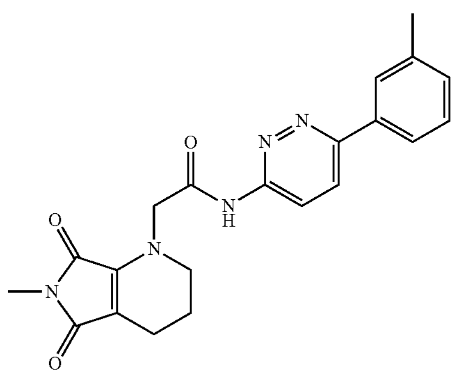 [SMILES: Cc1cccc(-c2ccc(NC(=O)CN3CCCC4=C3C(=O)N(C)C4=O)nn2)c1] | 2-(6-methyl-5,7-dioxo-2,3,4,5,6,7-hexahydro-1H-pyrrolo[3,4-b]pyridin-1-yl)-N-(6-(m-tolyl)pyridazin-3-yl)acetamide |
| 30 | 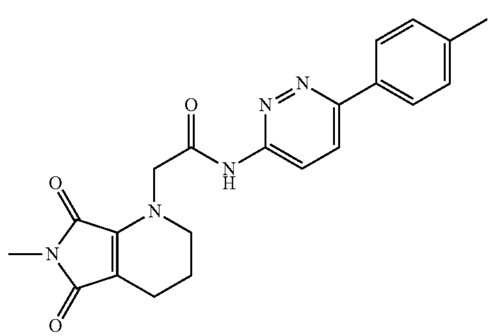 | 2-(6-methyl-5,7-dioxo-2,3,4,5,6,7-hexahydro-1H-pyrrolo[3,4-b]pyridin-1-yl)-N-(6-(p-tolyl)pyridazin-3-yl)acetamide |

-continued

| Cpd ID | Structure | IUPAC Name |
|---|---|---|
| 31 | 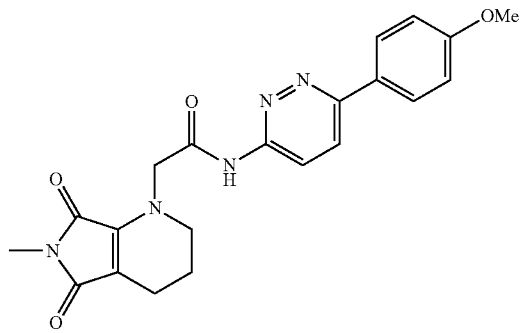 [SMILES: COc1ccc(-c2ccc(NC(=O)CN3CCCC4=C3C(=O)N(C)C4=O)nn2)cc1] | N-(6-(4-methoxyphenyl)pyridazin-3-yl)-2-(6-methyl-5,7-dioxo-2,3,4,5,6,7-hexahydro-1H-pyrrolo[3,4-b]pyridin-1-yl)acetamide |
| 32 | 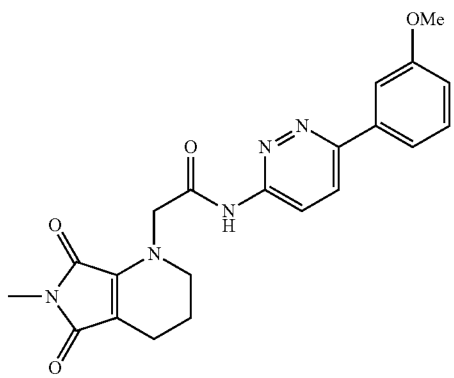 [SMILES: COc1cccc(-c2ccc(NC(=O)CN3CCCC4=C3C(=O)N(C)C4=O)nn2)c1] | N-(6-(3-methoxyphenyl)pyridazin-3-yl)-2-(6-methyl-5,7-dioxo-2,3,4,5,6,7-hexahydro-1H-pyrrolo[3,4-b]pyridin-1-yl)acetamide |
| 33 | 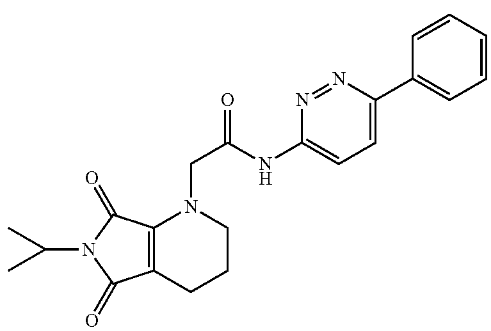 [SMILES: CC(C)N1C(=O)C2=C(C1=O)N(CC(=O)Nc1ccc(-c3ccccc3)nn1)CCC2] | 2-(6-isopropyl-5,7-dioxo-2,3,4,5,6,7-hexahydro-1H-pyrrolo[3,4-b]pyridin-1-yl)-N-(6-phenylpyridazin-3-yl)acetamide |
| 34 | 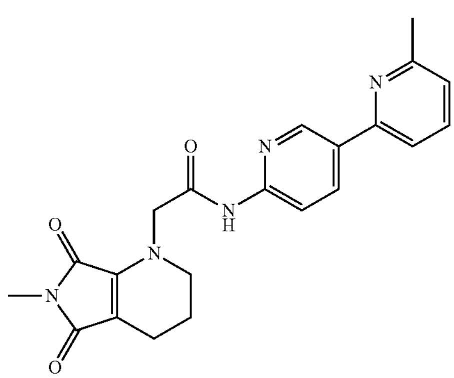 [SMILES: Cc1cccc(-c2ccc(NC(=O)CN3CCCC4=C3C(=O)N(C)C4=O)nc2)n1] | 2-(6-methyl-5,7-dioxo-2,3,4,5,6,7-hexahydro-1H-pyrrolo[3,4-b]pyridin-1-yl)-N-(6-methyl-[2,3'-bipyridin]-6'-yl)acetamide |

| Cpd ID | Structure | IUPAC Name |
|---|---|---|
| 35 | 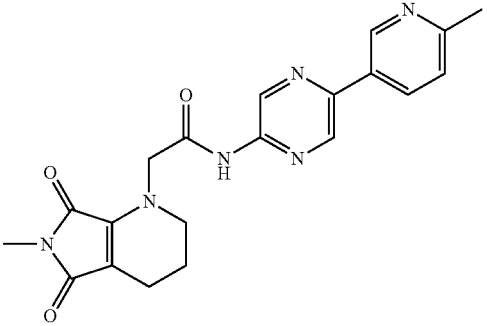 | N-(6-(3-methoxyphenyl)pyridazin-3-yl)-2-(6-methyl-5,7-dioxo-2,3,4,5,6,7-hexahydro-1H-pyrrolo[3,4-b]pyridin-1-yl)acetamide |
| 36 | 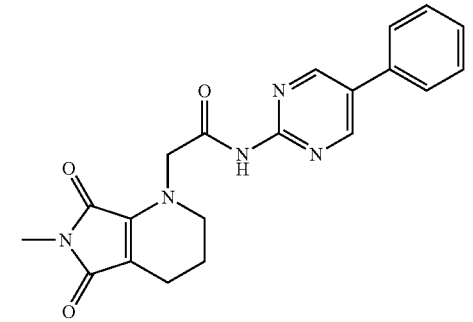 [SMILES: CN1C(=O)C2=C(C1=O)N(CC(=O)Nc1ncc(-c3ccccc3)cn1)CCC2] | 2-(6-methyl-5,7-dioxo-2,3,4,5,6,7-hexahydro-1H-pyrrolo[3,4-b]pyridin-1-yl)-N-(5-phenylpyrimidin-2-yl)acetamide |
| 37 | 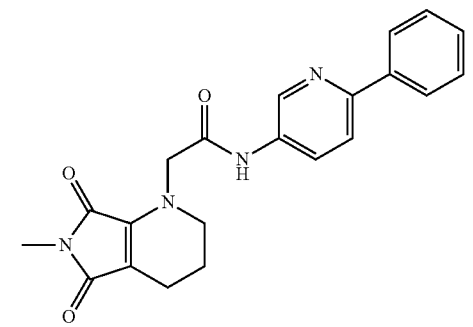 [SMILES: CN1C(=O)C2=C(C1=O)N(CC(=O)Nc1ccc(-c3ccccc3)nc1)CCC2] | 2-(6-methyl-5,7-dioxo-2,3,4,5,6,7-hexahydro-1H-pyrrolo[3,4-b]pyridin-1-yl)-N-(6-phenylpyridin-3-yl)acetamide |
| 38 | 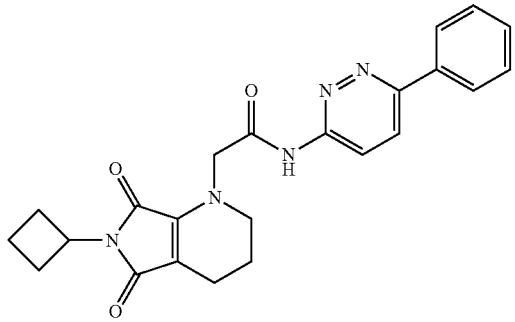 [SMILES: O=C(CN1CCCC2=C1C(=O)N(C1CCC1)C2=O)Nc1ccc(-c2ccccc2)nn1] | 2-(6-cyclobutyl-5,7-dioxo-2,3,4,5,6,7-hexahydro-1H-pyrrolo[3,4-b]pyridin-1-yl)-N-(6-phenylpyridazin-3-yl)acetamide |

| Cpd ID | Structure | IUPAC Name |
|---|---|---|
| 39 | 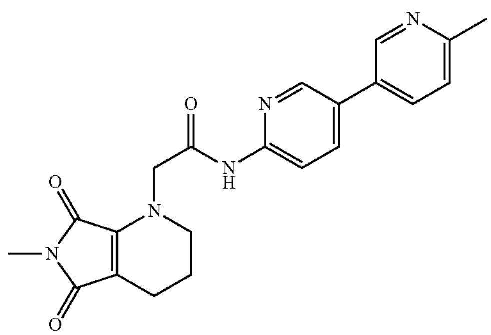 | 2-(6-methyl-5,7-dioxo-2,3,4,5,6,7-hexahydro-1H-pyrrolo[3,4-b]pyridin-1-yl)-N-(6'-methyl-[3,3'-bipyridin]-6-yl)acetamide |
| 40 | 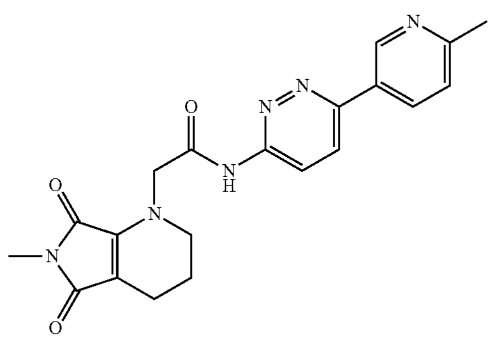 | 2-(6-methyl-5,7-dioxo-2,3,4,5,6,7-hexahydro-1H-pyrrolo[3,4-b]pyridin-1-yl)-N-(6-(6-methylpyridin-3-yl)pyridazin-3-yl)acetamide |
| 41 | 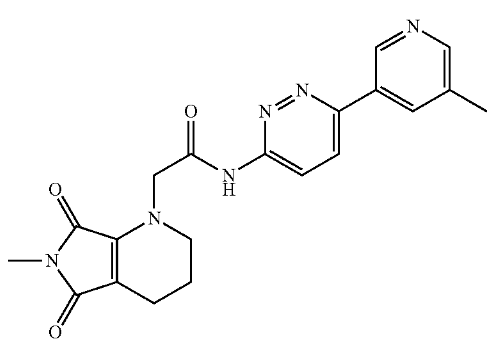 | 2-(6-methyl-5,7-dioxo-2,3,4,5,6,7-hexahydro-1H-pyrrolo[3,4-b]pyridin-1-yl)-N-(6-(5-methylpyridin-3-yl)pyridazin-3-yl)acetamide |
| 42 | 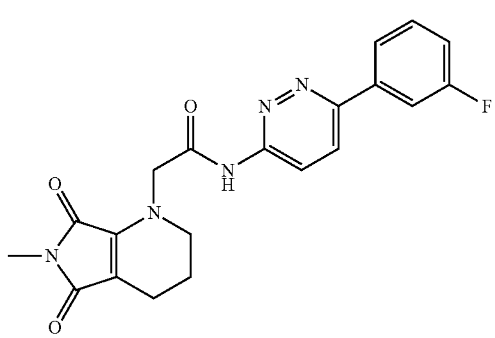 [SMILES: CN1C(=O)C2=C(C1=O)N(CC(=O)Nc1ccc(-c3cccc(F)c3)nn1)CCC2] | N-(6-(3-fluorophenyl)pyridazin-3-yl)-2-(6-methyl-5,7-dioxo-2,3,4,5,6,7-hexahydro-1H-pyrrolo[3,4-b]pyridin-1-yl)acetamide |

| Cpd ID | Structure | IUPAC Name |
| --- | --- | --- |
| 43 | 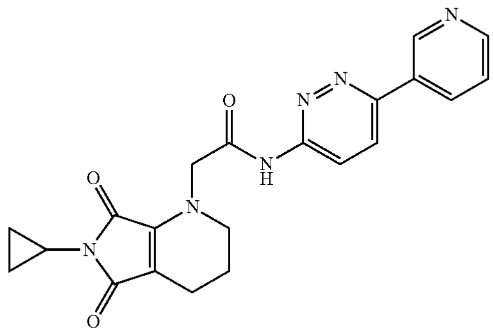 [SMILES: O=C(CN1CCCC2=C1C(=O)N(C1CC1)C2=O)Nc1ccc(-c2cccnc2)nn1] | 2-(6-cyclopropyl-5,7-dioxo-2,3,4,5,6,7-hexahydro-1H-pyrrolo[3,4-b]pyridin-1-yl)-N-(6-(pyridin-3-yl)pyridazin-3-yl)acetamide |
| 44 | 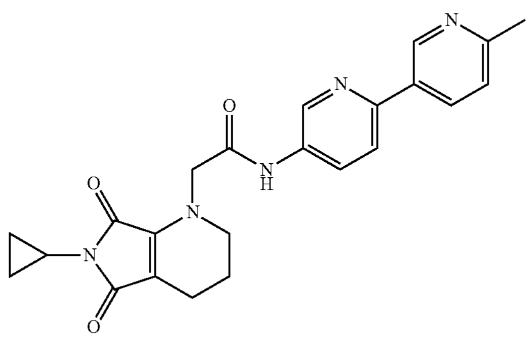 [SMILES: Cc1ccc(-c2ccc(NC(=O)CN3CCCC4=C3C(=O)N(C3CC3)C4=O)cn2)cn1] | 2-(6-cyclopropyl-5,7-dioxo-2,3,4,5,6,7-hexahydro-1H-pyrrolo[3,4-b]pyridin-1-yl)-N-(6'-methyl-[2,3'-bipyridin]-5-yl)acetamide |
| 45 | 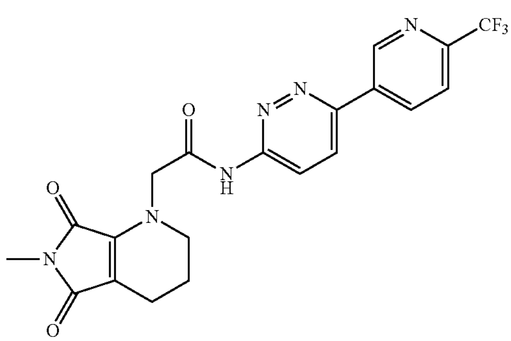 [SMILES: CN1C(=O)C2=C(C1=O)N(CC(=O)Nc1ccc(-c3ccc(C(F)(F)F)nc3)nn1)CCC2] | 2-(6-methyl-5,7-dioxo-2,3,4,5,6,7-hexahydro-1H-pyrrolo[3,4-b]pyridin-1-yl)-N-(6-(6-(trifluoromethyl)pyridin-3-yl)pyridazin-3-yl)acetamide |
| 46 | 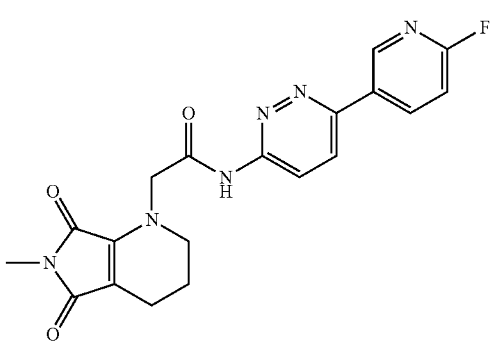 [SMILES: CN1C(=O)C2=C(C1=O)N(CC(=O)Nc1ccc(-c3ccc(F)nc3)nn1)CCC2] | N-(6-(6-fluoropyridin-3-yl)pyridazin-3-yl)-2-(6-methyl-5,7-dioxo-2,3,4,5,6,7-hexahydro-1H-pyrrolo[3,4-b]pyridin-1-yl)acetamide |

| Cpd ID | Structure | IUPAC Name |
| --- | --- | --- |
| 47 | 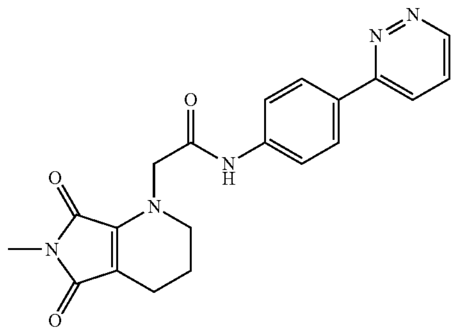 [SMILES: CN1C(=O)C2=C(C1=O)N(CC(=O)Nc1ccc(-c3cccnn3)cc1)CCC2] | 2-(6-methyl-5,7-dioxo-2,3,4,5,6,7-hexahydro-1H-pyrrolo[3,4-b]pyridin-1-yl)-N-(4-(pyridazin-3-yl)phenyl)acetamide |
| 48 | 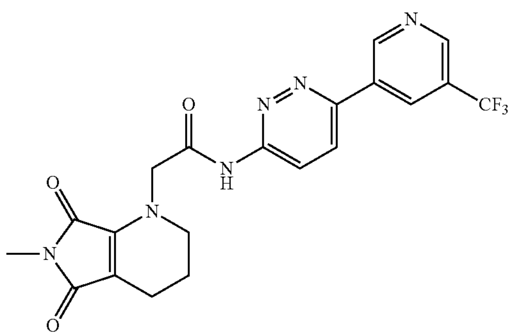 [SMILES: CN1C(=O)C2=C(C1=O)N(CC(=O)Nc1ccc(-c3cncc(C(F)(F)F)c3)nn1)CCC2] | 2-(6-methyl-5,7-dioxo-2,3,4,5,6,7-hexahydro-1H-pyrrolo[3,4-b]pyridin-1-yl)-N-(6-(5-(trifluoromethyl)pyridin-3-yl)pyridazin-3-yl)acetamide |
| 49 | 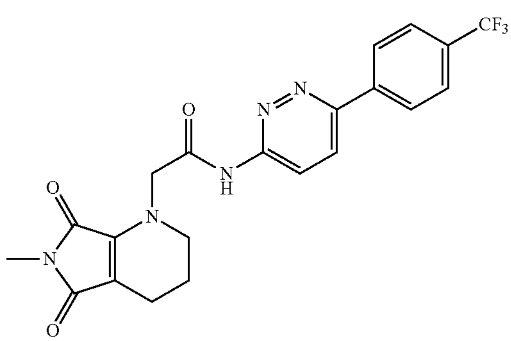 [SMILES: CN1C(=O)C2=C(C1=O)N(CC(=O)Nc1ccc(-c3ccc(C(F)(F)F)cc3)nn1)CCC2] | 2-(6-methyl-5,7-dioxo-2,3,4,5,6,7-hexahydro-1H-pyrrolo[3,4-b]pyridin-1-yl)-N-(6-(4-(trifluoromethyl)phenyl)pyridazin-3-yl)acetamide |
| 50 | 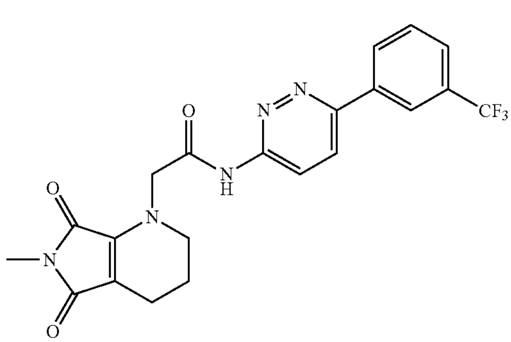 [SMILES: CN1C(=O)C2=C(C1=O)N(CC(=O)Nc1ccc(-c3cccc(C(F)(F)F)c3)nn1)CCC2] | 2-(6-methyl-5,7-dioxo-2,3,4,5,6,7-hexahydro-1H-pyrrolo[3,4-b]pyridin-1-yl)-N-(6-(3-(trifluoromethyl)phenyl)pyridazin-3-yl)acetamide |

| Cpd ID | Structure | IUPAC Name |
|---|---|---|
| 51 | 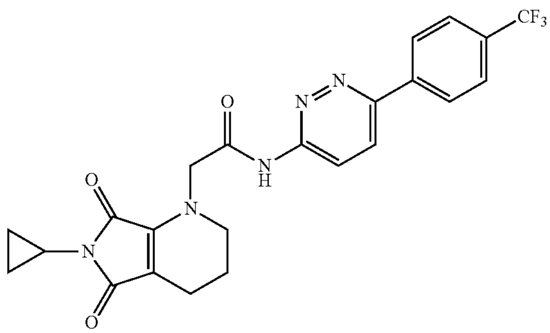 [SMILES: O=C(CN1CCCC2=C1C(=O)N(C1CC1)C2=O)Nc1ccc(-c2ccc(C(F)(F)F)cc2)nn1] | 2-(6-cyclopropyl-5,7-dioxo-2,3,4,5,6,7-hexahydro-1H-pyrrolo[3,4-b]pyridin-1-yl)-N-(6-(4-(trifluoromethyl)phenyl)pyridazin-3-yl)acetamide |
| 52 | 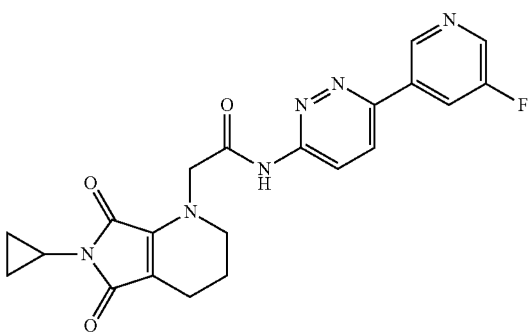 [SMILES: O=C(CN1CCCC2=C1C(=O)N(C1CC1)C2=O)Nc1ccc(-c2cncc(F)c2)nn1] | 2-(6-cyclopropyl-5,7-dioxo-2,3,4,5,6,7-hexahydro-1H-pyrrolo[3,4-b]pyridin-1-yl)-N-(6-(5-fluoropyridin-3-yl)pyridazin-3-yl)acetamide |
| 53 | 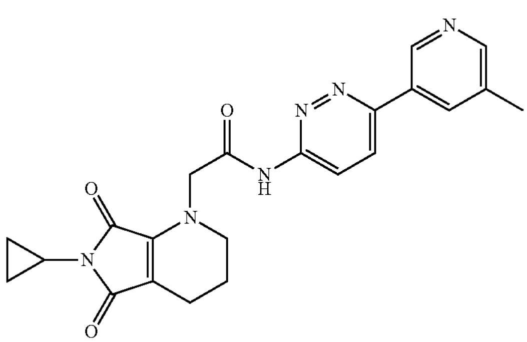 [SMILES: Cc1cncc(-c2ccc(NC(=O)CN3CCCC4=C3C(=O)N(C3CC3)C4=O)nn2)c1] | 2-(6-cyclopropyl-5,7-dioxo-2,3,4,5,6,7-hexahydro-1H-pyrrolo[3,4-b]pyridin-1-yl)-N-(6-(5-methylpyridin-3-yl)pyridazin-3-yl)acetamide |
| 54 | 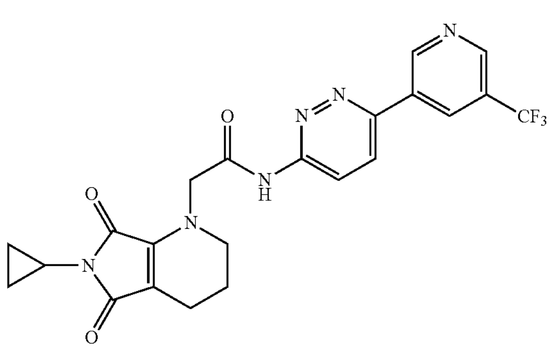 [SMILES: O=C(CN1CCCC2=C1C(=O)N(C1CC1)C2=O)Nc1ccc(-c2cncc(C(F)(F)F)c2)nn1] | 2-(6-cyclopropyl-5,7-dioxo-2,3,4,5,6,7-hexahydro-1H-pyrrolo[3,4-b]pyridin-1-yl)-N-(6-(5-(trifluoromethyl)pyridin-3-yl)pyridazin-3-yl)acetamide |

| Cpd ID | Structure | IUPAC Name |
|---|---|---|
| 55 | 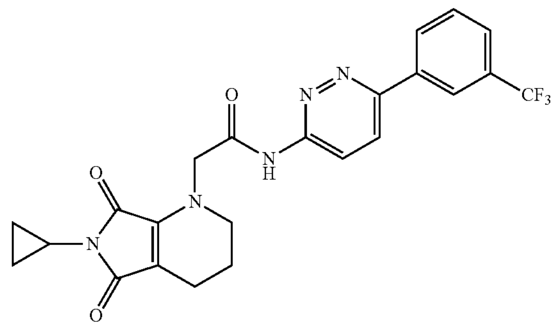 [SMILES: O=C(CN1CCCC2=C1C(=O)N(C1CC1)C2=O)Nc1ccc(-c2cccc(C(F)(F)F)c2)nn1] | 2-(6-cyclopropyl-5,7-dioxo-2,3,4,5,6,7-hexahydro-1H-pyrrolo[3,4-b]pyridin-1-yl)-N-(6-(3-(trifluoromethyl)phenyl)pyridazin-3-yl)acetamide |
| 56 | 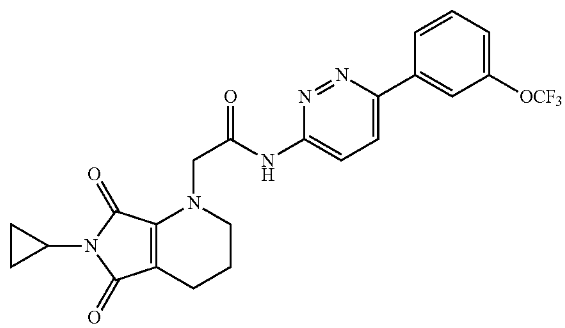 [SMILES: O=C(CN1CCCC2=C1C(=O)N(C1CC1)C2=O)Nc1ccc(-c2cccc(OC(F)(F)F)c2)nn1] | 2-(6-cyclopropyl-5,7-dioxo-2,3,4,5,6,7-hexahydro-1H-pyrrolo[3,4-b]pyridin-1-yl)-N-(6-(3-(trifluoromethoxy)phenyl)pyridazin-3-yl)acetamide |
| 57 | 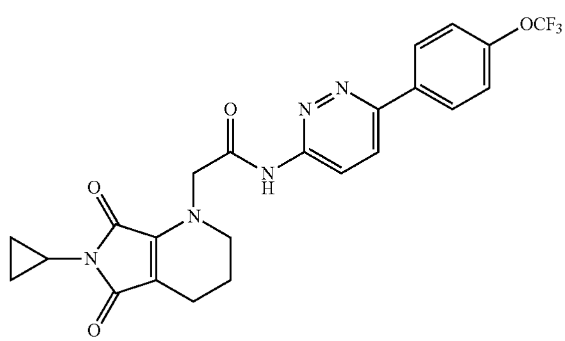 [SMILES: O=C(CN1CCCC2=C1C(=O)N(C1CC1)C2=O)Nc1ccc(-c2ccc(OC(F)(F)F)cc2)nn1] | 2-(6-cyclopropyl-5,7-dioxo-2,3,4,5,6,7-hexahydro-1H-pyrrolo[3,4-b]pyridin-1-yl)-N-(6-(4-(trifluoromethoxy)phenyl)pyridazin-3-yl)acetamide |
| 58 | 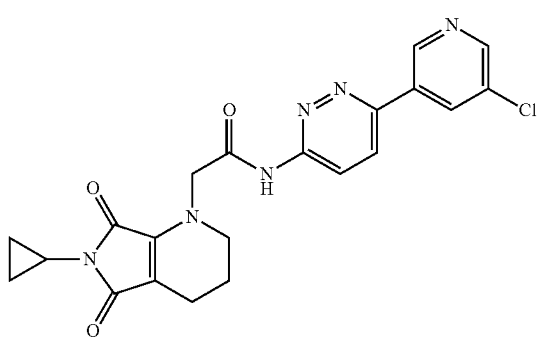 [SMILES: O=C(CN1CCCC2=C1C(=O)N(C1CC1)C2=O)Nc1ccc(-c2cncc(Cl)c2)nn1] | N-(6-(5-chloropyridin-3-yl)pyridazin-3-yl)-2-(6-cyclopropyl-5,7-dioxo-2,3,4,5,6,7-hexahydro-1H-pyrrolo[3,4-b]pyridin-1-yl)acetamide |

| Cpd ID | Structure | IUPAC Name |
| --- | --- | --- |
| 59 | 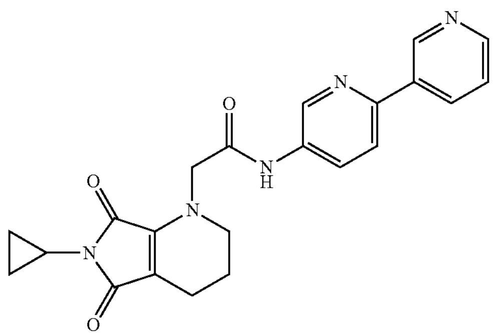 [SMILES: O=C(CN1CCCC2=C1C(=O)N(C1CC1)C2=O)Nc1ccc(-c2cccnc2)nc1] | N-(2,3'-bipyridin-5-yl)-2-(6-cyclopropyl-5,7-dioxo-2,3,4,5,6,7-hexahydro-1H-pyrrolo[3,4-b]pyridin-1-yl)acetamide |
| 60 | 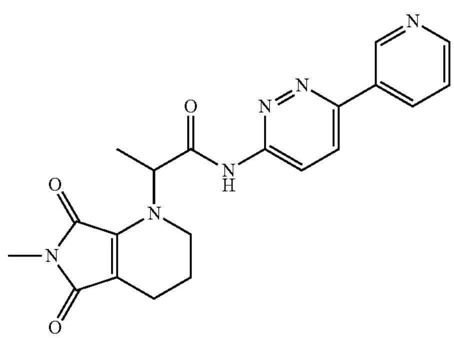 [SMILES: CC(C(=O)Nc1ccc(-c2cccnc2)nn1)N1CCCC2=C1C(=O)N(C)C2=O] | 2-(6-methyl-5,7-dioxo-2,3,4,5,6,7-hexahydro-1H-pyrrolo[3,4-b]pyridin-1-yl)-N-(6-(pyridin-3-yl)pyridazin-3-yl)propanamide |
| 61 | 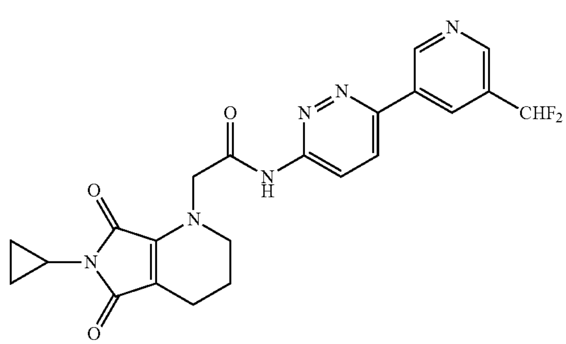 [SMILES: O=C(CN1CCCC2=C1C(=O)N(C1CC1)C2=O)Nc1ccc(-c2cncc(C(F)F)c2)nn1] | 2-(6-cyclopropyl-5,7-dioxo-2,3,4,5,6,7-hexahydro-1H-pyrrolo[3,4-b]pyridin-1-yl)-N-(6-(5-(difluoromethoxy)pyridin-3-yl)pyridazin-3-yl)acetamide |
| 62 | 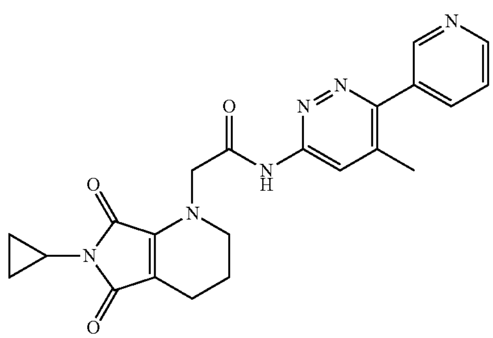 [SMILES: Cc1cc(NC(=O)CN2CCCC3=C2C(=O)N(C2CC2)C3=O)nnc1-c1cccnc1] | 2-(6-cyclopropyl-5,7-dioxo-2,3,4,5,6,7-hexahydro-1H-pyrrolo[3,4-b]pyridin-1-yl)-N-(5-methyl-6-(pyridin-3-yl)pyridazin-3-yl)acetamide |

| Cpd ID | Structure | IUPAC Name |
|---|---|---|
| 63 | 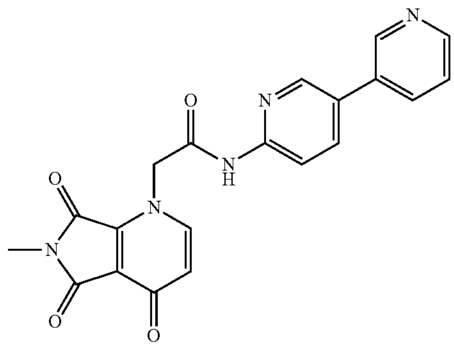 [SMILES: CN1C(=O)c2c(n(CC(=O)Nc3ccc(-c4cccnc4)cn3)ccc2=O)C1=O] | N-(3,3'-bipyridin-6-yl)-2-(6-methyl-4,5,7-trioxo-4,5,6,7-tetrahydro-1H-pyrrolo[3,4-b]pyridin-1-yl)acetamide |
| 64 | 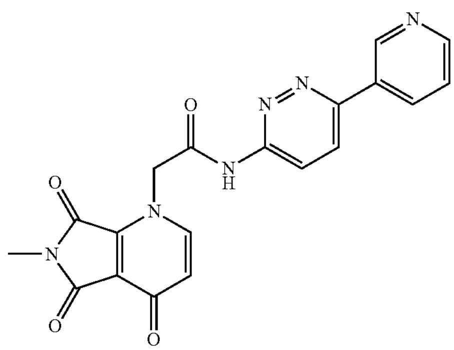 [SMILES: CN1C(=O)c2c(n(CC(=O)Nc3ccc(-c4cccnc4)nn3)ccc2=O)C1=O] | 2-(6-methyl-4,5,7-trioxo-4,5,6,7-tetrahydro-1H-pyrrolo[3,4-b]pyridin-1-yl)-N-(6-(pyridin-3-yl)pyridazin-3-yl)acetamide |
| 65 | 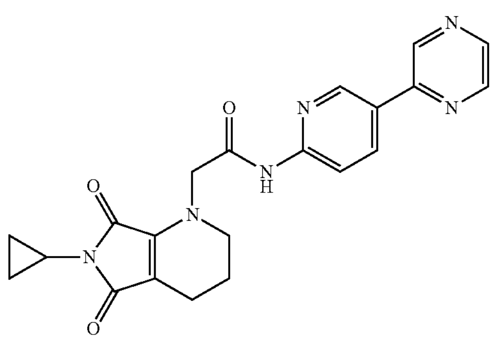 [SMILES: O=C(CN1CCCC2=C1C(=O)N(C1CC1)C2=O)Nc1ccc(-c2cnccn2)cn1] | 2-(6-cyclopropyl-5,7-dioxo-2,3,4,5,6,7-hexahydro-1H-pyrrolo[3,4-b]pyridin-1-yl)-N-(6-(pyrazin-2-yl)pyridin-3-yl)acetamide |
| 66 | 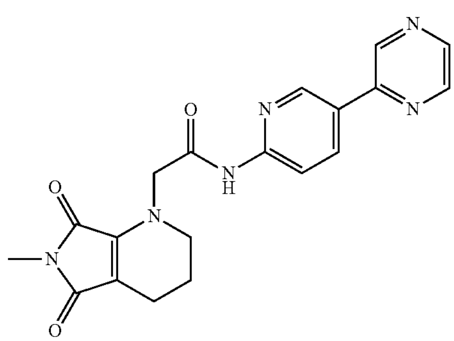 [SMILES: CN1C(=O)C2=C(C1=O)N(CC(=O)Nc1ccc(-c3cnccn3)cn1)CCC2] | 2-(6-methyl-5,7-dioxo-2,3,4,5,6,7-hexahydro-1H-pyrrolo[3,4-b]pyridin-1-yl)-N-(6-(pyrazin-2-yl)pyridin-3-yl)acetamide |

| Cpd ID | Structure | IUPAC Name |
|---|---|---|
| 67 | 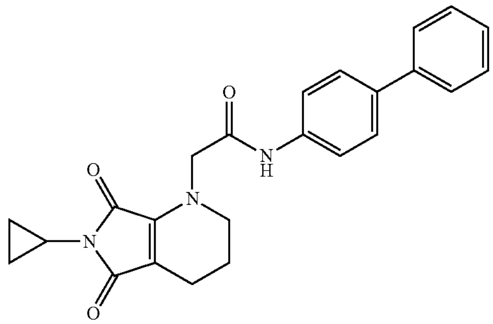 [SMILES: O=C(CN1CCCC2=C1C(=O)N(C1CC1)C2=O)Nc1ccc(-c2ccccc2)cc1] | N-([1,1'-biphenyl]-4-yl)-2-(6-cyclopropyl-5,7-dioxo-2,3,4,5,6,7-hexahydro-1H-pyrrolo[3,4-b]pyridin-1-yl)acetamide |
| 68 | 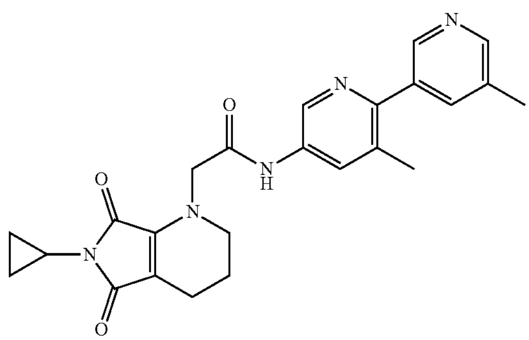 [SMILES: Cc1cncc(-c2ncc(NC(=O)CN3CCCC4=C3C(=O)N(C3CC3)C4=O)cc2C)c1] | 2-(6-cyclopropyl-5,7-dioxo-2,3,4,5,6,7-hexahydro-1H-pyrrolo[3,4-b]pyridin-1-yl)-N-(3,5'-dimethyl-[2,3'-bipyridin]-5-yl)acetamide |
| 69 | 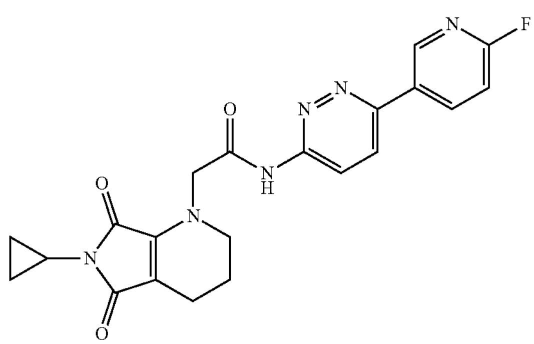 [SMILES: O=C(CN1CCCC2=C1C(=O)N(C1CC1)C2=O)Nc1ccc(-c2ccc(F)nc2)nn1] | 2-(6-cyclopropyl-5,7-dioxo-2,3,4,5,6,7-hexahydro-1H-pyrrolo[3,4-b]pyridin-1-yl)-N-(6-(6-fluoropyridin-3-yl)pyridazin-3-yl)acetamide |
| 70 | 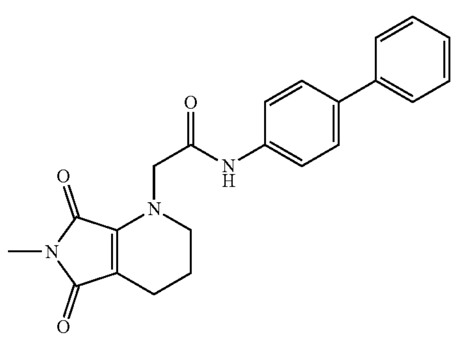 [SMILES: CN1C(=O)C2=C(C1=O)N(CC(=O)Nc1ccc(-c3ccccc3)cc1)CCC2] | N-([1,1'-biphenyl]-4-yl)-2-(6-methyl-5,7-dioxo-2,3,4,5,6,7-hexahydro-1H-pyrrolo[3,4-b]pyridin-1-yl)acetamide |

| Cpd ID | Structure | IUPAC Name |
|---|---|---|
| 71 | 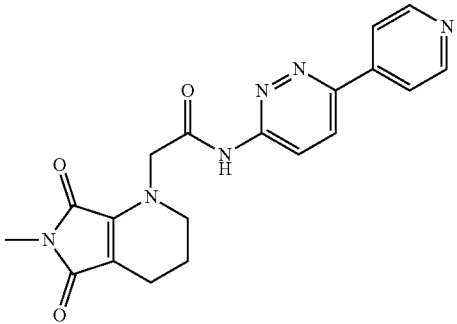 [SMILES: CN1C(=O)C2=C(C1=O)N(CC(=O)Nc1ccc(-c3ccncc3)nn1)CCC2] | 2-(6-methyl-5,7-dioxo-2,3,4,5,6,7-hexahydro-1H-pyrrolo[3,4-b]pyridin-1-yl)-N-(6-(pyridin-4-yl)pyridazin-3-yl)acetamide |
| 72 | 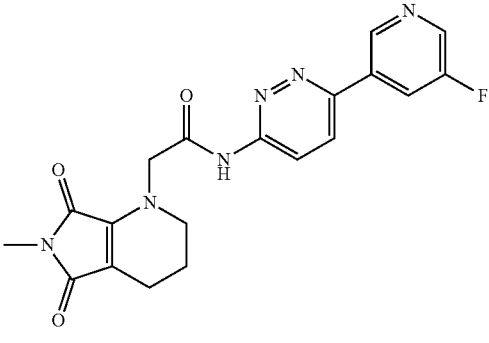 | N-(6-(5-fluoropyridin-3-yl)pyridazin-3-yl)-2-(6-methyl-5,7-dioxo-2,3,4,5,6,7-hexahydro-1H-pyrrolo[3,4-b]pyridin-1-yl)acetamide |
| 73 | 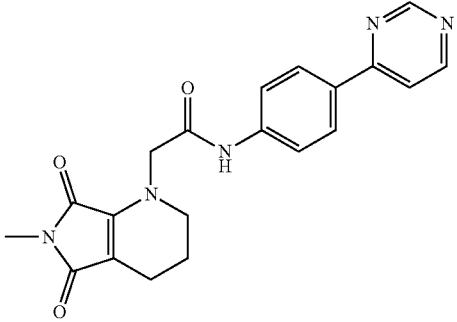 [SMILES: CN1C(=O)C2=C(C1=O)N(CC(=O)Nc1ccc(-c3ccncn3)cc1)CCC2] | 2-(6-methyl-5,7-dioxo-2,3,4,5,6,7-hexahydro-1H-pyrrolo[3,4-b]pyridin-1-yl)-N-(4-(pyrimidin-4-yl)phenyl)acetamide |
| 74 | 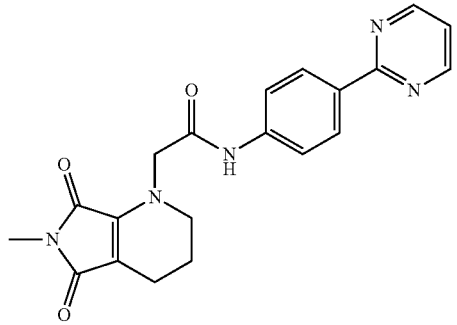 [SMILES: CN1C(=O)C2=C(C1=O)N(CC(=O)Nc1ccc(-c3ncccn3)cc1)CCC2] | 2-(6-methyl-5,7-dioxo-2,3,4,5,6,7-hexahydro-1H-pyrrolo[3,4-b]pyridin-1-yl)-N-(4-(pyrimidin-2-yl)phenyl)acetamide |

| Cpd ID | Structure | IUPAC Name |
|---|---|---|
| 75 | 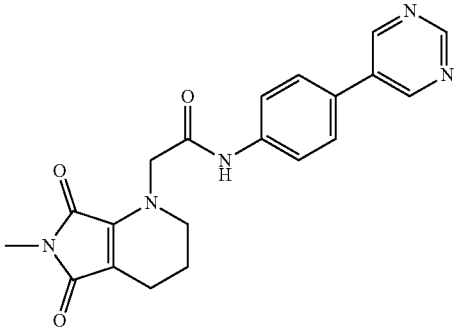 [SMILES: CN1C(=O)C2=C(C1=O)N(CC(=O)Nc1ccc(-c3cncnc3)cc1)CCC2] | 2-(6-methyl-5,7-dioxo-2,3,4,5,6,7-hexahydro-1H-pyrrolo[3,4-b]pyridin-1-yl)-N-(4-(pyrimidin-5-yl)phenyl)acetamide |
| 76 | 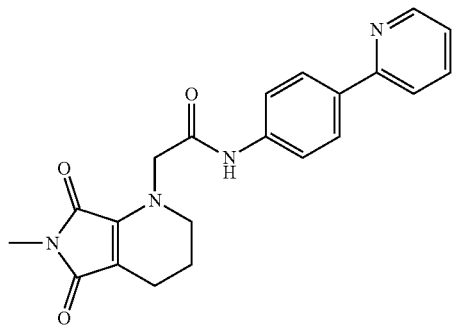 [SMILES: CN1C(=O)C2=C(C1=O)N(CC(=O)Nc1ccc(-c3ccccn3)cc1)CCC2] | 2-(6-methyl-5,7-dioxo-2,3,4,5,6,7-hexahydro-1H-pyrrolo[3,4-b]pyridin-1-yl)-N-(4-(pyridin-2-yl)phenyl)acetamide |
| 77 | 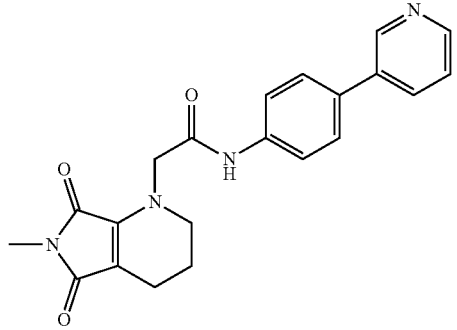 [SMILES: CN1C(=O)C2=C(C1=O)N(CC(=O)Nc1ccc(-c3cccnc3)cc1)CCC2] | 2-(6-methyl-5,7-dioxo-2,3,4,5,6,7-hexahydro-1H-pyrrolo[3,4-b]pyridin-1-yl)-N-(4-(pyridin-3-yl)phenyl)acetamide |
| 78 | 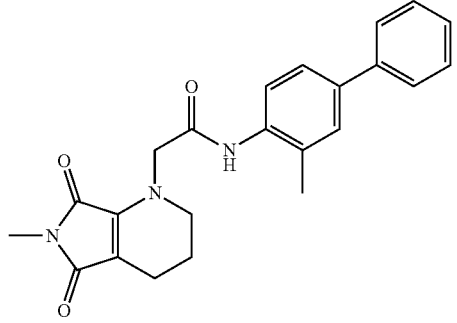 [SMILES: Cc1cc(-c2ccccc2)ccc1NC(=O)CN1CCCC2=C1C(=O)N(C)C2=O] | 2-(6-methyl-5,7-dioxo-2,3,4,5,6,7-hexahydro-1H-pyrrolo[3,4-b]pyridin-1-yl)-N-(3-methyl-[1,1'-biphenyl]-4-yl)acetamide |

| Cpd ID | Structure | IUPAC Name |
|---|---|---|
| 79 | 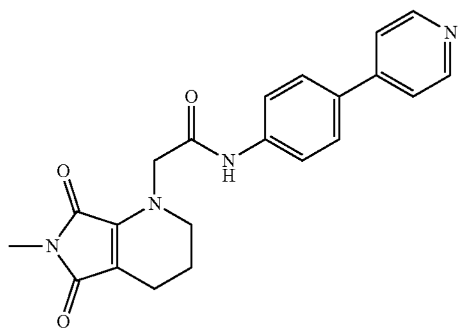 [SMILES: CN1C(=O)C2=C(C1=O)N(CC(=O)Nc1ccc(-c3ccncc3)cc1)CCC2] | 2-(6-methyl-5,7-dioxo-2,3,4,5,6,7-hexahydro-1H-pyrrolo[3,4-b]pyridin-1-yl)-N-(4-(pyridin-4-yl)phenyl)acetamide |
| 80 | 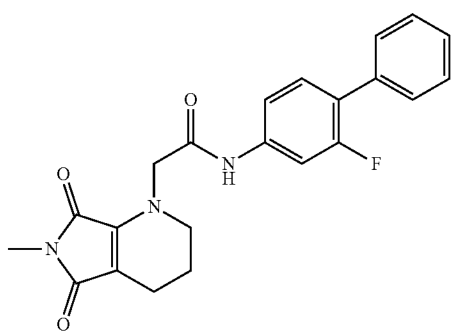 [SMILES: CN1C(=O)C2=C(C1=O)N(CC(=O)Nc1ccc(-c3ccccc3)c(F)c1)CCC2] | N-(2-fluoro-[1,1'-biphenyl]-4-yl)-2-(6-methyl-5,7-dioxo-2,3,4,5,6,7-hexahydro-1H-pyrrolo[3,4-b]pyridin-1-yl)acetamide |
| 81 | 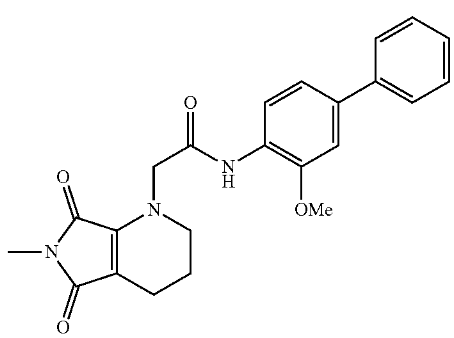 [SMILES: COc1cc(-c2ccccc2)ccc1NC(=O)CN1CCCC2=C1C(=O)N(C)C2=O] | N-(3-methoxy-[1,1'-biphenyl]-4-yl)-2-(6-methyl-5,7-dioxo-2,3,4,5,6,7-hexahydro-1H-pyrrolo[3,4-b]pyridin-1-yl)acetamide |
| 82 | 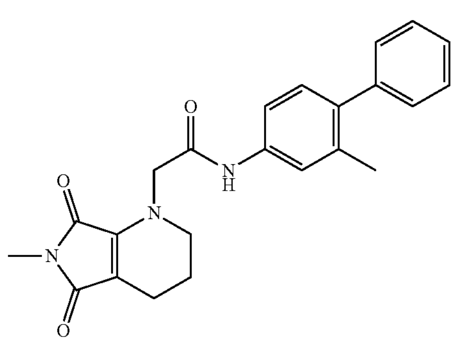 [SMILES: Cc1cc(NC(=O)CN2CCCC3=C2C(=O)N(C)C3=O)ccc1-c1ccccc1] | 2-(6-methyl-5,7-dioxo-2,3,4,5,6,7-hexahydro-1H-pyrrolo[3,4-b]pyridin-1-yl)-N-(2-methyl-[1,1'-biphenyl]-4-yl)acetamide |

| Cpd ID | Structure | IUPAC Name |
|---|---|---|
| 83 | 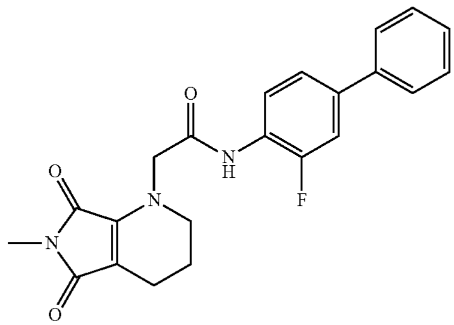 [SMILES: CN1C(=O)C2=C(C1=O)N(CC(=O)Nc1ccc(-c3ccccc3)cc1F)CCC2] | N-(3-fluorobiphenyl-4-yl)-2-(6-methyl-5,7-dioxo-2,3,4,5,6,7-hexahydro-1H-pyrrolo[3,4-b]pyridin-1-yl)acetamide |
| 84 | 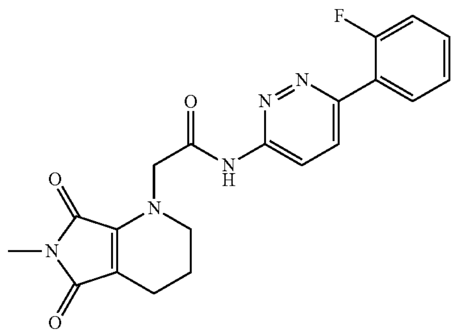 [SMILES: CN1C(=O)C2=C(C1=O)N(CC(=O)Nc1ccc(-c3ccccc3F)nn1)CCC2] | N-(6-(2-fluorophenyl)pyridazin-3-yl)-2-(6-methyl-5,7-dioxo-2,3,4,5,6,7-hexahydro-1H-pyrrolo[3,4-b]pyridin-1-yl)acetamide |
| 85 | 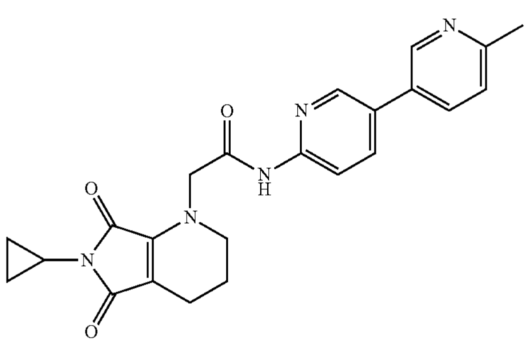 [SMILES: Cc1ccc(-c2ccc(NC(=O)CN3CCCC4=C3C(=O)N(C3CC3)C4=O)nc2)cn1] | 2-(6-cyclopropyl-5,7-dioxo-2,3,4,5,6,7-hexahydro-1H-pyrrolo[3,4-b]pyridin-1-yl)-N-(6'-methyl-[3,3'-bipyridin]-6-yl)acetamide |
| 86 | 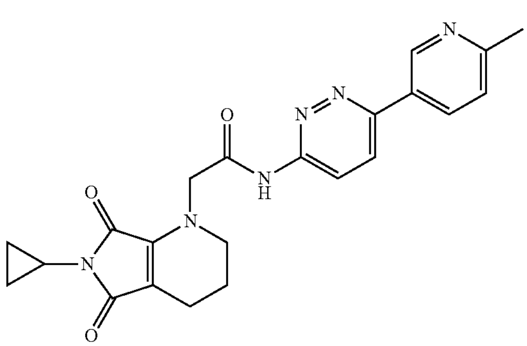 [SMILES: Cc1ccc(-c2ccc(NC(=O)CN3CCCC4=C3C(=O)N(C3CC3)C4=O)nn2)cn1] | 2-(6-cyclopropyl-5,7-dioxo-2,3,4,5,6,7-hexahydro-1H-pyrrolo[3,4-b]pyridin-1-yl)-N-(6-(6-methylpyridin-3-yl)pyridazin-3-yl)acetamide |

| Cpd ID | Structure | IUPAC Name |
|---|---|---|
| 87 | 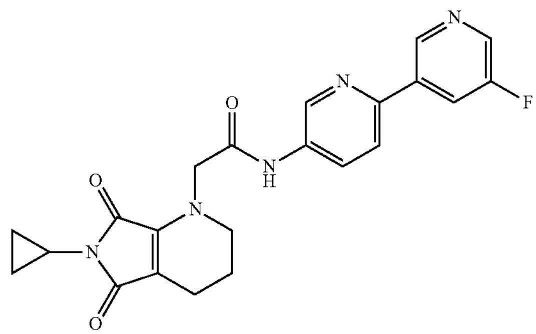 [SMILES: O=C(CN1CCCC2=C1C(=O)N(C1CC1)C2=O)Nc1ccc(-c2cncc(F)c2)nc1] | 2-(6-cyclopropyl-5,7-dioxo-2,3,4,5,6,7-hexahydro-1H-pyrrolo[3,4-b]pyridin-1-yl)-N-(5'-fluoro-[2,3'-bipyridin]-5-yl)acetamide |
| 88 | 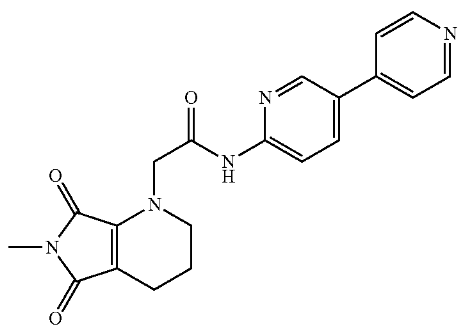 | N-([3,4'-bipyridin]-6-yl)-2-(6-methyl-5,7-dioxo-2,3,4,5,6,7-hexahydro-1H-pyrrolo[3,4-b]pyridin-1-yl)acetamide |
| 89 | 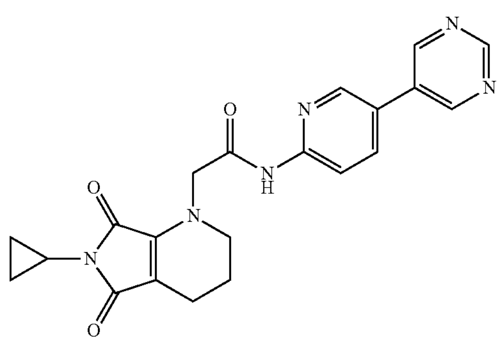 [SMILES: O=C(CN1CCCC2=C1C(=O)N(C1CC1)C2=O)Nc1ccc(-c2cncnc2)cn1] | 2-(6-cyclopropyl-5,7-dioxo-2,3,4,5,6,7-hexahydro-1H-pyrrolo[3,4-b]pyridin-1-yl)-N-(5-(pyrimidin-5-yl)pyridin-2-yl)acetamide |
| 90 | 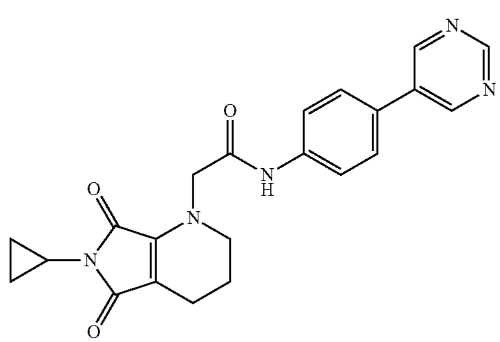 [SMILES: O=C(CN1CCCC2=C1C(=O)N(C1CC1)C2=O)Nc1ccc(-c2cncnc2)cc1] | 2-(6-cyclopropyl-5,7-dioxo-2,3,4,5,6,7-hexahydro-1H-pyrrolo[3,4-b]pyridin-1-yl)-N-(4-(pyrimidin-5-yl)phenyl)acetamide |

| Cpd ID | Structure | IUPAC Name |
|---|---|---|
| 91 | 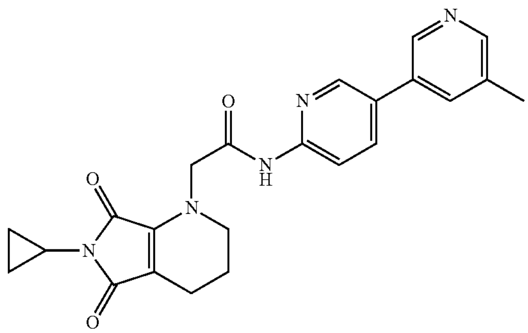 [SMILES: Cc1cncc(-c2ccc(NC(=O)CN3CCCC4=C3C(=O)N(C3CC3)C4=O)nc2)c1] | 2-(6-cyclopropyl-5,7-dioxo-2,3,4,5,6,7-hexahydro-1H-pyrrolo[3,4-b]pyridin-1-yl)-N-(5'-methyl-2,3'-bipyridin-5-yl)acetamide |
| 92 | 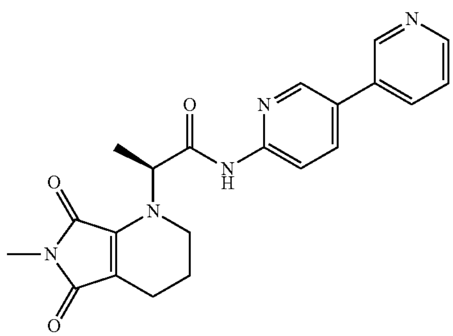 [SMILES: C[C@@H](C(=O)Nc1ccc(-c2cccnc2)cn1)N1CCCC2=C1C(=O)N(C)C2=O] | (S)-N-([3,3'-bipyridin]-6-yl)-2-(6-methyl-5,7-dioxo-2,3,4,5,6,7-hexahydro-1H-pyrrolo[3,4-b]pyridin-1-yl)propanamide |
| 93 | 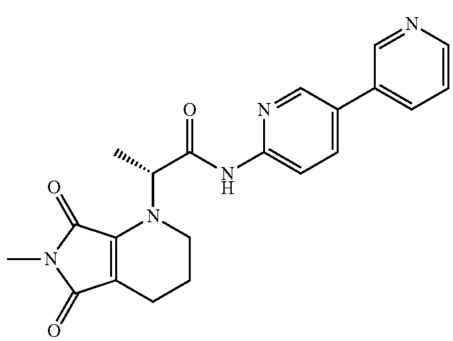 [SMILES: C[C@H](C(=O)Nc1ccc(-c2cccnc2)cn1)N1CCCC2=C1C(=O)N(C)C2=O] | (R)-N-([3,3'-bipyridin]-6-yl)-2-(6-methyl-5,7-dioxo-2,3,4,5,6,7-hexahydro-1H-pyrrolo[3,4-b]pyridin-1-yl)propanamide |
| 94 | 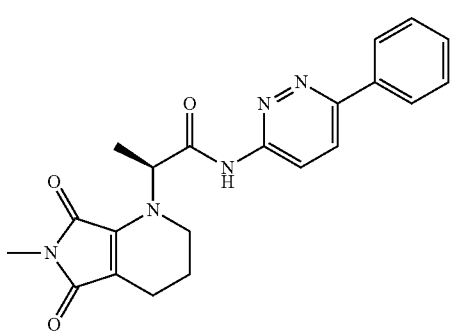 [SMILES: C[C@@H](C(=O)Nc1ccc(-c2ccccc2)nn1)N1CCCC2=C1C(=O)N(C)C2=O] | (S)-2-(6-methyl-5,7-dioxo-2,3,4,5,6,7-hexahydro-1H-pyrrolo[3,4-b]pyridin-1-yl)-N-(6-phenylpyridazin-3-yl)propanamide |

| Cpd ID | Structure | IUPAC Name |
|---|---|---|
| 95 | 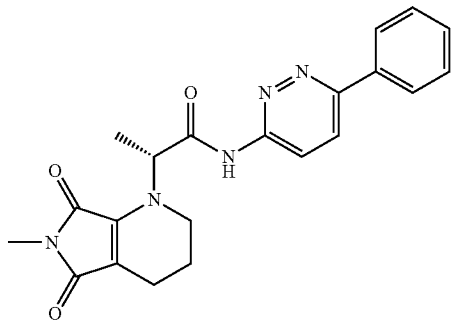 [SMILES: C[C@H](C(=O)Nc1ccc(-c2ccccc2)nn1)N1CCCC2=C1C(=O)N(C)C2=O] | (R)-2-(6-methyl-5,7-dioxo-2,3,4,5,6,7-hexahydro-1H-pyrrolo[3,4-b]pyridin-1-yl)-N-(6-phenylpyridazin-3-yl)propanamide |
| 96 | 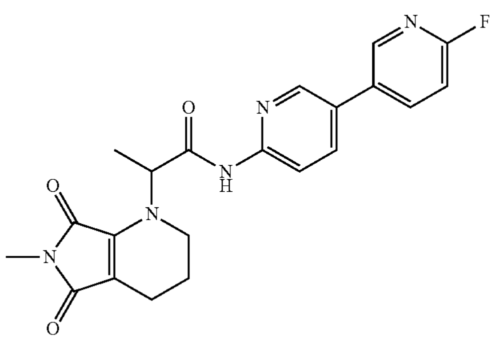 [SMILES: CC(C(=O)Nc1ccc(-c2ccc(F)nc2)cn1)N1CCCC2=C1C(=O)N(C)C2=O] | N-(6'-fluoro-3,3'-bipyridin-6-yl)-2-(6-methyl-5,7-dioxo-2,3,4,5,6,7-hexahydro-1H-pyrrolo[3,4-b]pyridin-1-yl)propanamide |
| 97 | 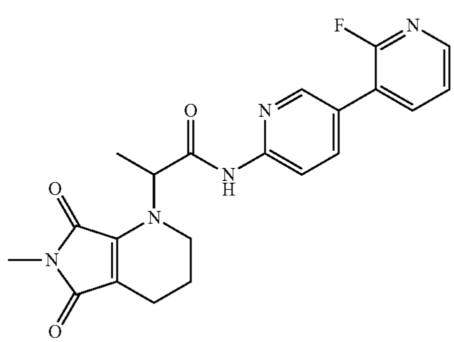 [SMILES: CC(C(=O)Nc1ccc(-c2cccnc2F)cn1)N1CCCC2=C1C(=O)N(C)C2=O] | N-(2'-fluoro-3,3'-bipyridin-6-yl)-2-(6-methyl-5,7-dioxo-2,3,4,5,6,7-hexahydro-1H-pyrrolo[3,4-b]pyridin-1-yl)propanamide |
| 99 | 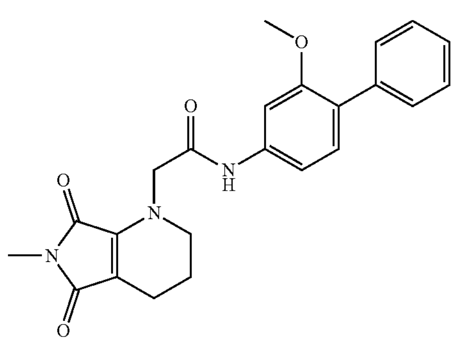 [SMILES: COc1cc(NC(=O)CN2CCCC3=C2C(=O)N(C)C3=O)ccc1-c1ccccc1] | N-(2-methoxy-[1,1'-biphenyl]-4-yl)-2-(6-methyl-5,7-dioxo-2,3,4,5,6,7-hexahydro-1H-pyrrolo[3,4-b]pyridin-1-yl)acetamide |

| Cpd ID | Structure | IUPAC Name |
|---|---|---|
| 100 | 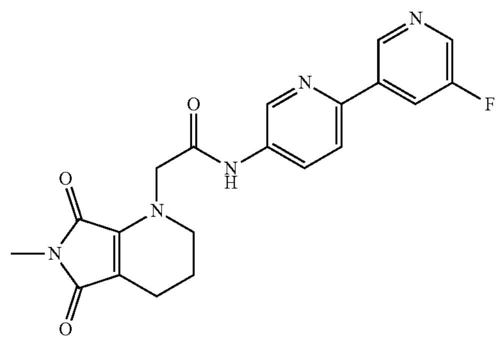 [SMILES: CN1C(=O)C2=C(C1=O)N(CC(=O)Nc1ccc(-c3cncc(F)c3)nc1)CCC2] | N-(5'-fluoro-[2,3'-bipyridin]-5-yl)-2-(6-methyl-5,7-dioxo-2,3,4,5,6,7-hexahydro-1H-pyrrolo[3,4-b]pyridin-1-yl)acetamide |
| 101 | 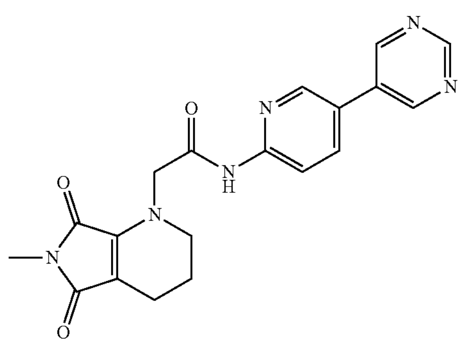 [SMILES: CN1C(=O)C2=C(C1=O)N(CC(=O)Nc1ccc(-c3cncnc3)cn1)CCC2] | 2-(6-methyl-5,7-dioxo-2,3,4,5,6,7-hexahydro-1H-pyrrolo[3,4-b]pyridin-1-yl)-N-(5-(pyrimidin-5-yl)pyridin-2-yl)acetamide |
| 102 | 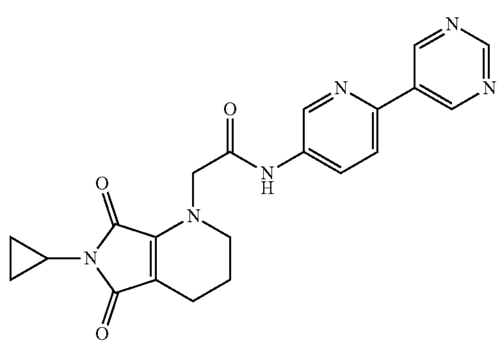 [SMILES: O=C(CN1CCCC2=C1C(=O)N(C1CC1)C2=O)Nc1ccc(-c2cncnc2)nc1] | 2-(6-cyclopropyl-5,7-dioxo-2,3,4,5,6,7-hexahydro-1H-pyrrolo[3,4-b]pyridin-1-yl)-N-(6-(pyrimidin-5-yl)pyridin-3-yl)acetamide |
| 103 | 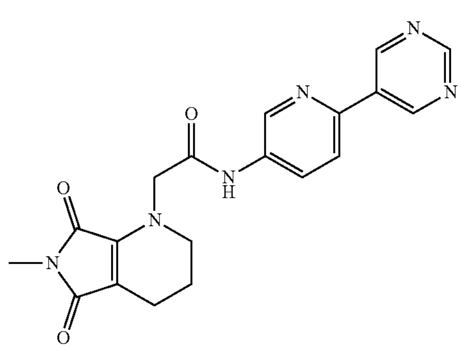 [SMILES: CN1C(=O)C2=C(C1=O)N(CC(=O)Nc1ccc(-c3cncnc3)nc1)CCC2] | 2-(6-methyl-5,7-dioxo-2,3,4,5,6,7-hexahydro-1H-pyrrolo[3,4-b]pyridin-1-yl)-N-(6-(pyrimidin-5-yl)pyridin-3-yl)acetamide |

| Cpd ID | Structure | IUPAC Name |
|---|---|---|
| 104 | 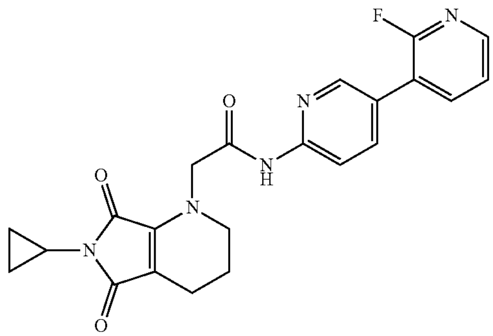 [SMILES: O=C(CN1CCCC2=C1C(=O)N(C1CC1)C2=O)Nc1ccc(-c2cccnc2F)cn1] | 2-(6-cyclopropyl-5,7-dioxo-2,3,4,5,6,7-hexahydro-1H-pyrrolo[3,4-b]pyridin-1-yl)-N-(2'-fluoro-[3,3'-bipyridin]-6-yl)acetamide |
| 105 | 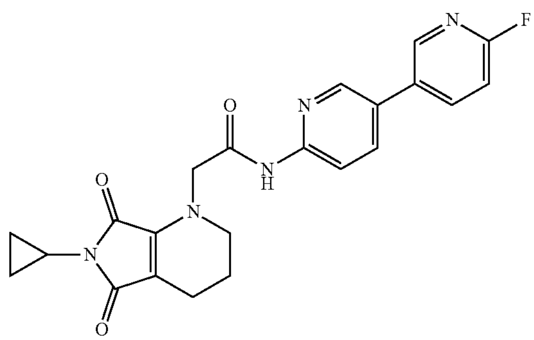 [SMILES: O=C(CN1CCCC2=C1C(=O)N(C1CC1)C2=O)Nc1ccc(-c2ccc(F)nc2)cn1] | 2-(6-cyclopropyl-5,7-dioxo-2,3,4,5,6,7-hexahydro-1H-pyrrolo[3,4-b]pyridin-1-yl)-N-(6'-fluoro-[3,3'-bipyridin]-6-yl)acetamide |
| 106 | 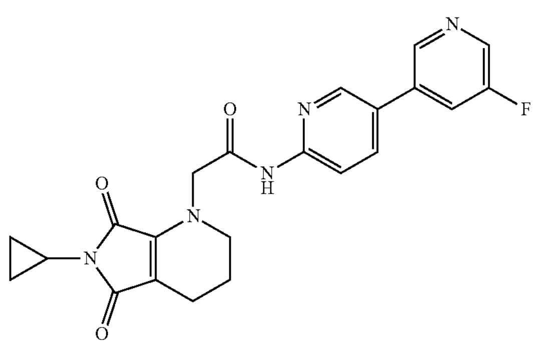 [SMILES: O=C(CN1CCCC2=C1C(=O)N(C1CC1)C2=O)Nc1ccc(-c2cncc(F)c2)cn1] | 2-(6-cyclopropyl-5,7-dioxo-2,3,4,5,6,7-hexahydro-1H-pyrrolo[3,4-b]pyridin-1-yl)-N-(5'-fluoro-[3,3'-bipyridin]-6-yl)acetamide |
| 107 | 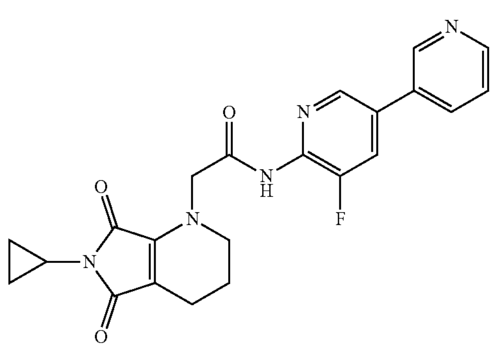 [SMILES: O=C(CN1CCCC2=C1C(=O)N(C1CC1)C2=O)Nc1ncc(-c2cccnc2)cc1F] | 2-(6-cyclopropyl-5,7-dioxo-2,3,4,5,6,7-hexahydro-1H-pyrrolo[3,4-b]pyridin-1-yl)-N-(5-fluoro-[3,3'-bipyridin]-6-yl)acetamide |

| Cpd ID | Structure | IUPAC Name |
|---|---|---|
| 108 | 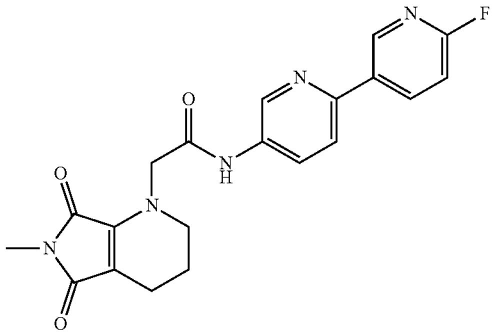 [SMILES: CN1C(=O)C2=C(C1=O)N(CC(=O)Nc1ccc(-c3ccc(F)nc3)nc1)CCC2] | N-(6'-fluoro-[2,3'-bipyridin]-5-yl)-2-(6-methyl-5,7-dioxo-2,3,4,5,6,7-hexahydro-1H-pyrrolo[3,4-b]pyridin-1-yl)acetamide |
| 109 | 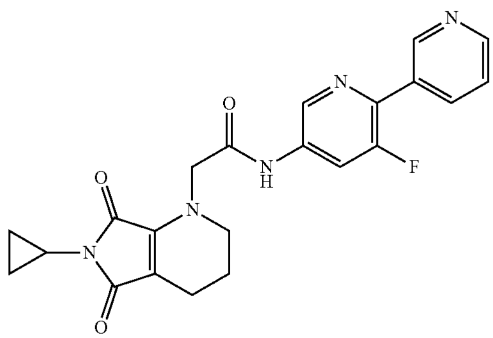 [SMILES: O=C(CN1CCCC2=C1C(=O)N(C1CC1)C2=O)Nc1cnc(-c2cccnc2)c(F)c1] | 2-(6-cyclopropyl-5,7-dioxo-2,3,4,5,6,7-hexahydro-1H-pyrrolo[3,4-b]pyridin-1-yl)-N-(4-fluoro-[3,3'-bipyridin]-6-yl)acetamide |
| 110 | 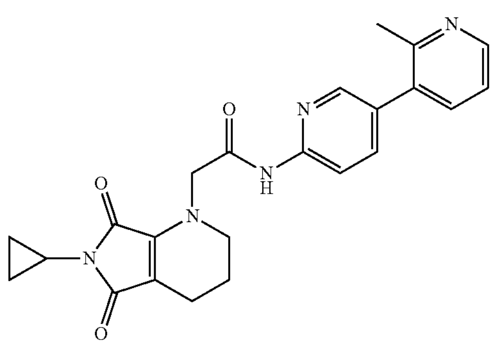 [SMILES: Cc1ncccc1-c1ccc(NC(=O)CN2CCCC3=C2C(=O)N(C2CC2)C3=O)nc1] | 2-(6-cyclopropyl-5,7-dioxo-2,3,4,5,6,7-hexahydro-1H-pyrrolo[3,4-b]pyridin-1-yl)-N-(2'-methyl-[3,3'-bipyridin]-6-yl)acetamide |
| 111 | 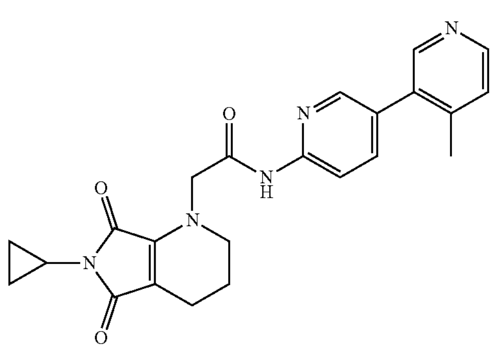 [SMILES: Cc1ccncc1-c1ccc(NC(=O)CN2CCCC3=C2C(=O)N(C2CC2)C3=O)nc1] | 2-(6-cyclopropyl-5,7-dioxo-2,3,4,5,6,7-hexahydro-1H-pyrrolo[3,4-b]pyridin-1-yl)-N-(4'-methyl-[3,3'-bipyridin]-6-yl)acetamide |

| Cpd ID | Structure | IUPAC Name |
|---|---|---|
| 112 | 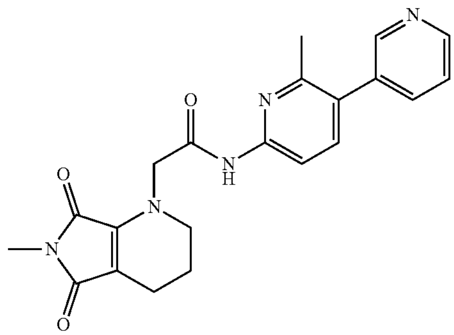 [SMILES: Cc1nc(NC(=O)CN2CCCC3=C2C(=O)N(C)C3=O)ccc1-c1cccnc1] | N-(6'-fluoro-[2,3'-bipyridin]-5-yl)-2-(6-methyl-5,7-dioxo-2,3,4,5,6,7-hexahydro-1H-pyrrolo[3,4-b]pyridin-1-yl)acetamide |
| 113 | 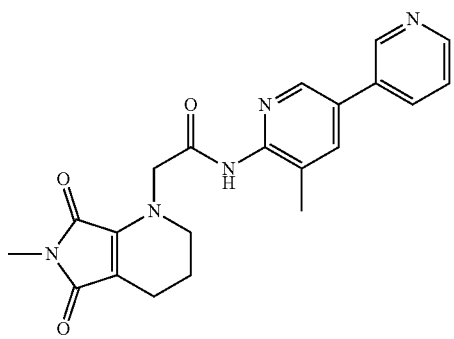 [SMILES: Cc1cc(-c2cccnc2)cnc1NC(=O)CN1CCCC2=C1C(=O)N(C)C2=O] | 2-(6-methyl-5,7-dioxo-2,3,4,5,6,7-hexahydro-1H-pyrrolo[3,4-b]pyridin-1-yl)-N-(5-methyl-[3,3'-bipyridin]-6-yl)acetamide |
| 114 | 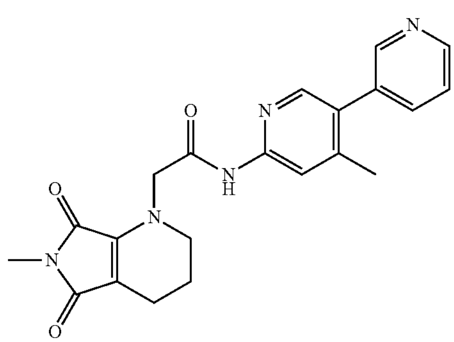 [SMILES: Cc1cc(NC(=O)CN2CCCC3=C2C(=O)N(C)C3=O)ncc1-c1cccnc1] | 2-(6-methyl-5,7-dioxo-2,3,4,5,6,7-hexahydro-1H-pyrrolo[3,4-b]pyridin-1-yl)-N-(4-methyl-[3,3'-bipyridin]-6-yl)acetamide |
| 115 | 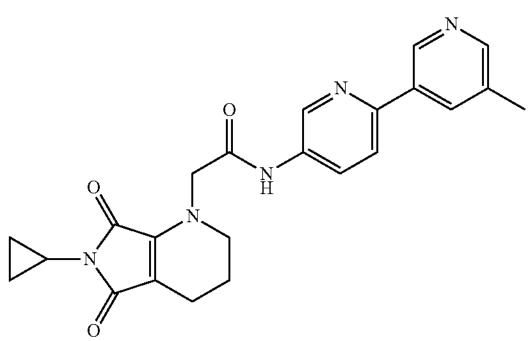 [SMILES: Cc1cncc(-c2ccc(NC(=O)CN3CCCC4=C3C(=O)N(C3CC3)C4=O)cn2)c1] | 2-(6-cyclopropyl-5,7-dioxo-2,3,4,5,6,7-hexahydro-1H-pyrrolo[3,4-b]pyridin-1-yl)-N-(5'-methyl-[3,3'-bipyridin]-6-yl)acetamide |

| Cpd ID | Structure | IUPAC Name |
|---|---|---|
| 116 | 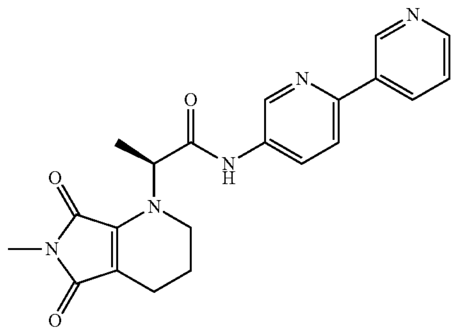 [SMILES: C[C@@H](C(=O)Nc1ccc(-c2cccnc2)nc1)N1CCCC2=C1C(=O)N(C)C2=O] | (S)-N-([2,3'-bipyridin]-5-yl)-2-(6-methyl-5,7-dioxo-2,3,4,5,6,7-hexahydro-1H-pyrrolo[3,4-b]pyridin-1-yl)propanamide |
| 117 | 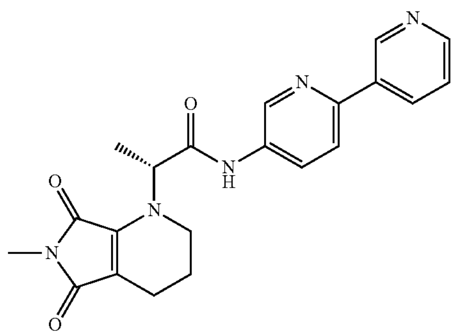 [SMILES: C[C@H](C(=O)Nc1ccc(-c2cccnc2)nc1)N1CCCC2=C1C(=O)N(C)C2=O] | (R)-N-([2,3'-bipyridin]-5-yl)-2-(6-methyl-5,7-dioxo-2,3,4,5,6,7-hexahydro-1H-pyrrolo[3,4-b]pyridin-1-yl)propanamide |
| 118 | 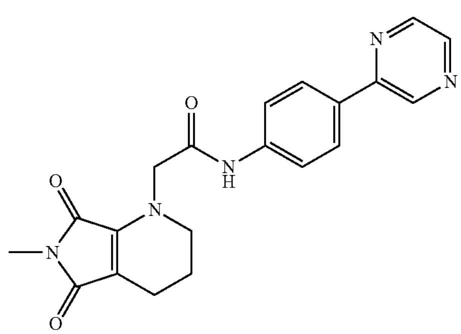 [SMILES: CN1C(=O)C2=C(C1=O)N(CC(=O)Nc1ccc(-c3cnccn3)cc1)CCC2] | 2-(6-methyl-5,7-dioxo-2,3,4,5,6,7-hexahydro-1H-pyrrolo[3,4-b]pyridin-1-yl)-N-(4-(pyrazin-2-yl)phenyl)acetamide |
| 119 | 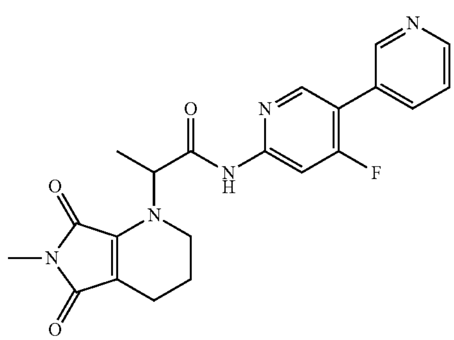 [SMILES: CC(C(=O)Nc1cc(F)c(-c2cccnc2)cn1)N1CCCC2=C1C(=O)N(C)C2=O] | N-(4-fluoro-3,3'-bipyridin-6-yl)-2-(6-methyl-5,7-dioxo-2,3,4,5,6,7-hexahydro-1H-pyrrolo[3,4-b]pyridin-1-yl)propanamide |

| Cpd ID | Structure | IUPAC Name |
| --- | --- | --- |
| 120 | 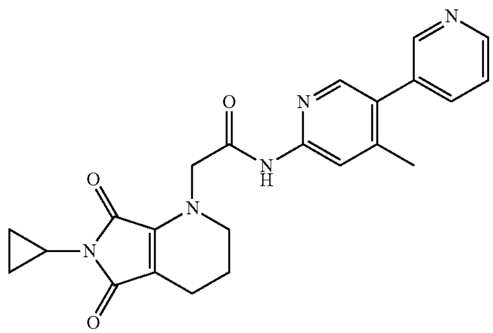 [SMILES: Cc1cc(NC(=O)CN2CCCC3=C2C(=O)N(C2CC2)C3=O)ncc1-c1cccnc1] | 2-(6-cyclopropyl-5,7-dioxo-2,3,4,5,6,7-hexahydro-1H-pyrrolo[3,4-b]pyridin-1-yl)-N-(4-methyl-[3,3'-bipyridin]-6-yl)acetamide |
| 121 | 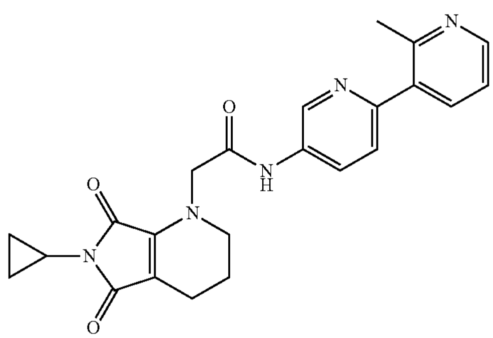 [SMILES: Cc1ncccc1-c1ccc(NC(=O)CN2CCCC3=C2C(=O)N(C2CC2)C3=O)cn1] | 2-(6-cyclopropyl-5,7-dioxo-2,3,4,5,6,7-hexahydro-1H-pyrrolo[3,4-b]pyridin-1-yl)-N-(2'-methyl-2,3'-bipyridin-5-yl)acetamide |
| 122 | 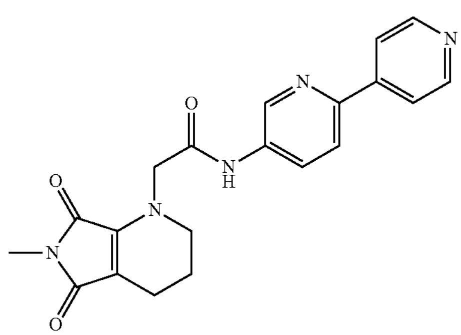 [SMILES: CN1C(=O)C2=C(C1=O)N(CC(=O)Nc1ccc(-c3ccncc3)nc1)CCC2] | N-(2,4'-bipyridin-5-yl)-2-(6-methyl-5,7-dioxo-2,3,4,5,6,7-hexahydro-1H-pyrrolo[3,4-b]pyridin-1-yl)acetamide |
| 123 | 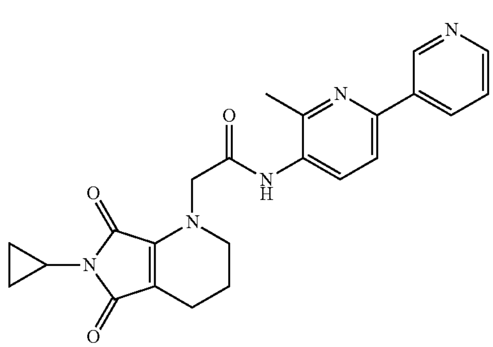 [SMILES: Cc1nc(-c2cccnc2)ccc1NC(=O)CN1CCCC2=C1C(=O)N(C1CC1)C2=O] | 2-(6-cyclopropyl-5,7-dioxo-2,3,4,5,6,7-hexahydro-1H-pyrrolo[3,4-b]pyridin-1-yl)-N-(6-methyl-2,3'-bipyridin-5-yl)acetamide |

| Cpd ID | Structure | IUPAC Name |
|---|---|---|
| 124 | 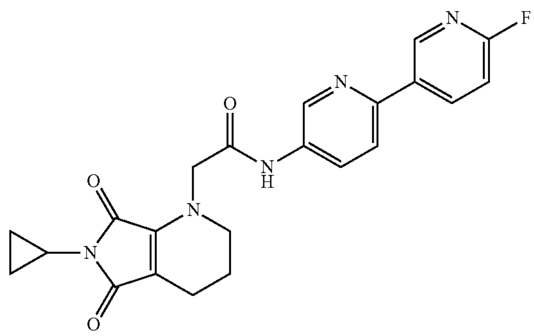 [SMILES: O=C(CN1CCCC2=C1C(=O)N(C1CC1)C2=O)Nc1ccc(-c2ccc(F)nc2)nc1] | 2-(6-cyclopropyl-5,7-dioxo-2,3,4,5,6,7-hexahydro-1H-pyrrolo[3,4-b]pyridin-1-yl)-N-(6'-fluoro-[2,3'-bipyridin]-5-yl)acetamide |
| 125 | 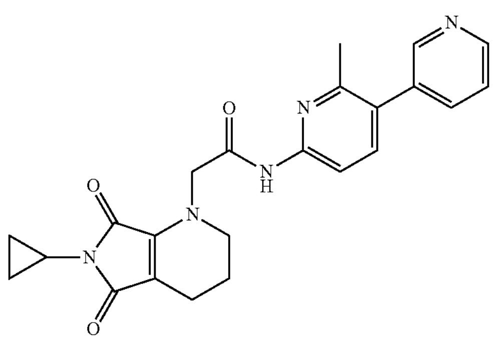 [SMILES: Cc1nc(NC(=O)CN2CCCC3=C2C(=O)N(C2CC2)C3=O)ccc1-c1cccnc1] | 2-(6-cyclopropyl-5,7-dioxo-2,3,4,5,6,7-hexahydro-1H-pyrrolo[3,4-b]pyridin-1-yl)-N-(2-methyl-[3,3'-bipyridin]-6-yl)acetamide |
| 126 | 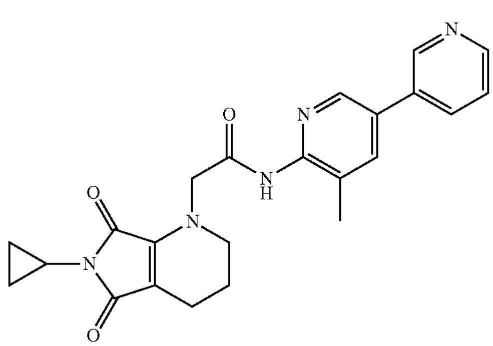 [SMILES: Cc1cc(-c2cccnc2)cnc1NC(=O)CN1CCCC2=C1C(=O)N(C1CC1)C2=O] | 2-(6-cyclopropyl-5,7-dioxo-2,3,4,5,6,7-hexahydro-1H-pyrrolo[3,4-b]pyridin-1-yl)-N-(2-methyl-[3,3'-bipyridin]-6-yl)acetamide |
| 127 | 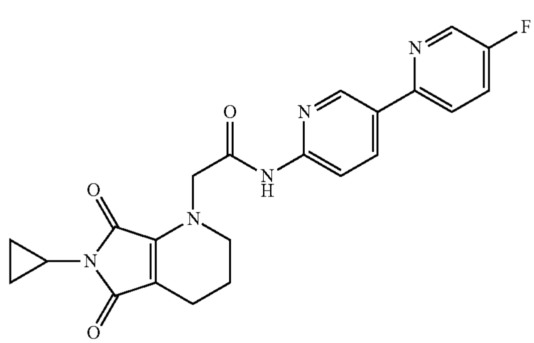 [SMILES: O=C(CN1CCCC2=C1C(=O)N(C1CC1)C2=O)Nc1ccc(-c2ccc(F)cn2)cn1] | 2-(6-cyclopropyl-5,7-dioxo-2,3,4,5,6,7-hexahydro-1H-pyrrolo[3,4-b]pyridin-1-yl)-N-(5-fluoro-[2,3'-bipyridin]-6'-yl)acetamide |

| Cpd ID | Structure | IUPAC Name |
| --- | --- | --- |
| 128 | 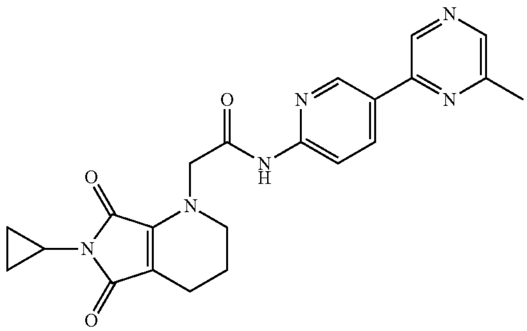 [SMILES: Cc1cncc(-c2ccc(NC(=O)CN3CCCC4=C3C(=O)N(C3CC3)C4=O)nc2)n1] | 2-(6-cyclopropyl-5,7-dioxo-2,3,4,5,6,7-hexahydro-1H-pyrrolo[3,4-b]pyridin-1-yl)-N-(5-(6-methylpyrazin-2-yl)pyridin-2-yl)acetamide |
| 129 | 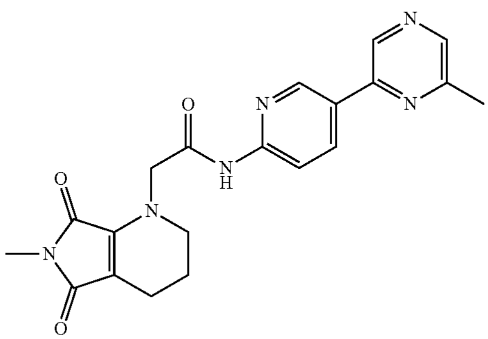 | 2-(6-methyl-5,7-dioxo-2,3,4,5,6,7-hexahydro-1H-pyrrolo[3,4-b]pyridin-1-yl)-N-(5-(6-methylpyrazin-2-yl)pyridin-2-yl)acetamide |
| 130 | 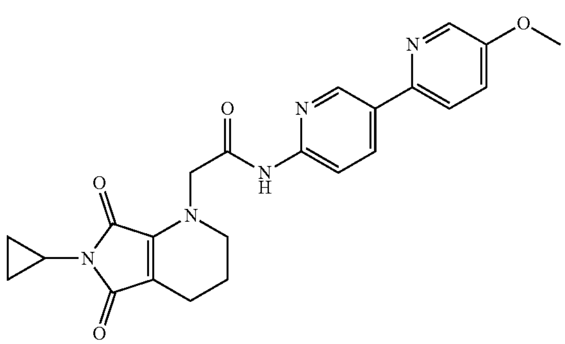 [SMILES: COc1ccc(-c2ccc(NC(=O)CN3CCCC4=C3C(=O)N(C3CC3)C4=O)nc2)nc1] | 2-(6-cyclopropyl-5,7-dioxo-2,3,4,5,6,7-hexahydro-1H-pyrrolo[3,4-b]pyridin-1-yl)-N-(5-methoxy-[2,3'-bipyridin]-6'-yl)acetamide |
| 131 | 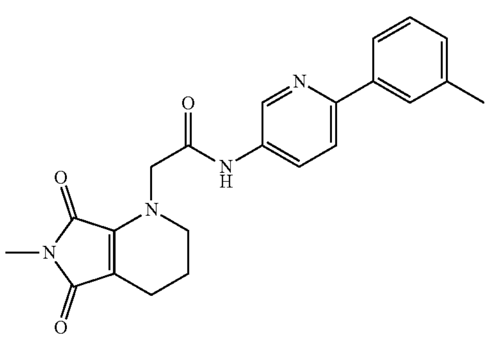 | 2-(6-methyl-5,7-dioxo-2,3,4,5,6,7-hexahydro-1H-pyrrolo[3,4-b]pyridin-1-yl)-N-(6-(m-tolyl)pyridin-3-yl)acetamide |

| Cpd ID | Structure | IUPAC Name |
|---|---|---|
| 132 | 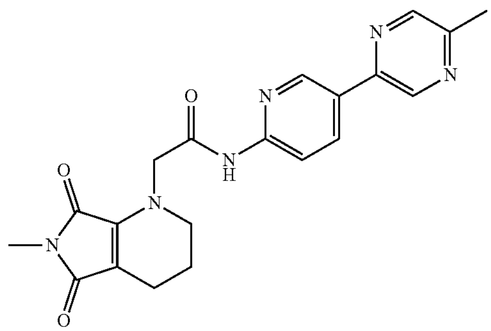 | 2-(6-methyl-5,7-dioxo-2,3,4,5,6,7-hexahydro-1H-pyrrolo[3,4-b]pyridin-1-yl)-N-(5-(5-methylpyrazin-2-yl)pyridin-2-yl)acetamide |
| 133 | 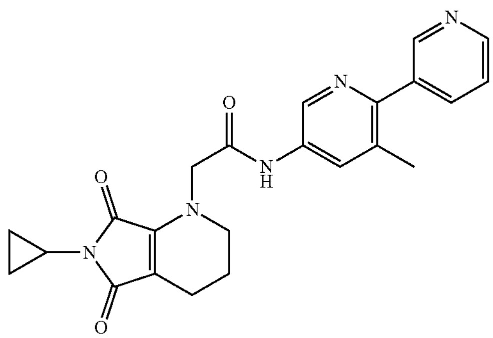 [SMILES: Cc1cc(NC(=O)CN2CCCC3=C2C(=O)N(C2CC2)C3=O)cnc1-c1cccnc1] | 2-(6-cyclopropyl-5,7-dioxo-2,3,4,5,6,7-hexahydro-1H-pyrrolo[3,4-b]pyridin-1-yl)-N-(3-methyl-2,3'-bipyridin-5-yl)acetamide |
| 134 | 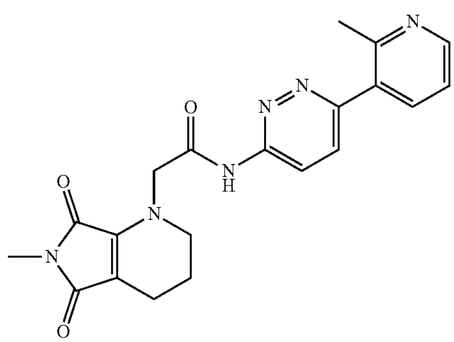 [SMILES: Cc1ncccc1-c1ccc(NC(=O)CN2CCCC3=C2C(=O)N(C)C3=O)nn1] | 2-(6-methyl-5,7-dioxo-2,3,4,5,6,7-hexahydro-1H-pyrrolo[3,4-b]pyridin-1-yl)-N-(6-(2-methylpyridin-3-yl)pyridazin-3-yl)acetamide |
| 135 | 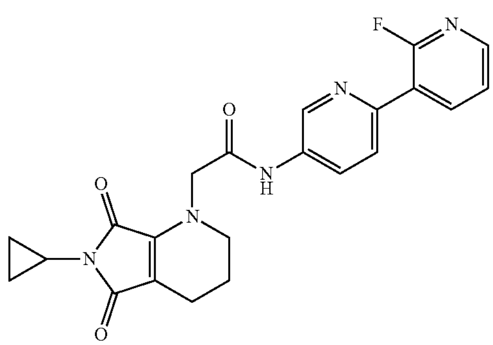 [SMILES: O=C(CN1CCCC2=C1C(=O)N(C1CC1)C2=O)Nc1ccc(-c2cccnc2F)nc1] | 2-(6-cyclopropyl-5,7-dioxo-2,3,4,5,6,7-hexahydro-1H-pyrrolo[3,4-b]pyridin-1-yl)-N-(2'-fluoro-2,3'-bipyridin-5-yl)acetamide |

| Cpd ID | Structure | IUPAC Name |
|---|---|---|
| 136 | 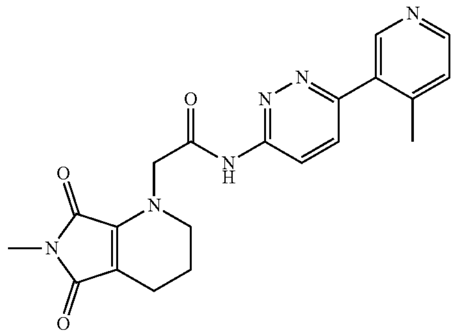 [SMILES: Cc1ccncc1-c1ccc(NC(=O)CN2CCCC3=C2C(=O)N(C)C3=O)nn1] | 2-(6-methyl-5,7-dioxo-2,3,4,5,6,7-hexahydro-1H-pyrrolo[3,4-b]pyridin-1-yl)-N-(6-(4-methylpyridin-3-yl)pyridazin-3-yl)acetamide |
| 137 | 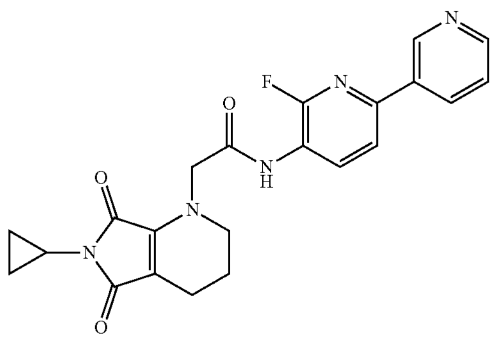 [SMILES: O=C(CN1CCCC2=C1C(=O)N(C1CC1)C2=O)Nc1ccc(-c2cccnc2)nc1F] | N-(6-fluoro-2,3'-bipyridin-5-yl)-2-(6-methyl-5,7-dioxo-2,3,4,5,6,7-hexahydro-1H-pyrrolo[3,4-b]pyridin-1-yl)acetamide |
| 138 | 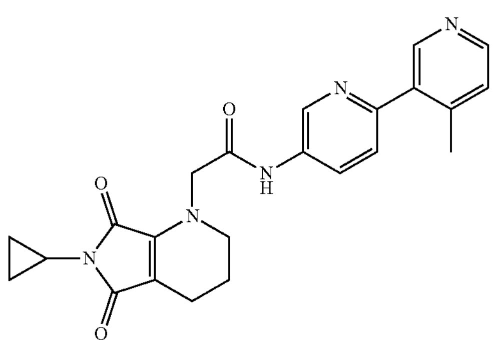 [SMILES: Cc1ccncc1-c1ccc(NC(=O)CN2CCCC3=C2C(=O)N(C2CC2)C3=O)cn1] | 2-(6-cyclopropyl-5,7-dioxo-2,3,4,5,6,7-hexahydro-1H-pyrrolo[3,4-b]pyridin-1-yl)-N-(4'-methyl-2,3'-bipyridin-5-yl)acetamide |
| 139 | 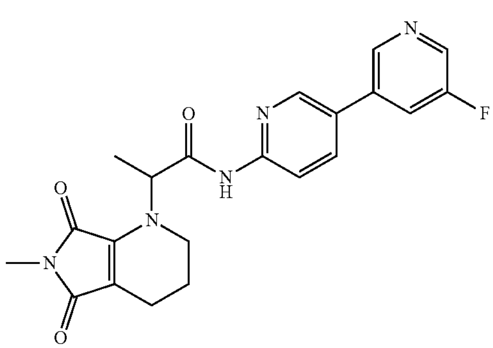 [SMILES: CC(C(=O)Nc1ccc(-c2cncc(F)c2)cn1)N1CCCC2=C1C(=O)N(C)C2=O] | N-(5'-fluoro-3,3'-bipyridin-6-yl)-2-(6-methyl-5,7-dioxo-2,3,4,5,6,7-hexahydro-1H-pyrrolo[3,4-b]pyridin-1-yl)propanamide |

| Cpd ID | Structure | IUPAC Name |
|---|---|---|
| 140 | 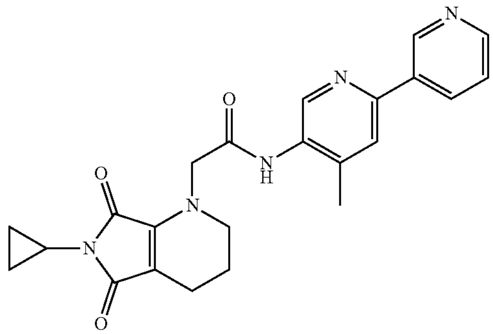 [SMILES: Cc1cc(-c2cccnc2)ncc1NC(=O)CN1CCCC2=C1C(=O)N(C1CC1)C2=O] | 2-(6-cyclopropyl-5,7-dioxo-2,3,4,5,6,7-hexahydro-1H-pyrrolo[3,4-b]pyridin-1-yl)-N-(4-methyl-2,3'-bipyridin-5-yl)acetamide |
| 141 | 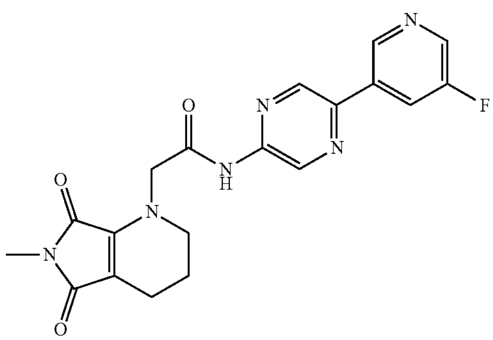 [SMILES: CN1C(=O)C2=C(C1=O)N(CC(=O)Nc1cnc(-c3cncc(F)c3)cn1)CCC2] | N-(5-(5-fluoropyridin-3-yl)pyrazin-2-yl)-2-(6-methyl-5,7-dioxo-2,3,4,5,6,7-hexahydro-1H-pyrrolo[3,4-b]pyridin-1-yl)acetamide |
| 142 | 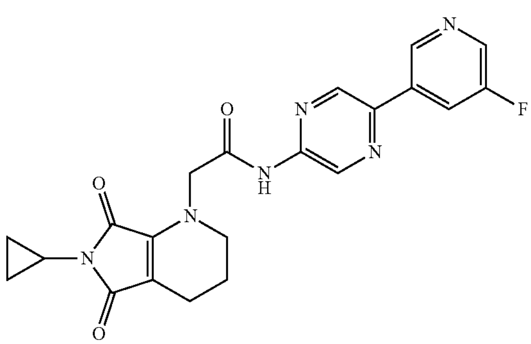 [SMILES: O=C(CN1CCCC2=C1C(=O)N(C1CC1)C2=O)Nc1cnc(-c2cncc(F)c2)cn1] | 2-(6-cyclopropyl-5,7-dioxo-2,3,4,5,6,7-hexahydro-1H-pyrrolo[3,4-b]pyridin-1-yl)-N-(5-(5-fluoropyridin-3-yl)pyrazin-2-yl)acetamide |
| 143 | 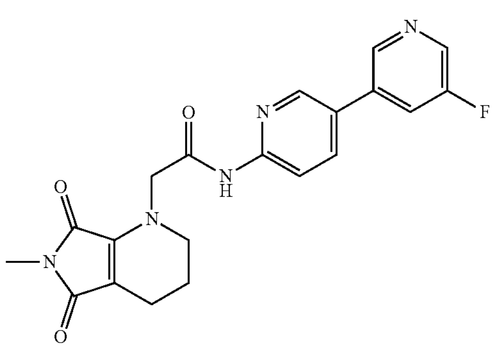 [SMILES: CN1C(=O)C2=C(C1=O)N(CC(=O)Nc1ccc(-c3cncc(F)c3)cn1)CCC2] | N-(5'-fluoro-3,3'-bipyridin-6-yl)-2-(6-methyl-5,7-dioxo-2,3,4,5,6,7-hexahydro-1H-pyrrolo[3,4-b]pyridin-1-yl)acetamide |

| Cpd ID | Structure | IUPAC Name |
|---|---|---|
| 144 | 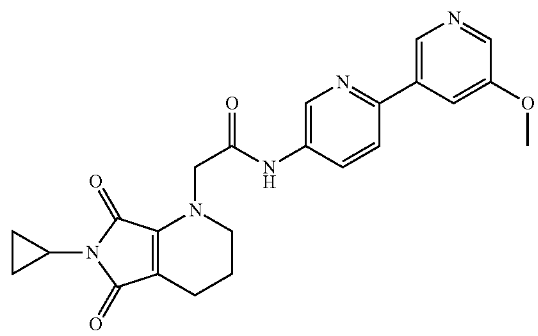 [SMILES: COc1cncc(-c2ccc(NC(=O)CN3CCCC4=C3C(=O)N(C3CC3)C4=O)cn2)c1] | 2-(6-cyclopropyl-5,7-dioxo-2,3,4,5,6,7-hexahydro-1H-pyrrolo[3,4-b]pyridin-1-yl)-N-(5'-methoxy-2,3'-bipyridin-5-yl)acetamide |
| 145 | 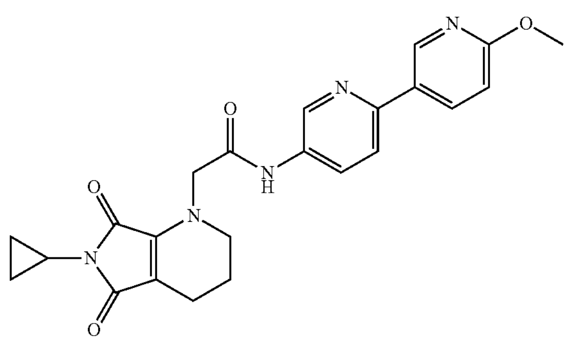 [SMILES: COc1ccc(-c2ccc(NC(=O)CN3CCCC4=C3C(=O)N(C3CC3)C4=O)cn2)cn1] | 2-(6-cyclopropyl-5,7-dioxo-2,3,4,5,6,7-hexahydro-1H-pyrrolo[3,4-b]pyridin-1-yl)-N-(6'-methoxy-2,3'-bipyridin-5-yl)acetamide |
| 146 | 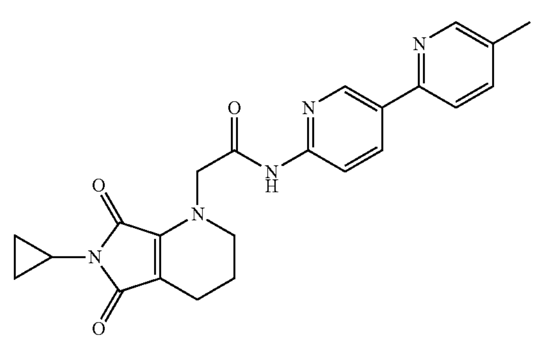 [SMILES: Cc1ccc(-c2ccc(NC(=O)CN3CCCC4=C3C(=O)N(C3CC3)C4=O)nc2)nc1] | 2-(6-cyclopropyl-5,7-dioxo-2,3,4,5,6,7-hexahydro-1H-pyrrolo[3,4-b]pyridin-1-yl)-N-(5-methyl-2,3'-bipyridin-6'-yl)acetamide |
| 147 | 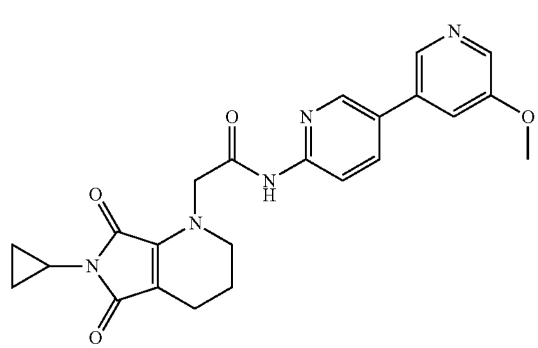 [SMILES: COc1cncc(-c2ccc(NC(=O)CN3CCCC4=C3C(=O)N(C3CC3)C4=O)nc2)c1] | 2-(6-cyclopropyl-5,7-dioxo-2,3,4,5,6,7-hexahydro-1H-pyrrolo[3,4-b]pyridin-1-yl)-N-(5'-methoxy-3,3'-bipyridin-6-yl)acetamide |

| Cpd ID | Structure | IUPAC Name |
|---|---|---|
| 148 | 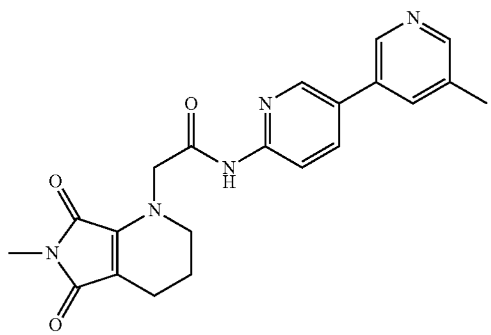 | 2-(6-methyl-5,7-dioxo-2,3,4,5,6,7-hexahydro-1H-pyrrolo[3,4-b]pyridin-1-yl)-N-(5'-methyl-[3,3'-bipyridin]-6-yl)acetamide |
| 149 | 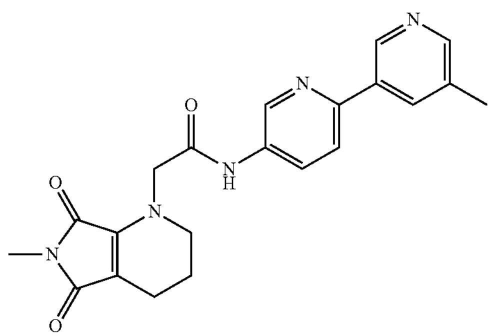 | 2-(6-methyl-5,7-dioxo-2,3,4,5,6,7-hexahydro-1H-pyrrolo[3,4-b]pyridin-1-yl)-N-(5'-methyl-[2,3'-bipyridin]-5-yl)acetamide |
| 150 | 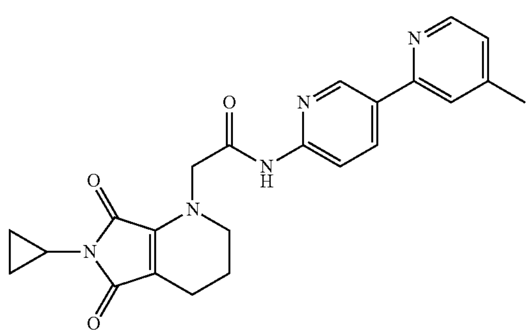 [SMILES: Cc1ccnc(-c2ccc(NC(=O)CN3CCCC4=C3C(=O)N(C3CC3)C4=O)nc2)c1] | 2-(6-cyclopropyl-5,7-dioxo-2,3,4,5,6,7-hexahydro-1H-pyrrolo[3,4-b]pyridin-1-yl)-N-(4-methyl-[2,3'-bipyridin]-6'-yl)acetamide |
| 151 | 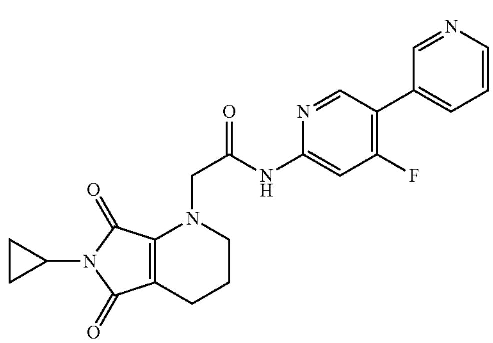 [SMILES: O=C(CN1CCCC2=C1C(=O)N(C1CC1)C2=O)Nc1cc(F)c(-c2cccnc2)cn1] | 2-(6-cyclopropyl-5,7-dioxo-2,3,4,5,6,7-hexahydro-1H-pyrrolo[3,4-b]pyridin-1-yl)-N-(4-fluoro-3,3'-bipyridin-6-yl)acetamide |

| Cpd ID | Structure | IUPAC Name |
|---|---|---|
| 152 | 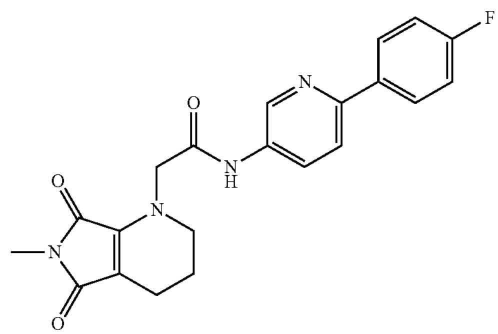 [SMILES: CN1C(=O)C2=C(C1=O)N(CC(=O)Nc1ccc(-c3ccc(F)cc3)nc1)CCC2] | N-(6-(4-fluorophenyl)pyridin-3-yl)-2-(6-methyl-5,7-dioxo-2,3,4,5,6,7-hexahydro-1H-pyrrolo[3,4-b]pyridin-1-yl)acetamide |
| 153 | 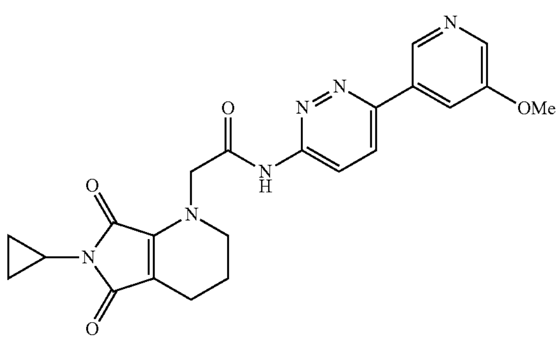 [SMILES: COc1cncc(-c2ccc(NC(=O)CN3CCCC4=C3C(=O)N(C3CC3)C4=O)nn2)c1] | 2-(6-cyclopropyl-5,7-dioxo-2,3,4,5,6,7-hexahydro-1H-pyrrolo[3,4-b]pyridin-1-yl)-N-(6-(5-methoxypyridin-3-yl)pyridazin-3-yl)acetamide |
| 154 | 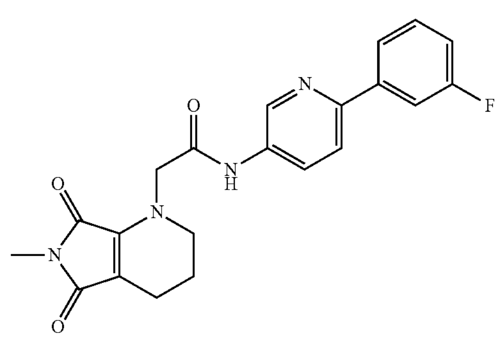 | N-(6-(3-fluorophenyl)pyridin-3-yl)-2-(6-methyl-5,7-dioxo-2,3,4,5,6,7-hexahydro-1H-pyrrolo[3,4-b]pyridin-1-yl)acetamide |
| 155 | 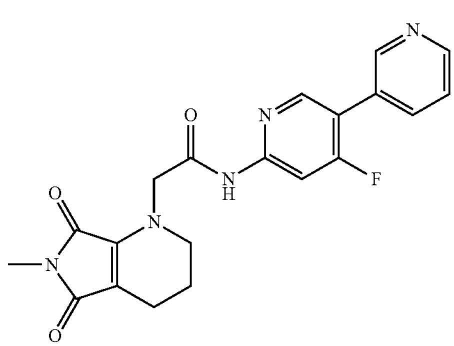 [SMILES: CN1C(=O)C2=C(C1=O)N(CC(=O)Nc1cc(F)c(-c3cccnc3)cn1)CCC2] | N-(4-fluoro-3,3'-bipyridin-6-yl)-2-(6-methyl-5,7-dioxo-2,3,4,5,6,7-hexahydro-1H-pyrrolo[3,4-b]pyridin-1-yl)acetamide |

-continued

| Cpd ID | Structure | IUPAC Name |
|---|---|---|
| 156 | 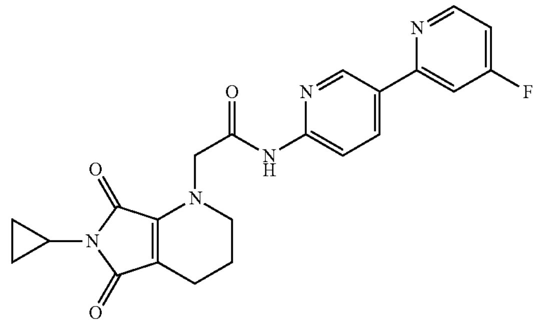 [SMILES: O=C(CN1CCCC2=C1C(=O)N(C1CC1)C2=O)Nc1ccc(-c2cc(F)ccn2)cn1] | 2-(6-cyclopropyl-5,7-dioxo-2,3,4,5,6,7-hexahydro-1H-pyrrolo[3,4-b]pyridin-1-yl)-N-(4-fluoro-[2,3'-bipyridin]-6'-yl)acetamide |
| 157 | 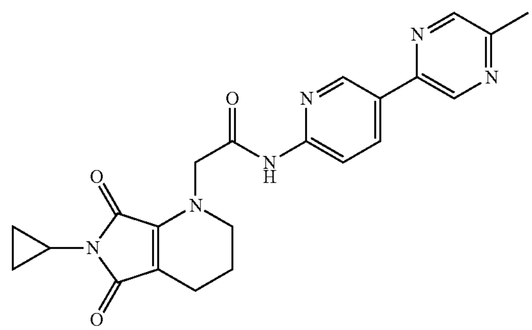 [SMILES: Cc1cnc(-c2ccc(NC(=O)CN3CCCC4=C3C(=O)N(C3CC3)C4=O)nc2)cn1] | 2-(6-cyclopropyl-5,7-dioxo-2,3,4,5,6,7-hexahydro-1H-pyrrolo[3,4-b]pyridin-1-yl)-N-(5-(5-methylpyrazin-2-yl)pyridin-2-yl)acetamide |
| 158 | | 2-(6-methyl-5,7-dioxo-2,3,4,5,6,7-hexahydro-1H-pyrrolo[3,4-b]pyridin-1-yl)-N-(6-(p-tolyl)pyridin-3-yl)acetamide | or a pharmaceutically acceptable salt thereof.

12. A compound as defined by claim 1 wherein the compound is N-([3,3'-bipyridin]-6-yl)-2-(6-cyclopropyl-5,7-dioxo-2,3,4,5,6,7-hexahydro-1H-pyrrolo[3,4-b]pyridin-1-yl)acetamide:

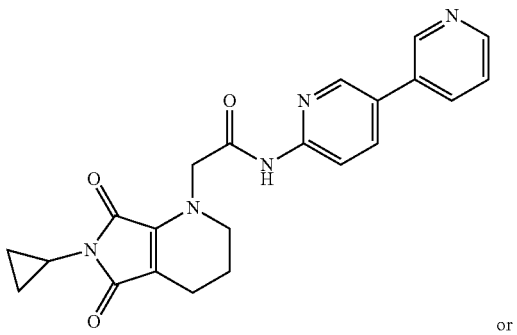

or

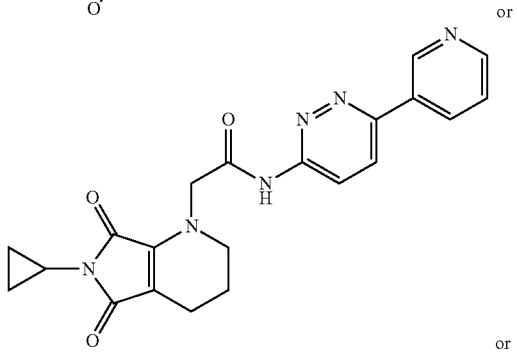

or

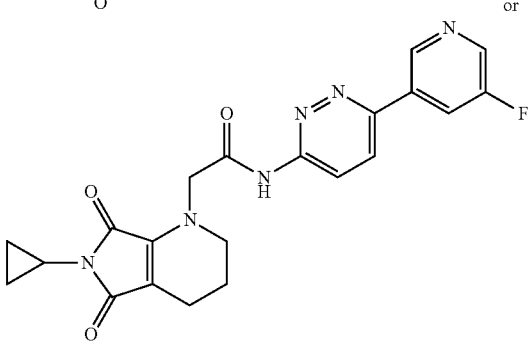

or a pharmaceutically acceptable salt thereof.

13. The compound of claim 1 or a pharmaceutically acceptable salt thereof having an $IC_{50}$ against HEK293-STF3A cells of less than about 10 micromolar.

14. A pharmaceutical composition comprising a compound according to claim 1 or a pharmaceutically acceptable salt thereof in combination with one or more therapeutically acceptable adjuvents, diluents or carriers.

15. A method of modulating WNT activity comprising exposing a WNT protein or a WNT receptor to a compound according to claim 1 or a pharmaceutically acceptable salt thereof.

16. A method according to claim 15 wherein the method is an in vivo method.

17. A method of treating a disease or condition associated with WNT pathway activity comprising administering to a subject in need thereof a therapeutically effective amount of a compound according to claim 1 or a pharmaceutically acceptable salt thereof.

18. The method of claim 17 wherein the disease or condition is selected from the group consisting of fibrosis, stem cell and diabetic retinopathy, rheumatoid arthritis, psoriasis and myocardial infarction.

19. A process for preparation of a compound according to claim 1 or a protected derivative thereof, wherein the process comprises reaction of a compound of Formula (II):

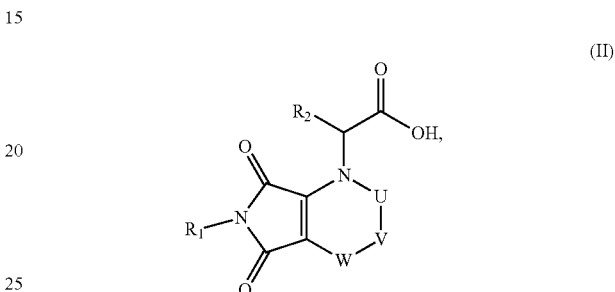

or a protected derivative thereof, wherein $R_1$, $R_2$, U, V and W are as defined in claim 1, with a compound of Formula (III):

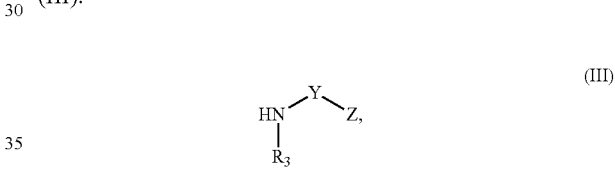

or a protected derivative thereof, wherein $R_3$, Y and Z are as defined in claim 1;

to effect condensation of the compounds of Formula (II) and Formula (III) to provide the compound of Formula (I), protected derivative thereof, or a pharmaceutically acceptable salt thereof:

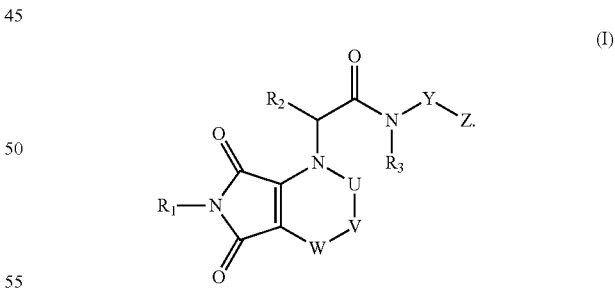

* * * * *